(12) United States Patent
Sham et al.

(10) Patent No.: US 9,796,706 B2
(45) Date of Patent: *Oct. 24, 2017

(54) INHIBITORS OF JUN N-TERMINAL KINASE

(71) Applicant: IMAGO PHARMACEUTICALS, INC., Jackson Hole, WY (US)

(72) Inventors: Hing L. Sham, Palo Alto, CA (US); Roy K. Hom, San Francisco, CA (US); Andrei W. Konradi, Burlingame, CA (US); Gary D. Probst, San Francisco, CA (US); Simeon Bowers, Oakland, CA (US); Anh Truong, Burlingame, CA (US); R. Jeffrey Neitz, San Francisco, CA (US); Jennifer Sealy, Oakland, CA (US); Gergely Toth, Palo Alto, CA (US)

(73) Assignee: IMAGO PHARMACEUTICALS, INC., Jackson Hole, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/391,645

(22) Filed: Dec. 27, 2016

(65) Prior Publication Data

US 2017/0107209 A1    Apr. 20, 2017

Related U.S. Application Data

(63) Continuation of application No. 14/725,691, filed on May 29, 2015, now abandoned, which is a
(Continued)

(51) Int. Cl.
| | |
|---|---|
| *C07D 409/04* | (2006.01) |
| *C07D 409/14* | (2006.01) |
| *C07D 413/04* | (2006.01) |
| *C07D 413/14* | (2006.01) |
| *C07D 417/04* | (2006.01) |
| *C07D 417/14* | (2006.01) |
| *C07D 471/04* | (2006.01) |
| *C07D 487/04* | (2006.01) |
| *A61K 31/381* | (2006.01) |
| *A61K 31/433* | (2006.01) |
| *A61K 31/401* | (2006.01) |
| *A61K 31/4196* | (2006.01) |
| *A61K 31/4245* | (2006.01) |

(Continued)

(52) U.S. Cl.
CPC .......... *C07D 409/04* (2013.01); *A61K 31/381* (2013.01); *A61K 31/401* (2013.01); *A61K 31/4196* (2013.01); *A61K 31/4245* (2013.01); *A61K 31/433* (2013.01); *A61K 31/4709* (2013.01); *A61K 31/4725* (2013.01); *A61K 31/498* (2013.01); *A61K 31/4985* (2013.01); *A61K 31/519* (2013.01); *C07D 409/14* (2013.01); *C07D 413/04* (2013.01); *C07D 413/14* (2013.01); *C07D 417/04* (2013.01); *C07D 417/14* (2013.01); *C07D 471/04* (2013.01); *C07D 487/04* (2013.01)

(58) Field of Classification Search
CPC .. C07D 409/04; C07D 409/14; C07D 487/04; C07D 413/04; C07D 413/14; C07D 417/04; C07D 417/14; C07D 471/04; A61K 31/381; A61K 31/401; A61K 31/4196; A61K 31/4245; A61K 31/433; A61K 31/4709; A61K 31/4725; A61K 31/498; A61K 31/4985; A61K 31/519
See application file for complete search history.

(56) References Cited

U.S. PATENT DOCUMENTS

| | | | |
|---|---|---|---|
| 5,068,239 | A | 11/1991 | Inukai et al. |
| 2009/0192164 | A1 | 7/2009 | Hasumi et al. |

FOREIGN PATENT DOCUMENTS

| | | |
|---|---|---|
| EP | 0 421 365 A2 | 4/1991 |
| JP | 3-204875 | 9/1991 |

(Continued)

OTHER PUBLICATIONS

Office Action issued Jul. 12, 2016 in European Patent Application No. 10 704 662.5.
Australian Office Action issued May 4, 2016 in Patent Application No. 2015215863.
Office Action issued Jan. 13, 2016 in Japanese Patent Application No. 2014-252997 (with English translation).
(Continued)

*Primary Examiner* — Sarah Pihonak
(74) *Attorney, Agent, or Firm* — Oblon, McClelland, Maier & Neustadt, L.L.P.

(57) ABSTRACT

The present disclosure provides inhibitors of c-Jun N-terminal kinases (JNK) having a structure according to the following formula:

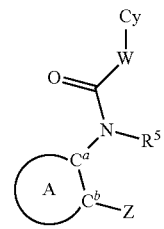

or a salt or solvate thereof, wherein ring A, $C^a$, $C^b$, Z, $R^5$, W and Cy are defined herein. The disclosure further provides pharmaceutical compositions including the compounds of the present disclosure and methods of making and using the compounds and compositions of the present disclosure, e.g., in the treatment and prevention of various disorders, such as Alzheimer's disease.

17 Claims, No Drawings

Related U.S. Application Data continuation of application No. 13/617,630, filed on Sep. 14, 2012, now Pat. No. 9,073,891, which is a continuation of application No. 12/701,474, filed on Feb. 5, 2010, now Pat. No. 8,450,363.

(60) Provisional application No. 61/244,390, filed on Sep. 21, 2009, provisional application No. 61/207,126, filed on Feb. 6, 2009.

(51) Int. Cl.
*A61K 31/4709* (2006.01)
*A61K 31/4725* (2006.01)
*A61K 31/498* (2006.01)
*A61K 31/4985* (2006.01)
*A61K 31/519* (2006.01)

(56) References Cited

FOREIGN PATENT DOCUMENTS

| | | |
|---|---|---|
| JP | 2005-022972 A | 1/2005 |
| WO | 00/39116 A1 | 7/2000 |
| WO | 02/06246 A1 | 1/2002 |
| WO | 03/035076 A1 | 5/2003 |
| WO | 03/062211 A1 | 7/2003 |
| WO | 2004/026226 A1 | 1/2004 |
| WO | 2004/041813 A1 | 5/2004 |
| WO | 2007/129195 A2 | 11/2007 |
| WO | 2008/001929 A1 | 1/2008 |

OTHER PUBLICATIONS

Office Action with Search History issued Jan. 14, 2016 in Canadian Patent Application No. 2,751,141.
Office Action issued Aug. 26, 2015 in Israeli Patent Application No. 214472 (with English translation).
CAS STN Abstract, Registry No. 886960-39-0 (pub. Jun. 6, 2006).
Office Action issued Dec. 22, 2014, in Chinese Patent Application No. 201080015664.5 (with English translation).
Collinge, Journal of Neurology, Neurosurgery, and Psychiatry, BMJ Publishing Group. vol. 76, pp. 906-919 (2005).
Singh, et al., Progress in Neurobiology, Elsevier, vol. 81, pp. 29-44 (2007).
Lindvall, et al., Nature, Nature Publishing Group, vol. 441, pp. 1094-1096 (2006).
Gaillard, et al., Journal of Medicinal Chemistry, American Chemical Society, vol. 48, pp. 4596-4607 (2005).
Sarvanan, et al., "Synthesis and Antimicrobial Activity of Some 2'-Substituted Amino (2-Methyl Oxadiazol-5-YL)-4,5,6,7-Tetrahydro Benzo (b) Thiophenes," 7 Indian Journal of Heterocyclic Chemistry 285-288 (1998).
SciFinder search report (Mar. 2012).
STN Columbus search report, for compounds RN 1007073-52-0 and RN 955782-19-1 (Mar. 2012).
Chemical Abstracts Servile, Database Accession No. 1179 424-94-2 (Sep. 2, 2009), XP-002580315.
Chemical Abstracts Servile, Database Accession No. 1179493-56-1 (Sep. 2, 2009), XP-002580316.
International Search Report dated Jun. 28, 2010, for International Application No. PCT/US2010/023404.
Vippagunta, et al., "Crystalline Solids," Advanced Drug Delivery Reviews, pp. 3-26, vol. 48 (2001).

INHIBITORS OF JUN N-TERMINAL KINASE

The present application is a continuation of U.S. patent application Ser. No. 14/725,691, filed on May 29, 2015, which is a continuation of U.S. patent application Ser. No. 13/617,630, filed on Sep. 14, 2012 (now U.S. Pat. No. 9,073,891), which is a continuation of U.S. patent application Ser. No. 12/701,474, filed on Feb. 5, 2010 (now U.S. Pat. No. 8,450,363), which claims priority from U.S. Provisional Patent Application No. 61/207,126 filed on Feb. 6, 2009, and from U.S. Provisional Patent Application No. 61/244,390 filed on Sep. 21, 2009, the disclosures each of which are incorporated herein by reference in their entirety.

BACKGROUND OF THE DISCLOSURE

The present disclosure relates to inhibitors of c-Jun N-terminal kinases (JNKs). The disclosure also provides pharmaceutical compositions comprising the inhibitors of the present disclosure and methods of utilizing those compositions in the treatment of various disorders, such as Alzheimer's disease.

Mammalian cells respond to extracellular stimuli by activating signaling cascades that are mediated by members of the mitogen-activated protein (MAP) kinase family, which include the extracellular signal regulated kinases (ERKs), the p38 MAP kinases and the c-Jun N-terminal kinases (JNKs). MAP kinases (MAPKs) are serine/threonine kinases and are activated by a variety of signals including growth factors, cytokines, UV radiation, and stress-inducing agents. MAPKs phosphorylate various substrates including transcription factors, which in turn regulate the expression of specific genes.

Members of the JNK family are activated by pro-inflammatory cytokines, such as tumor necrosis factor-alpha (TNF alpha) and interleukin-1 beta (IL-1 beta), as well as by environmental stress, including UV irradiation, hypoxia, and osmotic shock (see, e.g., Minden et al., *Biochemica et Biophysica Acta* 1997, 1333:F85-F104). Three distinct JNK genes, jnk1, jnk2 and jnk3 were identified and at least ten different splicing isoforms exist in mammalian cells (see, e.g., Gupta et al., *EMBO J.* 1996, 15:2760-2770).

Down-stream substrates of JNKs include transcription factors c-Jun, ATF-2, Elk1, p53 and a cell death domain protein (DENN) (see, e.g., Zhang et al. *Proc. Natl. Acad. Sci. USA* 1998, 95:2586-2591). Each JNK isoform binds to these substrates with different affinities, suggesting a regulation of signaling pathways by substrate specificity in vivo (Gupta et al., supra).

JNKs have been implicated in mediating a number of physiological responses and disorders including cellular-response to cancer, thrombin-induced platelet aggregation, immunodeficiency disorders, autoimmune diseases, cell death, allergies, osteoporosis and heart disease. The therapeutic targets related to activation of the JNK pathway include chronic myelogenous leukemia (CML), rheumatoid arthritis, asthma, osteoarthritis, ischemia, various cancers and neurodegenerative diseases.

Several reports have detailed the importance of JNK activation associated with liver disease or episodes of hepatic ischemia (see, e.g., *Nat. Genet.* 1999, 21:326-329; *FEBS Lett.* 1997, 420:201-204; *J. Clin. Invest.* 1998, 102: 1942-1950; *Hepatology* 1998, 28:1022-1030). A role for JNK in cardiovascular disease such as myocardial infarction or congestive heart failure has also been reported (see, e.g., *Circ. Res.* 1998, 83:167-178; Circulation 1998, 97:1731-7).

The JNK cascade also plays a role in T-cell activation, including activation of the IL-2 promoter (see, e.g., *J. Immunol.* 1999, 162:3176-87; *Eur. J. Immunol.* 1998, 28:3867-77; *J. Exp. Med.* 1997). A role for JNK activation in various forms of cancer has also been established. For example, constitutively activated JNK is associated with HTLV-1 mediated tumorigenesis (*Oncogene* 1996, 13:135-42). JNK may play a role in Kaposi's sarcoma (KS) because it is thought that the proliferative effects of bFGF and OSM on KS cells are mediated by their activation of the JNK signaling pathway (see e.g., *J. Clin. Invest.* 1997, 99:1798-804). Other proliferative effects of certain cytokines implicated in KS proliferation, such as vascular endothelial growth factor (VEGF), IL-6 and TNF alpha, may also be mediated by JNK. In addition, regulation of the c-jun gene in p210 BCR-ABL transformed cells corresponds with activity of JNK, suggesting a role for JNK inhibitors in the treatment for chronic myelogenous leukemia (CML) (see, e.g., Blood 1998, 92-2450-60).

While JNK1 and JNK2 are widely expressed in a variety of tissues, JNK3 is selectively expressed in the brain and, to a lesser extent, in the heart and testis (see, e.g., Gupta et al., supra; Mohit et al., *Neuron* 1995, 14:67-78; Martin et al., *Brain Res. Mol. Brain. Res.* 1996, 35:47-57). JNK3 has been linked to neuronal apoptosis induced by kainic acid, indicating a role of JNK in the pathogenesis of glutamate neurotoxicity. In the adult human brain, JNK3 expression is localized to a subpopulation of pyramidal neurons in the CA1, CA4 and subiculum regions of the hippocampus and layers 3 and 5 of the neocortex (Mohit et al., supra). The CA1 neurons of patients with acute hypoxia showed strong nuclear JNK3-immunoreactivity compared to minimal, diffuse cytoplasmic staining of the hippocampal neurons from brain tissues of normal patients (Zhang et al., supra). Thus, JNK3 appears to be involved in hypoxic and ischemic damage of CA1 neurons in the hippocampus.

Disruption of the JNK3 gene caused resistance of mice to the excitotoxic glutamate receptor agonist kainic acid, including the effects on seizure activity, AP-1 transcriptional activity and apoptosis of hippocampal neurons, indicating that the JNK3 signaling pathway is a critical component in the pathogenesis of glutamate neurotoxicity (Yang et al., *Nature* 1997, 389:865-870).

In addition, JNK3 co-localizes immunochemically with neurons vulnerable in Alzheimer's disease (Mohit et al., supra). Based on these findings, JNK signalling, especially that of JNK3, has been implicated in the areas of apoptosis-driven neurodegenerative diseases such as Alzheimer's Disease, Parkinson's Disease, amyotrophic lateral sclerosis (ALS), epilepsy, seizures, Huntington's Disease, traumatic brain injuries, as well as ischemic and hemorrhaging stroke.

Drug molecules that inhibit MAPKs, such as p38 are known (see, e.g., WO 98/27098 and WO 95/31451). However, inhibitors that are selective for JNKs versus other members of the MAPK family are rare (see, e.g., U.S. Patent Application Publication 20080033022). There is an unmet medical need for the development of potent, JNK specific inhibitors that are useful in treating the various conditions associated with JNK activation.

SUMMARY OF THE DISCLOSURE

In various aspects, the present disclosure provides for a compound having a structure according to Formula (I):

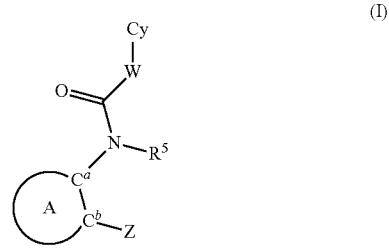

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and are part of ring A; Z is 5- or 6-membered heteroaryl, with the proviso that (i) when ring A is thiophene, then Z is not a heteroaryl chosen from benzoimidazole, thiazole, and benzothiazole; (ii) when ring A is thiazole, then Z is not benzoimidazole; (iii) when ring A is thiophene, then Z is not substituted oxadiazole; and (iv) when ring A is thiophene, then Z is not pyrimidinone; $R^5$ is chosen from H, acyl, $C_1$-$C_6$ alkyl, and $C_3$-$C_6$ cycloalkyl; W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, C(O)Nee, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; and $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl. The present disclosure further provides for a pharmaceutical composition comprising a compound according to Formula (I) and a pharmaceutically acceptable carrier.

The present disclosure also provides for compound having a structure according to Formula (VIII):

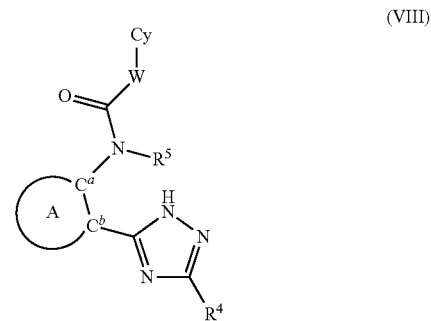

(VIII)

or a tautomer, mixture of tautomers, salt or solvate thereof, wherein ring A is 5- or 6-membered heteroaryl, wherein the heteroaryl is optionally substituted with 1-3 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and, which are part of ring A; $R^4$ is chosen from H, independently chosen from H, $C_1$-$C_4$ alkyl, $C_1$-$C_4$ alkenyl, $C_1$-$C_4$ alkynyl, $C_1$-$C_4$ haloalkyl, $C_3$-$C_6$ cycloalkyl, 3- to 6-membered heterocycloalkyl, aryl, and 5- or 6-membered heteroaryl, CN, halogen, $OR^{17}$, $SR^{17}$ and $NR^{17}R^{18}$, wherein $R^{17}$ and $R^{18}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{17}$ and $R^{18}$, together with the nitrogen atom to which they are bound form a 5- to 7-membered heterocyclic ring; $R^5$ is chosen from H, acyl, $C_1$-$C_6$ alkyl, and C$_3$-C$_6$ cycloalkyl; W is chosen from C$_1$-C$_4$ alkylene, wherein the alkylene is optionally substituted with from 1 to 4 substituents chosen from alkyl, alkenyl, alkynyl, haloalkyl, heteroalkyl, C$_3$-C$_6$-cycloalkyl, 3- to 8-membered heterocycloalkyl, aryl, 5- or 6-membered heteroaryl, CN, halogen, OR$^{42}$, SR$^{42}$, NR$^{42}$R$^{43}$, C(O)R$^{44}$, C(O)NR$^{42}$R$^{43}$, OC(O)NR$^{42}$R$^{43}$, C(O)OR$^{42}$, NR$^{45}$C(O)R$^{44}$, NR$^{45}$C(O)OR$^{42}$, NR$^{45}$C(O)NR$^{42}$R$^{43}$, NR$^{45}$C(S)NR$^{42}$R$^{43}$, NR$^{45}$S(O)$_2$R$^{44}$, S(O)$_2$NR$^{42}$R$^{43}$, S(O)R$^{44}$, and S(O)$_2$R$^{44}$, wherein R$^{42}$, R$^{43}$ and R$^{45}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{42}$ and R$^{43}$, together with the nitrogen atom to which they are bound are optionally joined to form a 5- to 7-membered heterocyclic ring; and R$^{44}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, OR$^{52}$, SR$^{52}$, NR$^{52}$R$^{53}$, C(O)R$^{54}$, C(O)NR$^{52}$R$^{53}$, OC(O)NR$^{52}$R$^{53}$, C(O)OR$^{52}$, NR$^{55}$C(O)R$^{54}$, NR$^{55}$C(O)OR$^{52}$, NR$^{55}$C(O)NR$^{52}$R$^{53}$, NR$^{55}$C(S)NR$^{52}$R$^{53}$, NR$^{55}$S(O)$_2$R$^{54}$, S(O)$_2$NR$^{52}$R$^{53}$, S(O)R$^{54}$ and S(O)$_2$R$^{54}$, wherein R$^{52}$, R$^{53}$ and R$^{55}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{52}$ and R$^{53}$, together with the nitrogen atom to which they are bound are optionally joined to form a 5- to 7-membered heterocyclic ring; and R$^{54}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl. The present disclosure further provides for a pharmaceutical composition comprising a compound according to Formula (VIII) and a pharmaceutically acceptable carrier.

The present disclosure further provides for a compound having a structure according to Formula (X) or Formula (XI):

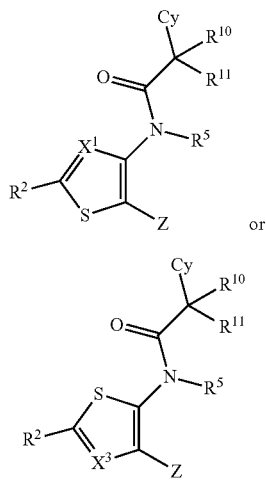

or a salt or solvate thereof, wherein X$^1$ is chosen from N and CR$^{2a}$; R$^2$ and R$^{2a}$ are independently chosen from H, C$_1$-C$_4$-alkyl, C$_1$-C$_4$-alkenyl, C$_1$-C$_4$-alkynyl, C$_1$-C$_4$-haloalkyl, 2- to 4-membered heteroalkyl, C$_3$-C$_6$-cycloalkyl, 3- to 6-membered heterocycloalkyl, CN, and halogen; R$^{10}$ and R$^{11}$ are independently chosen from H, C$_1$-C$_6$-alkyl, C$_1$-C$_6$-alkenyl, C$_1$-C$_6$-alkynyl, C$_1$-C$_6$-haloalkyl, 2- to 6-membered heteroalkyl, C$_3$-C$_6$-cycloalkyl, 3- to 8-membered heterocycloalkyl, aryl, 5- or 6-membered heteroaryl, CN, halogen, OR$^{42}$, SR$^{42}$, NR$^{42}$R$^{43}$, C(O)R$^{44}$, C(O)NR$^{42}$R$^{43}$, OC(O)NR$^{42}$R$^{43}$, C(O)OR$^{42}$, NR$^{45}$C(O)R$^{44}$, NR$^{45}$C(O)OR$^{42}$, NR$^{45}$C(O)NR$^{42}$R$^{43}$, NR$^{45}$C(S)NR$^{42}$R$^{43}$, NR$^{45}$S(O)$_2$R$^{44}$, S(O)$_2$NR$^{42}$R$^{43}$, S(O)R$^{44}$ and S(O)$_2$R$^{44}$, wherein R$^{42}$, R$^{43}$ and R$^{45}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, or R$^{42}$ and R$^{43}$, together with the nitrogen atom to which they are bound form a 5- to 7-membered heterocyclic ring; and R$^{44}$ is chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; R$^5$ is chosen from H and substituted or unsubstituted C$_1$-C$_6$ alkyl; Cy is chosen from cycloalkyl, heterocycloalkyl, aryl, and heteroaryl, wherein the cycloalkyl, heterocycloalkyl, aryl or heteroaryl is optionally substituted with from 1 to 6 substituents independently chosen from C$_1$-C$_6$-alkyl, C$_1$-C$_6$-alkenyl, C$_1$-C$_6$-alkynyl, C$_1$-C$_6$-haloalkyl, 2- to 6-membered heteroalkyl, C$_3$-C$_{12}$-cycloalkyl, 3- to 8-membered heterocycloalkyl, aryl, 5- or 6-membered heteroaryl, CN, halogen, OR$^{52}$, SR$^{52}$, NR$^{52}$R$^{53}$, C(O)R$^{54}$, C(O)NR$^{52}$R$^{53}$, OC(O)NR$^{52}$R$^{53}$, C(O)OR$^{52}$, NR$^{55}$C(O)R$^{54}$, NR$^{55}$C(O)OR$^{52}$, NR$^{55}$C(O)NR$^{52}$R$^{53}$, NR$^{55}$C(S)NR$^{52}$R$^{53}$, NR$^{55}$S(O)$_2$R$^{54}$, S(O)$_2$NR$^{52}$R$^{53}$, S(O)R$^{54}$ and S(O)$_2$R$^{54}$, wherein R$^{52}$, R$^{53}$ and R$^{55}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{52}$ and R$^{53}$, together with the nitrogen atom to which they are bound are optionally joined to form a 5- to 7-membered heterocyclic ring; and R$^{54}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; and Z is chosen from:

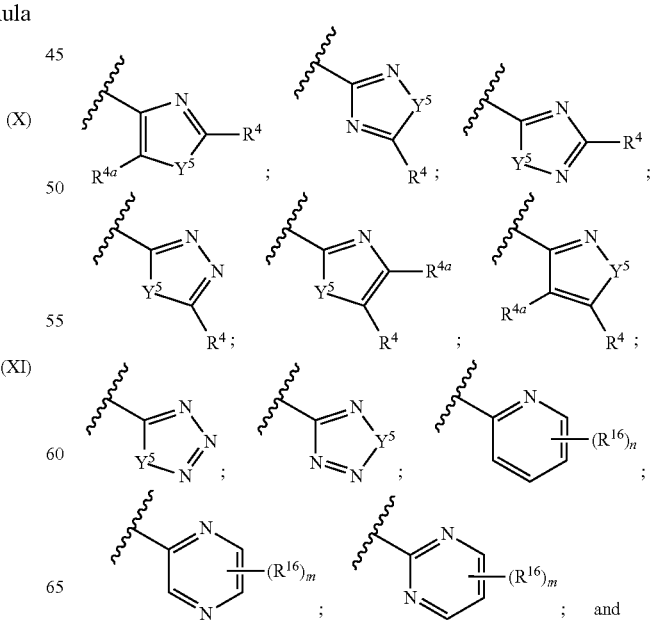

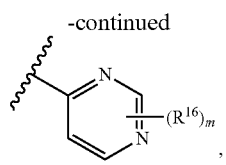

wherein $Y^5$ is chosen from O, S and $NR^3$, wherein $R^3$ is chosen from H, alkyl, alkenyl, alkynyl, haloalkyl, cycloalkyl, 3- to 8-membered heterocycloalkyl, aryl, and 5- or 6-membered heteroaryl; and $R^4$, $R^{4a}$ and $R^{16}$ are independently chosen from H, alkyl, alkenyl, alkynyl, haloalkyl, cycloalkyl, 3- to 8-membered heterocycloalkyl, aryl, 5- or 6-membered heteroaryl, CN, halogen, $OR^{17}$, $SR^{17}$ and $NR^{17}R^{18}$, wherein $R^{17}$ and $R^{18}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{17}$ and $R^{18}$, together with the nitrogen atom to which they are bound form a 5- to 7-membered heterocyclic ring, or two of $R^4$, $R^{4a}$ and $R^3$, together with the atoms to which they are attached, form a 5- to 7-membered ring, or adjacent $R^{16}$ groups, together with the carbon atoms to which they are attached, form a 5- to 7-membered ring; n is an integer chosen from 0 to 4; and m is an integer chosen from 0 to 3. The present disclosure further provides for a pharmaceutical composition comprising a compound according to Formula (X) or (XI) and a pharmaceutically acceptable carrier.

The present disclosure also provides for a method of treating a neurodegenerative disease comprising administering to a mammalian subject in need thereof a pharmaceutically effective amount of a compound having a structure according to Formula (I):

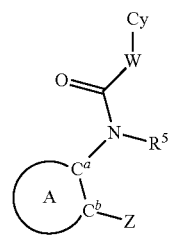

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and are part of ring A; Z is 5- or 6-membered heteroaryl; $R^5$ is chosen from H, acyl, $C_1$-$C_6$ alkyl, and $C_3$-$C_6$ cycloalkyl; W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; and $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl.

The present disclosure also provides for a method of reducing p-cjun concentration in brain tissue of a subject in need thereof, the method comprising administering to the subject a compound having a structure according to Formula (I):

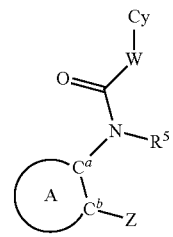

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, NR$^{15}$C(O)NR$^{12}$R$^{13}$, NR$^{15}$C(S)NR$^{12}$R$^{13}$, NR$^{15}$S(O)$_2$R$^{14}$, S(O)$_2$NR$^{12}$R$^{13}$, S(O)R$^{14}$ and S(O)$_2$R$^{14}$, wherein R$^{12}$, R$^{13}$ and R$^{15}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, or R$^{12}$ and R$^{13}$, together with the nitrogen atom to which they are bound form a 5- to 7-membered heterocyclic ring; and R$^{14}$ is chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; C$^a$ and C$^b$ are carbon atoms, which are adjacent to each other and are part of ring A; Z is 5- or 6-membered heteroaryl; R$^5$ is chosen from H, acyl, C$_1$-C$_6$ alkyl, and C$_3$-C$_6$ cycloalkyl; W is chosen from C$_1$-C$_4$ alkylene, wherein the alkylene is optionally substituted with 1-4 substituents independently chosen from alkyl, alkenyl, alkynyl, haloalkyl, heteroalkyl, C$_3$-C$_6$-cycloalkyl, 3- to 8-membered heterocycloalkyl, aryl, 5- or 6-membered heteroaryl, CN, halogen, OR$^{42}$, SR$^{42}$, NR$^{42}$R$^{43}$, C(O)R$^{44}$, C(O)NR$^{42}$R$^{43}$, OC(O)NR$^{42}$R$^{43}$, C(O)OR$^{42}$, NR$^{45}$C(O)R$^{44}$, NR$^{45}$C(O)OR$^{42}$, NR$^{45}$C(O)NR$^{42}$R$^{43}$, NR$^{45}$C(S)NR$^{42}$R$^{43}$, NR$^{45}$S(O)$_2$R$^{44}$, S(O)$_2$NR$^{42}$R$^{43}$, S(O)R$^{44}$, and S(O)$_2$R$^{44}$, wherein R$^{42}$, R$^{43}$ and R$^{45}$ are members independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{42}$ and R$^{43}$, together with the nitrogen atom to which they are bound are optionally joined to form a 5- to 7-membered heterocyclic ring; and R$^{44}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, OR$^{52}$, SR$^{52}$, NR$^{52}$R$^{53}$, C(O)R$^{54}$, C(O)NR$^{52}$R$^{53}$, OC(O)NR$^{52}$R$^{53}$, C(O)OR$^{52}$, NR$^{55}$C(O)R$^{54}$, NR$^{55}$C(O)OR$^{52}$, NR$^{55}$C(O)NR$^{52}$R$^{53}$, NR$^{55}$C(S)NR$^{52}$R$^{53}$, NR$^{55}$S(O)$_2$R$^{54}$, S(O)$_2$NR$^{52}$R$^{53}$, S(O)R$^{54}$ and S(O)$_2$R$^{54}$, wherein R$^{52}$, R$^{53}$ and R$^{55}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{52}$ and R$^{53}$, together with the nitrogen atom to which they are bound are optionally joined to form a 5- to 7-membered heterocyclic ring; and R$^{54}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl.

In addition, the present disclosure provides for use of a compound in an in vitro assay measuring kinase activity, said compound having a structure according to Formula (I):

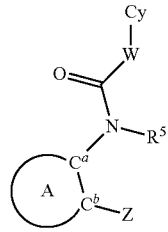

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, C$_3$-C$_{10}$-cycloalkyl, 3- to 8-membered heterocycloalkyl, aryl, 5- or 6-membered heteroaryl, CN, halogen, OR$^{12}$, SR$^{12}$, NR$^{12}$R$^{13}$, C(O)R$^{14}$, C(O)NR$^{12}$R$^{13}$, OC(O)NR$^{12}$R$^{13}$, C(O)OR$^{12}$, NR$^{15}$C(O)R$^{14}$, NR$^{15}$C(O)OR$^{12}$, NR$^{15}$C(O)NR$^{12}$R$^{13}$, NR$^{15}$C(S)NR$^{12}$R$^{13}$, NR$^{15}$S(O)$_2$R$^{14}$, S(O)$_2$NR$^{12}$R$^{13}$, S(O)R$^{14}$ and S(O)$_2$R$^{14}$, wherein R$^{12}$, R$^{13}$ and R$^{15}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, or R$^{12}$ and R$^{13}$, together with the nitrogen atom to which they are bound form a 5- to 7-membered heterocyclic ring; and R$^{14}$ is chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; C$^a$ and C$^b$ are carbon atoms, which are adjacent to each other and are part of ring A; Z is 5- or 6-membered heteroaryl; R$^5$ is chosen from H, acyl, C$_1$-C$_6$ alkyl, and C$_3$-C$_6$ cycloalkyl; W is chosen from C$_1$-C$_4$ alkylene, wherein the alkylene is optionally substituted with 1-4 substituents independently chosen from alkyl, alkenyl, alkynyl, haloalkyl, heteroalkyl, C$_3$-C$_6$-cycloalkyl, 3- to 8-membered heterocycloalkyl, aryl, 5- or 6-membered heteroaryl, CN, halogen, OR$^{42}$, SR$^{42}$, NR$^{42}$R$^{43}$, C(O)R$^{44}$, C(O)NR$^{42}$R$^{43}$, OC(O)NR$^{42}$R$^{43}$, C(O)OR$^{42}$, NR$^{45}$C(O)R$^{44}$, NR$^{45}$C(O)OR$^{42}$, NR$^{45}$C(O)NR$^{42}$R$^{43}$, NR$^{45}$C(S)NR$^{42}$R$^{43}$, NR$^{45}$S(O)$_2$R$^{44}$, S(O)$_2$NR$^{42}$R$^{43}$, S(O)R$^{44}$, and S(O)$_2$R$^{44}$, wherein R$^{42}$, R$^{43}$ and R$^{45}$ are members independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{42}$ and R$^{43}$, together with the nitrogen atom to which they are bound are optionally joined to form a 5- to 7-membered heterocyclic ring; and R$^{44}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, OR$^{52}$, SR$^{52}$, NR$^{52}$R$^{53}$, C(O)R$^{54}$, C(O)NR$^{52}$R$^{53}$, OC(O)NR$^{52}$R$^{53}$, C(O)OR$^{52}$, NR$^{55}$C(O)R$^{54}$, NR$^{55}$C(O)OR$^{52}$, NR$^{55}$C(O)NR$^{52}$R$^{53}$, NR$^{55}$C(S)NR$^{52}$R$^{53}$, NR$^{55}$S(O)$_2$R$^{54}$, S(O)$_2$NR$^{52}$R$^{53}$, S(O)R$^{54}$ and S(O)$_2$R$^{54}$, wherein R$^{52}$, R$^{53}$ and R$^{55}$ are independently chosen from H, acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl, wherein R$^{52}$ and R$^{53}$, together with the nitrogen atom to which they are bound are optionally joined to form a 5- to 7-membered heterocyclic ring; and R$^{54}$ is independently chosen from acyl, C$_1$-C$_6$-alkyl, 2- to 6-membered heteroalkyl, aryl, 5- or 6-membered heteroaryl, C$_3$-C$_8$ cycloalkyl and 3- to 8-membered heterocycloalkyl.

The present disclosure also provides for a use of a compound in an in vivo assay measuring kinase activity, said compound having a structure according to Formula (I):

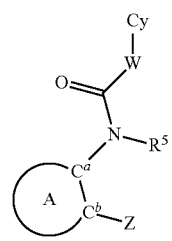

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and are part of ring A; Z is 5- or 6-membered heteroaryl; $R^5$ is chosen from H, acyl, $C_1$-$C_6$ alkyl, and $C_3$-$C_6$ cycloalkyl; W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; an $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroaryl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl.

The present disclosure further provides for an in vitro method for measuring phosphorylated kinase substrate comprising: (i) creating a mixture comprising a kinase and a compound having a structure according to Formula (I):

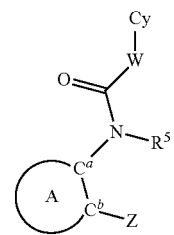

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and are part of ring A; Z is 5- or 6-membered heteroaryl; and (ii) when ring A is thiazole, then Z is not benzoimidazole; $R^5$ is chosen from H, acyl, $C_1$-$C_6$ alkyl, and $C_3$-$C_6$ cycloalkyl; W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; and $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; (ii) adding a kinase substrate and ATP or a derivative thereof to the mixture; and (iii) measuring an amount of phosphorylated kinase substrate. In one example, the method further comprises measuring phosphorylated kinase substrate, such as phospho-cJun.

The present invention also provides for an in vitro method comprising contacting a cell with a compound having a structure according to Formula (I):

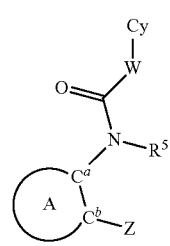

(I)

or a salt or solvate thereof, wherein ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; $C^a$ and $C^b$ are carbon atoms, which are adjacent to each other and are part of ring A; Z is 5- or 6-membered heteroaryl; $R^5$ is chosen from H, acyl, $C_1$-$C_6$ alkyl, and $C_3$-$C_6$ cycloalkyl; W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; and $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl; Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl. In one example, the method further comprises measuring phosphorylated kinase substrate, such as phospho-cJun.

DETAILED DESCRIPTION OF THE DISCLOSURE

Definitions

The definitions and explanations below are for the terms as used throughout this entire document including both the specification and the claims. Throughout the specification and the appended claims, a given formula or name shall encompass all isomers thereof, such as stereoisomers, geometrical isomers, optical isomers, tautomers, and mixtures thereof where such isomers exist, as well as pharmaceutically acceptable salts and solvates thereof, such as hydrates.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Where multiple substituents are indicated as being attached to a structure, those substituents are independently chosen. For example "ring A is optionally substituted with 1, 2 or 3 $R_q$ groups" indicates that ring A is substituted with 1, 2 or 3 $R_q$ groups, wherein the $R_q$ groups are independently chosen (i.e., can be the same or different).

Compounds were named using Autonom 2000 4.01.305, which is available from Beilstein Information Systems, Inc, Englewood, Colo.; ChemDraw v.10.0, (available from Cambridgesoft at 100 Cambridge Park Drive, Cambridge, Mass.

02140), or ACD Name pro, which is available from Advanced Chemistry Development, Inc., at 110 Yonge Street, 14$^{th}$ floor, Toronto, Ontario, Canada M5c 1T4. Alternatively, the names were generated based on the IUPAC rules or were derived from names originally generated using the aforementioned nomenclature programs. A person of skill in the art will appreciate that chemical names for tautomeric forms of the current compounds will vary slightly, but will nevertheless describe the same compound. For example, the names N-(2-(3-methyl-1H-1,2,4-triazol-5-yl)thiophen-3-yl)-2-(naphthalen-1-yl)acetamide and N-(2-(5-methyl-4H-1,2,4-triazol-3-yl)thiophen-3-yl)-2-(naphthalen-1-yl)acetamide describe two tautomeric forms of the same compound.

Where substituent groups are specified by their conventional chemical formulae, written from left to right, they equally encompass the chemically identical substituents, which would result from writing the structure from right to left. For example, "—$CH_2O$—" is intended to also recite "—$OCH_2$—".

The term "alkyl," by itself or as part of another substituent, means, unless otherwise stated, a straight or branched chain hydrocarbon radical having the number of carbon atoms designated (e.g., $C_1$-$C_{10}$ means one to ten carbon atoms). Typically, an alkyl group will have from 1 to 24 carbon atoms, for example having from 1 to 10 carbon atoms, from 1 to 8 carbon atoms or from 1 to 6 carbon atoms. A "lower alkyl" group is an alkyl group having from 1 to 4 carbon atoms. The term "alkyl" includes di- and multivalent radicals. For example, the term "alkyl" includes "alkylene" wherever appropriate, e.g., when the formula indicates that the alkyl group is divalent or when substituents are joined to form a ring. Examples of alkyl radicals include, but are not limited to, methyl, ethyl, n-propyl, iso-propyl, n-butyl, tert-butyl, iso-butyl, sec-butyl, as well as homologs and isomers of, for example, n-pentyl, n-hexyl, n-heptyl and n-octyl.

The term "alkylene" by itself or as part of another substituent means a divalent (diradical) alkyl group, wherein alkyl is defined herein. "Alkylene" is exemplified, but not limited, by —$CH_2CH_2CH_2CH_2$—. Typically, an "alkylene" group will have from 1 to 24 carbon atoms, for example, having 10 or fewer carbon atoms (e.g., 1 to 8 or 1 to 6 carbon atoms). A "lower alkylene" group is an alkylene group having from 1 to 4 carbon atoms.

The term "alkenyl" by itself or as part of another substituent refers to a straight or branched chain hydrocarbon radical having from 2 to 24 carbon atoms and at least one double bond. A typical alkenyl group has from 2 to 10 carbon atoms and at least one double bond. In one embodiment, alkenyl groups have from 2 to 8 carbon atoms or from 2 to 6 carbon atoms and from 1 to 3 double bonds. Exemplary alkenyl groups include vinyl, 2-propenyl, 1-but-3-enyl, crotyl, 2-(butadienyl), 2,4-pentadienyl, 3-(1,4-pentadienyl), 2-isopentenyl, 1-pent-3-enyl, 1-hex-5-enyl and the like.

The term "alkynyl" by itself or as part of another substituent refers to a straight or branched chain, unsaturated or polyunsaturated hydrocarbon radical having from 2 to 24 carbon atoms and at least one triple bond. A typical "alkynyl" group has from 2 to 10 carbon atoms and at least one triple bond. In one aspect of the disclosure, alkynyl groups have from 2 to 6 carbon atoms and at least one triple bond. Exemplary alkynyl groups include prop-1-ynyl, prop-2-ynyl (i.e., propargyl), ethynyl and 3-butynyl.

The terms "alkoxy," "alkylamino" and "alkylthio" (or thioalkoxy) are used in their conventional sense, and refer to alkyl groups that are attached to the remainder of the molecule via an oxygen atom, an amino group, or a sulfur atom, respectively.

The term "heteroalkyl," by itself or in combination with another term, means a stable, straight or branched chain hydrocarbon radical consisting of the stated number of carbon atoms (e.g., $C_2$-$C_{10}$, or $C_2$-$C_8$) and at least one heteroatom chosen, e.g., from N, O, S, Si, B and P (in one embodiment, N, O and S), wherein the nitrogen, sulfur and phosphorus atoms are optionally oxidized, and the nitrogen atom(s) are optionally quaternized. The heteroatom(s) is/are placed at any interior position of the heteroalkyl group. Examples of heteroalkyl groups include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$—S(O)—$CH_3$, —$CH_2$—$CH_2$—S(O)$_2$—$CH_3$, —CH=CH—O—$CH_3$, —$CH_2$—Si($CH_3$)$_3$, —$CH_2$—CH=N—$OCH_3$, and —CH=CH—N($CH_3$)—$CH_3$. Up to two heteroatoms can be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. Typically, a heteroalkyl group will have from 3 to 24 atoms (carbon and heteroatoms, excluding hydrogen) (3- to 24-membered heteroalkyl). In another example, the heteroalkyl group has a total of 3 to 10 atoms (3- to 10-membered heteroalkyl) or from 3 to 8 atoms (3- to 8-membered heteroalkyl). The term "heteroalkyl" includes "heteroalkylene" wherever appropriate, e.g., when the formula indicates that the heteroalkyl group is divalent or when substituents are joined to form a ring.

The term "cycloalkyl" by itself or in combination with other terms, represents a saturated or unsaturated, non-aromatic carbocyclic radical having from 3 to 24 carbon atoms, for example, having from 3 to 12 carbon atoms (e.g., $C_3$-$C_8$ cycloalkyl or $C_3$-$C_6$ cycloalkyl). Examples of cycloalkyl include, but are not limited to, cyclopropyl, cyclobutyl, cyclopentyl, cyclohexyl, cycloheptyl, 1-cyclohexenyl, 3-cyclohexenyl, cycloheptyl and the like. The term "cycloalkyl" also includes bridged, polycyclic (e.g., bicyclic) structures, such as norbornyl, adamantyl and bicyclo[2.2.1]heptyl. The "cycloalkyl" group can be fused to at least one (e.g., 1 to 3) other ring chosen from aryl (e.g., phenyl), heteroaryl (e.g., pyridyl) and non-aromatic (e.g., carbocyclic or heterocyclic) rings. When the "cycloalkyl" group includes a fused aryl, heteroaryl or heterocyclic ring, then the "cycloalkyl" group is attached to the remainder of the molecule via the carbocyclic ring.

The term "heterocycloalkyl", "heterocyclic", "heterocycle", or "heterocyclyl", by itself or in combination with other terms, represents a carbocyclic, non-aromatic ring (e.g., 3- to 8-membered ring and for example, 4-, 5-, 6- or 7-membered ring) containing at least one and up to 5 heteroatoms chosen from, e.g., N, O, S, Si, B and P (for example, N, O and S), wherein the nitrogen, sulfur and phosphorus atoms are optionally oxidized, and the nitrogen atom(s) are optionally quaternized (e.g., from 1 to 4 heteroatoms chosen from nitrogen, oxygen and sulfur), or a fused ring system of 4- to 8-membered rings, containing at least one and up to 10 heteroatoms (e.g., from 1 to 5 heteroatoms chosen from N, O and S) in stable combinations known to those of skill in the art. Exemplary heterocycloalkyl groups include a fused phenyl ring. When the "heterocyclic" group includes a fused aryl, heteroaryl or cycloalkyl ring, then the "heterocyclic" group is attached to the remainder of the molecule via a heterocycle. A heteroatom can occupy the position at which the heterocycle is attached to the remainder of the molecule. Exemplary heterocycloalkyl or heterocyclic groups of the present disclosure include morpholinyl, thiomorpholinyl, thiomorpholinyl S-oxide, thiomorpholinyl S,S-dioxide, piperazinyl, homopiperazinyl, pyrrolidinyl, pyrrolinyl, imidazolidinyl, tetrahydropyranyl, piperidinyl, tetrahydrofuranyl, tetrahydrothienyl, piperidinyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazolyl, dihydropyridyl, dihydropyrimidinyl, dihydrofuryl, dihydropyranyl, tetrahydrothienyl S-oxide, tetrahydrothienyl S,S-dioxide, homothiomorpholinyl S-oxide, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

By "aryl" is meant a 5-, 6- or 7-membered, aromatic carbocyclic group having a single ring (e.g., phenyl) or being fused to other aromatic or non-aromatic rings (e.g., from 1 to 3 other rings). When the "aryl" group includes a non-aromatic ring (such as in 1,2,3,4-tetrahydronaphthyl) or heteroaryl group then the "aryl" group is linked to the remainder of the molecule via an aryl ring (e.g., a phenyl ring). The aryl group is optionally substituted (e.g., with 1 to 5 substituents described herein). In one example, the aryl group has from 6 to 10 carbon atoms. Non-limiting examples of aryl groups include phenyl, 1-naphthyl, 2-naphthyl, quinoline, indanyl, indenyl, dihydronaphthyl, fluorenyl, tetralinyl, benzo[d][1,3]dioxolyl or 6,7,8,9-tetrahydro-5H-benzo[a]cycloheptenyl. In one embodiment, the aryl group is chosen from phenyl, benzo[d][1,3]dioxolyl and naphthyl. The aryl group, in yet another embodiment, is phenyl.

The term "arylalkyl" is meant to include those radicals in which an aryl group or heteroaryl group is attached to an alkyl group to create the radicals -alkyl-aryl and -alkyl-heteroaryl, wherein alkyl, aryl and heteroaryl are defined herein. Exemplary "arylalkyl" groups include benzyl, phenethyl, pyridylmethyl and the like.

By "aryloxy" is meant the group —O-aryl, where aryl is as defined herein. In one example, the aryl portion of the aryloxy group is phenyl or naphthyl. The aryl portion of the aryloxy group, in one embodiment, is phenyl.

The term "heteroaryl" or "heteroaromatic" refers to a polyunsaturated, 5-, 6- or 7-membered aromatic moiety containing at least one heteroatom (e.g., 1 to 5 heteroatoms, such as 1-3 heteroatoms) chosen from N, O, S, Si and B (for example, N, O and S), wherein the nitrogen and sulfur atoms are optionally oxidized, and the nitrogen atom(s) are optionally quaternized. The "heteroaryl" group can be a single ring or be fused to other aryl, heteroaryl, cycloalkyl or heterocycloalkyl rings (e.g., from 1 to 3 other rings). When the "heteroaryl" group includes a fused aryl, cycloalkyl or heterocycloalkyl ring, then the "heteroaryl" group is attached to the remainder of the molecule via the heteroaryl ring. A heteroaryl group can be attached to the remainder of the molecule through a carbon- or heteroatom. In one example, the heteroaryl group has from 4 to 10 carbon atoms and from 1 to 5 heteroatoms chosen from O, S and N. Non-limiting examples of heteroaryl groups include pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridyl, benzotetrahydrofuranyl, benzotetrahydrothienyl, purinyl, benzodioxolyl, triazinyl, pteridinyl, benzothiazolyl, imidazopyridyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. Exemplary heteroaryl groups include imidazolyl, pyrazolyl, thiadiazolyl, triazolyl, isoxazolyl, isothiazolyl, imidazolyl, thiazolyl, oxadiazolyl, and pyridyl. Other exemplary heteroaryl groups include 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, pyridin-4-yl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are chosen from the group of acceptable aryl group substituents described below.

For brevity, the term "aryl" when used in combination with other terms (e.g., aryloxy, arylthioxy, arylalkyl) includes both aryl and heteroaryl rings as defined above.

Each of the above terms (e.g., "alkyl", "cycloalkyl", "heteroalkyl", heterocycloalkyl", "aryl" and "heteroaryl") are meant to include both substituted and unsubstituted forms of the indicated radical. The term "substituted" for each type of radical is explained below. When a compound of the present disclosure includes more than one substituent, then each of the substituents is independently chosen.

The term "substituted" in connection with alkyl, alkenyl, alkynyl, cycloalkyl, heteroalkyl and heterocycloalkyl radicals (including those groups referred to as alkylene, heteroalkylene, heteroalkenyl, cycloalkenyl, heterocycloalkenyl, and the like) refers to one or more substituents, wherein each substituent is independently chosen from, but not limited to, 3- to 10-membered heteroalkyl, $C_3$-$C_{10}$ cycloalkyl, 3- to 10-membered heterocycloalkyl, aryl, heteroaryl, —OR$^a$, —SR$^a$, =O, =NR$^a$, =N—OR$^a$, —NR$^a$R$^b$, -halogen, —SiR$^a$R$^b$R$^c$, —OC(O)R$^a$, —C(O)R$^e$, —C(O)OR$^a$, —C(O)NR$^a$R$^b$, —OC(O)NR$^a$R$^b$, —NR$^c$(O)R$^e$, —NR$^c$C(O)NR$^a$R$^b$, —NR$^c$C(S)NR$^a$R$^b$, —NR$^c$C(O)OR$^a$, —NR$^c$C(NR$^a$R$^b$)=NR$^d$, —S(O)R$^e$, —S(O)$_2$R$^e$, —S(O)$_2$NR$^a$R$^b$, —NR$^c$S(O)$_2$R$^a$, —CN and —NO$_2$. R$^a$, R$^b$, R$^c$, R$^d$ and R$^e$ each independently refer to hydrogen, $C_1$-$C_{24}$ alkyl (e.g., $C_1$-$C_{10}$ alkyl or $C_1$-$C_6$ alkyl), $C_3$-$C_{10}$ cycloalkyl, $C_1$-$C_{24}$ heteroalkyl (e.g., $C_1$-$C_{10}$ heteroalkyl or $C_1$-$C_6$ heteroalkyl), $C_3$-$C_{10}$ heterocycloalkyl, aryl, heteroaryl, arylalkyl and heteroarylalkyl, wherein, in one embodiment, R$^e$ is not hydrogen. When two of the above R groups (e.g., R$^a$ and $R^b$) are attached to the same nitrogen atom, they can be combined with the nitrogen atom to form a 5-, 6-, or 7-membered ring. For example, —$NR^aR^b$ is meant to include pyrrolidinyl, N-alkyl-piperidinyl and morpholinyl.

The term "substituted" in connection with aryl and heteroaryl groups, refers to one or more substituents, wherein each substituent is independently chosen from, but not limited to, alkyl (e.g., $C_1$-$C_{24}$ alkyl, $C_1$-$C_{10}$ alkyl or $C_1$-$C_6$ alkyl), cycloalkyl (e.g., $C_3$-$C_{10}$ cycloalkyl, or $C_3$-$C_8$ cycloalkyl), alkenyl (e.g., $C_1$-$C_{10}$ alkenyl or $C_1$-$C_6$ alkenyl), alkynyl (e.g., $C_1$-$C_{10}$ alkynyl or $C_1$-$C_6$ alkynyl), heteroalkyl (e.g., 3- to 10-membered heteroalkyl), heterocycloalkyl (e.g., $C_3$-$C_8$ heterocycloalkyl), aryl, heteroaryl, —$R^a$, —$OR^a$, —$SR^a$, =O, =$NR^a$, =N—$OR^a$, —$NR^aR^b$, -halogen, —$SiR^aR^bR^c$, —$OC(O)R^a$, —$C(O)R^e$, —$C(O)OR^a$, —$C(O)NR^aR^b$, —$OC(O)NR^aR^b$, —$NR^cC(O)R^e$, —$NR^cC(O)NR^aR^b$, —$NR^cC(S)NR^aR^b$, —$NR^cC(O)OR^a$, —$NR^cC(NR^aR^b)$=$NR^d$, —$S(O)R^e$, —$S(O)_2R^e$, —$S(O)_2NR^aR^b$, —$NR^cS(O)_2R^a$, —CN, —$NO_2$, —$N_3$, —$CH(Ph)_2$, fluoro ($C_1$-$C_4$)alkoxy, and fluoro($C_1$-$C_4$)alkyl, in a number ranging from zero to the total number of open valences on the aromatic ring system, wherein $R^a$, $R^b$, $R^c$, $R^d$ and $R^e$ each independently refer to hydrogen, $C_1$-$C_{24}$ alkyl (e.g., $C_1$-$C_{10}$ alkyl or $C_1$-$C_6$ alkyl), $C_3$-$C_{10}$ cycloalkyl, $C_1$-$C_{24}$ heteroalkyl (e.g., $C_1$-$C_{10}$ heteroalkyl or $C_1$-$C_6$ heteroalkyl), $C_3$-$C_{10}$ heterocycloalkyl, aryl, heteroaryl, arylalkyl and heteroarylalkyl, wherein, in one embodiment, $R^e$ is not hydrogen. When two R groups (e.g., $R^a$ and $R^b$) are attached to the same nitrogen atom, they can be combined with the nitrogen atom to form a 5-, 6-, or 7-membered ring. For example, —$NR^aR^b$ is meant to include pyrrolidinyl, N-alkyl-piperidinyl and morpholinyl.

The term "substituted" in connection with aryl and heteroaryl groups also refers to one or more fused ring(s), in which two hydrogen atoms on adjacent atoms of the aryl or heteroaryl ring are optionally replaced with a substituent of the formula -T-C(O)—(CRR')$_q$—U—, wherein T and U are independently —NR—, —O—, —CRR'— or a single bond, and q is an integer from 0 to 3. Alternatively, two of the hydrogen atoms on adjacent atoms of the aryl or heteroaryl ring can optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer from 1 to 4. One of the single bonds of the ring so formed can optionally be replaced with a double bond. Alternatively, two of the hydrogen atoms on adjacent atoms of the aryl or heteroaryl ring can optionally be replaced with a substituent of the formula —(CRR')$_s$—X—(CR"R''')$_d$—, where s and d are independently integers from 0 to 3, and X is —O—, —NR'—, —S—, —S(O)—, —S(O)$_2$—, or —S(O)$_2$NR'—, wherein the substituents R, R', R" and R''' in each of the formulas above are independently chosen from hydrogen and ($C_1$-$C_6$)alkyl.

The terms "halo" or "halogen," by themselves or as part of another substituent, mean at least one of fluorine, chlorine, bromine and iodine.

By "haloalkyl" is meant an alkyl radical, wherein alkyl is as defined above and wherein at least one hydrogen atom is replaced by a halogen atom. The term "haloalkyl," is meant to include monohaloalkyl and polyhaloalkyl. For example, the term "halo($C_1$-$C_4$)alkyl" is mean to include, but not limited to, chloromethyl, 1-bromoethyl, fluoromethyl, difluoromethyl, trifluoromethyl, 1,1,1-trifluoroethyl and 4-chlorobutyl, 3-bromopropyl.

As used herein, the term "acyl" describes the group —$C(O)R^e$, wherein $R^e$ is chosen from hydrogen, $C_1$-$C_{24}$ alkyl (e.g., $C_1$-$C_{10}$ alkyl or $C_1$-$C_6$ alkyl), $C_1$-$C_{24}$ alkenyl (e.g., $C_1$-$C_{10}$ alkenyl or $C_1$-$C_6$ alkenyl), $C_1$-$C_{24}$ alkynyl (e.g., $C_1$-$C_{10}$ alkynyl or $C_1$-$C_6$ alkynyl), $C_3$-$C_{10}$ cycloalkyl, $C_1$-$C_{24}$ heteroalkyl (e.g., $C_1$-$C_{10}$ heteroalkyl or $C_1$-$C_6$ heteroalkyl), $C_3$-$C_{10}$ heterocycloalkyl, aryl, heteroaryl, arylalkyl and heteroarylalkyl. In one embodiment, $R^e$ is not hydrogen.

By "alkanoyl" is meant an acyl radical —C(O)-Alk-, wherein Alk is an alkyl radical as defined herein. Examples of alkanoyl include acetyl, propionyl, butyryl, isobutyryl, valeryl, isovaleryl, 2-methyl-butyryl, 2,2-dimethylpropionyl, hexanoyl, heptanoyl, octanoyl and the like.

As used herein, the term "heteroatom" includes oxygen (O), nitrogen (N), sulfur (S), silicon (Si), boron (B) and phosphorus (P). In one embodiment, heteroatoms are O, S and N.

By "oxo" is meant the group =O.

The symbol "R" is a general abbreviation that represents a substituent group as described herein. Exemplary substituent groups include alkyl, alkenyl, alkynyl, cycloalkyl, heteroalkyl, aryl, heteroaryl and heterocycloalkyl groups, each as defined herein.

As used herein, the term "aromatic ring" or "non-aromatic ring" is consistent with the definition commonly used in the art. For example, aromatic rings include phenyl and pyridyl. Non-aromatic rings include cyclohexanes.

As used herein, the term "fused ring system" means at least two rings, wherein each ring has at least 2 atoms in common with another ring. "Fused ring systems can include aromatic as well as non-aromatic rings. Examples of "fused ring systems" are naphthalenes, indoles, quinolines, chromenes and the like. Likewise, the term "fused ring" refers to a ring that has at least two atoms in common with the ring to which it is fused.

The phrase "therapeutically effective amount" as used herein means that amount of a compound, material, or composition of the present disclosure, which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

The terms "treatment" or "treating" when referring to a disease or condition, means producing a desired therapeutic effect. Exemplary therapeutic effects include delaying onset or reducing at least one symptom associated with the disease, positively affecting (e.g., reducing or delaying onset) a clinical marker associated with the disease and slowing or reversing disease progression.

The term "pharmaceutically acceptable" refers to those properties and/or substances that are acceptable to a patient (e.g., human patient) from a toxicological and/or safety point of view.

The term "pharmaceutically acceptable salts" means salts of the compounds of the present disclosure, which may be prepared with relatively nontoxic acids or bases, depending on the particular substituents found on the compounds described herein. When compounds of the present disclosure contain relatively acidic functionalities (e.g., —COOH group), base addition salts can be obtained by contacting the compound (e.g., neutral form of such compound) with a sufficient amount of the desired base, either neat or in a suitable inert solvent. Examples of pharmaceutically acceptable base addition salts include lithium, sodium, potassium, calcium, ammonium, organic amino, magnesium and aluminum salts and the like. When compounds of the present disclosure contain relatively basic functionalities (e.g., amines), acid addition salts can be obtained, e.g., by contacting the compound (e.g., neutral form of such compound) with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, diphosphoric, monohydrogenphosphoric, dihydrogenphosphoric, sulfuric, monohydrogensulfuric, hydriodic and the like, as well as the salts derived from relatively nontoxic organic acids like formic, acetic, propionic, isobutyric, malic, maleic, malonic, benzoic, succinic, suberic, fumaric, lactic, mandelic, phthalic, benzenesulfonic, p-tolylsulfonic, citric, tartaric, methanesulfonic, 2-hydroxyethylsulfonic, salicylic, stearic and the like. Also included are salts of amino acids such as arginate and the like, and salts of organic acids like glucuronic or galactunoric acids and the like (see, for example, Berge et al., *Journal of Pharmaceutical Science*, 1977, 66: 1-19). Certain specific compounds of the present disclosure contain both, basic and acidic, functionalities that allow the compounds to be converted into either base or acid addition salts.

The neutral forms of the compounds can be regenerated, for example, by contacting the salt with a base or acid and isolating the parent compound in the conventional manner. The parent form of the compound can differ from the various salt forms in certain physical properties, such as solubility in polar solvents, but otherwise the salts are equivalent to the parent form of the compound for the purposes of the present disclosure.

When a substituent includes a negatively charged oxygen atom "O⁻", e.g., in "—COO⁻", then the formula is meant to optionally include a proton or an organic or inorganic cationic counterion (e.g., Na+). In one example, the resulting salt form of the compound is pharmaceutically acceptable. Further, when a compound of the present disclosure includes an acidic group, such as a carboxylic acid group, e.g., written as the substituent "—COOH", "—CO$_2$H" or "—C(O)$_2$H", then the formula is meant to optionally include the corresponding "de-protonated" form of that acidic group, e.g., "—COO⁻", "—CO$_2$⁻" or "—C(O)$_2$⁻", respectively.

In addition to salt forms, the present disclosure provides compounds, which are in a prodrug form. Prodrugs of the compounds described herein are those compounds that readily undergo chemical changes under physiological conditions to provide the compounds of the present disclosure. Non-limiting examples of "pharmaceutically acceptable derivative" or "prodrug" include pharmaceutically acceptable esters, phosphate esters or sulfonate esters thereof as well as other derivatives of a compound of this present disclosure which, upon administration to a recipient, is capable of providing, either directly or indirectly, a compound of this present disclosure. In one embodiment, derivatives or prodrugs are those that increase the bioavailability of the compounds of this present disclosure when such compounds are administered to a mammal (e.g., by allowing an orally administered compound to be more readily absorbed into the blood stream) or which enhance delivery of the parent compound to a biological compartment (e.g., the brain or lymphatic system) relative to the parent species.

Prodrugs include a variety of esters (i.e., carboxylic acid ester). Ester groups, which are suitable as prodrug groups are generally known in the art and include benzyloxy, di($C_1$-$C_6$)alkylaminoethyloxy, acetoxymethyl, pivaloyloxymethyl, phthalidyl, ethoxycarbonyloxyethyl, 5-methyl-2-oxo-1,3-dioxol-4-yl methyl, and ($C_1$-$C_6$)alkoxy esters, optionally substituted by N-morpholino and amide-forming groups such as di($C_1$-$C_6$)alkylamino. For example, ester prodrug groups include $C_1$-$C_6$ alkoxy esters. Those skilled in the art will recognize various synthetic methodologies that may be employed to form pharmaceutically acceptable prodrugs of the compounds of the present disclosure (e.g., via esterification of a carboxylic acid group).

In an exemplary embodiment, the prodrug is suitable for treatment/prevention of those diseases and conditions that require the drug molecule to cross the blood brain barrier. In one embodiment, the prodrug enters the brain, where it is converted into the active form of the drug molecule. In another example, a prodrug is used to enable an active drug molecule to reach the inside of the eye after topical application of the prodrug to the eye. Additionally, prodrugs can be converted to the compounds of the present disclosure by chemical or biochemical methods in an ex vivo environment. For example, prodrugs can be slowly converted to the compounds of the present disclosure when placed in a transdermal patch reservoir with a suitable enzyme or chemical reagent.

Certain compounds of the present disclosure can exist in unsolvated forms as well as solvated forms, including hydrated forms. In general, the solvated forms are equivalent to unsolvated forms and are encompassed within the scope of the present disclosure. Certain compounds of the present disclosure can exist in multiple crystalline or amorphous forms ("polymorphs"). In general, all physical forms are of use in the methods contemplated by the present disclosure and are intended to be within the scope of the present disclosure. "Compound or a pharmaceutically acceptable salt, hydrate, polymorph or solvate of a compound" intends the inclusive meaning of "and/or", in that materials meeting more than one of the stated criteria are included, e.g., a material that is both a salt and a solvate is encompassed.

The compounds of the present disclosure can contain unnatural proportions of atomic isotopes at one or more of the atoms that constitute such compounds. For example, the compounds can be radiolabeled with radioactive isotopes, such as for example tritium ($^3$H), iodine-125 ($^{125}$I) or carbon-14 ($^{14}$C). All isotopic variations of the compounds of the present disclosure, whether radioactive or not, are intended to be encompassed within the scope of the present disclosure. Compounds described herein, in which one or more of the hydrogen atoms are replaced with another stable isotope of hydrogen (i.e., deuterium) or a radioactive isotope (i.e., tritium), are part of this disclosure.

Compositions Including Stereoisomers

Compounds of the present disclosure can exist in particular geometric or stereoisomeric forms. The present disclosure contemplates all such compounds, including cis- and trans-isomers, (−)- and (+)-enantiomers, diastereomers, (D)-isomers, (L)-isomers, the racemic mixtures thereof, and other mixtures thereof, such as enantiomerically or diastereomerically enriched mixtures, as falling within the scope of the present disclosure. Additional asymmetric carbon atoms can be present in a substituent such as an alkyl group. All such isomers, as well as mixtures thereof, are intended to be included in this disclosure. When the compounds described herein contain olefinic double bonds or other centers of geometric asymmetry, and unless specified otherwise, it is intended that the compounds include both E and Z geometric isomers. Likewise, all tautomeric forms and mixtures of tautomers are included.

Optically active (R)- and (S)-isomers and d and/isomers can be prepared using chiral synthons or chiral reagents, or resolved using conventional techniques. Resolution of the racemates can be accomplished, for example, by conventional methods such as crystallization in the presence of a resolving agent; chromatography, using, for example a chiral HPLC column; or derivatizing the racemic mixture with a resolving reagent to generate diastereomers, separating the diastereomers via chromatography, and removing the resolving agent to generate the original compound in enantiomerically enriched form. Any of the above procedures can be repeated to increase the enantiomeric purity of a compound. If, for instance, a particular enantiomer of a compound of the present disclosure is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, or an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

As used herein, the term "chiral", "enantiomerically enriched" or "diastereomerically enriched" refers to a compound having an enantiomeric excess (ee) or a diastereomeric excess (de) of greater than about 50%, for example, greater than about 70%, such as greater than about 90%. In one embodiment, the compositions have higher than about 90% enantiomeric or diastereomeric excess, e.g., those compositions with greater than about 95%, greater than about 97% and greater than about 99% ee or de.

The terms "enantiomeric excess" and "diastereomeric excess" are used in their conventional sense. Compounds with a single stereocenter are referred to as being present in "enantiomeric excess", those with at least two stereocenters are referred to as being present in "diastereomeric excess". The value of ee will be a number from 0 to 100, zero being racemic and 100 being enantiomerically pure. For example, a 90% ee reflects the presence of 95% of one enantiomer and 5% of the other(s) in the material in question.

Hence, in one embodiment, the disclosure provides a composition including a first stereoisomer and at least one additional stereoisomer of a compound of the present disclosure. The first stereoisomer can be present in a diastereomeric or enantiomeric excess of at least about 80%, such as at least about 90%, and for example, at least about 95%. In another embodiment, the first stereoisomer is present in a diastereomeric or enantiomeric excess of at least about 96%, at least about 97%, at least about 98%, at least about 99% or at least about 99.5%. In yet another embodiment, the compounds of the present disclosure is enantiomerically or diastereomerically pure (diastereomeric or enantiomeric excess is about 100%). Enantiomeric or diastereomeric excess can be determined relative to exactly one other stereoisomer, or can be determined relative to the sum of at least two other stereoisomers. In an exemplary embodiment, enantiomeric or diastereomeric excess is determined relative to all other detectable stereoisomers, which are present in the mixture. Stereoisomers are detectable if a concentration of such stereoisomer in the analyzed mixture can be determined using common analytical methods, such as chiral HPLC.

The term "JNK-mediated condition", "c-Jun N-terminal kinase mediated disorder" or any other variation thereof, as used herein means any disease or other condition in which JNK is known to play a role, or a disease state that is associated with elevated activity or expression of JNK. For example, a "JNK-mediated condition" may be relieved by inhibiting JNK activity. Such conditions include, without limitation, inflammatory diseases, autoimmune diseases, destructive bone disorders, proliferative disorders, cancer, infectious diseases, neurodegenerative diseases, allergies, reperfusion/ischemia in stroke, heart attacks, angiogenic disorders, organ hypoxia, vascular hyperplasia, cardiac hypertrophy, thrombin-induced platelet aggregation, and conditions associated with prostaglandin endoperoxidase synthase-2.

The term "neurological disorder" refers to any undesirable condition of the central or peripheral nervous system of a mammal. The term "neurological disorder" includes neurodegenerative diseases (e.g., Alzheimer's disease, Parkinson's disease and amyotrophic lateral sclerosis), neuropsychiatric diseases (e.g. schizophrenia and anxieties, such as general anxiety disorder). Exemplary neurological disorders include MLS (cerebellar ataxia), Huntington's disease, Down syndrome, multi-infarct dementia, status epilecticus, contusive injuries (e.g. spinal cord injury and head injury), viral infection induced neurodegeneration, (e.g. AIDS, encephalopathies), epilepsy, benign forgetfulness, closed head injury, sleep disorders, depression (e.g., bipolar disorder), dementias, movement disorders, psychoses, alcoholism, post-traumatic stress disorder and the like. "Neurological disorder" also includes any undesirable condition associated with the disorder. For instance, a method of treating a neurodegenerative disorder includes methods of treating loss of memory and/or loss of cognition associated with a neurodegenerative disorder. Such method would also include treating or preventing loss of neuronal function characteristic of neurodegenerative disorder.

The term "neurodegenerative diseases" includes any disease or condition characterized by problems with movements, such as ataxia, and conditions affecting cognitive abilities (e.g., memory) as well as conditions generally related to all types of dementia. "Neurodegenerative diseases" may be associated with impairment or loss of cognitive abilities, potential loss of cognitive abilities and/or impairment or loss of brain cells. Exemplary "neurodegenerative diseases" include Alzheimer's disease (AD), diffuse Lewy body type of Alzheimer's disease, Parkinson's disease, Down syndrome, dementia, mild cognitive impairment (MCI), amyotrophic lateral sclerosis (ALS), traumatic brain injuries, ischemia, stroke, cerebral ischemic brain damage, ischemic or hemorrhaging stroke, multi-infarct dementia, hereditary cerebral hemorrhage with amyloidosis of the dutch-type, cerebral amyloid angiopathy (including single and recurrent lobar hemorrhages), neurodegeneration induced by viral infection (e.g. AIDS, encephalopathies) and other degenerative dementias, including dementias of mixed vascular and degenerative origin, dementia associated with Parkinson's disease, dementia associated with progressive supranuclear palsy and dementia associated with cortical basal degeneration, epilepsy, seizures, and Huntington's disease.

"Pain" is an unpleasant sensory and emotional experience. Pain classifications have been based on duration, etiology or pathophysiology, mechanism, intensity, and symptoms. The term "pain" as used herein refers to all categories of pain, including pain that is described in terms of stimulus or nerve response, e.g., somatic pain (normal nerve response to a noxious stimulus) and neuropathic pain (abnormal response of a injured or altered sensory pathway, often without clear noxious input); pain that is categorized temporally, e.g., chronic pain and acute pain; pain that is categorized in terms of its severity, e.g., mild, moderate, or severe; and pain that is a symptom or a result of a disease state or syndrome, e.g., inflammatory pain, cancer pain, AIDS pain, arthropathy, migraine, trigeminal neuralgia, cardiac ischaemia, and diabetic peripheral neuropathic pain (see, e.g., Harrison's Principles of Internal Medicine, pp. 93-98 (Wilson et al., eds., 12th ed. 1991); Williams et al., *J. of Med. Chem.* 42: 1481-1485 (1999), herein each incorporated by reference in their entirety). "Pain" is also meant to include mixed etiology pain, dual mechanism pain, allodynia, causalgia, central pain, hyperesthesia, hyperpathia, dysesthesia, and hyperalgesia.

Compositions

In various aspects, the present disclosure provides a compound having a structure according to Formula (I):

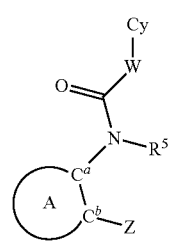
(I)

or a salt or solvate thereof.

In Formula (I), ring A is chosen from substituted or unsubstituted aryl (e.g., phenyl) and substituted or unsubstituted heteroaryl. In one example, ring A is a 5-membered heteroaromatic ring. In one example, the 5-membered heteroaromatic ring comprising from 1 to 3 heteroatoms chosen from O, S and N (e.g., thiophene, thiazole, or oxazole). In another example, ring A is a 5-membered heteroaromatic ring containing at least one sulfur atom (e.g., thiophene, thiazole). In another example, ring A is a 6-membered heteroaromatic ring. In one example, the 6-membered heteroaromatic ring comprises from 1 to 4 heteroatoms chosen from O, S and N (e.g., pyridyl or pyrimidyl). The above 6-membered heteroaromatic ring is optionally substituted with from 1 to 3 substituents, and the above 5-membered heteroaromatic ring is optionally substituted with 1 or 2 substituents, wherein each substituent is independently chosen from substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$, wherein $R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{12}$ and $R^{13}$, together with the nitrogen atom to which they are bound are optionally joined to form a 5- to 7-membered heterocyclic ring. $R^{14}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl.

In Formula (I), $C^a$ and $C^b$ are carbon atoms, which are adjacent to each other and are both part of ring A.

In Formula (I), Z is a 5- or 6-membered heteroaromatic ring (e.g., triazole, oxazole, oxadiazole, imidazole, tetrazole, pyrazole, pyridine, pyrazine and the like). Exemplary Z groups are described herein below.

In one example, when ring A is thiophene, then Z is not a thiazole-2-yl or benzo[d]thiazol-2-yl. In another example, when ring A is thiophene, then Z is not 1H-benzo[d]imidazole-2-yl. In yet another example, when ring A is thiophene, then Z is not methyl or ethyl-substituted thiazole. In another example, when ring A is thiophene, then Z is not substituted (e.g., alkyl-substituted) or unsubstituted thiazoles and substituted or unsubstituted benzothiazoles. In another example, when ring A is thiophene, then Z is not substituted or unsubstituted benzimidazoles. In a further example, when ring A is thiazole, then Z is not substituted or unsubstituted benzimidazoles. In yet another example, when ring A is thiazole, then Z is not 1H-benzo[d]imidazole-2-yl.

In one example, when A is thiophene, then Z is not:

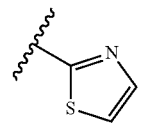

In another example, when A is thiophene, then Z is not:

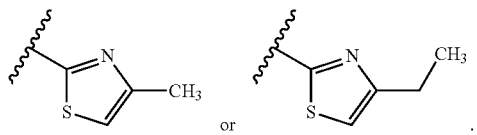

or

In a further example, when A is thiophene, then Z is not:

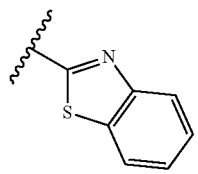

In another example, when A is thiophene or thiazole, then Z is not:

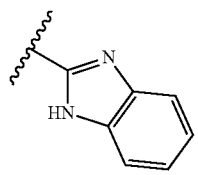

In one example, when ring A is thiophene, then Z is other than oxadiazole. In another example, when ring A is thiophene, then Z is other than substituted (e.g., phenyl-substituted) oxadiazole. In yet another example, when ring A is thiophene, then Z is other than oxadiazole substituted with phenyl or substituted phenyl. In yet another example, when ring A is thiophene, then Z is other than oxadiazole, wherein the oxadiazole is substituted with a phenyl, 4-methyl-phenyl, or a 4-ethyl-phenyl group. In another example, when ring A is methyl- or ethyl-substituted thiophene, then Z is other than oxadiazole.

In another example, when ring A is thiophene, then Z is other than pyrimidinone. In another example, when ring A is thiophene, then Z is other than substituted pyrimidinone (e.g., pyrimidinone substituted with at least one of hydroxy, carboxy or hydroxy-methylene).

In Formula (I), $R^5$ is chosen from H, substituted or unsubstituted alkyl (e.g., $C_1$-$C_6$ alkyl), substituted or unsubstituted $C_3$-$C_6$ cycloalkyl and acyl (e.g., acetyl).

In Formula (I), W is chosen from substituted or unsubstituted alkylene (e.g., substituted or unsubstituted $C_1$-$C_{10}$ alkylene). In one example, W is $C_1$-$C_{10}$ alkylene optionally substituted with from 1 to 6 substituents chosen from $R^{10}$ and $R^{11}$ defined as hereinbelow for Formulae (X) and (XI). In another example, W is straight chain alkylene represented by the formula —$(CR^{10}R^{11})_n$—, wherein n is chosen from 1 to 10 and $R^{10}$ and $R^{11}$ are defined as hereinbelow for Formulae (X) and (XI). In yet another example, W is a straight carbon chain represented by —$(CH_2)_n$—, wherein n is from 1 to 10 (e.g., n is chosen from 1 to 3 or n is 1 or 2). In another example W is $C_1$-$C_4$ alkylene optionally substituted with from 1 to 4 substituents chosen from $R^{10}$ and $R^{11}$ as defined herein. In a further example, W is substituted or unsubstituted methylene, e.g., —$CR^{10}R^{11}$—, wherein $R^{10}$ and $R^{11}$ are defined as hereinbelow for Formulae (X) and (XI). In a further example, W is methylene, optionally substituted with one or two substituents chosen from $C_1$-$C_6$ alkyl, $C_3$-$C_6$ cycloalkyl, $C_1$-$C_6$ alkoxy, CN and halogen (e.g., F, Cl or Br). In a one example, W is unsubstituted methylene (—$CH_2$—).

Cy in Formula (I) represents a ring or fused ring system. In one example, Cy is chosen from substituted or unsubstituted cycloalkyl (e.g., substituted or unsubstituted $C_3$-$C_8$ cycloalkyl), substituted or unsubstituted heterocycloalkyl (e.g., substituted or unsubstituted 3- to 8-membered heterocycloalkyl), substituted or unsubstituted aryl (e.g., phenyl), substituted or unsubstituted heteroaryl (e.g., pyridyl) and a fused ring system. Exemplary Cy are described hereinbelow.

In one example, ring Z in Formula (I) is a 5-membered heteroaromatic ring and the compound of the present disclosure has a structure according to Formula (II):

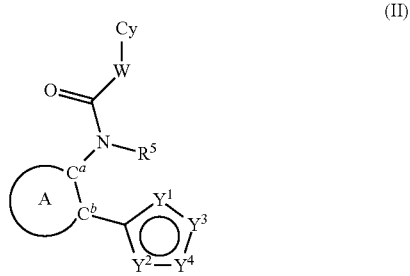

(II)

or a salt or solvate thereof, wherein A, $C^a$, $C^b$, $R^5$, W and Cy are defined as for Formula (I), above.

In Formula (II), $Y^1$ is chosen from N, O and S. $Y^2$, $Y^3$ and $Y^4$ are independently chosen from S, O, N, $NR^3$ and $CR^4$. In one example, at least one of $Y^1$ and $Y^2$ is N. Each $R^3$ and each $R^4$ is independently chosen from H, substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{17}$, $SR^{17}$, $NR^{17}R^{18}$, $C(O)R^{19}$, $C(O)NR^{17}R^{18}$, $OC(O)NR^{17}R^{18}$, $C(O)OR^{17}$, $NR^{20}C(O)R^{19}$, $NR^{20}C(O)OR^{17}$, $NR^{20}C(O)NR^{17}R^{18}$, $NR^{20}C(S)NR^{17}R^{18}$, $NR^{20}S(O)_2R^{19}$, $S(O)_2NR^{17}R^{18}$, $S(O)R^{19}$ and $S(O)_2R^{19}$, wherein $R^{17}$, $R^{18}$ and $R^{20}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{17}$ and $R^{18}$, together with the nitrogen atom to which they are bound are optionally joined to form a 5- to 7-membered heterocyclic ring. $R^{19}$ is independently chosen from acyl, $C_1$-$C_6$-alkyl, 2- to 6-membered heteroalkyl, aryl (e.g., phenyl), 5- or 6-membered heteroaryl, $C_3$-$C_8$ cycloalkyl and 3- to 8-membered heterocycloalkyl. In one example, each $R^3$ is independently chosen from H, alkyl (e.g., $C_1$-$C_6$-alkyl), alkenyl (e.g., $C_1$-$C_6$-alkenyl), alkynyl (e.g., $C_1$-$C_6$-alkynyl), haloalkyl (e.g., $C_1$-$C_6$-haloalkyl), heterocycloalkyl (e.g., 3- to 8-membered heterocycloalkyl), cycloalkyl (e.g., $C_3$-$C_6$-cycloalkyl), aryl (e.g., phenyl) and heteroaryl. In another example, each $R^4$ is independently chosen from H, alkyl (e.g., $C_1$-$C_6$-alkyl), alkenyl (e.g., $C_1$-$C_6$-alkenyl), alkynyl (e.g., $C_1$-$C_6$-alkynyl), haloalkyl (e.g., $C_1$-$C_6$-haloalkyl), heterocycloalkyl (e.g., 3- to 8-membered heterocycloalkyl), cycloalkyl (e.g., $C_3$-$C_6$-cycloalkyl), aryl (e.g., phenyl), heteroaryl, CN, halogen, $OR^{17}$, $SR^{17}$ and $NR^{17}R^{18}$, wherein $R^{17}$ and $R^{18}$ are defined as above.

Alternatively, any of the $R^3$ substituents and/or $R^4$ substituents, together with the atoms to which they are attached, form a 5- to 7-membered ring. For example, if two of $Y^2$, $Y^3$, and $Y^4$ are $NR^3$, then the two $R^3$ groups may form a 5- to 7-membered ring. In another embodiment, if two of $Y^2$, $Y^3$, and $Y^4$ are $CR^4$, then the two $R^4$ groups may form a 5- to 7-membered ring. In yet another embodiment, if one of $Y^2$, $Y^3$, and $Y^4$ is $NR^3$ and a second of $Y^2$, $Y^3$, and $Y^4$ is $CR^4$, then the $R^3$ and $R^4$ groups may form a 5- to 7-membered ring.

In another example, in Formula (II), $Y^1$ is N. In a further example, $Y^1$ is N and $Y^2$, $Y^3$ and $Y^4$ form a triazole, thiazole, oxazole, oxadiazole, imidazole, pyrazole or tetrazole ring. In yet another example, $Y^1$ is N and $Y^2$, $Y^3$ and $Y^4$ form a triazole ring.

In one example, in Formula (II), when $Y^3$ and $Y^4$ are both $CR^4$ and $Y^1$ is N, then $Y^2$ is other than S. In another example, when $Y^3$ and $Y^4$ are both $CR^4$ and $Y^2$ is N, then $Y^1$ is other than S. In a further example, when A is thiophene, then the moiety:

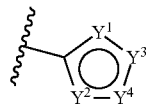

is not thiazole. In a further example, when A is thiophene, then the above moiety is not benzothiazole. In a further example, when A is thiophene, then the above moiety is not benzimidazole. In a further example, when A is thiazole, then the moiety is other than benzimidazole. In a further example, when A is thiophene or thiazole, then the above moiety is not thiazole-2-yl, benzo[d]thiazol-2-yl or 1H-benzo[d]imidazole-2-yl.

In another example, in Formula (II), when $Y^2$ is $NR^3$, then $R^3$ is H. In another example, in Formula (II), when $Y^2$ is $CR^4$, then $R^4$ is H.

In another example, in Formula (II), W is substituted or unsubstituted methylene. In a further example, W is —$CH_2$—. In another example, each $R^3$ is H. In yet another example, each $R^4$ is chosen from H and methyl. In a further example, in Formula (II), $R^5$ is H. In another example, in Formula (II), W is methylene and $R^5$ is H.

Ring A

In one example, in Formula (I) and Formula (II), ring A is a 5-membered heteroaromatic ring. In another example, in Formula (I) and Formula (II), ring A is a 6-membered aromatic or heteroaromatic ring. Exemplary rings for A include phenyl, pyridine, thiophene, thiazole and oxazole. In a one example, in Formula (I) or (II), ring A is chosen from thiophene and thiazole. In another example, in Formula (I) or (II), ring A is chosen from thiophene and thiazole, wherein the thiophene is optionally substituted with 1 or 2 substituents and the thiazole is optionally substituted with 1 substituent, wherein each substituent is independently chosen from $C_1$-$C_4$ alkyl (e.g., methyl, ethyl, iso-propyl, tert-butyl), $C_3$-$C_6$ cycloalkyl (e.g., cyclopropyl), $C_1$-$C_4$ haloalkyl (e.g., $CF_3$, $CHF_2$, $CH_2F$, $CH_2CF_3$), halogen (e.g., F, Cl. Br) and CN. In another example, ring A is thiophene or thiazole, $Y^1$ is N and $Y^2$, $Y^3$ and $Y^4$ form a triazole ring.

In yet another example, ring A is a 5-membered heteroaromatic ring and the compounds of Formula (II) have a structure according to Formula (IIIa) or Formula (IIIb):

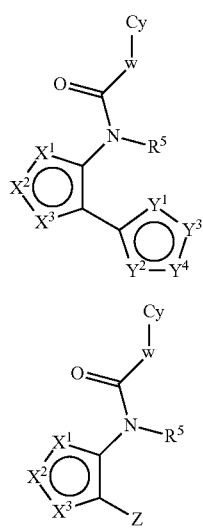

or a salt or solvate thereof, wherein Z, $R^5$, W, Cy, $Y^1$, $Y^2$, $Y^3$ and $Y^4$ are defined as for Formula (I) and Formula (II), above.

In Formula (IIIa) and (IIIb), $X^1$, $X^2$ and $X^3$ are independently chosen from S, O, N, $NR^1$ and $CR^2$, with the proviso that at least one of $X^1$, $X^2$ and $X^3$ is other than $CR^2$. $R^1$ is chosen from H, substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., pyridyl). In one example, $R^1$ is chosen from H, substituted or unsubstituted $C_1$-$C_6$ alkyl (e.g., methyl or ethyl) and $C_1$-$C_3$ haloalkyl.

In Formula (IIIa) and (IIIb), each $R_2$ is independently chosen from aryl group substituents as defined herein. In one example, each $R^2$ is independently chosen from H, substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{22}$, $SR^{22}$, $NR^{22}R^{23}$, $C(O)R^{24}$, $C(O)NR^{22}R^{23}$, $OC(O)NR^{22}R^{23}$, $C(O)OR^{22}$, $NR^{25}C(O)R^{24}$, $NR^{25}C(O)OR^{22}$, $NR^{25}C(O)NR^{22}R^{23}$, $NR^{25}C(S)NR^{22}R^{23}$, $NR^{25}S(O)_2R^{24}$, $S(O)_2NR^{22}R^{23}$, $S(O)R^{24}$ and $S(O)_2R^{24}$, wherein $R^{22}$, $R^{23}$ and $R^{25}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{12}$ and $R^{13}$, together with the nitrogen atom to which they are bound are optionally joined to form a 5- to 7-membered heterocyclic ring. $R^{24}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl. In one example, each $R^2$ is independently chosen from H, $C_1$-$C_4$ alkyl (e.g., methyl, ethyl, iso-propyl, tert-butyl), $C_3$-$C_6$ cycloalkyl (e.g., cyclopropyl), $C_1$-$C_4$ haloalkyl (e.g., $CF_3$, $CHF_2$, $CH_2F$, $CH_2CF_3$), halogen (e.g., F, Cl. Br) and CN.

In a further example, the compounds of the present disclosure have a structure according to Formula (IV), Formula (V), Formula (VI) or Formula (VII):

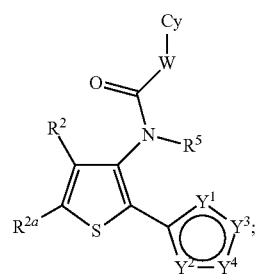

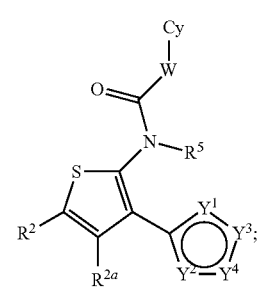

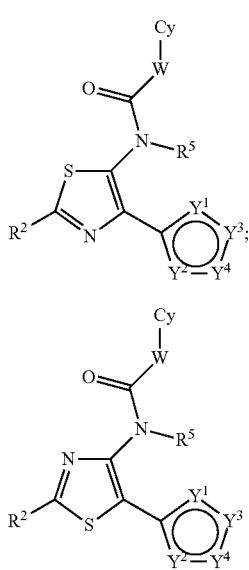

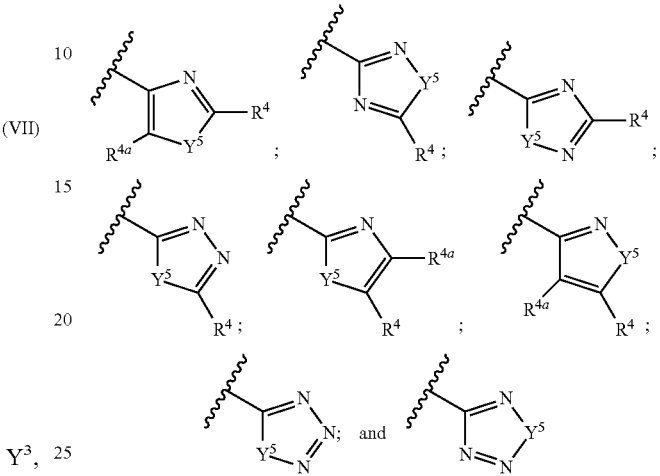

wherein $Y^5$ is chosen from O, S and $NR^3$, wherein $R^3$ is defined as for Formula (II), above. In one example, each $R^3$ is independently chosen from H, alkyl (e.g., $C_1$-$C_6$-alkyl), alkenyl (e.g., $C_1$-$C_6$-alkenyl), alkynyl (e.g., $C_1$-$C_6$-alkynyl), haloalkyl (e.g., $C_1$-$C_6$-haloalkyl), heterocycloalkyl (e.g., 3- to 8-membered heterocycloalkyl), cycloalkyl (e.g., $C_3$-$C_6$-cycloalkyl), aryl (e.g., phenyl) and heteroaryl. In another example, $R^3$ in the above structures is chosen from H, $C_1$-$C_3$ alkyl (e.g., methyl) and $C_1$-$C_3$ haloalkyl.

In the above structures, $R^4$ and $R^{4a}$ are independently chosen and are each defined as $R^4$ in Formula (II), above. In one example, $R^4$ and $R^{4a}$ are independently chosen from H, alkyl (e.g., $C_1$-$C_6$-alkyl), alkenyl (e.g., $C_1$-$C_6$-alkenyl), alkynyl (e.g., $C_1$-$C_6$-alkynyl), haloalkyl (e.g., $C_1$-$C_6$-haloalkyl), heterocycloalkyl (e.g., 3- to 8-membered heterocycloalkyl), cycloalkyl (e.g., $C_3$-$C_6$-cycloalkyl), aryl (e.g., phenyl), heteroaryl, CN, halogen, $OR^{17}$, $SR^{17}$ and $NR^{17}R^{18}$, wherein $R^{17}$ and $R^{18}$ are defined as above. In another example, $R^4$ and $R^{4a}$ in the above structures are independently chosen from H, substituted or unsubstituted $C_1$-$C_3$ alkyl (e.g., methyl), $C_3$-$C_6$ cycloalkyl (e.g., cyclopropyl) and $NR^{17}R^{18}$. In another example, $R^{4a}$ in the above structures is H. In yet another example in the above structures, $R^4$ is H. In yet another example $R^3$ in the above structures is H. In a further example in the above structures, $R^3$, $R^4$ and $R^{4a}$ are each H.

Alternatively, any of the $R^3$ substituents and/or $R^4$ substituents, together with the atoms to which they are attached, form a 5- to 7-membered ring. For example, if two of $Y^2$, $Y^3$, and $Y^4$ are $NR^3$, then the two $R^3$ groups may form a 5- to 7-membered ring. In another embodiment, if two of $Y^2$, $Y^3$, and $Y^4$ are $CR^4$, then the two $R^4$ groups may form a 5- to 7-membered ring. In yet another embodiment, if one of $Y^2$, $Y^3$, and $Y^4$ is $NR^3$ and a second of $Y^2$, $Y^3$, and $Y^4$ is $CR^4$, then the $R^3$ and $R^4$ groups may form a 5- to 7-membered ring.

In one example, ring Z in Formula (I) or (IIIb) or the moiety:

or a salt or solvate thereof, wherein Cy, W, $R^5$, $Y^1$, $Y^2$, $Y^3$, and $Y^4$ are defined as hereinabove in Formulae (I), (II) and (III), respectively.

In Formulae (IV) to (VII), $R^2$ and $R^{2a}$ are each defined as $R^2$ in Formula (IIIa) and (IIIb). In one example, $R^2$ and $R^{2a}$ are independently chosen from H, $C_1$-$C_4$ alkyl (e.g., methyl, ethyl, iso-propyl, tert-butyl), $C_3$-$C_6$ cycloalkyl (e.g., cyclopropyl), $C_1$-$C_4$ haloalkyl (e.g., $CF_3$, $CHF_2$, $CH_2F$, $CH_2CF_3$), halogen (e.g., F, Cl. Br) and CN. In another example, $R^2$ and $R^{2a}$ are both H. In yet another example, at least one of $R^2$ and $R^{2a}$ is halogen (e.g., F, Cl, Br). In a further example, at least one of $R^2$ and $R^{2a}$ is CN. In another example, at least one of $R^2$ and $R^{2a}$ is methyl.

Ring Z

In one embodiment, ring Z is chosen from 5-membered and 6-membered heteroaromatic rings. Exemplary 6-membered heteroaromatic rings for Z include pyridines and pyrazines. In vitro biological activity of the compounds of the present disclosure is generally higher when ring Z is connected to ring A via a carbon atom of ring Z (as shown above in Formulae II-VII) as opposed to being connected via a nitrogen atom of ring Z. Hence, in one example, ring Z is connected to the remainder of the molecule via a carbon atom.

In vitro biological activity of a compound of the present disclosure is generally higher when Z does not include a substituent (e.g., a methyl group) at the atom, which is immediately adjacent to the ring connection connecting rings Z and A. Hence, in another example, when $Y^2$ is $NR^3$, then $R^3$ is H. In another example, when $Y^2$ is $CR^4$, then $R^4$ is H.

Exemplary 5-membered heteroaromatic rings for Z in Formula (I) or (IIIb) or the moiety:

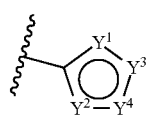

in Formulae (II), (IIIa) and (IV) to (VII) include triazoles (e.g., 1,2,3-triazoles or 1,2,4-triazoles), oxazoles, isoxazoles, thiazoles, isothiazoles, tetrazoles, oxadiazoles (e.g., 1,2,4-oxadiazoles or 1,3,4-oxadiazoles), thiadiazoles (e.g., 1,2,4-thiadiazoles or 1,3,4-thiadiazoles), pyrazoles, imidazoles and tetrazoles. In another example, ring Z has a structure, which is chosen from:

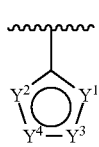

in any of the above formulae and embodiments, is chosen from:

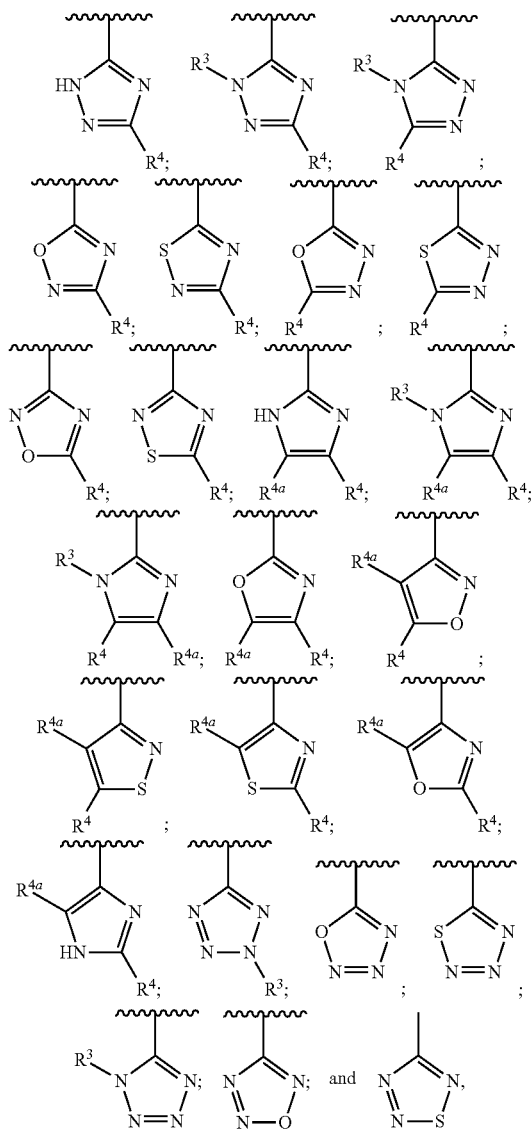

or a tautomer or mixture of tautomers thereof, wherein $R^4$, $R^{4a}$ and $R^3$ are defined as hereinabove. In one example, $R^4$, $R^{4a}$ and $R^3$ are independently chosen from H, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, $OR^{17}$ and $NR^{17}R^{18}$, wherein $R^{17}$ and $R^{18}$ are independently chosen from H, substituted or unsubstituted alkyl, substituted or unsubstituted heteroalkyl, substituted or unsubstituted aryl, substituted or unsubstituted heteroaryl, substituted or unsubstituted cycloalkyl, substituted or unsubstituted heterocycloalkyl, and wherein $R^{17}$ and $R^{18}$, together with the nitrogen atom to which they are attached, are optionally joined to form a 5- to 7-membered ring. In the above structures, at least two of $R^3$, $R^4$ and $R^{4a}$, $R^{17}$ and $R^{18}$, together with the atoms to which they are attached, are optionally joined to form a 5- to 7-membered ring. For example, one of $R^3$, $R^4$ and $R^{4a}$ and one of $R^{17}$ and $R^{18}$, together with the atoms to which they are attached, are optionally joined to form a 5- to 7-membered ring. In another example, $R^3$ and $R^4$ or $R^4$ and $R^{4a}$, together with the atoms to which they are attached, are optionally joined to form a 5- to 7-membered ring. In one embodiment, in any of the above structures, $R^3$ is H.

In one embodiment, in the above structures, $R^{4a}$ is H. In another embodiment, in the above structures, $R^4$ is H, methyl, cyclopropyl or amino. In yet another embodiment, in the above structures, $R^{4a}$ (when present) is H and $R^4$ is H. In yet another embodiment, in the above structures, $R^{4a}$ (when present) is H and $R^4$ is methyl. In a further embodiment, in the above structures, $R^{4a}$ (when present) is H and $R^4$ is cyclopropyl.

In one example, Z in Formula (I) or (IIIb) or the moiety:

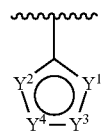

in any of the above formulae and embodiments, is chosen from:

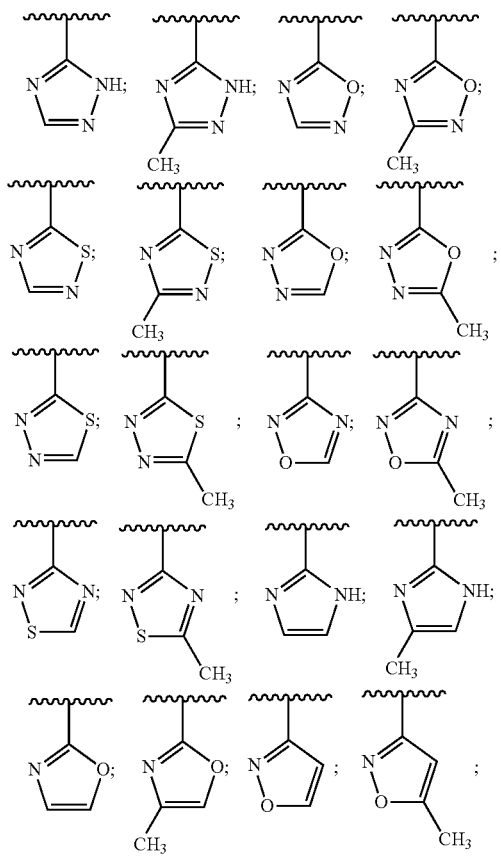

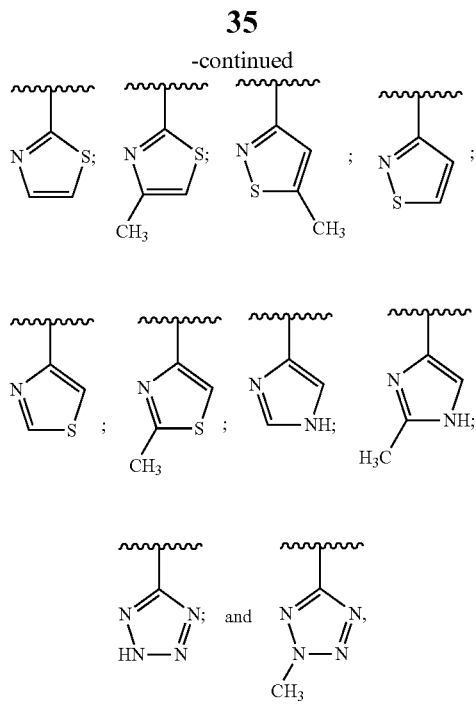

or a tautomer or mixture of tautomers thereof.

In one embodiment, Z in Formula (I) or (IIIb) or any of the formulae above is a triazole. In one example according to this embodiment, Z has the formula:

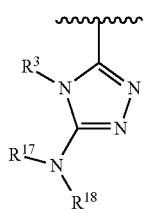

wherein $R^3$, $R^{17}$ and $R^{18}$ are defined as herein above. In one example, in the above structure, $R^3$ and one of $R^{17}$ and $R^{18}$, together with the atoms to which they are attached, are optionally joined to form a 5- to 7-membered ring. In another example, in the above structure, $R^3$ is H.

In another example, Z in Formula (I) is a triazole and the compounds of the present disclosure have a structure according to Formula (VIIIa), Formula (VIIIb) or Formula (VIIIc):

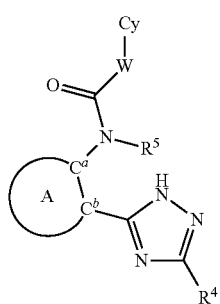
(VIIIa)

(VIIIb)

(VIIIc)

or a tautomer, mixture of tautomers, salt or solvate thereof.

In Formulae (VIIIa), (VIIIb) and (VIIIc), ring A, $C^a$, $C^b$, $R^3$, $R^4$, $R^5$, W and Cy are defined as hereinabove. In one example, $R^4$ is H. In another example, $R^4$ is methyl. In Formula (VIIIb), $R^3$ and $R^4$, together with the atoms to which they are attached, are optionally joined to form a 5- to 7-membered ring.

In one example, in Formula (VIIIa), ring A is chosen from thiophenes and thiazoles. In a further example, the compounds of the present disclosure have a structure according to one of Formula (IVa), Formula (Va), Formula (VIa) and Formula (VIIa):

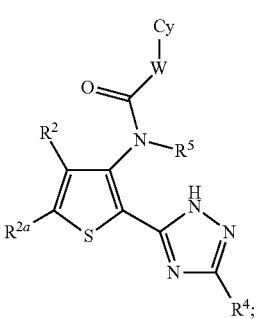
(IVa)

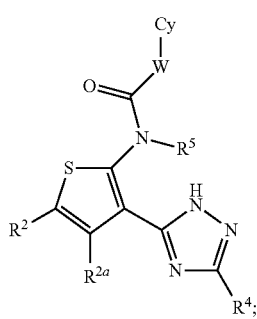
(Va)

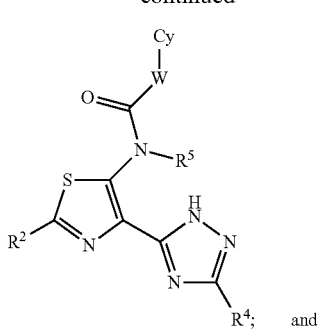

(VIa)

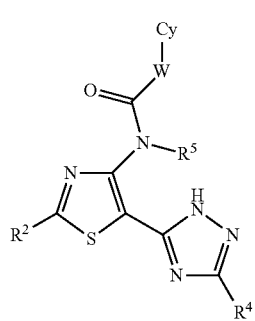

(VIIa)

or a tautomer, mixture of tautomers, salt or solvate thereof, wherein Cy, W, $R^4$ and $R^5$ are defined as for Formula (I), above. $R^2$ and $R^{2a}$ are defined as in Formulae (IV) to (VII) hereinabove. In one example, $R^4$ is H or methyl.

Exemplary 6-membered heteroaromatic rings for Z, e.g., in Formula (I) and Formula (IIIb), include pyridines, pyrazines, pyrimidines, pyridazines and triazines (e.g., 1,2,3-triazines; 1,2,4-triazines or 1,3,5-triazines). In one example, Z in Formula (I) or (IIIb) has a structure, which is chosen from:

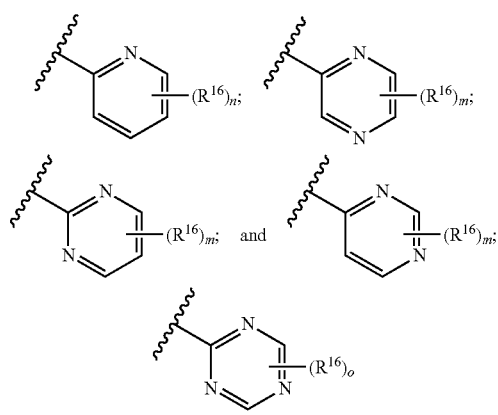

wherein n is an integer chosen from 0 to 4, m is an integer chosen from 0 to 3 and o is an integer chosen from 0 to 2. Each $R^{16}$ is independently chosen from H, substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{32}$, $SR^{32}$, $NR^{32}R^{33}$, $C(O)R^{34}$, $C(O)NR^{32}R^{33}$, $OC(O)NR^{32}R^{33}$, $C(O)OR^{32}$, $NR^{35}C(O)R^{34}$, $NR^{35}C(O)OR^{32}$, $NR^{35}C(O)NR^{32}R^{33}$, $NR^{35}C(S)NR^{32}R^{33}$, $NR^{35}S(O)_2R^{34}$, $S(O)_2NR^{32}R^{33}$, $S(O)R^{34}$ and $S(O)_2R^{34}$, wherein $R^{32}$, $R^{33}$ and $R^{35}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{32}$ and $R^{33}$, together with the nitrogen atom to which they are bound are optionally joined to form a 5- to 7-membered heterocyclic ring. $R^{34}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl. Adjacent $R^{16}$, together with the carbon atoms to which they are attached, are optionally joined to form a 5- to 7-membered ring.

In another example, Z is a fused ring system, which includes at least one of the above 5- or 6-membered rings. In one example, Z is chosen from benzo- or pyrido-imidazole, benzo- or pyrido-oxazole, benzo- or pyrido-thiazole, benzo- or pyrido-isoxazole and benzo- or pyrido-isothiazole.

In one example, when ring A is thiophene, then Z is other than oxadiazole. In another example, when ring A is thiophene, then Z is other than substituted (e.g., phenyl-substituted) oxadiazole. In yet another example, when ring A is thiophene, then Z is other than oxadiazole substituted with phenyl or substituted phenyl. In yet another example, when ring A is thiophene, then Z is other than oxadiazole, wherein the oxadiazole is substituted with a phenyl, 4-methyl-phenyl, or a 4-ethyl-phenyl group. In another example, when ring A is methyl- or ethyl-substituted thiophene, then Z is other than oxadiazole.

In another example, when ring A is thiophene, then Z is other than pyrimidinone. In another example, when ring A is thiophene, then Z is other than substituted pyrimidinone (e.g., pyrimidinone substituted with at least one of hydroxy, carboxy or hydroxy-methylene)

W

In another example according to any of the above embodiments of Formulae (I) to (IX), W is straight chain alkylene represented by —$(CR^{10}R^{11})_n$—, wherein n is chosen from 1 to 10 and $R^{10}$ and $R^{11}$ are defined as hereinbelow for Formulae (X) and (XI). In another example, W is straight chain alkylene represented by —$(CH_2)_n$—, wherein n is chosen from 1 to 10. In one embodiment, n is 1 or 2. In yet another example according to any of the above embodiments of Formula (I) to (IX), W is unsubstituted methylene (—$CH_2$—).

The present disclosure further provides a compound, having a structure according to Formula (X) or Formula (XI):

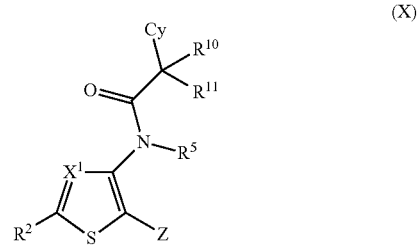

(X)

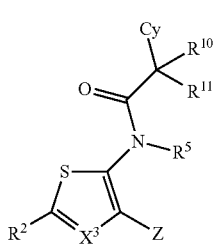

(XI)

or a salt or solvate thereof, wherein Z, $R^5$ and Cy are defined as for Formula (I) above.

In Formula (X) and Formula (XI), $X^1$ and $X^3$ are independently chosen from N and $CR^{2a}$. $R^2$ and $R^{2a}$ are each independently defined as $R^2$ in Formula (IIIa) and Formula (IIIb). In one example, $R^2$ and $R^{2a}$ are independently chosen from H, substituted or unsubstituted $C_1$-$C_{10}$ alkyl, substituted or unsubstituted 3- to 10-membered heteroalkyl, substituted or unsubstituted $C_3$-$C_8$ cycloalkyl, substituted or unsubstituted 3- to 8-membered heterocycloalkyl, substituted or unsubstituted aryl (e.g., phenyl), substituted or unsubstituted heteroaryl (e.g., pyridyl), CN and halogen. In another example, $R^2$ and $R^{2a}$ are independently chosen from H, $C_1$-$C_4$ alkyl (e.g., methyl, ethyl, iso-propyl, tert-butyl), $C_3$-$C_6$ cycloalkyl (e.g., cyclopropyl), $C_1$-$C_4$ haloalkyl (e.g., $CF_3$, $CHF_2$, $CH_2F$, $CH_2CF_3$), halogen (e.g., F, Cl or Br) and CN. In one example, $R^2$ and $R^{2a}$ are independently chosen from H, methyl, halogen and CN.

In Formula (X) and Formula (XI), $R^{10}$ and $R^{11}$ are independently chosen from H, substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$ and $S(O)_2R^{44}$, wherein $R^{42}$, $R^{43}$ and $R^{45}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring. $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl. In one example, $R^{10}$ and $R^{11}$ are both H.

In Formula (X) and Formula (XI), Z is chosen from those Z-groups described herein, above. In one example, Z in Formula (X) or Formula (XI) is chosen from:

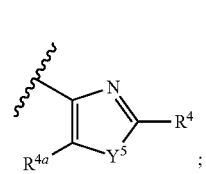
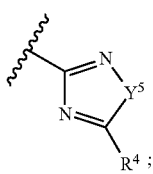
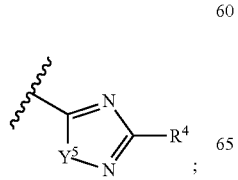

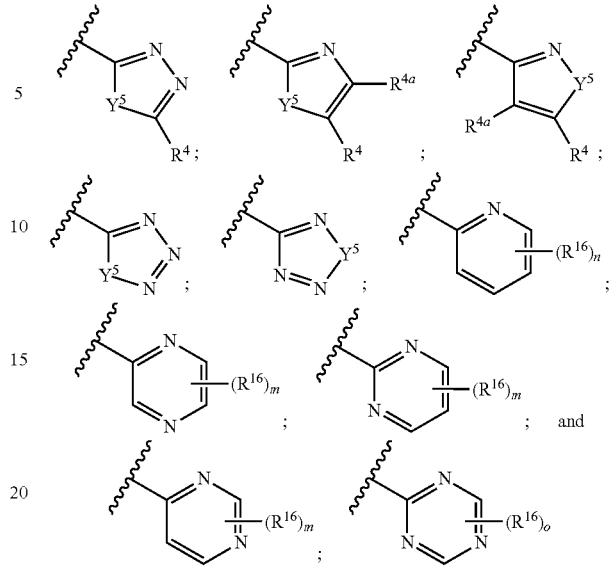

wherein n, m, o, $Y^5$, $R^4$, $R^{4a}$, and $R^{16}$ are defined as hereinabove. In another example, Z in Formula is a triazole.

Substituent $R^5$

In any of the embodiments of Formula (I) to (XI), $R^5$ is defined as for Formula (I). In one example, according to any of the above embodiments of Formulae (I) to (XI), $R^5$ is H or $C_1$-$C_3$ alkyl. In another example, according to any of the above embodiments of Formulae (I) to (XI), $R^5$ is H. In another example according to any of the above embodiments of Formula (I) to (XI), $R^5$ is H and W is methylene ($-CH_2-$).

In one example, the compounds of the present disclosure have a structure according to Formula (XII), Formula (XIII), Formula (XIV) or Formula (XV):

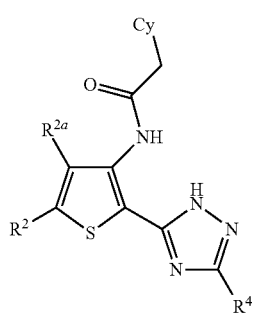

(XII)

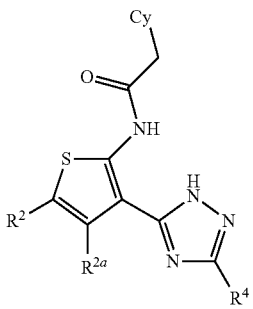

(XIII)

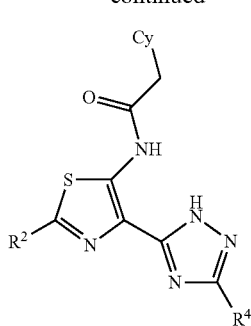

(XIV)

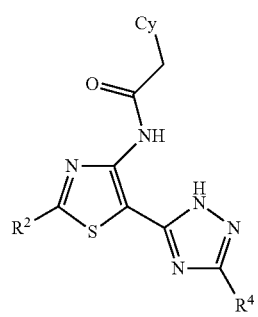

(XV)

or a tautomer, mixture of tautomers, salt or solvate thereof, wherein Cy and $R^4$ are defined as for Formula (I) hereinabove. $R^2$ and $R^{2a}$ are defined as for Formulae (IV) to (VII) hereinabove. In one example in the above structures, $R^2$ and $R^{2a}$ (when present) are independently chosen from H, halogen (e.g., F, Cl, Br), methyl and halogen-substituted methyl (e.g., $CF_3$ or $CHF_2$). In another example, $R^4$ is H or methyl. In yet another example, $R^2$ and $R^{2a}$ (when present) are independently H, halogen (e.g., F, Cl, Br) or halogen-substituted methyl, and $R^4$ is H or methyl.

Ring Cy

Cy in any of the embodiments of Formula (I) to (XV) represents a ring or a fused ring system. In one example according to any of the above embodiments of Formula (I) to (XV), Cy is chosen from substituted or unsubstituted $C_3$-$C_{12}$ cycloalkyl (e.g., substituted or unsubstituted cyclopentane, cyclohexane, norbornane or adamantane), substituted or unsubstituted 3- to 12-membered heterocycloalkyl (e.g., substituted or unsubstituted morpholino), substituted or unsubstituted aryl (e.g., substituted or unsubstituted phenyl or substituted or unsubstituted naphthyl), substituted or unsubstituted heteroaryl (e.g., substituted or unsubstituted pyridyl, substituted or unsubstituted quinoline, substituted or unsubstituted isoquinoline, substituted or unsubstituted quinoxaline, substituted or unsubstituted quinazoline) and other fused ring systems (e.g., substituted or unsubstituted 3,4-dihydroquinolin-2-one, and substituted or unsubstituted 3,4-dihydro-1,6-naphthyridin-2-one). In one example, each of the above cycloalkyl, heterocycloalkyl, aryl or heteroaryl groups is optionally substituted with from 1 to 8 $R^{20}$ groups, wherein each $R^{20}$ is independently chosen from substituted or unsubstituted alkyl (e.g., $C_1$-$C_6$-alkyl), substituted or unsubstituted alkenyl (e.g., $C_1$-$C_6$-alkenyl), substituted or unsubstituted alkynyl (e.g., $C_1$-$C_6$-alkynyl), haloalkyl (e.g., $C_1$-$C_6$-haloalkyl), substituted or unsubstituted heteroalkyl (e.g., 2- to 6-membered heteroalkyl), substituted or unsubstituted cycloalkyl (e.g., $C_3$-$C_6$-cycloalkyl), substituted or unsubstituted heterocycloalkyl (e.g., 3- to 8-membered heterocycloalkyl), substituted or unsubstituted aryl (e.g., phenyl), substituted or unsubstituted heteroaryl (e.g., 5- or 6-membered heteroaryl), CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring. $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl.

In one example, Cy in any of the above embodiments of Formula (I) to (XV) has a structure chosen from:

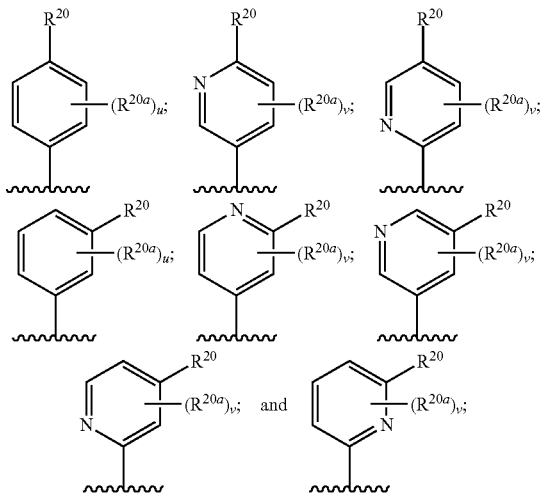

wherein q is an integer chosen from 0 to 5, r is an integer chosen from 0 to 4, s is an integer chosen from 0 to 6, t is an integer chosen from 0 to 8 and each $R^{20}$ is independently defined as above. At least two $R^{20}$, together with the atoms to which they are attached, are optionally joined to form a 5- to 7-membered ring. In one example, two $R^{20}$, together with the atoms to which they are attached, are joined to form a 5- or 6-membered, aromatic (e.g., phenyl) or heteroaromatic (e.g., pyridyl, pyrimidyl, pyrazyl, thienyl or pyrazole) ring.

In a further example, Cy in any of the above embodiments of Formula (I) to (XV) is 4-substituted or 3-substituted phenyl or pyridyl. For example, Cy has a structure chosen from:

wherein u is an integer chosen from 0 to 4 and v is an integer chosen from 0 to 3. $R^{20}$ is defined as herein above. In one example, $R^{20}$ in the above structures is $OR^{51}$, wherein $R^{51}$ is defined as herein above. In one example, $R^{51}$ is chosen from substituted or unsubstituted alkyl (e.g., $C_1$-$C_6$ alkyl). In one embodiment, $R^{20}$ in the above structures is chosen from methoxy and ethoxy. Each $R^{20a}$ in the above structures is independently chosen from $R^{20}$ groups as defined herein above. In one example, the integer u or the integer v are 0 and $R^{20a}$ in the above structures is absent.

In a further example, Cy in any of the above embodiments of Formula (I) to (XV) is chosen from:

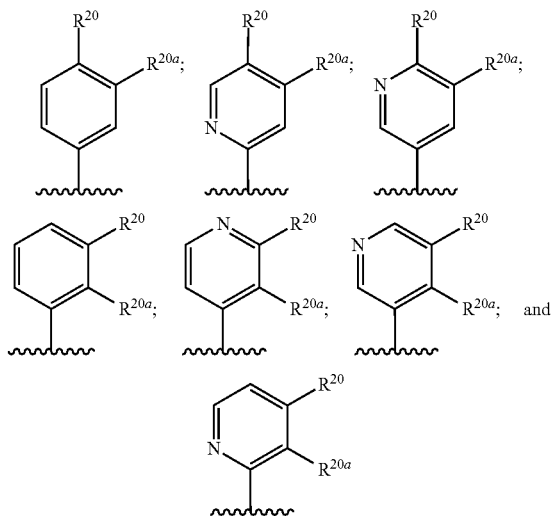

wherein $R^{20}$ and $R^{20a}$ are defined as herein above. $R^{20}$ and $R^{20a}$, together with the atoms to which they are attached, are optionally joined to form a 5- to 7-membered ring.

In yet another example, Cy in any of the above embodiments of Formula (I) to (XV) is chosen from:

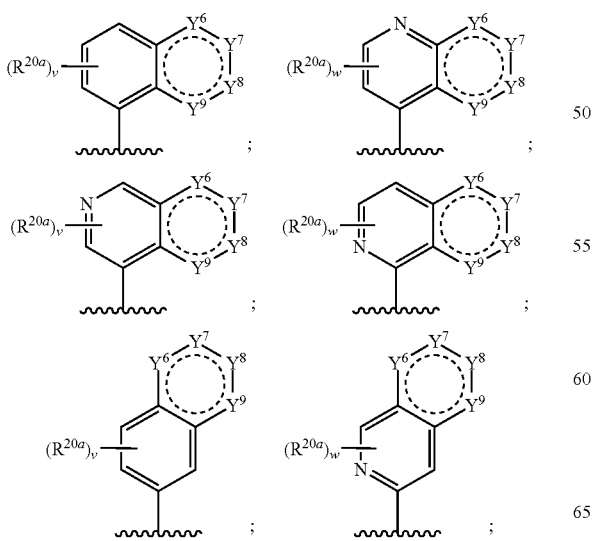

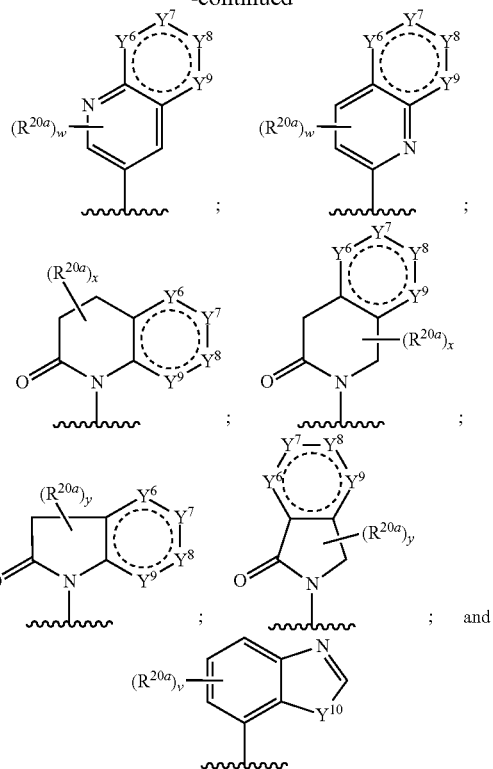

wherein v is an integer chosen from 0 to 3, w is an integer chosen from 0 to 2, x is an integer chosen from 0 to 4, and y is an integer chosen from 0 to 2. Each $R^{20a}$ in the above structures is independently chosen and is defined as herein above. In one example, each $R^{20a}$ in the above structures is absent. $Y^6$, $Y^7$, $Y^8$ and $Y^9$ are independently chosen from N and $CR^{20b}$, wherein each $R^{20b}$ is independently chosen from H and $R^{20}$ as defined herein above. In one example, $Y^6$, $Y^7$, $Y^8$ and $Y^9$ are chosen from N and CH. $Y^{10}$ is a chosen from O and S. In another example, $Y^{10}$ is S.

In a further example, Cy in any of the above embodiments of Formula (I) to (XV) is chosen from:

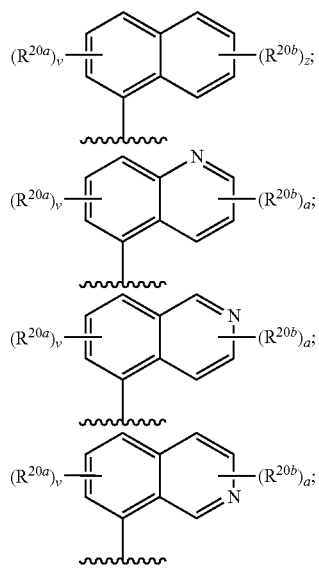

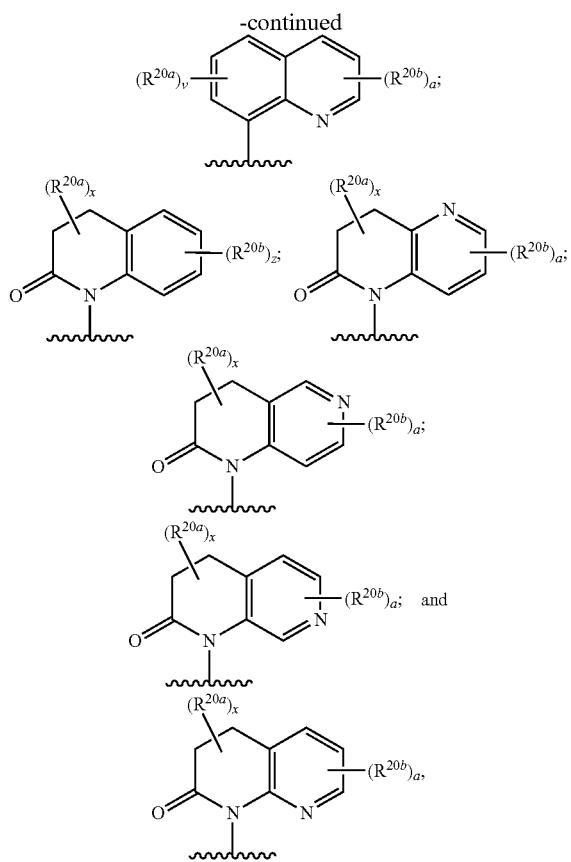

wherein v, x, $R^{20a}$ and $R^{20b}$ are defined as herein above. The integer z is chosen from 0 to 4 and the integer a is chosen from 0 to 3. In one example in the above structures $R^{20a}$ is absent. In another example, each $R^{20b}$ in the above structures is H. In yet another example, in the above structures, each $R^{20a}$ is absent and each $R^{20b}$ is H.

In Vitro Activities

Certain compounds of the present disclosure exhibit various in vitro biological activities as demonstrated, e.g., in Example 14 and Table 1. For example, certain compounds of the present disclosure exhibit inhibitory activity against Jun N-terminal kinases (JNKs). In vitro assays for the determination of JNK activities are known in the art and exemplary assay formats are described herein (see e.g., Example 14). Many compounds of the present disclosure are especially active against JNK3 (e.g., aJNK3 or cJNK3) but may also inhibit JNK1 and JNK2.

In one example, the compounds of the present disclosure may be inhibitors of aJNK3 with an $IC_{50}$ of less than about 50 μM, less than about 40 μM, less than about 30 μM, less than about 20 μM or less than about 10 μM. In another example, the compounds of the present disclosure may exhibit inhibitory activity against aJNK3 with an $IC_{50}$ of less than about 9 μM, less than about 8 μM, less than about 7 μM, less than about 6 μM, less than about 5 μM, less than about 4 μM, less than about 3 μM, less than about 2 μM, or less than about 1 μM. In yet another example, the compounds of the present disclosure may exhibit inhibitory activity against aJNK3 with an $IC_{50}$ of less than about 0.9 μM, less than about 0.8 μM, less than about 0.7 μM, less than about 0.6 μM, less than about 0.5 μM, less than about 0.4 μM, less than about 0.3 μM, less than about 0.2 μM. For example, the compounds of the present disclosure may exhibit inhibitory activity against aJNK3 with an $IC_{50}$ of less than about 0.1 μM (100 nM). In another example, the compounds of the present disclosure may exhibit inhibitory activity against a JNK3 with an $IC_{50}$ of less than about 90 nM, less than about 80 nM, less than about 70 nM, less than about 60 nM, less than about 50 nM, less than about 40 nM, less than about 30 nM or less than about 20 nM. In another example, the compounds of the present disclosure may exhibit inhibitory activity against aJNK3 with an $IC_{50}$ of less than about 10 nM.

Certain compounds of the present disclosure do not only exhibit inhibitory activity against JNK, but at the same time have little or no inhibitory activity against certain other members of the MAP kinase family of proteins. For example, certain compounds of the present disclosure are active against aJNK3 and show little or no inhibitory activity against p38 and/or MAPK. For the purpose of this application the selectivity of the instant compounds for JNK over other kinases is expressed in a ratio of $IC_{50}$ values. Those can be determined using assays known in the art or those described herein (see e.g., Example 14).

Certain compounds of the present disclosure are characterized by the following inhibitory activities involving aJNK3 and p38. In one example, the ratio of $IC_{50}$ (aJNK3)/$IC_{50}$ (p38) is less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (aJNK3)/$IC_{50}$ (p38) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (aJNK3)/$IC_{50}$ (p38) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (aJNK3)/$IC_{50}$ (p38) is less than about 0.0009, less than about 0.0008, less than about 0.0007, less than about 0.0006, less than about 0.0005, less than about 0.0004, less than about 0.0003, less than about 0.0002 or less than about 0.0001.

Certain compounds of the present disclosure are characterized by the following inhibitory activities involving aJNK3 and MAPK. In one example, the ratio of $IC_{50}$ (aJNK3)/$IC_{50}$ (MAPK) is less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (aJNK3)/$IC_{50}$ (MAPK) is less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (aJNK3)/$IC_{50}$ (MAPK) is less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (aJNK3)/$IC_{50}$ (MAPK) is less than about 0.0009, less than about 0.0008, less than about 0.0007, less than about 0.0006, less than about 0.0005, less than about 0.0004, less than about 0.0003, less than about 0.0002 or less than about 0.0001.

Certain compounds of the present disclosure are characterized by the following inhibitory activities involving aJNK3, p38 and MAPK. In one example, the ratio of $IC_{50}$ (aJNK3)/$IC_{50}$ (MAPK) and the ratio of $IC_{50}$ (aJNK3)/$IC_{50}$ (p38) is each less than about 1, less than about 0.9, less than about 0.8, less than about 0.7, less than about 0.6, less than about 0.5, less than about 0.4, less than about 0.3, less than about 0.2 or less than about 0.1. In another example, the ratio of $IC_{50}$ (aJNK3)/$IC_{50}$ (MAPK) and the ratio of $IC_{50}$ (aJNK3)/$IC_{50}$ (p38) is each less than about 0.09, less than about 0.08, less than about 0.07, less than about 0.06, less than about 0.05, less than about 0.04, less than about 0.03, less than about 0.02 or less than about 0.01. In a further example, the ratio of $IC_{50}$ (aJNK3)/$IC_{50}$ (MAPK) and the ratio of $IC_{50}$ (aJNK3)/$IC_{50}$ (p38) is each less than about 0.009, less than about 0.008, less than about 0.007, less than about 0.006, less than about 0.005, less than about 0.004, less than about 0.003, less than about 0.002 or less than about 0.001. In yet another example, the ratio of $IC_{50}$ (aJNK3)/$IC_{50}$ (MAPK) and the ratio of $IC_{50}$ (aJNK3)/$IC_{50}$ (p38) is each less than about 0.0009, less than about 0.0008, less than about 0.0007, less than about 0.0006, less than about 0.0005, less than about 0.0004, less than about 0.0003, less than about 0.0002 or less than about 0.0001.

Exemplary compounds of the present disclosure and their in vitro biological activities are listed in Table 1, below. $IC_{50}$ values in Table 1 were determined using the procedures of Example 14.

TABLE 1

| InVitro Biological Activities | | | |
|---|---|---|---|
| Compound Name | JNK3 $IC_{50}$ (μM) | JNK1 $IC_{50}$ (μM) | JNK2 $IC_{50}$ (μM) |
| N-(2-(1H-1,2,4-triazol-5-yl)thiophen-3-yl)-2-(naphthalen-1-yl)acetamide | (++) | (++) | (++) |
| N-(2-(3-methyl-1H-1,2,4-triazol-5-yl)thiophen-3-yl)-2-(naphthalen-1-yl)acetamide | (++) | (++) | (++) |
| N-(2-(1,3-dimethyl-1H-1,2,4-triazol-5-yl)thiophen-3-yl)-2-(naphthalen-1-yl)acetamide | (+) | (+) | (−) |
| N-(2-(1-methyl-1H-1,2,4-triazol-5-yl)thiophen-3-yl)-2-(naphthalen-1-yl)acetamide | (−) | (−) | (−) |
| 2-(4-methoxyphenyl)-N-(2-(3-methyl-1H-1,2,4-triazol-5-yl)thiophen-3-yl)acetamide | (++) | (++) | (++) |
| N-(2-(1H-1,2,4-triazol-5-yl)thiophen-3-yl)-2-(4-methoxyphenyl)acetamide | (++) | (++) | (++) |
| N-(2-(1H-1,2,4-triazol-1-yl)thiophen-3-yl)-2-(4-methoxyphenyl)acetamide | (+) | (+) | (−) |
| 2-(4-methoxyphenyl)-N-(4-methyl-3-(3-methyl-1H-1,2,4-triazol-5-yl)thiophen-2-yl)acetamide | (++) | (++) | (++) |
| N-(2-(2H-1,2,3-triazol-2-yl)thiophen-3-yl)-2-(4-methoxyphenyl)acetamide | (++) | (++) | (++) |
| N-(2-(3-cyclopropyl-1H-1,2,4-triazol-5-yl)thiophen-3-yl)-2-(4-methoxyphenyl)acetamide | (++) | (++) | (++) |
| N-(2-(3-ethyl-1H-1,2,4-triazol-5-yl)thiophen-3-yl)-2-(4-methoxyphenyl)acetamide | (++) | (++) | (++) |
| N-(2-(3-tert-butyl-1H-1,2,4-triazol-5-yl)thiophen-3-yl)-2-(4-methoxyphenyl)acetamide | (++) | (++) | (+) |
| 2-(4-methoxyphenyl)-N-(2-(3-(tetrahydrofuran-2-yl)-1H-1,2,4-triazol-5-yl)thiophen-3-yl)acetamide | (++) | (++) | (++) |
| 2-(4-methoxyphenyl)-N-(2-(3-(trifluoromethyl)-1H-1,2,4-triazol-5-yl)thiophen-3-yl)acetamide | (++) | (++) | (+) |
| N-(4-methyl-3-(1H-1,2,4-triazol-5-yl)thiophen-2-yl)-2-(2-oxo-3,4-dihydroquinolin-1(2H)-yl)acetamide | (+++) | (+++) | (++)-(+++) |
| N-(4-methyl-3-(3-methyl-1H-1,2,4-triazol-5-yl)thiophen-2-yl)-2-(2-oxo-3,4-dihydroquinolin-1(2H)-yl)acetamide | (+++) | (+++) | (+++) |
| 2-(4-methoxyphenyl)-N-(2-(3-(pyridin-4-yl)-1H-1,2,4-triazol-5-yl)thiophen-3-yl)acetamide | (+) | (++) | (−) |
| N-(2-(3-amino-1H-1,2,4-triazol-5-yl)thiophen-3-yl)-2-(4-methoxyphenyl)acetamide | (++) | (++) | (++) |
| N-(4-chloro-3-(1H-1,2,4-triazol-5-yl)thiophen-2-yl)-2-(2-oxo-3,4-dihydroquinolin-1(2H)-yl)acetamide | (+++) | (+++) | (+++) |
| N-(3-(1H-1,2,4-triazol-5-yl)thiophen-2-yl)-2-(2-oxo-3,4-dihydroquinolin-1(2H)-yl)acetamide | (++) | (+++) | (++) |
| N-(4-chloro-3-(1H-1,2,4-triazol-5-yl)thiophen-2-yl)-2-(isoquinolin-5-yl)acetamide | (+++) | (+++) | (+++) |
| N-(4-chloro-3-(1H-1,2,4-triazol-5-yl)thiophen-2-yl)-2-(quinolin-5-yl)acetamide | (+++) | (+++) | (+++) |
| N-(2-(1H-1,2,4-triazol-5-yl)thiophen-3-yl)-2-(2,3-dihydrobenzo[b][1,4]dioxin-6-yl)acetamide | (++) | (++) | (++) |
| N-(4-methyl-3-(1H-1,2,4-triazol-5-yl)thiophen-2-yl)-2-(quinolin-5-yl)acetamide | (++) | (++) | (++) |
| 2-(2,3-dihydrobenzo[b][1,4]dioxin-6-yl)-N-(2-(3-methyl-1H-1,2,4-triazol-5-yl)thiophen-3-yl)acetamide | (++) | (++) | (++) |
| N-(2-(1H-1,2,4-triazol-5-yl)thiophen-3-yl)-2-(quinolin-5-yl)acetamide | (++) | (++) | (++) |
| N-(4-methyl-3-(3-methyl-1H-1,2,4-triazol-5-yl)thiophen-2-yl)-2-(quinolin-5-yl)acetamide | (+++) | (+++) | (++) |
| N-(4-methyl-3-(1H-1,2,4-triazol-5-yl)thiophen-2-yl)-2-(quinoxalin-5-yl)acetamide | (++) | (++) | (++) |
| N-(4-methyl-3-(3-methyl-1H-1,2,4-triazol-5-yl)thiophen-2-yl)-2-(quinoxalin-5-yl)acetamide | (++) | (++) | (++) |

TABLE 1-continued

InVitro Biological Activities

| Compound Name | JNK3 IC$_{50}$ (μM) | JNK1 IC$_{50}$ (μM) | JNK2 IC$_{50}$ (μM) |
|---|---|---|---|
| N-(4-methyl-3-(1H-1,2,4-triazol-5-yl)thiophen-2-yl)-2-(4-(3-(piperidin-1-yl)propoxy)phenyl)acetamide | (++) | (++) | (++) |
| N-(4-methyl-3-(3-methyl-1H-1,2,4-triazol-5-yl)thiophen-2-yl)-2-(4-(3-(piperidin-1-yl)propoxy)phenyl)acetamide | (++) | (++) | (++) |
| 2-(4-(2-(1H-imidazol-1-yl)ethoxy)phenyl)-N-(4-methyl-3-(1H-1,2,4-triazol-5-yl)thiophen-2-yl)acetamide | (++) | (++) | (++) |
| N-(4-bromo-3-(1H-1,2,4-triazol-5-yl)thiophen-2-yl)-2-(isoquinolin-5-yl)acetamide | (+++) | (+++) | (+++) |
| N-(4-bromo-3-(1H-1,2,4-triazol-5-yl)thiophen-2-yl)-2-(quinolin-5-yl)acetamide | (+++) | (+++) | (+++) |
| N-(4-bromo-3-(1H-1,2,4-triazol-5-yl)thiophen-2-yl)-2-(2-oxo-3,4-dihydroquinolin-1(2H)-yl)acetamide | (+++) | (+++) | (+++) |
| N-(4-cyano-3-(1H-1,2,4-triazol-5-yl)thiophen-2-yl)-2-(isoquinolin-5-yl)acetamide | (+++) | (+++) | (+++) |
| N-(4-cyano-3-(1H-1,2,4-triazol-5-yl)thiophen-2-yl)-2-(2-oxo-3,4-dihydroquinolin-1(2H)-yl)acetamide | (+++) | (+++) | (+++) |
| N-(2-(3-methyl-1H-1,2,4-triazol-5-yl)thiophen-3-yl)-2-(4-(2-oxopyrrolidin-1-yl)phenyl)acetamide | (++) | (++) | (++) |
| N-(4-methyl-3-(5-methyl-4H-1,2,4-triazol-3-yl)thiophen-2-yl)-2-(4-(pyridin-4-yl)phenyl)acetamide | (++) | (++) | (++) |
| N-(4-cyano-3-(4H-1,2,4-triazol-3-yl)thiophen-2-yl)-2-(quinolin-5-yl)acetamide | (+++) | (+++) | (+++) |
| N-(4-bromo-3-(1H-1,2,4-triazol-5-yl)thiophen-2-yl)-2-(2-oxo-7-(trifluoromethyl)quinolin-1(2H)-yl)acetamide | (+++) | (+++) | (+++) |
| N-(4-bromo-3-(1H-1,2,4-triazol-5-yl)thiophen-2-yl)-2-(6-fluoro-2-oxo-3,4-dihydroquinolin-1(2H)-yl)acetamide | (+++) | (+++) | (+++) |
| N-(4-bromo-3-(1H-1,2,4-triazol-5-yl)thiophen-2-yl)-2-(7-fluoro-2-oxoquinolin-1(2H)-yl)acetamide | (+++) | (+++) | (+++) |
| N-(4-bromo-3-(1H-1,2,4-triazol-5-yl)thiophen-2-yl)-2-(7-chloro-2-oxo-3,4-dihydroquinolin-1(2H)-yl)acetamide | (+++) | (+++) | (+++) |
| N-(4-bromo-3-(1H-1,2,4-triazol-5-yl)thiophen-2-yl)-2-(6,7-difluoro-2-oxoquinolin-1(2H)-yl)acetamide | (+++) | (+++) | (+++) |
| N-(4-bromo-3-(1H-1,2,4-triazol-5-yl)thiophen-2-yl)-2-(2-oxo-6-(trifluoromethyl)quinolin-1(2H)-yl)acetamide | (+++) | (+++) | (+++) |
| N-(4-bromo-3-(1H-1,2,4-triazol-5-yl)thiophen-2-yl)-2-(6-fluoro-2-oxoquinolin-1(2H)-yl)acetamide | (+++) | (+++) | (+++) |
| 2-(isoquinolin-5-yl)-N-(2-(4-methylthiazol-2-yl)thiophen-3-yl)acetamide | (++) | (++) | (++) |
| 2-(isoquinolin-5-yl)-N-(2-(thiazol-4-yl)thiophen-3-yl)acetamide | (++) | (++) | (++) |
| 2-(2-oxo-3,4-dihydro-1,6-naphthyridin-1(2H)-yl)-N-(2-(thiazol-4-yl)thiophen-3-yl)acetamide | (++) | (++) | (++) |
| 2-(2-oxo-3,4-dihydroquinolin-1(2H)-yl)-N-(2-(thiazol-4-yl)thiophen-3-yl)acetamide | (++) | (++) | (++) |
| 2-(isoquinolin-5-yl)-N-(2-(2-methoxythiazol-4-yl)thiophen-3-yl)acetamide | (++) | (++) | (+) |
| N-(2-(2-chlorothiazol-4-yl)thiophen-3-yl)-2-(isoquinolin-5-yl)acetamide | (++) | (++) | (+) |
| 2-(isoquinolin-5-yl)-N-(2-(thiazol-2-yl)thiophen-3-yl)acetamide | (++) | (++) | (++) |
| 2-(isoquinolin-5-yl)-N-(2-(5-methylthiazol-2-yl)thiophen-3-yl)acetamide | (++) | (++) | (++) |
| 2-(4-(3-(piperidin-1-yl)propoxy)phenyl)-N-(2-(thiazol-4-yl)thiophen-3-yl)acetamide | (++) | (++) | (++) |
| N-(3-(benzo[d]thiazol-2-yl)-4-methylthiophen-2-yl)-2-(isoquinolin-5-yl)acetamide | (++) | (++) | (+) |
| 2-(4-methoxyphenyl)-N-(2-(oxazol-2-yl)thiophen-3-yl)acetamide | (++) | (++) | (+) |
| 2-(isoquinolin-5-yl)-N-(2-(oxazol-2-yl)thiophen-3-yl)acetamide | (++) | (++) | (++) |
| 2-(4-methoxyphenyl)-N-(3-(5-methyl-1,2,4-oxadiazol-3-yl)thiophen-2-yl)acetamide | (++) | (++) | (++) |
| N-(2-(1,3,4-oxadiazol-2-yl)thiophen-3-yl)-2-(naphthalen-1-yl)acetamide | (++) | (++) | (+) |
| 2-(4-methoxyphenyl)-N-(2-(5-methyl-1,3,4-oxadiazol-2-yl)thiophen-3-yl)acetamide | (++) | (++) | (−) |
| N-(2-(5-isopropyl-1,3,4-oxadiazol-2-yl)thiophen-3-yl)-2-(4-methoxyphenyl)acetamide | (+) | (+) | (−) |
| N-(2-(5-methyl-1,3,4-oxadiazol-2-yl)thiophen-3-yl)-2-(naphthalen-1-yl)acetamide | (++) | (++) | (+) |
| N-(4-methyl-3-(3-methyl-1,2,4-oxadiazol-5-yl)thiophen-2-yl)-2-(naphthalen-1-yl)acetamide | (++) | (++) | (++) |

TABLE 1-continued

InVitro Biological Activities

| Compound Name | JNK3 IC$_{50}$ (µM) | JNK1 IC$_{50}$ (µM) | JNK2 IC$_{50}$ (µM) |
|---|---|---|---|
| N-(4-methyl-3-(3-methyl-1,2,4-oxadiazol-5-yl)thiophen-2-yl)-2-(4-(pyridin-4-yl)phenyl)acetamide | (++) | (++) | (++) |
| N-(2-(3-methyl-1,2,4-oxadiazol-5-yl)thiophen-3-yl)-2-(naphthalen-1-yl)acetamide | (++) | (++) | (−) |
| N-(4-(1H-1,2,4-triazol-5-yl)thiazol-5-yl)-2-(isoquinolin-5-yl)acetamide | (++) | (++) | (++) |
| 2-(isoquinolin-5-yl)-N-(4-(1-methyl-1H-1,2,4-triazol-5-yl)thiazol-5-yl)acetamide | (++) | (++) | (++) |
| 2-(2-pyridyl)-3-(1-naphthylacetylamino)thiophene | (++) | | |
| N-(2-(1H-pyrazol-1-yl)thiophen-3-yl)-2-(4-methoxyphenyl)-acetamide | (+) | (+) | (−) |
| 2-(4-methoxyphenyl)-N-(2-(4-methyl-1H-pyrazol-1-yl)thiophen-3-yl)acetamide | (+) | (+) | (+) |
| N-(2-(1H-pyrazol-3-yl)thiophen-3-yl)-2-(naphthalen-1-yl)acetamide | (++) | (++) | (−) |
| N-(2-(1-methyl-1H-pyrazol-3-yl)thiophen-3-yl)-2-(naphthalen-1-yl)acetamide | (+) | (+) | (−) |
| N-(2-(5-methyl-1H-pyrazol-3-yl)thiophen-3-yl)-2-(naphthalen-1-yl)acetamide | (++) | (++) | (−) |
| N-(3-(2H-tetrazol-5-yl)thiophen-2-yl)-2-(4-methoxyphenyl)-acetamide | (++) | (++) | (−) |
| 2-(4-methoxyphenyl)-N-(3-(2-methyl-2H-tetrazol-5-yl)thiophen-2-yl)acetamide | (++) | (++) | (+) |
| N-(3-(2-(methoxymethyl)-2H-tetrazol-5-yl)thiophen-2-yl)-2-(4-methoxyphenyl)acetamide | (−) | (−) | (−) |
| N-(3-(1-(methoxymethyl)-1H-tetrazol-5-yl)thiophen-2-yl)-2-(4-methoxyphenyl)acetamide | (++) | (++) | (−) |
| N-(2-(1-methyl-1H-imidazol-2-yl)thiophen-3-yl)-2-(naphthalen-1-yl)acetamide | (+) | (+) | (−) |
| 2-(4-methoxyphenyl)-N-(2-(1-methyl-1H-imidazol-4-yl)thiophen-3-yl)acetamide | (+) | (+) | (−) |
| N-(2-(1H-imidazol-4-yl)thiophen-3-yl)-2-(4-methoxyphenyl)-acetamide | (+) | (+) | (−) |
| N-(2-(1H-imidazol-4-yl)thiophen-3-yl)-2-(2-oxo-3,4-dihydroquinolin-1(2H)-yl)acetamide | (++) | (++) | (+) |
| 2-(4-methoxyphenyl)-N-(2-(2-methyl-1H-imidazol-4-yl)thiophen-3-yl)acetamide | (+) | (+) | (−) |
| N-(2-(2-methyl-1H-imidazol-4-yl)thiophen-3-yl)-2-(2-oxo-3,4-dihydroquinolin-1(2H)-yl)acetamide | (+) | (+) | (−) |
| N-(2-(1H-imidazol-1-yl)thiophen-3-yl)2-(naphthalen-1-yl)acetamide | (++) | (+) | (−) |
| 2-(4-methoxyphenyl)-N-(2-(4-methyl-1H-imidazol-1-yl)thiophen-3-yl)acetamide | (−) | (−) | (−) |
| 2-(4-methoxyphenyl)-N-(2-(pyrazin-2-yl)thiophen-3-yl)acetamide | (++) | (++) | (++) |
| 2-(isoquinolin-5-yl)-N-(4-(pyrazin-2-yl)thiazol-5-yl)acetamide | (++) | (++) | (++) |
| N-(4,4'-bithiazol-5-yl)-2-(isoquinolin-5-yl)acetamide | (+++) | (+++) | (++) |
| 2-(4-methoxyphenyl)-N-(2-(2-oxooxazolidin-3-yl)thiophen-3-yl)acetamide | (+) | (−) | (−) |
| 2-(7-bromo-2-oxo-3,4-dihydroquinolin-1(2H)-yl)-N-(4-bromo-3-(1H-1,2,4-triazol-5-yl)thiophen-2-yl)acetamide | (++) | (++) | (++) |
| N-(4-bromo-3-(4H-1,2,4-triazol-3-yl)thiophen-2-yl)-2-(quinolin-4-yl)acetamide | (+++) | (+++) | (++) |
| N-(4-bromo-3-(1H-1,2,4-triazol-5-yl)thiophen-2-yl)-2-(2-oxo-6-(trifluoromethyl)quinolin-1(2H)-yl)acetamide | (+++) | (+++) | (+++) |
| N-(4-bromo-3-(1H-1,2,4-triazol-5-yl)thiophen-2-yl)-2-(8-fluoroisoquinolin-5-yl)acetamide | (+++) | (+++) | (+++) |
| N-(4-bromo-3-(1H-1,2,4-triazol-5-yl)thiophen-2-yl)-2-(2-oxo-1,6-naphthyridin-1(2H)-yl)acetamide | (+++) | (+++) | (+++) |
| N-(4-bromo-3-(1H-1,2,4-triazol-5-yl)thiophen-2-yl)-2-(8-fluoroquinolin-5-yl)acetamide | (+++) | (+++) | (++) |
| N-(4-bromo-3-(4H-1,2,4-triazol-3-yl)thiophen-2-yl)-2-(7-(trifluoromethyl)quinolin-5-yl)acetamide | (++) | (++) | (++) |
| N-(4-bromo-3-(4H-1,2,4-triazol-3-yl)thiophen-2-yl)-2-(5-(trifluoromethyl)quinolin-7-yl)acetamide | (++) | (++) | (++) |
| N-(4-bromo-3-(1H-1,2,4-triazol-5-yl)thiophen-2-yl)-2-(2-oxo-1,5-naphthyridin-1(2H)-yl)acetamide | (+++) | (+++) | (+++) |
| N-(4-bromo-3-(1H-1,2,4-triazol-5-yl)thiophen-2-yl)-2-(2-oxo-3,4-dihydro-1,6-naphthyridin-1(2H)-yl)acetamide | (+++) | (+++) | (+++) |
| N-(4-bromo-3-(1H-1,2,4-triazol-5-yl)thiophen-2-yl)-2-(2-oxo-3,4-dihydro-1,5-naphthyridin-1(2H)-yl)acetamide | (+++) | (+++) | (+++) |

TABLE 1-continued

InVitro Biological Activities

| Compound Name | JNK3 IC$_{50}$ (μM) | JNK1 IC$_{50}$ (μM) | JNK2 IC$_{50}$ (μM) |
|---|---|---|---|
| N-(4-bromo-3-(1H-1,2,4-triazol-5-yl)thiophen-2-yl)-2-(6-chloro-2-oxoquinolin-1(2H)-yl)acetamide | (+++) | (+++) | (+++) |
| N-(4-bromo-3-(1H-1,2,4-triazol-5-yl)thiophen-2-yl)-2-(5-fluoro-2-oxoquinolin-1(2H)-yl)acetamide | (+++) | (+++) | (+++) |
| N-(4-bromo-3-(1H-1,2,4-triazol-3-yl)thiophen-2-yl)-2-(3-fluoroquinolin-8-yl)acetamide | (++) | (+++) | (++) |
| N-(4-bromo-3-(1H-1,2,4-triazol-5-yl)thiophen-2-yl)-2-(2-oxo-6-(trifluoromethoxy)quinolin-1(2H)-yl)acetamide | (+++) | (+++) | (+++) |
| N-(4-bromo-3-(4H-1,2,4-triazol-3-yl)thiophen-2-yl)-2-(isoquinolin-4-yl)acetamide | (+++) | (+++) | (++) |
| N-(5-chloro-3-(1H-1,2,4-triazol-5-yl)thiophen-2-yl)-2-(2-oxo-6-(trifluoromethyl)quinolin-1(2H)-yl)acetamide | (++) | (+++) | (++) |
| N-(4-bromo-3-(1H-1,2,4-triazol-3-yl)thiophen-2-yl)-2-(3-fluoroquinolin-5-yl)acetamide | (+++) | (+++) | (+++) |
| N-(4-bromo-3-(1H-1,2,4-triazol-5-yl)thiophen-2-yl)-2-(2-oxo-7-(trifluoromethoxy)quinolin-1(2H)-yl)acetamide | (+++) | (+++) | (+++) |
| N-(4-bromo-3-(1H-1,2,4-triazol-5-yl)thiophen:2-yl)-2-(7-cyano-2-oxoquinolin-1(2H)-yl)acetamide | (+++) | (+++) | (+++) |
| N-(4-bromo-3-(1H-1,2,4-triazol-5-yl)thiophen-2-yl)-2-(isoquinolin-8-yl)acetamide | (+++) | (+++) | (++) |
| N-(4-bromo-3-(1H-1,2,4-triazol-5-yl)thiophen-2-yl)-2-(6-cyano-2-oxoquinolin-1(2H)-yl)acetamide | (+++) | (+++) | (+++) |
| N-(4-bromo-3-(1H-1,2,4-triazol-5-yl)thiophen-2-yl)-2-(quinolin-8-yl)acetamide | (++) |  | (++) |
| N-(4-bromo-3-(1H-1,2,4-triazol-5-yl)thiophen-2-yl)-2-(2-oxo-5-(trifluoromethyl)quinolin-1(2H)-yl)acetamide | (+++) | (+++) | (++) |
| N-(4-bromo-3-(1H-1,2,4-triazol-5-yl)thiophen-2-yl)-2-(2-oxo-6-(trifluoromethyl)-3,4-dihydroquinolin-1(2H)-yl)acetamide | (+++) | (+++) | (+++) |
| N-(4-cyano-3-(1-methyl-1H-1,2,4-triazol-3-yl)thiophen-2-yl)-2-(quinolin-5-yl)acetamide | (+++) | (+++) | (+++) |
| N-(4-bromo-3-(1H-1,2,4-triazol-3-yl)thiophen-2-yl)-2-(2-(trifluoromethyl)quinolin-7-yl)acetamide | (++) | (++) | (++) |
| N-(4-bromo-3-(1H-1,2,4-triazol-5-yl)thiophen-2-yl)-2-(7-fluoroquinolin-5-yl)acetamide | (+++) | (+++) | (++) |
| N-(4-bromo-3-(1H-1,2,4-triazol-3-yl)thiophen-2-yl)-2-(3-(trifluoromethyl)quinolin-5-yl)acetamide | (+++) | (+++) | (++) |
| N-(4-bromo-3-(1H-1,2,4-triazol-5-yl)thiophen-2-yl)-2-(6-fluoroquinolin-5-yl)acetamide | (+++) | (+++) | (+++) |
| N-(4-bromo-3-(1H-1,2,4-triazol-5-yl)thiophen-2-yl)-2-(6-fluoroquinolin-7-yl)acetamide | (++) | (+++) | (++) |
| N-(4-bromo-3-(1H-1,2,4-triazol-5-yl)thiophen-2-yl)-2-(6-ethynyl-2-oxoquinolin-1(2H)-yl)acetamide | (+++) | (+++) | (+++) |
| N-(4-bromo-3-(1H-1,2,4-triazol-5-yl)thiophen-2-yl)-2-(2-oxo-7-(trifluoromethyl)-1,6-naphthyridin-1(2H)-yl)acetamide | (+++) | (+++) | (+++) |
| N-(4-bromo-3-(1H-1,2,4-triazol-5-yl)thiophen-2-yl)-2-(5-oxopyrazolo[1,5-a]pyrimidin-4(5H)-yl)acetamide | (+++) | (+++) | (+++) |
| N-(4-bromo-3-(1H-1,2,4-triazol-3-yl)thiophen-2-yl)-2-(3-(trifluoromethyl)quinolin-8-yl)acetamide | (++) | (++) | (++) |
| N-(4-bromo-3-(1H-1,2,4-triazol-5-yl)thiophen-2-yl)-2-(6-methylimidazo[2,1-b]thiazol-3-yl)acetamide | (++) | (+++) | (++) |
| 2-(2-oxo-6-(trifluoromethyl)quinolin-1(2H)-yl)-N-(2-(thiazol-4-yl)thiophen-3-yl)acetamide | (+++) | (+++) | (++) |
| N-(4-cyano-3-(pyrazin-2-yl)thiophen-2-yl)-2-(quinolin-5-yl)acetamide | (+++) | (+++) | (++) |
| 2-(2-oxo-1,6-naphthyridin-1(2H)-yl)-N-(2-(thiazol-4-yl)thiophen-3-yl)acetamide | (++) | (+++) | (++) |
| N-(4-bromo-3-(4H-1,2,4-triazol-3-yl)thiophen-2-yl)-2-(3,3-difluoro-2-oxoindolin-1-yl)acetamide | (++) | (+++) | (++) |
| 2-(benzo[d]thiazol-7-yl)-N-(4-bromo-3-(1H-1,2,4-triazol-5-yl)thiophen-2-yl)acetamide | (+++) | (+++) | (++) |
| N-(4-chloro-3-(1H-1,2,4-triazol-5-yl)thiophen-2-yl)-2-(2-oxo-6-(trifluoromethyl)quinolin-1(2H)-yl)acetamide | (+++) | (+++) | (+++) |
| N-(4-cyano-3-(oxazol-2-yl)thiophen-2-yl)-2-(2-oxo-6-(trifluoromethyl)quinolin-1(2H)-yl)acetamide | (+++) | (+++) | (+++) |
| N-(4-bromo-3-(1H-1,2,4-triazol-5-yl)thiophen-2-yl)-2-(2-oxo-6-(trifluoromethyl)-1,5-naphthyridin-1(2H)-yl)acetamide | (+++) | (+++) | (+++) |
| N-(3-(1,2,4-oxadiazol-3-yl)thiophen-2-yl)-2-(6,7-difluoro-2-oxoquinolin-1(2H)-yl)acetamide | (++) | (+++) | (++) |
| N-(4-cyano-3-(thiazol-2-yl)thiophen-2-yl)-2-(2-oxo-6-(trifluoromethyl)quinolin-1(2H)-yl)acetamide | (+++) | (+++) | (+++) |

TABLE 1-continued

InVitro Biological Activities

| Compound Name | JNK3 IC$_{50}$ (μM) | JNK1 IC$_{50}$ (μM) | JNK2 IC$_{50}$ (μM) |
|---|---|---|---|
| N-(4-bromo-3-(1H-1,2,4-triazol-5-yl)thiophen-2-yl)-2-(5-oxo-2-(trifluoromethyl)pyrazolo[1,5-a]pyrimidin-4(5H)-yl)acetamide | (+++) | (+++) | (+++) |
| N-(4-cyano-3-(thiazol-4-yl)thiophen-2-yl)-2-(2-oxo-6-(trifluoromethyl)quinolin-1(2H)-yl)acetamide | (+++) | (+++) | (+++) |
| N-(4-bromo-3-(1H-1,2,4-triazol-5-yl)thiophen-2-yl)-2-(imidazo[1,2-a]pyridin-5-yl)acetamide | (++) | (+++) | (++) |
| N-(4-bromo-3-(1H-1,2,4-triazol-5-yl)thiophen-2-yl)-2-(7-fluoro-2-oxo-6-(trifluoromethyl)quinolin-1(2H)-yl)acetamide | (+++) | (+++) | (+++) |
| N-(4-bromo-3-(1-methyl-1H-1,2,4-triazol-3-yl)thiophen-2-yl)-2-(2-oxo-3,4-dihydro-1,5-naphthyridin-1(2H)-yl)acetamide | (+++) | (+++) | (+++) |
| N-(4-cyano-3-(thiazol-5-yl)thiophen-2-yl)-2-(2-oxo-6-(trifluoromethyl)quinolin-1(2H)-yl)acetamide | (++) | (++) | (++) |
| N-(4-cyano-3-(1H-1,2,3-triazol-1-yl)thiophen-2-yl)-2-(2-oxo-6-(trifluoromethyl)quinolin-1(2H)-yl)acetamide | (++) | (++) | (++) |
| N-(3-(1H-benzo[d][1,2,3]triazol-1-yl)-4-cyanothiophen-2-yl)-2-(2-oxo-6-(trifluoromethyl)quinolin-1(2H)-yl)acetamide | (++) | (++) | (++) |
| N-(4-bromo-3-(1H-1,2,4-triazol-5-yl)thiophen-2-yl)-2-(6-fluoroisoquinolin-5-yl)acetamide; and N-(4-bromo-3-(1H-1,2,4-triazol-5-yl)thiophen-2-yl)-2-(6-fluoroisoquinolin-7-yl)acetamide | (+++) | (+++) | (+++) |
| N-(4-cyano-3-(2H-1,2,3-triazol-2-yl)thiophen-2-yl)-2-(2-oxo-6-(trifluoromethyl)quinolin-1(2H)-yl)acetamide | (+++) | (+++) | (+++) |
| N-(4-chloro-3-(1H-1,2,4-triazol-3-yl)thiophen-2-yl)-2-(2-oxo-3,4-dihydro-1,5-naphthyridin-1(2H)-yl)acetamide | (+++) | (+++) | (+++) |
| N-(4-cyano-3-(thiazol-2-yl)thiophen-2-yl)-2-(2-oxo-3,4-dihydro-1,5-naphthyridin-1(2H)-yl)acetamide | (+++) | (+++) | (+++) |
| N-(4-chloro-3-(1-methyl-1H-1,2,4-triazol-3-yl)thiophen-2-yl)-2-(2-oxo-3,4-dihydro-1,5-naphthyridin-1(2H)-yl)acetamide | (+++) | (+++) | (+++) |
| N-(4-chloro-3-(1H-1,2,4-triazol-5-yl)thiophen-2-yl)-2-(5-oxopyrazolo[1,5-a]pyrimidin-4(5H)-yl)acetamide | (+++) | (+++) | (+++) |
| N-(4-bromo-3-(oxazol-2-yl)thiophen-2-yl)-2-(2-oxo-3,4-dihydro-1,5-naphthyridin-1(2H)-yl)acetamide | (+++) | (+++) | (+++) |
| N-(4-bromo-3-(thiazol-2-yl)thiophen-2-yl)-2-(2-oxo-3,4-dihydro-1,5-naphthyridin-1(2H)-yl)acetamide | (+++) | (+++) | (++) |
| N-(4-chloro-3-(thiazol-2-yl)thiophen-2-yl)-2-(2-oxo-3,4-dihydro-1,5-naphthyridin-1(2H)-yl)acetamide | (+++) | (+++) | (+++) |
| N-(3-(benzo[d]thiazol-2-yl)-4-cyanothiophen-2-yl)-2-(2-oxo-3,4-dihydro-1,5-naphthyridin-1(2H)-yl)acetamide | (++) | (++) | (++) |
| N-(4-chloro-3-(3-methyl-1H-1,2,4-triazol-5-yl)thiophen-2-yl)-2-(2-oxo-3,4-dihydro-1,5-naphthyridin-1(2H)-yl)acetamide | (+++) | (+++) | (+++) |
| N-(4-chloro-3-(1-(3-(dimethylamino)propyl)-1H-1,2,4-triazol-3-yl)thiophen-2-yl)-2-(2-oxo-6-(trifluoromethyl)quinolin-1(2H)-yl)acetamide | (+++) | (+++) | (+++) |
| N-(4-chloro-3-(1-(3-(4-methylpiperazin-1-yl)propyl)-1H-1,2,4-triazol-3-yl)thiophen-2-yl)-2-(2-oxo-6-(trifluoromethyl)quinolin-1(2H)-yl)acetamide | (+++) | (+++) | (++) |
| N-(4-chloro-3-(3-ethyl-1H-1,2,4-triazol-5-yl)thiophen-2-yl)-2-(2-oxo-3,4-dihydro-1,5-naphthyridin-1(2H)-yl)acetamide | (+++) | (+++) | (++) |
| N-(4-chloro-3-(1-(2-(dimethylamino)ethyl)-1H-1,2,4-triazol-3-yl)thiophen-2-yl)-2-(2-oxo-6-(trifluoromethyl)quinolin-1(2H)-yl)acetamide | (+++) | (+++) | (+++) |
| N-(4-chloro-3-(1H-1,2,4-triazol-3-yl)thiophen-2-yl)-N-(2-(dimethylamino)ethyl)-2-(2-oxo-6-(trifluoromethyl)quinolin-1(2H)-yl)acetamide | (++) | (++) | (++) |
| N-(4-cyano-3-(1H-1,2,4-triazol-3-yl)thiophen-2-yl)-2-(2-oxo-3,4-dihydro-1,5-naphthyridin-1(2H)-yl)acetamide | (+++) | (+++) | (+++) |
| N-(4-chloro-3-(1-methyl-1H-1,2,4-triazol-3-yl)thiophen-2-yl)-2-(5-oxopyrazolo[1,5-a]pyrimidin-4(5H)-yl)acetamide | (+++) | (+++) | (+++) |
| N-(4-chloro-3-(1-(3-morpholinopropyl)-1H-1,2,4-triazol-3-yl)thiophen-2-yl)-2-(2-oxo-6-(trifluoromethyl)quinolin-1(2H)-yl)acetamide | (+++) | (+++) | (+++) |

TABLE 1-continued

InVitro Biological Activities

| Compound Name | JNK3 IC$_{50}$ (μM) | JNK1 IC$_{50}$ (μM) | JNK2 IC$_{50}$ (μM) |
|---|---|---|---|
| N-(4-chloro-3-(1H-1,2,4-triazol-3-yl)thiophen-2-yl)-2-(2-oxo-6-(trifluoromethyl)quinolin-1(2H)-yl)-N-(3-(pyrrolidin-1-yl)propyl)acetamide | (++) | (++) | (++) |
| N-(4-chloro-3-(1-(3-(pyrrolidin-1-yl)propyl)-1H-1,2,4-triazol-3-yl)thiophen-2-yl)-2-(2-oxo-6-(trifluoromethyl)quinolin-1(2H)-yl)acetamide | (+++) | (+++) | (+++) |
| N-(4-chloro-3-(1-methyl-1H-1,2,4-triazol-3-yl)thiophen-2-yl)-2-(2-oxo-6-(trifluoromethyl)-1,5-naphthyridin-1(2H)-yl)acetamide | (+++) | (+++) | (+++) |
| N-(4-chloro-3-(1H-1,2,4-triazol-5-yl)thiophen-2-yl)-2-(8-(trifluoromethyl)quinolin-5-yl)acetamide | (++) | (+++) | (++) |
| N-(4-bromo-3-(2H-1,2,3-triazol-2-yl)thiophen-2-yl)-2-(2-oxo-6-(trifluoromethyl)quinolin-1(2H)-yl)acetamide | (+++) | (+++) | (++) |
| N-(4-chloro-3-(1H-1,2,4-triazol-5-yl)thiophen-2-yl)-2-(2-oxo-6-(trifluoromethyl)-1,5-naphthyridin-1(2H)-yl)acetamide | (+++) | (+++) | (+++) |
| N-(4-chloro-3-(3-isopropyl-1H-1,2,4-triazol-5-yl)thiophen-2-yl)-2-(2-oxo-3,4-dihydro-1,5-naphthyridin-1(2H)-yl)acetamide | (++) | (+++) | (++) |
| 2-(6-bromo-2-oxoquinolin-1(2H)-yl)-N-(4-bromo-3-(1H-1,2,4-triazol-3-yl)thiophen-2-yl)acetamide | (+++) | (+++) | (+++) |
| N-(4-cyano-3-(1-methyl-1H-1,2,4-triazol-3-yl)thiophen-2-yl)-2-(2-oxo-3,4-dihydro-1,5-naphthyridin-1(2H)-yl)acetamide | (+++) | (+++) | (+++) |
| 2-(6-bromo-2-oxoquinolin-1(2H)-yl)-N-(4-chloro-3-(1H-1,2,4-triazol-3-yl)thiophen-2-yl)acetamide | (+++) | (+++) | (+++) |
| N-(4-chloro-3-(1H-1,2,4-triazol-3-yl)thiophen-2-yl)-2-(6-cyano-2-oxoquinolin-1(2H)-yl)acetamide | (+++) | (+++) | (+++) |
| N-(4-chloro-3-(1H-1,2,4-triazol-5-yl)thiophen-2-yl)-2-(5-oxo-2-(trifluoromethyl)pyrazolo[1,5-a]pyrimidin-4(5H)-yl)acetamide | (+++) | (+++) | (+++) |
| N-(4-chloro-3-(1H-1,2,4-triazol-3-yl)thiophen-2-yl)-2-(2-oxo-7-(trifluoromethyl)-1,6-naphthyridin-1(2H)-yl)acetamide | (+++) | (+++) | (+++) |
| N-(4-chloro-3-(1-methyl-1H-1,2,4-triazol-3-yl)thiophen-2-yl)-2-(5-oxo-2-(trifluoromethyl)pyrazolo[1,5-a]pyrimidin-4(5H)-yl)acetamide | (+++) | (+++) | (+++) |
| N-(4-chloro-3-(1-methyl-1H-1,2,4-triazol-3-yl)thiophen-2-yl)-2-(2-oxo-7-(trifluoromethyl)-1,6-naphthyridin-1(2H)-yl)acetamide | (+++) | (+++) | (+++) |

(+++)IC$_{50}$ < 0.1 μM
(++)IC$_{50}$ 0.1 μM-10 μM
(+)IC$_{50}$ > 10 μM
(−)Activity below level of detection in assay used (IC$_{50}$ > 50 μM)

In Vivo Activities

Certain compounds of the present disclosure exhibit in vivo biological activities, such as the inhibition of excitotoxic cell death. An in vivo model, which can be used to assess the potential in vivo beneficial effect of the compounds of the present disclosure is described in Example 15. Excitotoxic cell death can be induced experimentally by the administration of kainic acid. Peripheral injection of kainic acid results in the degeneration of neurons in the hippocampus. Mice lacking the Jnk3 gene are resistant to kainic acid-induced upregulation of phosphorylated c-jun (p-cjun) and hippocampal neuronal apotosis (see e.g., Yang D. D. et al., Nature 1997, 389: 865-870). Phosphorylated c-jun in wildtype mice is upregulated after kainic acid administration and demonstrate that this upregulation is inhibited by certain compounds of the present disclosure.

Certain compounds of the present disclosure are characterized by the following in vivo biological activities involving the concentration of p-cjun in the brain tissue (e.g., hippocampus) of a test animal (e.g., rodent, such as mice, rat, rabbit and the like) after treatment of the test animal with an excitatory amino acid or analog thereof (e.g., kainic acid). In one example, administration of a compound of the present disclosure to a test animal (e.g., at a dose of at least about 100, 200 or 300 mg/kg), results in a reduction of kainic acid-induced p-cjun concentration in the brain tissue of the test animal by at least about 1%, at least about 2%, at least about 3%, at least about 4%, at least about 5%, at least about 6%, at least about 7%, at least about 8%, at least about 9% or at least about 10% relative to the p-cjun concentration found in brain tissue of a comparable, untreated (vehicle treated) test animal. In another example, administration of a compound of the present disclosure to a test animal (e.g., at a dose of at least about 100, 200 or 300 mg/kg), results in a reduction of kainic acid-induced p-cjun concentration in the brain tissue of the test animal by at least about 11%, at least about 12%, at least about 13%, at least about 14%, at least about 15%, at least about 16%, at least about 17%, at least about 18%, at least about 19% or at least about 20%, relative to the p-cjun concentration found in brain tissue of a comparable, untreated (vehicle treated) test animal. In yet another example, administration of a compound of the present disclosure to a test animal (e.g., at a dose of at least about 100, 200 or 300 mg/kg), results in a reduction of kainic acid-induced p-cjun concentration in the brain tissue of the test animal by at least about 21%, at least about 22%, at least about 23%, at least about 24%, at least about 25%, at least about 26%, at least about 27%, at least about 28%, at least about 29% or at least about 30% relative to the p-cjun concentration found in brain tissue of a comparable, untreated (vehicle treated) test animal. In a further example, administration of a compound of the present disclosure to a test animal at a dose of at least about (100, 200 or 300 mg/kg), results in a reduction of kainic acid-induced p-cjun concentration in the brain tissue of the test animal by at least about 31%, at least about 32%, at least about 33%, at least about 34%, at least about 35%, at least about 36%, at least about 37%, at least about 38%, at least about 39% or at least about 40% relative to the p-cjun concentration found in brain tissue of a comparable, untreated (vehicle treated) test animal. In yet another example, administration of a compound of the present disclosure to a test animal (e.g., at a dose of at least about 100, 200 or 300 mg/kg), results in a reduction of kainic acid-induced p-cjun concentration in the brain tissue of the test animal by at least about 41%, at least about 42%, at least about 43%, at least about 44%, at least about 45%, at least about 46%, at least about 47%, at least about 48%, at least about 49% or at least about 50% relative to the p-cjun concentration found in brain tissue of a comparable, untreated (vehicle treated) test animal. In yet another example, administration of a compound of the present disclosure to a test animal (e.g., at a dose of at least about 300 mg/kg), results in a reduction of kainic acid-induced p-cjun concentration in the brain tissue of the test animal by at least about 51%, at least about 52%, at least about 53%, at least about 54%, at least about 55%, at least about 56%, at least about 57%, at least about 58%, at least about 59% or at least about 60% relative to the p-cjun concentration found in brain tissue of a comparable, untreated (vehicle treated) test animal.

Synthesis of Compounds

The compounds of the present disclosure can be prepared using methods known in the art of organic synthesis and those described herein (see, e.g., Examples 1 to 13). The starting materials and various intermediates may be obtained from commercial sources, prepared from commercially available compounds, and/or prepared using known synthetic methods. For example, the compounds of the present disclosure, as well as all intermediates, can be synthesized by known processes using either solution or solid phase techniques. Exemplary procedures for preparing compounds of the present disclosure are outlined in the following schemes.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, *Protecting Groups in Organic Synthesis*, Third Edition, Wiley, New York, 1999, and references cited therein.

In one example, the compounds of the present disclosure are prepared using a procedure outlined in Scheme 1a, below:

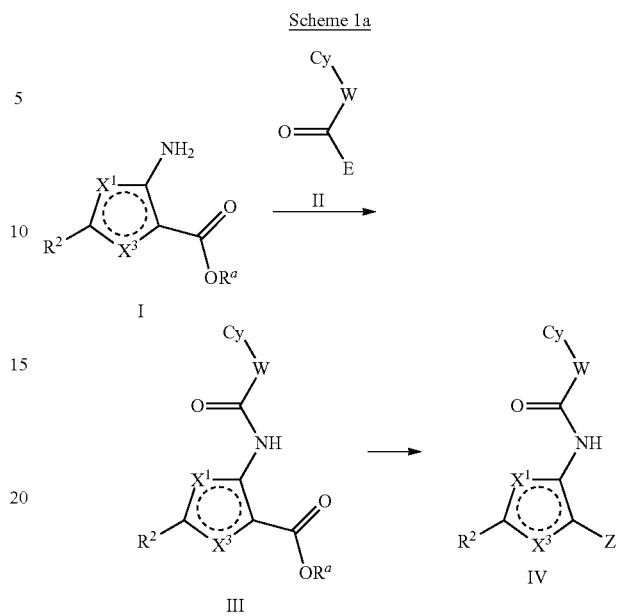

In Scheme 1a, Cy and W are defined as herein above. $X^1$ and $X^3$ are independently chosen from $CR^2$, S and N with the proviso that at least one of $X^1$ and $X^3$ is S. $R^2$ is defined as herein above. $R^a$ is chosen from substituted or unsubstituted alkyl, substituted or unsubstituted cycloalkyl, substituted or unsubstituted heterocycloalkyl, substituted or unsubstituted aryl and substituted or unsubstituted heteroaryl. In one example, $R^a$ in Scheme 1a is $C_1$-$C_4$ alkyl (e.g., methyl or ethyl). The moiety —C(O)E of compound II represents a carboxylic acid group (in which E is OH), an acid chloride (in which E is Cl) or an activated ester, such as a N-hydroxysuccinimide ester (NHS-ester), a carbodiimide, a triazolol and the like. The activated ester is optionally formed in situ from the corresponding acid, in which E is OH. In one example, compound III is formed by contacting compound I and compound II (wherein E is OH) in the presence of a coupling reagent and optionally an organic base, such as an amine (e.g., diisopropylethyl amine, DIPEA). Coupling reagents suitable for amide bond formation are known to those of skill in the art and include dicyclohexylcarbodiimide (DCCI), diisopropylcarbodiimide (DIC), 1-hydroxybenzo-triazole (HOBT), 1-hydroxy-7-azabenzotriazole (HOAt), 6-chloro-1-hydroxybenzotriazole (Cl-HOBT), 1-ethyl-3-(3'-dimethylaminopropyl)carbodiimide (EDC), N-[(1H-benzotriazol-1-yl)(dimethylamino)methylene]-N-methylmethanaminium hexafluorophosphate N-oxide (HBTU), N-[(dimethylamino)-1H-1,2,3-triazolo[4,5-b]pyridine-1-ylmethylene]-N-methylmethanaminium hexafluorophosphate (HATU), benzotriazol-1-yl-N-oxy-tris(pyrrolidino)phosphonium hexafluorophosphate (PyBOP) and combinations thereof. Alternatively, $POCl_3$ and a base (e.g., pyridine) can be used to form an amide bond.

After coupling the ester group of compound III can be converted to a hetero-aromatic group Z. Exemplary groups Z are described herein above. Schemes 2 to 8 outline the formation of various Z groups. A person of skill in the art will appreciate that the conversions shown in Schemes 2 to 8 are exemplary and that compounds, which include other Z groups can be synthesized using known methodologies and methods modified from those presented.

In one example, Z can be covalently linked to the core moiety via an aryl-aryl cross coupling reaction, such as a Suzuki or Stille-type reaction. An exemplary reaction is outlined in Scheme 1b, below.

Scheme 1b

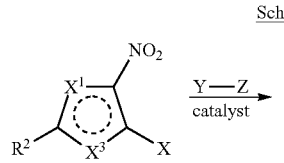

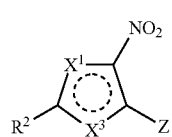

In Scheme 1b, Z, $X^1$, $X^3$ and $R^2$ are as defined as herein above (see, e.g., Scheme 1a). X is halogen (e.g., Cl, Br or I). Y is a leaving group suitable for a cross-coupling reaction. In one example, Y is a leaving group suitable for a Stille-type cross-coupling reaction, e.g., a trialkylstannyl (e.g., tributylstannyl). In another example, Y is a leaving group suitable for a Suzuki-type cross-coupling reaction, e.g., a boronic acid group. It is well within the capabilities of a skilled person to select a suitable catalyst. Typically, the cross-coupling reaction will be palladium-catalyzed. However, other transition metal catalysts can also be used. In one example, the catalyst is a palladium phosphine, such as triphenyl phosphine, $Pd(PPh_3)_4$. In another example, the catalyst is a copper-based catalyst. The reducing agent can be any reagent suitable for the reduction of a nitro group to an amino group. Exemplary reagents include hydrogen in combination with a metal catalyst, such as palladium on carbon (Pd/C); and tin(II) reagents, such as $SnCl_2$.

In Scheme 1b, the nitro analog is first coupled to Z, followed by reduction of the nitro group to an amino group. The resulting amine can then be coupled to a suitable carboxylic acid derivative, e.g., as outlined in Scheme 1a.

In another example, the coupling reaction is performed after the amide has been formed as outlined in Scheme 1c, below.

Scheme 1c

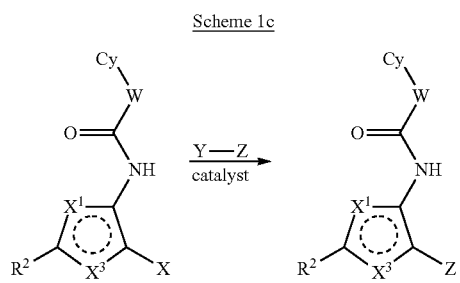

In Scheme 1c, Z, Y, $X^1$, $X^3$, $R^2$, X and the catalyst are defined as herein above (see, e.g., Scheme 1b).

In another example, the compounds of the present disclosure are prepared according to a procedure outlined in Scheme 1d, below:

Scheme 1d

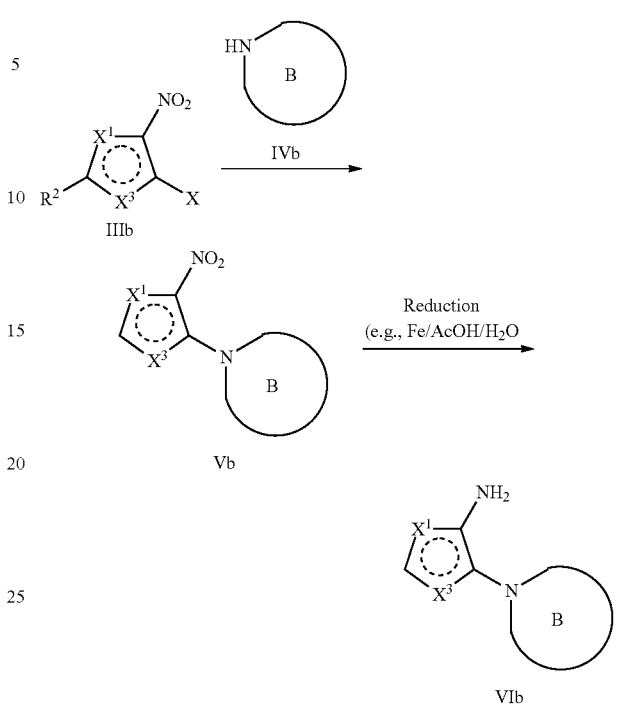

In Scheme 1d, $R^2$, $X^1$ and $X^3$ are defined as herein above and X is a leaving group, such as halogen (e.g., Cl, Br, I), tosylate, mesylate and the like. Ring B represents any heterocyclic or heteroaromatic ring, (e.g., imidazole, pyrazole). Ring B can optionally be part of a larger ring system (e.g., indolyl). In Scheme 1d, compound IIIb is reacted with compound IVb, e.g., by heating the components in a suitable solvent, such as acetonitrile, to afford compound Vb. The nitro group of Compound Vb can then be reduced to an amino group, e.g., using a metal reducing agent, such as iron (Fe) or zinc to afford compound VIb. Compound VIb can be further converted to a compound of the present disclosure by means of coupling with a suitable carboxylic acid or acid derivative, similarly to the reaction outlined in Scheme 1a.

Triazoles

In another example, the compounds of the present disclosure include a triazole moiety as the ring Z and are prepared using a procedure outlined in Schemes 2a or 2b, below.

Scheme 2a

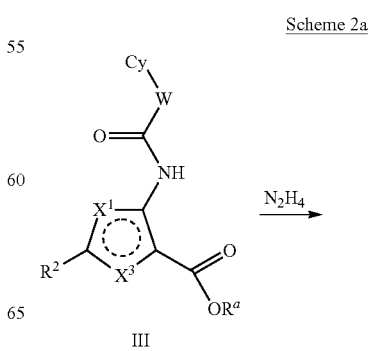

-continued

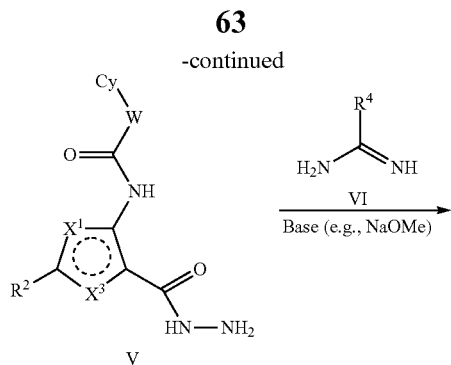

V

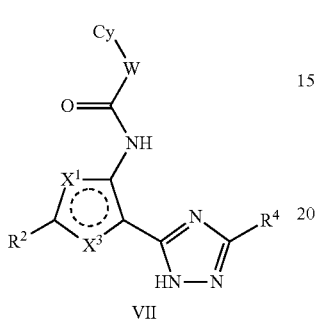

VII

In Scheme 2a, the ester III is first converted to the hydrazide V (e.g., using a hydrazine), which is further reacted with an imidamide (e.g., acetimidamide or propionimidamide) in the presence of a base in order to give the triazole VII. In Scheme 2a, $X^1$, $X^3$, $R^2$, $R^4$, Cy and W are defined as herein above. In one example, $R^4$ is chosen from substituted or unsubstituted alkyl, substituted or unsubstituted aryl, substituted or unsubstituted heteroaryl and amino (e.g., alkyl-amino). When $R^4$ is amino, the imidamide reagent VI of Scheme 2a can be a guanidine. In Scheme 2a, $X^1$ and $X^3$ are independently chosen from $CR^2$, S and N, with the proviso that at least one of $X^1$ and $X^3$ is S. $R^2$ is defined as herein above.

Alternatively, the carboxylic acid IIIa can be converted to a primary amide, which is then reacted with hydrazine to form a triazole, e.g., as outlined in Scheme 2b, below:

Scheme 2b

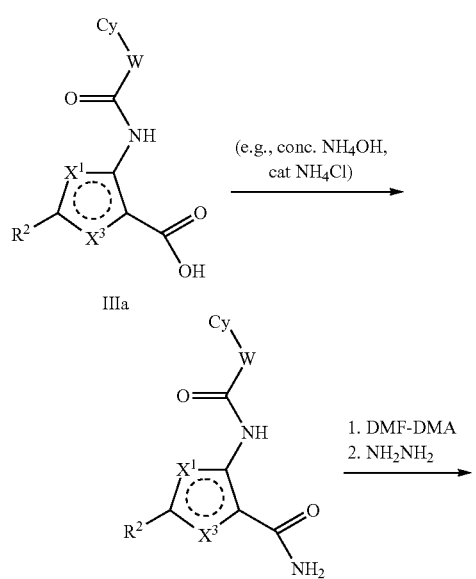

In Scheme 2b, $X^1$, $X^3$, $R^2$, Cy and W are defined as herein above.

Oxadiazole

In another example, the compounds of the present disclosure include an oxadiazole moiety as the ring Z. Such compounds can be prepared using procedures outlined in Schemes 3a to 3e, below.

Scheme 3a

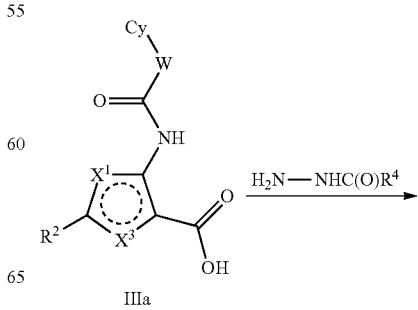

VIII

In Scheme 3a, $X^1$, $X^3$, $R^2$, Cy and W are defined as herein above. In Scheme 3a, the hydrazide V is reacted with trialkoxy-methane (e.g., triethoxymethane) to form the 1,3,4-oxadiazole analog VIII.

Alternatively, the carboxylic acid IIIa can be reacted with an acyl hydrazide to prepare a substituted 1,3,4-oxadiazole analog VIIIa as outlined in Scheme 3b, below.

Scheme 3b

Scheme 3d

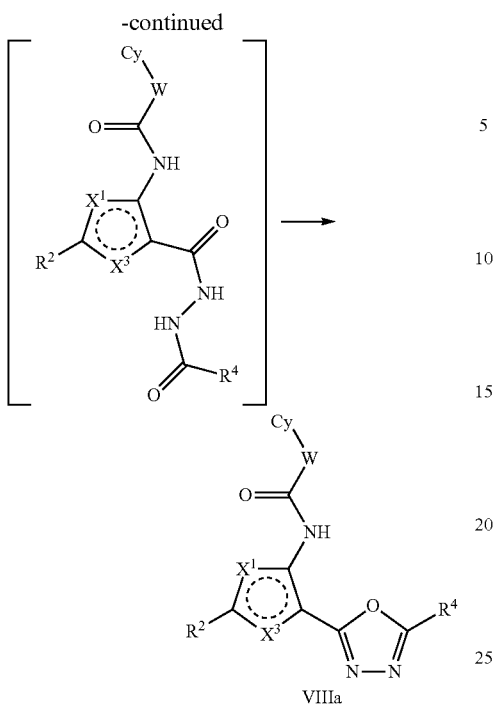

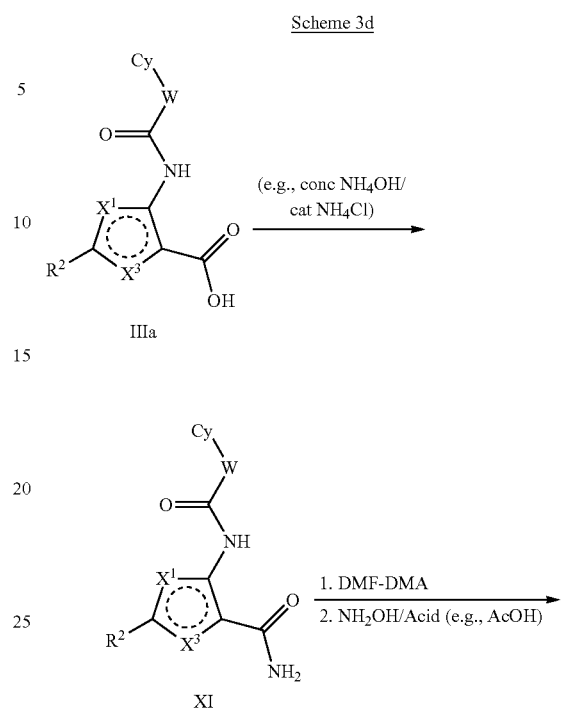

In Scheme 3b, $X^1$, $X^3$, $R^2$, Cy and W are defined as herein above. Alternatively, the unsubstituted oxadiazole ($R^4$=H in Formula VIIIa) can be prepared by reacting the above carboxylic acid with isocyanoimino-triphenyl-phosphorane.

Scheme 3c

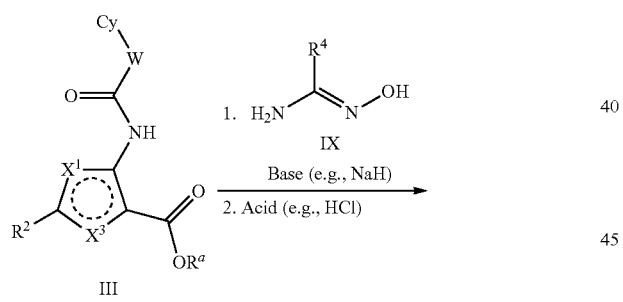

In Scheme 3d, $X^1$, $X^3$, $R^2$, Cy and W are defined as herein above. In Scheme 3d, the carboxylic acid IIIa, which can optionally be prepared through saponification of ester III, is first converted to the primary amide XI (e.g., using ammonium hydroxide and a catalytic amount of ammonium chloride) and then further converted to the 1,2,4-oxadiazole analog XII, e.g., by means of N,N-dimethylformamide dimethyl acetal (DMF-DMA) followed by hydroxylamine.

Scheme 3e

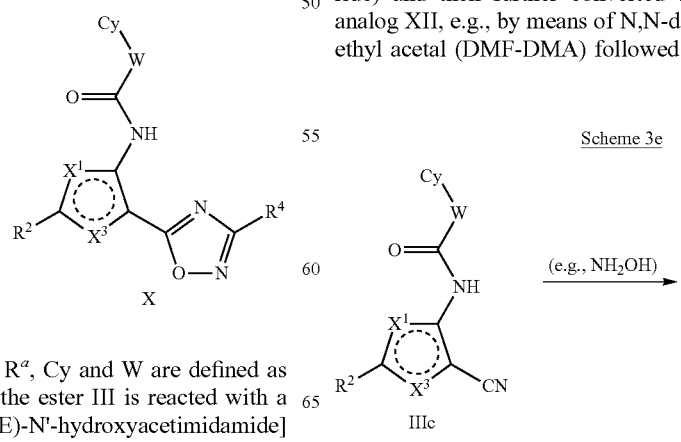

In Scheme 3c, $X^1$, $X^3$, $R^2$, $R^a$, Cy and W are defined as herein above. In Scheme 3c, the ester III is reacted with a hydroxyimidamide IX [e.g., (E)-N'-hydroxyacetimidamide] to form the 1,2,4-oxadiazole analog X.

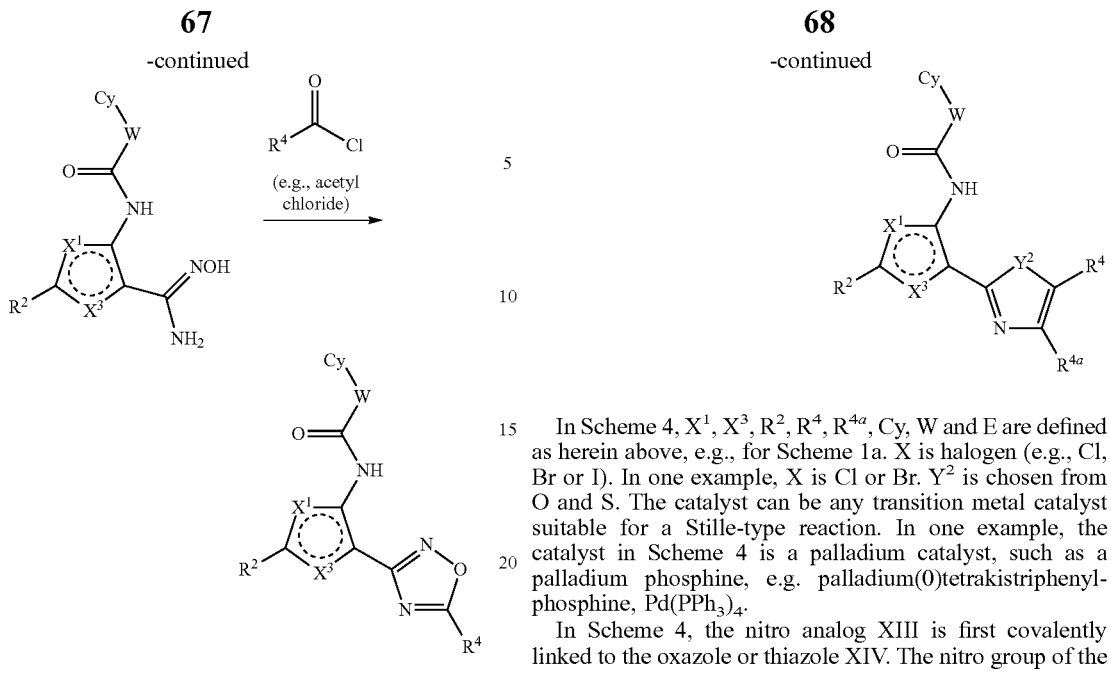

In Scheme 3e, the nitrile IIIc, is first converted to the corresponding imidamide (e.g., using hydroxylamine), which is further reacted with an acid chloride (e.g., acetyl chloride) to give an oxadiazole. In Scheme 3e, $X^1$, $X^3$, $R^2$, $R^4$, Cy and W are defined as herein above. In one example, $R^4$ is $C_1$-$C_4$ alkyl (e.g., methyl).

Oxazole/Thiazole

In yet another example, the compounds of the present disclosure include an oxazole or a thiazole moiety as the ring Z and are prepared using a procedure outlined in Scheme 4, below.

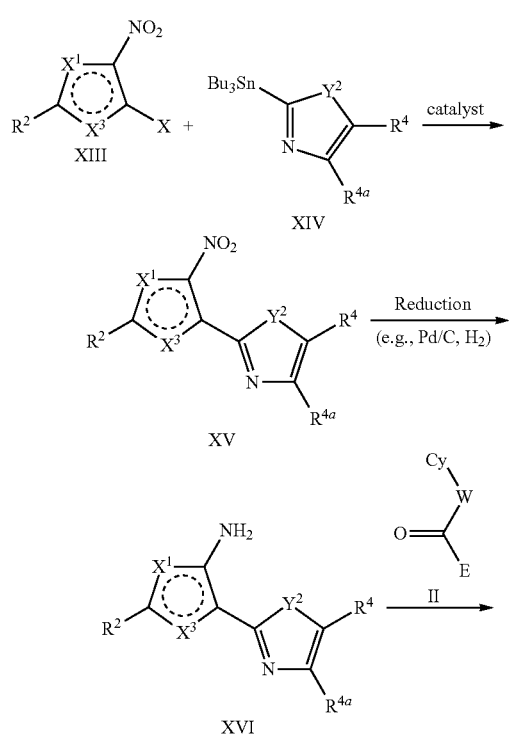

Scheme 4

In Scheme 4, $X^1$, $X^3$, $R^2$, $R^4$, $R^{4a}$, Cy, W and E are defined as herein above, e.g., for Scheme 1a. X is halogen (e.g., Cl, Br or I). In one example, X is Cl or Br. $Y^2$ is chosen from O and S. The catalyst can be any transition metal catalyst suitable for a Stille-type reaction. In one example, the catalyst in Scheme 4 is a palladium catalyst, such as a palladium phosphine, e.g. palladium(0)tetrakistriphenyl-phosphine, $Pd(PPh_3)_4$.

In Scheme 4, the nitro analog XIII is first covalently linked to the oxazole or thiazole XIV. The nitro group of the resulting cross-coupled product XV is reduced to an amino group using an appropriate reducing agent, such as hydrogen in combination with a metal catalyst, such as Pd/C. The reduced analog XVI can then be coupled to an appropriate carboxylic acid analog, e.g., compound II, e.g., as outlined in Scheme 1a, to produce the desired oxazole or thiazole.

A person of ordinary skill in the art will appreciate that compound XIV in Scheme 4 can be replaced with another oxazole, thiazole, isoxazole or isothiazole derivative to produce the corresponding products. Exemplary reagents are:

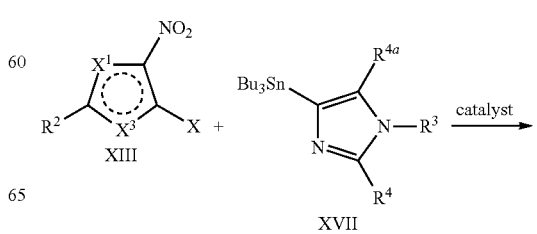

wherein $R^4$ is defined as hereinabove and $Y^2$ is O or S.

Imidazole

In a further example, the compounds of the present disclosure include an imidazole moiety as the ring Z and are prepared using a related procedure outlined in Scheme 5, below.

Scheme 5

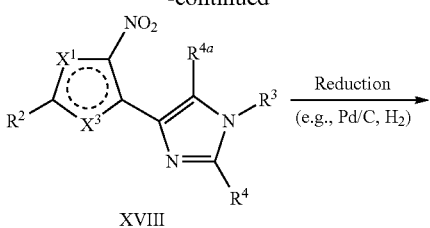

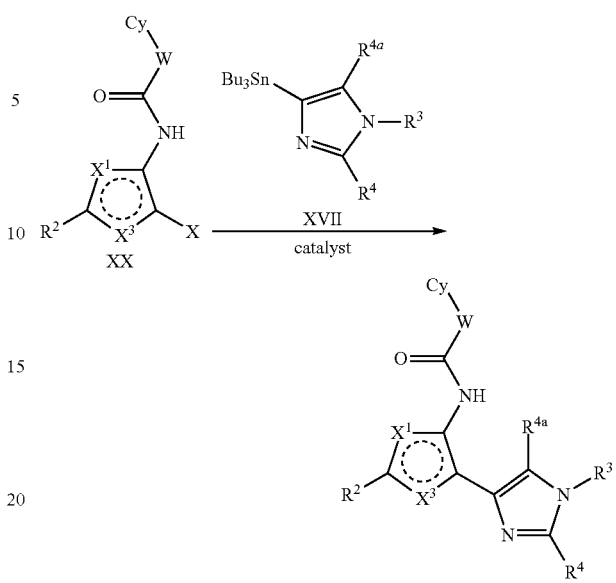

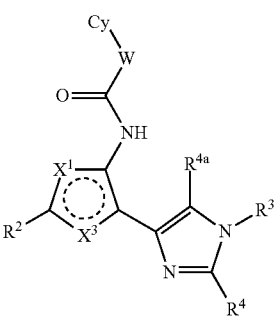

In Scheme 5, $X^1$, $X^3$, $R^2$, $R^3$, $R^4$, $R^{4a}$, Cy, W and E are defined as herein above (see, e.g., Scheme 1a). X is halogen (e.g., Cl, Br or I). In one example, X is Cl or Br. The catalyst can be any transition metal catalyst suitable for a Stille-type reaction. In one example, the catalyst in Scheme 5 is a palladium catalyst, such as a palladium phosphine, e.g. $Pd(PPh_3)_4$.

A person of ordinary skill in the art will appreciate that compound XVII in Scheme 5 can be replaced with another imidazole derivative to produce the corresponding product. An exemplary reagent is:

XVIIa

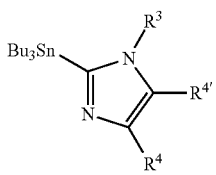

wherein $R^3$, $R^4$ and $R^{4a}$ are defined as hereinabove.

Alternatively, in Schemes 4 and 5, the coupling reaction with the imidazole, thiazole, oxazole and the like is performed subsequent to the amide formation, starting with compound XX. An exemplary coupling reaction is outlined below.

Tetrazole

In another example, the compounds of the present disclosure include a tetrazole moiety as the ring Z. The tetrazole moiety can be prepared from the corresponding nitrile through reaction with an azido-trialkylstannane. An exemplary procedure is outlined in Scheme 6, below. For example, the nitrile XXI is reacted with azidotributylstannane ($Bu_3SnN_3$) to form the tetrazole XXII. The tetrazole hydrogen can be replaced with another substituent (e.g., an alkyl group) by contacting the tetrazole with an electrophile and, optionally, an organic or inorganic base (e.g., carbonate or triethylamine). Exemplary electrophiles include X—$R^4$, wherein $R^4$ is defined as herein above and X is a leaving group, such as halogen (e.g., Cl, Br, I). In one example, X—$R^4$ is a halogen-substituted alkyl or heteroalkyl reagents (e.g., MeI).

Scheme 6

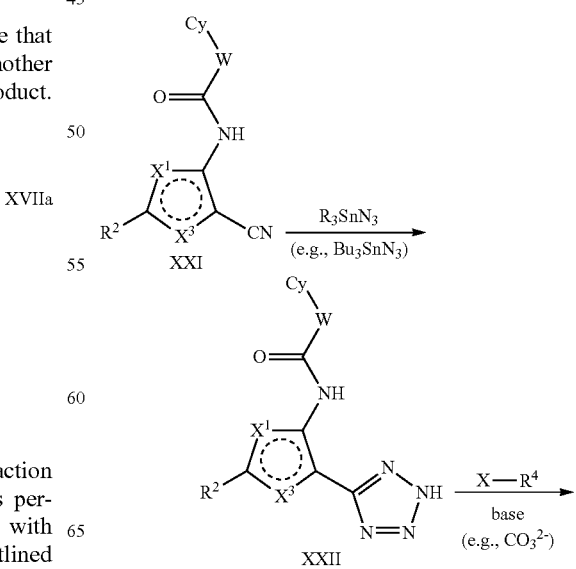

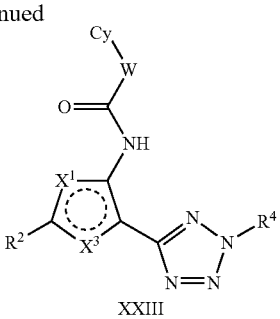

XXIII

In Scheme 6, $X^1$, $X^3$, $R^2$, $R^4$, Cy and W are defined as herein above (see, e.g., Scheme 1a). R is alkyl (e.g., $C_1$-$C_{10}$ alkyl). A person of skill in the art will appreciate that the tetrazole moiety can alternatively be formed prior to amide formation (e.g., starting with an appropriate cyano nitro analog).

Pyrazole

In another example, the compounds of the present disclosure include a pyrazole moiety as the ring Z, and can be prepared using a procedures outlined in Scheme 7, below.

Scheme 7

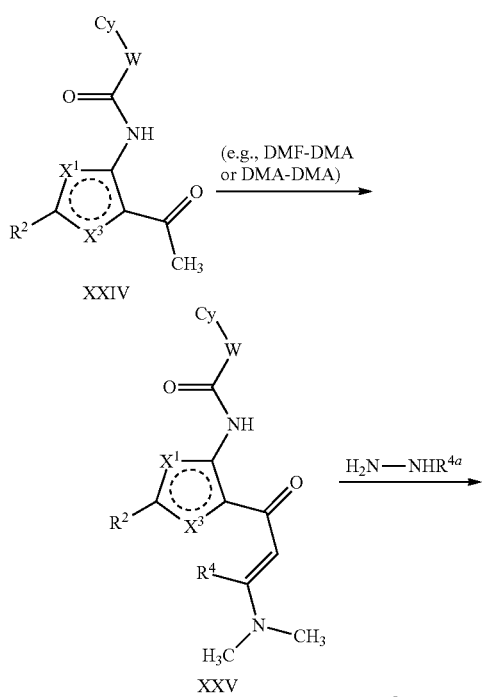

In Scheme 7, $X^1$, $X^3$, $R^2$, $R^4$, $R^{4a}$, Cy and W are defined as herein above (see, e.g., Scheme 1a). In one example, $R^4$ is H or methyl. In Scheme 7, the acetyl analog XXIV is first converted to the dimethylamino acryloyl analog XXV, which is then converted to the pyrazole XXVI by reaction with a hydrazide. A person of skill in the art will appreciate that the pyrazole moiety can alternatively be formed prior to amide formation.

In another example, the pyrazole moiety can be coupled to the remainder of the molecule via a nitrogen atom, e.g., as outlined in Scheme 7b.

Scheme 7b

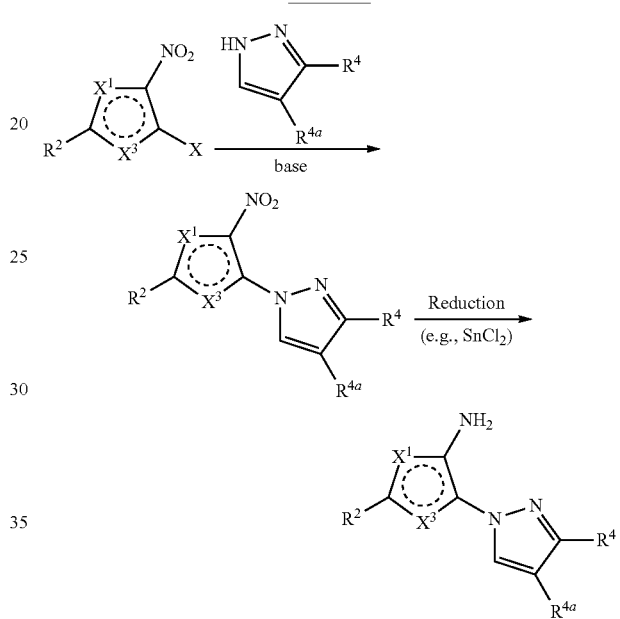

In Scheme 7b, $X^1$, $X^3$, $R^2$, $R^4$ and $R^{4a}$ are defined as herein above (see, e.g., Scheme 1a).

Pyridine/Pyrazine

In another example, the compounds of the present disclosure include a 6-membered heteroaromatic ring, such as a pyridine or pyrazine moiety as the ring Z. Such molecules can be prepared using a procedure outlined in Schemes 8a or 8b, below.

Scheme 8a

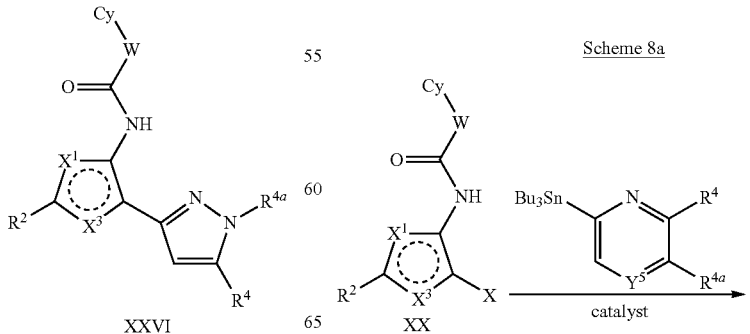

XX

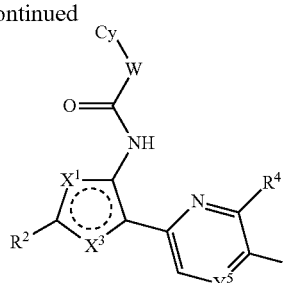

In Scheme 8a, $Y^5$ is N or $CR^4$. $X^1$, $X^3$, $R^2$, $R^4$, $R^{4a}$, Cy, W and the catalyst are defined as herein above (see, e.g., Scheme 1a and Scheme 1b). In one example, the catalyst is a palladium phosphine, e.g., $Pd(PPh_3)_4$.

Alternatively, the pyridine or pyrazine moiety can be coupled prior to amide formation starting from the nitro analog XIII as outlined in Scheme 8b, below.

Scheme 8b

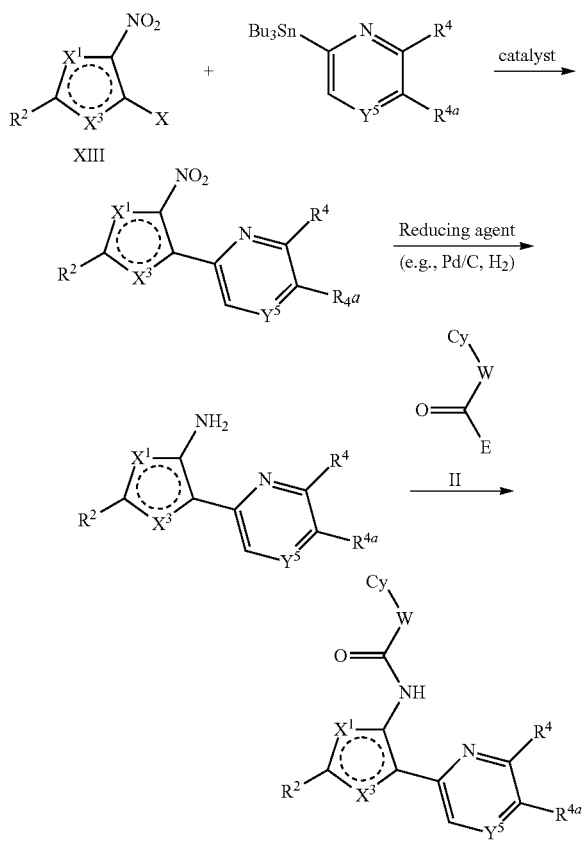

In Scheme 8b, $Y^5$ is N or $CR^4$. $X^1$, $X^3$, $R^2$, $R^4$, $R^{4a}$, Cy, W and the catalyst are defined as herein above (see, e.g., Scheme 1a and Scheme 1b). In one example, the catalyst is a palladium phosphine, e.g., $Pd(PPh_3)_4$.

Synthesis of Substituted Thiophene Analogs

In one example, the compounds of the present disclosure include a substituted thiophene ring. For example, in Formulae (II) to (XV), $R^2$ and/or $R^{2a}$ is other than H. Halogen-substituted analogs may be prepared using the procedure outlined in Scheme 9.

Scheme 9

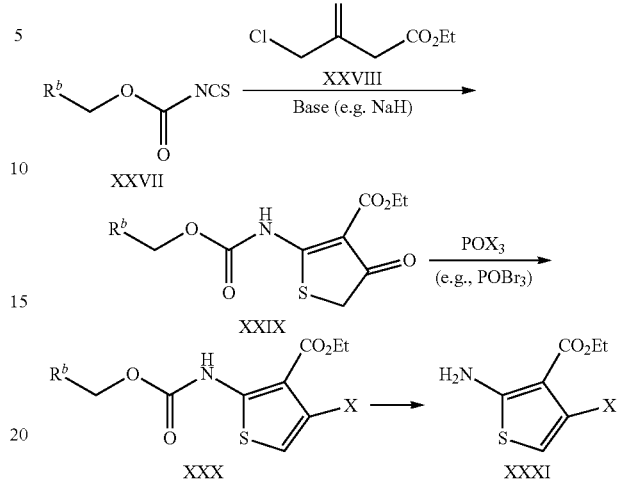

In Scheme 9, $R^b$ is a ring and X is a halogen (e.g., Br or Cl). In one example, X in Scheme 9 is Br. In another example, $R^b$ is chosen from substituted or unsubstituted cycloalkyl, substituted or unsubstituted heterocycloalkyl, substituted or unsubstituted aryl and substituted or unsubstituted heteroaryl. For example, $R^b$ is 9H-fluorene. In Scheme 9, the isothiocyanate XXVII is cyclized with the chloro beta-ketoester XXVIII in the presence of a base to give the carbamate XXIX. Deprotection of the amino group (e.g., using morpholine to remove fluorene protecting group) affords the halogenated thiophene ester XXXI. Compound XXXI can be further converted to an amide by coupling to an appropriate carboxylic acid, similarly to the reaction outlined in Scheme 1.

Alternatively the halogen can be replaced with another moiety (e.g., either before deprotection of the amino group, or after coupling of the amine with an appropriate carboxylic acid to form an amide). In one example, the halogen X (e.g., Br) in Scheme 9, can be replaced with a trifluoro-methyl ($-CF_3$) group, e.g., using $CF_3-CO_2-CuI$ or methyl 2,2-difluoro-2-(fluorosulfonyl)acetate/CuI. In another example, halogen X is replaced with halogen X* or CN, e.g., utilizing Sandmeyer or Sandmeyer-type reactions. For example, Br can be replaced with Cl, using a reagent including CuCl (CuCl/DMF) or with CN using a reagent including CuCN (e.g., CuCN/DMF). The substitution of one halogen for another can be performed at different stages of the synthesis. For example, compound XXXI in Scheme 9 can first be converted to an amide and the resulting analog can be subjected to halogen exchange. Subsequently the ester moiety can be converted to an heteroaryl group (e.g., a triazole moiety), e.g., using the methods described herein.

Analogs including an alkyl group as $R^2$ can be prepared using appropriate starting materials such as methyl-2-amino-4-methyl-3-thiophene carboxylate, which is commercially available (e.g., Oakwood, Fluorochem):

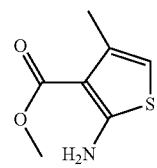

Pharmaceutical Compositions

The disclosure further provides pharmaceutical compositions including a compound of the present disclosure, e.g., those of Formulae (I) to (XV) (or any embodiment thereof), and at least one pharmaceutically acceptable carrier. The term "pharmaceutically acceptable carrier" means all pharmaceutically acceptable ingredients known to those of skill in the art, which are typically considered non-active ingredients. The term "pharmaceutically acceptable carrier" includes solvents, solid or liquid diluents, vehicles, adjuvants, excipients, glidants, binders, granulating agents, dispersing agents, suspending agents, wetting agents, lubricating agents, disintegrants, solubilizers, stabilizers, emulsifiers, fillers, preservatives (e.g., anti-oxidants), flavoring agents, sweetening agents, thickening agents, buffering agents, coloring agents and the like, as well as any mixtures thereof. Exemplary carriers (i.e., excipients) are described in, e.g., *Handbook of Pharmaceutical Manufacturing Formulations*, Volumes 1-6, Niazi, Sarfaraz K., Taylor & Francis Group 2005, which is incorporated herein by reference in its entirety. A pharmaceutical composition of the present disclosure may include one or more compounds of the present disclosure in association with one or more pharmaceutically acceptable carrier and optionally other active ingredients.

The compounds of the present disclosure may be administered orally, topically, parenterally, by inhalation or spray or rectally in dosage unit formulations containing at least one pharmaceutically acceptable carrier. The term "parenteral" as used herein includes percutaneous, subcutaneous, intravascular (e.g., intravenous), intramuscular, or intrathecal injection or infusion techniques and the like. The pharmaceutical compositions containing compounds of the present disclosure may be in a form suitable for oral use, for example, as tablets, troches, lozenges, aqueous or oily suspensions, dispersible powders or granules, emulsion, hard or soft capsules, or syrups or elixirs.

Compositions intended for oral use may be prepared according to any method known to the art for the manufacture of pharmaceutical compositions and such compositions may contain one or more agents chosen from the group consisting of sweetening agents, flavoring agents, coloring agents and preservative agents in order to provide pharmaceutically elegant and palatable preparations. Tablets contain the active ingredient in admixture with non-toxic pharmaceutically acceptable excipients that are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques. In some cases such coatings may be prepared by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules, wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil. Formulations for oral use may also be presented as lozenges.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, may also be present.

Pharmaceutical compositions of the present disclosure may also be in the form of oil-in-water emulsions. The oily phase may be a vegetable oil or a mineral oil or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol, glucose or sucrose. Such formulations may also contain a demulcent, a preservative and flavoring and coloring agents. The pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be a sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present disclosure may also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Compounds of the present disclosure may be administered parenterally in a sterile medium. The compound, depending on the vehicle and concentration used, can either be suspended or dissolved in the vehicle. In one embodiment, adjuvants such as local anesthetics, preservatives and buffering agents can be dissolved in the vehicle.

For disorders of the eye or other external tissues, e.g., mouth and skin, the formulations are applied, for example, as a topical gel, spray, ointment or cream, or as a scleral suppository, containing the active ingredients in a total amount of, for example, 0.075 to 30% w/w, 0.2 to 20% w/w or such as 0.4 to 15% w/w. When formulated in an ointment, the active ingredients may be employed with either paraffinic or a water-miscible ointment base.

Alternatively, the active ingredients may be formulated in a cream with an oil-in-water cream base. If desired, the aqueous phase of the cream base may include, for example at least 30% w/w of a polyhydric alcohol such as propylene glycol, butane-1,3-diol, mannitol, sorbitol, glycerol, polyethylene glycol and mixtures thereof. The topical formulation may desirably include a compound, which enhances absorption or penetration of the active ingredient through the skin or other affected areas. Examples of such dermal penetration enhancers include dimethylsulfoxide and related analogs. The compounds of this present disclosure can also be administered by a transdermal device. In one embodiment, topical administration will be accomplished using a patch either of the reservoir and porous membrane type or of a solid matrix variety. In either case, the active agent is delivered continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane. The transdermal patch may include the compound in a suitable solvent system with an adhesive system, such as an acrylic emulsion, and a polyester patch. The oily phase of the emulsions of this present disclosure may be constituted from known ingredients in a known manner. While the phase may comprise merely an emulsifier, it may comprise a mixture of at least one emulsifier with a fat or oil or with both a fat and an oil. In one embodiment, a hydrophilic emulsifier is included together with a lipophilic emulsifier, which acts as a stabilizer. The phase may, for example, include both an oil and a fat. Together, the emulsifier(s) with or without stabilizer(s) make-up the so-called emulsifying wax, and the wax together with the oil and fat make up the so-called emulsifying ointment base, which forms the oily, dispersed phase of the cream formulations. Emulsifiers and emulsion stabilizers suitable for use in the formulation of the present disclosure include Tween 60, Span 80, cetostearyl alcohol, myristyl alcohol, glyceryl monostearate, and sodium lauryl sulfate, among others. The choice of suitable oils or fats for the formulation is based on achieving the desired cosmetic properties, since the solubility of the active compound in most oils likely to be used in pharmaceutical emulsion formulations is very low. Thus, the cream may, for example, be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients. The anti-inflammatory active ingredients may, for example, be present in such formulations in a concentration of 0.5 to 20%, such as 0.5 to 10%, for example about 1.5% w/w. For therapeutic purposes, the active compounds of the present disclosure are ordinarily combined with one or more adjuvants appropriate to the indicated route of administration. The compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Dosage levels of the order of from about 0.005 mg to about 80 mg per kilogram of body weight per day are useful in the treatment of the diseases and conditions described herein (e.g., about 0.35 mg to about 5.6 g per human patient per day, based on an average adult person weight of 70 kg). The amount of active ingredient that may be combined with the carrier materials to produce a single dosage form will vary depending upon the host treated and the particular mode of administration. Dosage unit forms will generally contain between from about 1 mg to about 500 mg of an active ingredient. The daily dose can be administered in one to four doses per day. In the case of skin conditions, it may, for example, be applied as a topical preparation of compounds of this present disclosure on the affected area one to four times a day.

Formulations suitable for inhalation or insufflation include solutions and suspensions in pharmaceutically acceptable aqueous or organic solvents, or mixtures thereof, and powders. The liquid or solid compositions may contain suitable pharmaceutically acceptable excipients as describe above. The compositions may be administered by oral or nasal respiratory route for local or systemic effect. Compositions may be nebulized by use of inert gases or vaporized, and breathed directly from the nebulizing/vaporizing device or the nebulizing device may be attached to a facemask tert or intermittent positive pressure-breathing machine.

It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition may also be added to the animal feed or drinking water. It may be convenient to formulate the animal feed and drinking water compositions so that the animal takes in a therapeutically appropriate quantity of the composition along with its diet. It may also be convenient to present the composition as a premix for addition to the feed or drinking water.

Methods

Over-activation of JNK is believed to be an important mechanism in autoimmune, inflammatory, metabolic, neurological diseases as well as cancer and pain. Certain compounds of the present disclosure exhibit inhibitory activity against JNK (e.g., JNK1, JNK2 and JNK3). Kinase activity can be determined using a kinase assay, which typically employs a kinase substrate and a phosphate group donor, such as ATP (or a derivative thereof). Exemplary kinase substrates for various kinases are described in Example 14. The kinase catalyzes the transfer of a phosphate group from the phosphate group donor (e.g., ATP) unto the substrate forming a covalent bond. Certain compounds of the present disclosure can inhibit the activity of the kinase, slowing the above described reaction and resulting in a smaller number of phosphate groups being transferred. Hence, the current disclosure provides a method (i.e., an in vitro assay) that includes: (i) contacting a compound of the present disclosure with a kinase (e.g., JNK, p38, MAPK and the like) thereby forming a mixture. The method may further include (ii) contacting the mixture with a kinase substrate (e.g., peptide substrate) and ATP (or a derivative thereof), thereby forming an amount of phosphorylated kinase substrate. The method can further include (iii) measuring the amount of phosphorylated kinase substrate. The amount of phosphorylated substrate may be accomplished using a detection reagent. Suitable detection reagents can include a metal reagent, such as a lanthanoid (e.g., Eu-63), a radioactive probe, a labeled (e.g., fluorescently labelled) antibody and combinations thereof. In one example, the assay is a fluorescence resonance energy transfer (FRET) assay (e.g., TR-FRET). Examples of such assays are described in Example 14. In another embodiment, compounds of the present disclosure is used as a reference standard to determine the in vitro activity of other compounds in a kinase assay as described above. In another example, the compounds of the present disclosure is used in an in vitro assay for identifying candidate compounds that are capable of inhibiting JNK.

Over-activation of JNK is believed to be an important mechanism in autoimmune, inflammatory, metabolic, neurological diseases as well as cancer and pain. Hence, compounds and compositions of the present disclosure may be useful in the treatment and/or prevention of c-Jun N-terminal kinase mediated disorders, such as autoimmune disorders, inflammatory disorders, metabolic disorders, neurological diseases, pain and cancer.

One member of the JNK family, Jnk3, may be required for stress-induced neuronal apoptosis, as it is selectively expressed in the nervous system. Thus, the compounds of the present disclosure may be useful for the treatment of neurodegenerative diseases, such as Alzheimer's disease, Parkinson's disease and other diseases and conditions characterized by neuronal cell death, such as stroke. An in vivo model, which can be used to assess the potential in vivo beneficial effect of the compounds of the present disclosure, is described in Example 15.

Excitotoxic cell death can be induced experimentally by the administration of kainic acid, a potent agonist of the kainate class of glutamate receptors. Peripheral injection of kainic acid results in recurrent seizures and degeneration of select populations of neurons in the hippocampus. Activation of jnk is observed after kainic acid treatment in vivo (see, e.g., Jeon S. H. et al., *Experimental and Molecular Medicine* 2000, 32(4): 227-230 and Kim Y.-H. et al., *Molecules and Cells* 2001, 11(2): 144-150). Mice lacking the Jnk3 gene are resistant to kainic acid-induced upregulation of phosphorylated c-jun (p-cjun) and hippocampal neuronal apotosis (see e.g., Yang D. D. et al., *Nature* 1997, 389: 865-870). Phosphorylated c-jun in wildtype mice is upregulated after kainic acid administration and demonstrate that this upregulation is inhibited by compounds of the present disclosure.

The disclosure provides a method for reducing the upregulation of phosphorylated c-jun (e.g., which is induced by an excitatory amino acid or an analog thereof), in the brain of a test animal, such as a rodent (e.g., mice, rat, rabbit and the like). The method includes administering to the test animal a compound or composition of the present disclosure. The method can further include administering to the test animal an excitatory amino acid, such as kainic acid. The method can further include measuring the amount of phosphorylated c-jun in the brain (e.g., hippocampus) of the test animal.

In one example, the disclosure provides a method of treating a disease. The method includes administering to a mammalian subject (e.g., human) in need thereof a therapeutically effective amount of a compound or salt of the present disclosure, for example those according to any one of Formulae I to XV (or any embodiment thereof), or a composition comprising such compounds or salts.

In one example, the disease is a neurodegenerative disease. In another example, the disease is an infectious disease (e.g., sepsis, septic shock and Shigellosis). In yet another example, the disease is an autoimmune disease. In a further example, the disease is a destructive bone disorder, such as osteoporosis, osteoarthritis and multiple myeloma-related bone disorders.

Neurodegenerative diseases which may be treated by the compounds of this disclosure include, but are not limited to Alzheimer's disease (AD), diffuse Lewy body type of Alzheimer's disease, Parkinson's disease, Down syndrome, dementia, mild cognitive impairment (MCI), amyotrophic lateral sclerosis (ALS), traumatic brain injuries, cerebral ischemic brain damage, ischemic or hemorrhaging stroke, multi-infarct dementia, hereditary cerebral hemorrhage with amyloidosis of the dutch-type, cerebral amyloid angiopathy (including single and recurrent lobar hemorrhages), neurodegeneration induced by viral infection (e.g. AIDS, encephalopathies) and other degenerative dementias, including dementias of mixed vascular and degenerative origin, dementia associated with Parkinson's disease, dementia associated with progressive supranuclear palsy, dementia associated with cortical basal degeneration. Neurodegenerative diseases also includes epilepsy, seizures, neurodegenerative disease caused by traumatic injury, ischemia/reperfusion in stroke, cerebral ischemias, acute hypoxia and ischemia or glutamate neurotoxicity. In a one example, the neurodegenerative disease is Alzheimer's disease or diffuse Lewy body type of Alzheimer's disease. In one example, the neurodegenerative disease which can be treated using the compounds of this disclosure is Alzheimer's disease. The treatment of Alzheimer's disease (AD) can include methods of treating a patient who has AD, methods of preventing a patient from getting AD, methods of preventing or delaying the onset of AD; e.g., delaying or preventing the progression from MCI to AD. In another example, the neurodegenerative disease is diffuse Lewy body type of Alzheimer's disease. In yet another example, the disease is mild cognitive impairment (MCI).

In another embodiment, the disclosure provides a method of treating a disease chosen from epilepsy, seizures, Huntington's disease, multiple sclerosis, cancer, age-related macular degeneration, diabetic retinopathy and retinal neurodegeneration related to glaucoma or ocular trauma, the method comprising administering to a mammalian subject (e.g., a human subject) in need thereof a pharmaceutically effective amount of a compound or salt of any one of Formulae I to XV (or an embodiment thereof) or a pharmaceutical composition comprising at least one compound of Formulae I to XV (or an embodiment thereof). Other diseases, which may be treated using the compounds of the present disclosure include alcoholism, Alexander's disease, Alper's disease, ataxia telangiectasia, Batten disease (also known as Spielmeyer-Vogt-Sjogren-Batten disease), prion diseases, bovine spongiform encephalopathy (BSE), Canavan disease, cerebral palsy, Cockayne syndrome, corticobasal degeneration, Creutzfeldt-Jakob disease, frontotemporal lobar degeneration, Huntington's disease, HIV-associated dementia, Kennedy's disease, Krabbe's disease, Lewy body dementia, neuroborreliosis, Machado-Joseph disease (e.g., spinocerebellar ataxia type 3), multiple system atrophy, multiple sclerosis, narcolepsy, Niemann Pick disease, Pelizaeus-Merzbacher disease, Pick's disease, primary lateral sclerosis, progressive supranuclear palsy, Refsum's disease, Sandhoffs disease, Schilder's disease, subacute combined degeneration of spinal cord secondary to pernicious anaemia, spinocerebellar ataxia (multiple types with varying characteristics), spinal muscular atrophy, Steele-Richardson-Olszewski disease and tabes dorsalis.

Autoimmune diseases which may be treated or prevented by the compounds of this present disclosure include, but are not limited to, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis and graft versus host disease (GVHD). The compounds and compositions of the present disclosure may also be useful to treat pathologic immune responses such as that caused by T cell activation and thrombin-induced platelet aggregation.

Additional specific conditions or diseases that may be treated with the compounds or compositions of the present disclosure include, without limitation, myocardial ischemia, ischemia/reperfusion in heart attacks, organ hypoxia, vascular hyperplasia, cardiac and renal reperfusion injury, thrombosis, cardiac hypertrophy, hepatic ischemia, liver disease, congestive heart failure, thrombin induced platelet aggregation, endotoxemia and/or toxic shock syndrome, and conditions associated with prostaglandin endoperoxidase synthase-2.

In other embodiments, the specific conditions or diseases that may be treated with the compounds or compositions of the present disclosure include, without limitation, angiogenic disorders, including solid tumors, liquid tumors, tumor metastasis, ocular neovasculization, infantile haemangiomas. Proliferative diseases which may be treated or prevented by the compounds of this disclosure include, but are not limited to, acute myelogenous leukemia, chronic myelogenous leukemia, metastatic melanoma, Kaposi's sarcoma, multiple myeloma and HTLV-1 mediated tumorigenesis.

Other specific conditions or diseases that may be treated with the compounds or compositions of the present disclosure include, without limitation, acute pancreatitis, chronic pancreatitis, asthma, allergies, adult respiratory distress syndrome, chronic obstructive pulmonary disease, glomerulonephritis, rheumatoid arthritis, systemic lupus erythematosis, scleroderma, chronic thyroiditis, Grave's disease, diabetes, thrombocytopenia, atopic dermatitis, chronic active hepatitis, myasthenia gravis, multiple sclerosis, inflammatory bowel disease, ulcerative colitis, Crohn's disease, psoriasis, graft versus host disease (GVHD), inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic beta-cell disease; diseases characterized by massive neutrophil infiltration, rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder.

In addition, JNK inhibitors of the instant disclosure may be capable of inhibiting the expression of inducible pro-inflammatory proteins. Therefore, other "JNK-mediated conditions" which may be treated by the compounds of this disclosure include edema, analgesia, fever and pain, such as neuromuscular pain, migrains, cancer pain, dental pain and arthritis pain.

In addition to the compounds of this disclosure, pharmaceutically acceptable derivatives or prodrugs of the compounds of this disclosure may also be employed in compositions to treat or prevent the above-identified disorders.

The disclosures in this document of all articles and references, including patents, are incorporated herein by reference in their entirety.

The instant disclosure is illustrated further by the following examples, which are not to be construed as limiting the present disclosure in scope or spirit to the specific procedures described in them. Analogous structures and alternative synthetic routes within the scope of the present disclosure will be apparent to those skilled in the art.

EXAMPLES

General:

Reagents and solvents obtained from commercial suppliers were used without further purification unless otherwise stated. Thin layer chromatography was performed on pre-coated 0.25 mm silica gel plates (E. Merck, silica gel 60, $F_{254}$). Visualization was achieved using UV illumination or staining with phosphomolybdic acid, ninhydrin or other common staining reagents. Flash chromatography was performed using either a Biotage Flash 40 system and prepacked silica gel columns or hand packed columns (E. Merck silica gel 60, 230-400 mesh). Preparatory HPLC was performed on a Varian Prepstar high performance liquid chromatograph. $^1$H and $^{13}$C NMR spectra were recorded at 300 MHz and 75 MHz, respectively, on a Varian Gemini or Bruker Avance spectrometer. Chemical shifts are reported in parts per million (ppm) downfield relative to tetramethylsilane (TMS) or to proton resonances resulting from incomplete deuteration of the NMR solvent (δ scale). Mass spectra were recorded on an Agilent series 1100 mass spectrometer connected to an Agilent series 1100 HPLC.

Compound purity was typically determined by HPLC/MS analysis using a variety of analytical methods. Exemplary methods are described below.

[1]=20% [B]: 80% [A] to 70% [B]: 30% [A] gradient in 1.75 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[2]=50% [B]: 50% [A] to 95% [B]: 5% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[3]=5% [B]: 95% [A] to 20% [B]: 80% [A] gradient in 2.5 min, then hold, at 2 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[4]=20% [B]: 80% [A] to 70% [B]: 30% [A] gradient in 2.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[5]=50% [B]: 50% [A] to 95% [B]: 5% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[6]=5% [B]: 95% [A] to 20% [B]: 80% [A] gradient in 3.33 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×30 cm column, 3 micron packing, 210 nm detection, at 35° C.

[7]=20% [B]: 80% [A] to 70% [B]: 30% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

[8]=10% [B]: 90% [A] to 40% [B]: 60% [A] gradient in 10.0 min, then hold, at 1.5 mL/min, where [A]=0.1% trifluoroacetic acid in water; [B]=0.1% trifluoroacetic acid in acetonitrile on a Phenomenex Luna C18 (2) 4.6 mm×3 cm column, 3 micron packing, 210 nm detection, at 35° C.

[9]=23% [B]: 77% [A] to 30% [B]: 70% [A] gradient in 15.0 min, then hold, at 1.0 mL/min, where [A]=0.1% trifluoroacetic acid in water; [B]=0.1% trifluoroacetic acid in acetonitrile on a Zorbex SB-phenyl C18 2.1 mm×5 cm column, 5 micron packing, 210 nm detection, at 30° C.

[10]=50% [B]: 50% [A] to 95% [B]: 5% [A] gradient in 10.0 min, then hold, at 1.5 mL/min, where [A]=0.1% trifluoroacetic acid in water; [B]=0.1% trifluoroacetic acid in acetonitrile a Phenomenex Luna C18 (2) 4.6 mm×3 cm column, 3 micron packing, 210 nm detection, at 35° C.

[11]=5% [B]: 95% [A] to 20% [B]: 80% [A] gradient in 10.0 min, then hold, at 1.5 mL/min, where [A]=0.1% trifluoroacetic acid in water; [B]=0.1% trifluoroacetic acid in acetonitrile a Phenomenex Luna C18 (2) 4.6 mm×3 cm column, 3 micron packing, 210 nm detection, at 35° C.

[12]=30% [B]: 70% [A] to 60%[B]: 40%[A] gradient in 30 min, then hold, at 16 mL/min, where [A]=0.1% trifluoroacetic acid in water; [B]=0.1% trifluoroacetic acid in acetonitrile on a Phenomenex synergi Hydro-RP 2×25 cm column, 4.0 micron pacing, 210 nm detection, at 35° C.

[13]=10% [B]: 90% [A] to 40% [B]: 60% [A] gradient in 10.0 min, then hold, at 1.5 mL/min, where [A]=0.1% trifluoroacetic acid in water; [B]=0.1% trifluoroacetic acid in acetonitrile a Phenomenex Synergi Polar-RP 4.6 mm×5 cm column, 2.5 micron packing, 210 nm detection, at 35° C.

General Procedures:

Protocol A

To a solution of the carboxylic acid (e.g., 1.00 mmol) and the amine (e.g., 1.00 mmol) in pyridine (e.g., 0.5 M) at about 0° C. was added phosphorus oxychloride (POCl$_3$, e.g., 1.1 mmol) and the resulting solution was stirred at about 0° C. for about 30 minutes. Water was added to the reaction mixture and the resulting solution was diluted (e.g., with methylene chloride). The mixture was washed with saturated aqueous NaHCO$_3$ and the aqueous phase was separated and extracted with methylene chloride. The combined organic phases were dried (e.g., Na$_2$SO$_4$), filtered, concentrated under vacuum and the residue was optionally purified (e.g., silica gel column chromatography and/or preparative HPLC).

Protocol B

To a solution of the carboxylic acid (e.g., 1.00 mmol) and the amine (e.g., 1.00 mmol) in methylene chloride (0.3 M) was added 1-(3-dimethylaminopropyl)-3-ethylcarbodiimide hydrochloride (EDCI, e.g., 1.20 mmol) and 1-hydroxybenzotriazole (HOBt, e.g., 0.10 mmol). The reaction mixture was stirred at room temperature for about 18 h and was subsequently washed with 1 N aqueous HCl and saturated NaHCO$_3$. The organic phase was separated, dried (Na$_2$SO$_4$), filtered, concentrated under vacuum and the residue was optionally purified (e.g., silica gel column chromatography).

Protocol C

The carboxamide (e.g., 1.00 mmol) was dissolved in dimethylformamide dimethylacetal (DMF-DMA, e.g., 10.0 mmol) and the resulting solution was heated to about 110° C. for about 30 minutes. The solution was concentrated under vacuum and the residue was dissolved in acetic acid (e.g., 0.5 M). Hydrazine monohydrate (e.g., 1.10 mmol) was added to the solution and the mixture was heated to about 90° C. for about 30 minutes. The reaction mixture was concentrated under vacuum and the residue was optionally purified (e.g., by preparative HPLC).

Protocol D

The carboxamide (1.00 mmol) was dissolved in dimethylacetamide dimethylacetal (DMA-DMA, 10.0 mmol) and the resulting solution was heated to 110° C. for 30 minutes. The solution was concentrated under vacuum and the residue was dissolved in acetic acid (0.5 M). Hydrazine monohydrate (1.10 mmol) was added to the solution and the mixture was heated to 90° C. for 30 minutes. The reaction mixture was concentrated under vacuum and the residue was purified by preparative HPLC.

Protocol E

The chlorothiophene (e.g., 1.00 mmol), stannane (e.g., 1.00 mmol), and Pd(PPh$_3$)$_4$ (e.g., 0.1 mmol) were dissolved in DMF (e.g., 0.5 M) and the reaction vessel was evacuated and purged with nitrogen three times. The reaction mixture was heated to about 95° C. for about 18 h and the resulting solution was cooled to room temperature and diluted with Et$_2$O. The solution was washed with brine and the organic phase was separated, dried (Na₂SO₄), filtered, concentrated under vacuum and optionally purified (e.g., silica gel column chromatography).

Protocol F

The nitrothiophene and 10% palladium on carbon in ethyl acetate (e.g., 3 mL) was shaken under a hydrogen atmosphere (e.g., 40 psi) for about 2 h. The resulting suspension was filtered through a pad of diatomaceous earth and the filtrate was concentrated under vacuum.

Protocol G

CuCl (e.g., 5 mmol) was added to a solution of the bromothiophene (e.g., 1 mmol) in DMF (e.g., 0.3 M) and the resulting suspension was placed into a heated oil bath (e.g., 140° C.). The mixture was stirred for about 15 minutes and then removed from the oil bath. The resulting solution was diluted with Et₂O and washed with brine. The organic phase was separated, dried (Na₂SO₄), filtered, concentrated under vacuum and optionally purified (e.g., silica gel column chromatography).

Protocol H

Ammonium chloride (e.g., 0.05 mmol) was added to a solution of the methyl ester (e.g., 1 mmol) in concentrated aqueous ammonium hydroxide (e.g., 0.3 M) in a glass pressure tube. The tube was sealed and the reaction mixture was placed in a heated oil bath (e.g., 90° C.). After stirring for about 2 h the reaction was cooled to room temperature and diluted with water. The resulting solution was extracted with ethyl acetate and the organic phases were combined, dried (Na₂SO₄), filtered, concentrated under vacuum and optionally purified (e.g., silica gel column chromatography).

Protocol I

DMF-DMA (e.g., 1.00 mmol) was added to a solution of the carboxamide (e.g., 1.00 mmol) in methylene chloride (e.g., 0.2 M) and the resulting solution was stirred at room temperature for about 30 minutes. The solution was concentrated under vacuum and the residue was dissolved in acetic acid (e.g., 0.5 M). Hydrazine monohydrate (e.g., 1.10 mmol) was added to the solution and the mixture was stirred at room temperature for about 5 minutes. The reaction mixture was concentrated under vacuum and the residue was optionally purified (e.g., preparative HPLC).

Protocol J

DMF-DMA (e.g., 2.00 mmol) was added to a solution of the carboxamide (e.g., 1.00 mmol) in methylene chloride (e.g., 0.2 M) and the resulting solution was stirred at room temperature for about 30 minutes. The solution was concentrated under vacuum and the residue was dissolved in acetic acid (e.g., 0.5 M). Methylhydrazine (e.g., 2.0 mmol) was added to the solution and the mixture was stirred at room temperature for about 5 minutes. The reaction mixture was concentrated under vacuum and the residue was optionally purified (e.g., preparative HPLC).

Protocol K

Sodium hydride (e.g., 2 mmol) was added to a solution of the lactam (e.g., 1 mmol) in DMF (e.g., 0.2 M) at about 0° C. The resulting suspension was stirred for about 15 minutes after which methyl 2-bromoacetate (e.g., 1.2 mmol) was added. The reaction mixture was stirred at room temperature for about 1 h and was then diluted (e.g., with Et₂O). The solution was washed with brine and the organic phase was separated, dried (e.g., Na₂SO₄), filtered, concentrated under vacuum and purified (e.g., silica gel column).

Protocol L

To a solution of the carboxylic acid (e.g., 1.00 mmol) and the amine (e.g., 1.00 mmol) in DMF (e.g., 0.3 M) was added EDCI (e.g., 3.5 mmol), DMAP (e.g., 0.5 mmol) and HOBt (e.g., 0.5 mmol). The reaction mixture was stirred at room temperature for about 8 h and was subsequently diluted (e.g., with ethyl acetate) and washed with brine. The organic phase was separated, dried (e.g., Na₂SO₄), filtered, concentrated under vacuum and the residue was purified (e.g., silica gel column and/or preparative HPLC).

Protocol M

The aryl halide (e.g., 1.00 mmol), triethylamine (e.g., 2.00 mmol) and P(o-tol)₃ (e.g., 0.30 mmol) were dissolved in acetonitrile (e.g., 0.5 M) in a glass pressure tube and nitrogen gas was bubbled through the solution via a gas dispersion tube for 10 minutes. Ethyl acrylate (e.g., 1.25 mmol) and palladium acetate (e.g., 0.10 mmol) were added to the reaction mixture and the tube was sealed and placed into an oil bath pre-heated to about 120° C. for about 18 h. The resulting solution was concentrated under vacuum and purified (e.g., silica gel column).

Protocol N

Sodium ethoxide (e.g., 4 mmol of a 21% solution in ethanol) was added to a solution of the acrylate (e.g., 1.00 mmol) in ethanol (e.g., 0.5 M) and the resulting solution was heated to about 60° C. for about 2 h. The reaction mixture was diluted (e.g., with ethyl acetate) and washed with brine. The organic phase was separated, dried (e.g., Na₂SO₄), filtered, concentrated under vacuum and the residue was purified (e.g., silica gel column).

Synthesis of Various Intermediates 2-(6-Fluoroquinolin-5-yl)acetic acid and 2-(6-fluoroquinolin-7-yl)acetic acid Protocol O:

To a solution of o-fluoro benzoic acid (30.0 g, 0.19 mol) in conc. sulfuric acid (50 mL) and water (10 mL) was added dropwise a solution of fuming nitric acid (10 mL) in water (10 mL) at 0° C. The reaction mixture was stirred at 0° C. for 30 min. The resulting precipitate was filtered off and washed with cold water, dried in vacuum to give 2-(2-fluoro-5-nitrophenyl)acetic acid as a white solid (35.2 g, 91%).

To a suspension of 2-(2-fluoro-5-nitrophenyl)acetic acid (15.0 g, 75.3 mmol) in ethanol (800 mL), THF (400 mL), and water (200 mL) was added ammonium chloride (4.46 g, 83.4 mmol) and ferrous powder (25.04 g, 405.4 mmol). The resulting mixture was heated at 80° C. for 1 hr and the progress of the reaction was monitored by TLC. Upon complete consumption of starting material, the reaction mixture was filtered off while it was hot. The filtrate was evaporated under vacuum and the crude residue was diluted with ethyl acetate (200 mL) and washed with water (3×100 mL). The combined organic layer was washed with brine, dried over Na₂SO₄ and evaporated under vacuum to afford 2-(5-amino-2-fluorophenyl)acetic acid as a grey solid which was used for the next step without further purification (6.13 g, 48%).

To a solution of 2-(5-amino-2-fluorophenyl)acetic acid (6.13 g, 36.2 mmol) in ethanol (15 mL) was added conc. sulfuric acid (2 mL) dropwise. The reaction mixture was stirred under N₂ at 80° C. for 1 hr. After the reaction mixture was cooled to RT and neutralized with aqueous Na₂CO₃ to pH 7-8, the aqueous solution was extracted with ethyl acetate (3×100 mL). The combined organic layer was washed with brine, dried over Na₂SO₄ and evaporated under vacuum to afford ethyl 2-(5-amino-2-fluorophenyl)acetate as a yellow oil which was used for the next step without further purification (6.13 g, 95%).

To a mixture of ethyl 2-(5-amino-2-fluorophenyl)acetate (3.7 g, 18.8 mmol), glycerol (6.92 g, 75.2 mmol), nitrobenzene (4.63 g, 37.6 mmol) and ferrous sulfate (1.06 g, 3.76 mmol) was added conc. sulfuric acid (4.5 mL) dropwise. The reaction mixture was heated at 120° C. for 15 hr. After cooled to RT, the reaction mixture was diluted with ethanol (20 mL), and 2N aq. NaOH was introduced to adjust pH about 13. The resulting mixture was stirred at RT for 1 hr. Then the reaction was neutralized with aq. HCl and filtered, and the dark brown precipitate was washed with methanol. The combined filtrate was concentrated to dryness in vacuum. The resulting residue was washed adequately with methanol and the combined filtrate was concentrated to dryness to give crude product, which was isolated by flash column chromatography to give 2-(6-fluoroquinolin-5-yl) acetic acid and 2-(6-fluoroquinolin-7-yl)acetic acid (1.7 g, 44%). LC-MS (0.05% TFA): [M+1]$^+$ 206.1. $^1$H-NMR (DMSO-d6, 400 MHz): δ12.66 (brs, 1H), 8.90 (m, 1H), 8.35 (m, 1H), 8.04 (m, 1H), 7.76 (m, 1H), 7.56 (m, 1H), 3.88 (s, 2H).

2-(8-Fluoroquinolin-5-yl)acetic acid

The title compound (1.2 g) was prepared from p-fluorobenzoic acid (10.1 g, 65.5 mmol) according to Protocol O, above. LCMS (0.05% TFA): [M+1]$^+$ 206.0. $^1$H-NMR (CD$_3$OD, 400 MHz): δ 8.91 (d, 1H, J=2.8 Hz), 8.58 (d, 1H, J=6.8 Hz), 7.68 (m, 1H), 7.53 (m, 1H), 7.50 (m, 1H), 4.12 (s, 2H).

2-(8-(Trifluoromethyl)quinolin-5-yl)acetic acid

To a solution of 1, 4-dibromo-2-nitrobenzene (5 g, 17.8 mmol) in N-methylpyrrolidinone (40 mL) were added methyl difluoro(fluorosulfonyl)acetate (4.5 mL, 35.6 mmol) and copper(I) iodide. The mixture was heated at 80° C. overnight, decolorized with activated charcoal, diluted with brine and extracted with ethyl acetate (3×30 mL). The combined extracts was dried over MgSO$_4$, concentrated in vacuum and purified by flash chromatography (0-100 percent ethyl acetate in petroleum) to give 4-bromo-2-nitro-1-(trifluoromethyl)benzene (4.1 g, 85%) as a yellow oil.

To a suspension of 4-bromo-2-nitro-1-(trifluoromethyl) benzene (4.0 g, 14.9 mmol) in ethanol (230 mL), THF (85 mL), and water (40 mL) was added ammonium chloride (1.0 g, 18.8 mmol) and ferrous powder (5.06 g, 90 mmol). The resulting mixture was heated at 80° C. for 1 hr and the progress of the reaction was monitored by TLC. Upon complete consumption of staring material, the reaction mixture was filtered off while it was hot. The filtrate was evaporated under vacuum and the crude residue was diluted with ethyl acetate (100 mL) and washed with water (3×50 mL). The combined organic layer was washed with brine, dried over Na$_2$SO$_4$ and evaporated under vacuum to afford 5-bromo-2-(trifluoromethyl)aniline as a solid (3.2 g, 90%).

To a mixture of 5-bromo-2-(trifluoromethyl)aniline (3.0 g, 12.6 mmol), glycerol (4.64 g, 50.0 mmol), and ferrous sulfate (0.56 g, 2.0 mmol) was added conc. sulfuric acid (2.2 mL) dropwise. The reaction mixture was heated at 120° C. for 4 hr. After cooled to RT, the reaction was diluted with ethyl acetate (150 mL), and 2N aq. NaOH was introduced to adjust pH about 13. The organic layer was separated and washed with brine and dried over Na$_2$SO$_4$ and evaporated to give the crude product, which was purified with flash column chromatography to give 5-bromo-8-(trifluoromethyl)quinoline (1.2 g, 48%).

5-Bromo-8-(trifluoromethyl)quinoline (1.0 g, 3.6 mmol) was subjected to protocol P to give tert-butyl 2-(8-(trifluoromethyl)quinolin-5-yl)acetate (450 mg, 40%).

To a solution of tert-butyl 2-(8-(trifluoromethyl)quinolin-5-yl)acetate (400 mg, 1.28 mmol) in DCM (5 mL) was added TFA (10 mL) dropwise. The reaction was stirred at room temperature overnight. After the reaction was complete, the solvent was removed and the residue was purified (silica gel chromatography) to give the final product 2-(8-(trifluoromethyl)quinolin-5-yl)acetic acid (180 mg, 54%). LC-MS (0.05% TFA): [M+1]$^+$ 256.1. $^1$H-NMR (DMSO-d6, 400 MHz): δ 12.70 (s, 1H), 9.07 (m, 1H), 8.56 (m, 1H), 8.15 (d, 1H), 7.74 (m, 1H), 7.68 (m, 1H), 4.23 (s, 2H). $^{13}$C-NMR (DMSO-d6, 100 MHz): δ171.9, 151.0, 144.0, 138.3, 133.5, 127.87, 127.83, 127.78, 125.3, 123.1, 122.2, 37.7.

2-(Isoquinolin-4-yl)acetic acid 5.2 g of Zn powder was put into a 250 mL of three-neck flask under N$_2$ protection, and then 0.5 mL of TMSCl being dissolved in 20 mL of dry THF was injected into the flask. The suspension mixture was stirred at room temperature for 20 minutes, and then 6 mL of tert-butyl 2-bromoacetate in 50 mL of dry THF was dropped into the flask for about 30 minutes at 25-40° C. After the addition was complete, the reaction mixture was stirred at 40° C. for another 30 minutes.

4-Bromoisoquinoline (2.0 g, 9.7 mmol) was subjected to protocol P to give a residue which was purified with silica gel chromatography to give tert-butyl 2-(isoquinolin-4-yl) acetate (1.9 g, 81%).

To a solution of tert-butyl 2-(isoquinolin-4-yl)acetate (1.8 g, 7.4 mmol) in DCM (10 mL) was added TFA (10 mL) dropwise. The reaction was stirred at room temperature overnight. After the reaction completed, the solvent was evaporated and the residue was neutralized with aqueous ammonia to pH 3-4, then the precipitate was filtered, washed with water and ether, and the ether extract was collected to give the title compound (1.3 g, 93%) LC-MS (0.05% TFA): [M+1]$^+$ 188.1. $^1$H-NMR (DMSO-d6, 400 MHz): δ9.39 (s, 1H), 8.48 (s, 1H), 8.24 (d, 1H, J=6.4 Hz), 7.93 (t, 1H), 7.79 (m, 1H), 4.11 (s, 2H).

2-(Isoquinolin-8-yl)acetic acid 2-bromobenzaldehyde (18.4 g, 0.1 mol) and 2, 2-dimethoxyethanamine (11.55 g, 0.11 mol) in 200 mL of toluene was heated to reflux for 4 hr. The reaction mixture was evaporated under vacuum to give an oil of 2-bromo-N-(2, 2-dimethyoxyethylidene)aniline which was used for the next step without purification. The oil was dropped into 50 mL of concentrated H$_2$SO$_4$ and the mixture was heated to 130-140° C. for 30 mins, then the reaction mixture was poured into 500 mL if ice-water and adjust to pH~8 with 5N sodium hydroxide solution. The aqueous solution was extracted with DCM (250 mL×5) and washed with water (3×50 mL). The combined organic layer was washed with brine, dried over Na$_2$SO$_4$ and the solvent was evaporated under vacuum. The crude solid was purified with silica gel to give 8-bromoisoquinoline (2.2 g, two steps 10.6%).

Protocol P

To a suspension of 8-bromoisoquinoline (2.0 g, 9.7 mmol), Q-phos (68 mg, 0.096 mmol) and Pd(dba)$_2$ (132 mg, 0.14 mmol) in dry THF (30 mL) was added 40 mL of (2-tert-butoxy-2-oxoethyl)zinc(II) bromide solution under N$_2$ protection. The resulting mixture was heated at 80° C. overnight. The solvent was evaporated under vacuum and the crude residue was diluted with ethyl acetate (100 mL) and washed with water (3×50 mL). The combined organic layer was washed with brine, dried over Na$_2$SO$_4$ and the solvent was evaporated under vacuum to give a residue which was purified with silica gel chromatography to give tert-butyl 2-(isoquinolin-8-yl)acetate (1.85 g, 78%).

To a solution of tert-butyl 2-(isoquinolin-8-yl)acetate (1.8 g) in DCM (10 mL) was added TFA (10 mL) dropwise. The reaction was stirred at room temperature overnight. After the reaction was complete, the solvent was removed to give a residue which was adjusted to pH 3-4 with aqueous ammonia. The precipitate was filtered off and washed with water. The final product was purified (silica gel column chromatography) to afford 2-(isoquinolin-8-yl)acetic acid as a solid (1.2 g, 87%). LC-MS (0.05% TFA): [M+1]$^+$ 188.1. $^1$H-NMR (DMSO-d6, 400 MHz): $\delta$13.0 (brs, 1H), 9.65 (s, 1H), 8.61 (d, 1H, J=4.8 Hz), 8.16 (d, 1H, J=4.8 Hz), 8.05 (d, 1H, J=6.8 Hz), 7.92 (t, 1H), 7.72 (d, 1H, J=6.8 Hz), 4.29 (s, 2H).

2-(Quinolin-8-yl)acetic acid

The title compound (278 mg) was prepared from 8-bromoquinoline (3.0 g, 14.5 mmol) according to protocol P above. LCMS (0.05% TFA): [M+1]$^+$ 188.1. $^1$H-NMR (CD$_3$OD, 400 MHz): $\delta$ 9.01 (d, 1H, J=3.6 Hz), 8.72 (d, 1H, J=6.4 Hz), 8.06 (d, 1H, J=6.8 Hz), 7.87 (d, 1H, J=5.6 Hz), 7.77 (m, 2H), 4.31 (s, 2H).

Preparation of 2-(benzo[d]thiazol-7-yl)acetic acid

To a solution of 6-nitrobenzothiazole (3.8 g, 0.02 mol) in 40 ml 2N HCl was added SnCl$_2$ (15.9 g, 0.06 mol), and the mixture was stirred at room temperature overnight. The reaction mixture was treated with concentrated NH$_4$OH to pH 11 and extracted with ethyl acetate (3×150 ml). The combined organic phase was concentrated under reduced pressure. The residue was purified (silica gel chromatography) to give benzo[d]thiazol-6-amine (3 g, 72%).

To a solution of benzo[d]thiazol-6-amine (100 mg, 0.67 mmol) in 6 ml CHCl$_3$ was added Br$_2$ (42 mg, 0.27 mmol) in CHCl$_3$ (10 ml) dropwise about 15 min. The mixture was concentrated under reduced pressure, and the residue was crystallized from DCM:MeOH (5:1) to give 7-bromobenzo[d]thiazol-6-amine (80 mg, 80%).

To a solution of bromobenzo[d]thiazol-6-amine (30 mg, 0.13 mmol) was added 50% H$_2$SO$_4$ (38 mg, 0.39 mmol), and then NaNO$_2$ (18 mg, 0.26 mmol) was added to the mixture at 0-5° C. The reaction mixture was stirred about 15 min at 0-5° C., 50% H$_3$PO$_2$ (17 mg, 0.26 mmol) was added. The mixture was stirred at room temperature overnight, quenched with aq. NaHCO$_3$ solution, extracted with ethyl acetate. The combined organic layer was concentrated under vacuum to give a residue which was purified with chromatography (ethyl acetate/petroleum ether=0.06) to give 7-bromobenzo[d]thiazole (10 mg, 30%).

The title compound (20 mg) was prepared from 7-bromobenzo[d]thiazole according to protocol P. LCMS (0.05% TFA): [M+1]$^+$ 194.1. $^1$H-NMR (CDCl$_3$, 400 MHz): $\delta$9.05 (s, 1H), 8.10 (d, 1H, J=6.8 Hz), 7.53 (m, 1H), 7.39 (d, 1H, J=6.8 Hz), 3.96 (s, 2H).

4-Bromo-3-(4H-1,2,4-triazol-3-yl)thiophen-2-amine

2-Aminothiophene-3-carbonitrile (2.75 g, 22.1 mmol) in formic acid (15 ml) and concentrated sulfuric acid (1 ml) was heated in a microwave for 15 min at 100° C. The solution was diluted with water, filtered, and the filtrated was concentrated under reduced pressure to yield thieno[2,3-d]pyrimidin-4 (3H)-one as a purple film. Method [6] retention time 2.09 min by HPLC (M+ 153).

Thieno[2,3-d]pyrimidin-4(3H)-one, sodium acetate (20.92 g, 255 mmol), and bromine (3.0 ml, 58.2 mmol) in glacial acetic acid (100 ml) was stirred for 24 h. A second portion of bromine (10 ml, 194 mmol) was added and the heterogeneous mixture heated to reflux for 3 h, then cooled to ambient temperature. The mixture was diluted with saturated aqueous sodium sulfite and extracted with methylene chloride. The combined organic extracts were dried over magnesium sulfate, filtered, and concentrated under reduced pressure. The residue was flash chromatographed with 99:1: 0.1, 49:1:0.1, 24:1:0.1, and 23:2:0.2 methylene chloride: methanol:concentrated ammonium hydroxide as the eluant to afford 1.96 g (29% yield over two steps) of 5,6-dibromothieno[2,3-d]pyrimidin-4(3H)-one as a yellow solid. Method [8] retention time 6.19 min by HPLC (M+ 309, 311, and 313).

Zinc dust (210 mg, 3.21 mmol) was added to a solution of 5,6-dibromothieno[2,3-d]pyrimidin-4(3H)-one (910 mg, 2.94 mmol) in glacial acetic acid (8 ml) and water (2 ml). After stirring for 4 h, a second portion of zinc dust (214 mg, 3.27 mmol) was added and the heterogeneous mixture was placed into a preheated oil bath at 60° C. The heterogeneous mixture became a clear solution in 30 min. The solution was diluted with water and extracted with ethyl acetate. The combined organic extracts were dried over magnesium sulfate, filtered, and concentrated under reduced pressure to afford 5-bromothieno[2,3-d]pyrimidin-4(3H)-one as a white solid. Method [8] retention time 2.68 min by HPLC (M+ 231 and 233).

5-Bromothieno[2,3-d]pyrimidin-4(3H)-one in phosphorus(V) oxychloride (10 ml) was heated in a microwave at 100° C. for 30 min. The solution was concentrated under reduced pressure to yield 5-bromo-4-chlorothieno[2,3-d] pyrimidine. Method [8] retention time 8.72 min by HPLC (M+ 249, 251, and 253) major peak intensities.

5-Bromo-4-chlorothieno[2,3-d]pyrimidine and hydrazine monohydrate (2 ml, 41.2 mmol) in absolute ethanol (10 ml) was heated to 75° C. After stirring for 1 h, the solution was concentrated to yield 5-bromo-4-hydrazinylthieno[2,3-d]pyrimidine. Method [8] retention time 0.80 min by HPLC (M+ 245 and 247).

5-bromo-4-hydrazinylthieno[2,3-d]pyrimidine and triethylorthoformate (40 ml) in ethanol (10 ml) was placed into a preheated oil bath at 100° C. for 24 h. The solution was concentrated and the residue was flash chromatographed with 9:1, 4:1, and 7:3 methylene chloride:ethyl acetate as the eluant to afford 578 mg (38% yield over 4 steps) of 9-bromothieno[3,2-e][1,2,4]triazolo[4,3-c]pyrimidine as a yellow solid. Method [8] retention time 4.17 min by HPLC (M+ 255 and 257).

9-Bromothieno[3,2-e][1,2,4]triazolo[4,3-c]pyrimidine (551 mg, 2.16 mmol) and N-methylethane-1,2-diamine (1 ml, 11.3 mmol) in methanol (20 ml) was placed into a preheated oil bath at 60° C. After stirring for 15 min, the solution was diluted with saturated ammonium chloride and extracted with methylene chloride. The combined organic extracts were dried over magnesium sulfate, filtered, and concentrated under reduced pressure to afford 525 mg (99% yield) of 4-bromo-3-(4H-1,2,4-triazol-3-yl)thiophen-2-amine as a brown solid. Method [8] retention time 2.25 min by HPLC (M+245 and 247).

Example 1

Synthesis of Thiophene Triazoles

1.1. Synthesis of N-(2-(1H-1,2,4-triazol-5-yl)thiophen-3-yl)-2-(naphthalen-1-yl)acetamide (1)

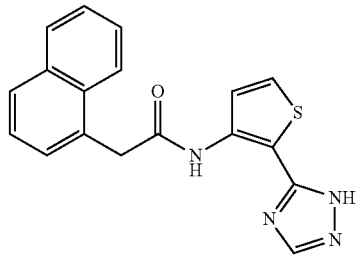 [SMILES: O=C(Cc1cccc2ccccc12)Nc1ccsc1-c1ncn[nH]1]

1.1.1. 3-(2-(Naphthalen-1-yl)acetamido)thiophene-2-carboxylic acid

Methyl 3-(2-(naphthalen-1-yl)acetamido)thiophene-2-carboxylate (210 mg, 0.645 mmol) was dissolved in THF/H$_2$O (2.5 mL, 4/1, v/v). Sodium hydroxide (129 mg, 3.22 mmol) was added and the reaction mixture was stirred at 50° C. for 20 h. The resulting solution was acidified with 10% aqueous HCl and extracted with ethyl acetate. The organic phase was separated, dried (Na$_2$SO$_4$), filtered and concentrated under vacuum to give 3-(2-(naphthalen-1-yl)acetamido)thiophene-2-carboxylic acid. Retention time=1.962 min, method [1], MS(ESI) 312.1 (M+H).

1.1.2. 3-(2-(Naphthalen-1-yl)acetamido)thiophene-2-carboxamide 3-(2-(Naphthalen-1-yl)acetamido)thiophene-2-carboxylic acid (151 mg, 0.485 mmol) was dissolved in thionyl chloride (2 mL) and the resulting solution was stirred at 60° C. for 30 minutes. The resulting solution was concentrated under vacuum and the residue was dissolved in acetonitrile (2 mL). Concentrated aqueous ammonium hydroxide (2 mL) was added to the resulting solution and the mixture was stirred at room temperature for 2 h. The solution was concentrated to 1 mL, diluted with ethyl acetate and washed with brine. The organic phase was separated and dried (Na$_2$SO$_4$), filtered, concentrated under vacuum and the residue was purified on a silica gel column (eluant hexane/ethyl acetate, 8/2 to 1/1) to give 3-(2-(naphthalen-1-yl)acetamido)thiophene-2-carboxamide (81 mg, 0.26 mmol, 54%). Retention time (min)=4.917, method [7], MS(ESI) 311.1 (M+H).

1.1.3. N-(2-(1H-1,2,4-Triazol-5-yl)thiophen-3-yl)-2-(naphthalen-1-yl)acetamide The title compound was prepared from 3-(2-(naphthalen-1-yl)acetamido)thiophene-2-carboxamide (104 mg, 0.335 mmol) according to protocol C. Method [7] retention time (min)=5.105, MS(ESI) 335.1 (M+H); $^1$H NMR (300 MHz, CDCl$_3$) δ 10.43 (s, 1H), 8.15 (d, J=5.4 Hz, 1H), 8.05-8.08 (m, 1H), 7.90-7.94 (m, 1H), 7.80 (s, 1H), 7.29-7.60 (m, 4H), 7.27 (s, 1H), 4.32 (s, 2H).

1.2. Synthesis of N-(2-(3-methyl-1H-1,2,4-triazol-5-yl)thiophen-3-yl)-2-(naphthalen-1-yl)acetamide (2)

The title compound was prepared from 3-(2-(naphthalen-1-yl)acetamido)thiophene-2-carboxamide (72 mg, 0.23 mmol) according to protocol D. Retention time (min)=4.919, method [7], MS(ESI) 349.0 (M+H); $^1$H NMR (300 MHz, CDCl$_3$) δ 10.32 (s, 1H), 8.16 (d, J=5.5 Hz, 1H), 8.08-8.11 (m, 1H), 7.87-7.92 (m, 2H), 7.52-7.61 (m, 4H), 7.24 (d, J=5.5 Hz, 1H), 4.28 (s, 2H), 2.32 (s, 3H).

1.3. Synthesis of N-(2-(1,3-dimethyl-1H-1,2,4-triazol-5-yl)thiophen-3-yl)-2-(naphthalen-1-yl)acetamide (3)

The title compound was prepared from 3-(2-(naphthalen-1-yl)acetamido)thiophene-2-carboxamide (71 mg, 0.22 mmol) using protocol D except that methyl hydrazine was used instead of hydrazine. The crude product was purified by preparative HPLC to give N-(2-(3-methyl-1H-1,2,4-triazol-5-yl)thiophen-3-yl)-2-(naphthalen-1-yl)acetamide. Retention time (min)=6.636, method [7], MS(ESI) 363.1 (M+H); $^1$H NMR (300 MHz, CDCl$_3$) δ 11.20 (s, 1H), 8.30 (d, J=5.5 Hz, 1H), 8.12 (d, J=8.2 Hz, 1H), 7.85-7.91 (m, 2H), 7.48-7.62 (m, 4H), 7.40 (d, J=5.5 Hz, 1H), 4.27 (s, 2H), 3.96 (s, 3H), 2.19 (s, 3H).

1.4. Synthesis of N-(2-(1-methyl-1H-1,2,4-triazol-5-yl)thiophen-3-yl)-2-(naphthalen-1-yl)acetamide (4)

The title compound was prepared from 3-(2-(naphthalen-1-yl)acetamido)thiophene-2-carboxamide (104 mg, 0.335 mmol) according to protocol C except that methyl hydrazine was used instead of hydrazine. The reaction mixture was purified by preparative HPLC to give N-(2-(1-methyl-1H-1,2,4-triazol-5-yl)thiophen-3-yl)-2-(naphthalen-1-yl)acetamide. Retention time (min)=6.494, method [7], MS(ESI) 349.1 (M+H); $^1$H NMR (300 MHz, CDCl$_3$) δ 11.26 (s, 1H), 8.30 (d, J=5.5 Hz, 1H), 7.88-8.06 (m, 3H), 7.42-7.59 (m, 5H), 7.41 (d, J=5.5 Hz, 1H), 4.30 (s, 2H), 3.98 (s, 3H).

Synthesis of 2-(4-Methoxyphenyl)-N-(2-(3-methyl-1H-1,2,4-triazol-5-yl)thiophen-3-yl)acetamide (5)

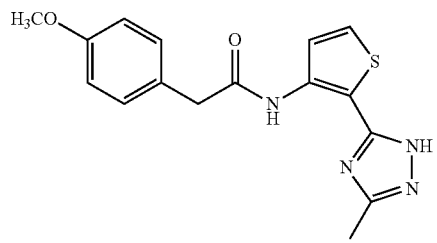 [SMILES: COc1ccc(CC(=O)Nc2ccsc2-c2nc(C)n[nH]2)cc1]

1.5.1. Methyl 3-(2-(4-methoxyphenyl)acetamido)thiophene-2-carboxylate

The title compound was prepared from 2-(4-methoxyphenyl)acetic acid (3.18 g, 19.2 mmol) and methyl 3-aminothiophene-2-carboxylate (3.02 g, 19.2 mmol) according to protocol B. Retention time (min)=2.143, method [1], MS(ESI) 306.1 (M+H).

1.5.2. 3-(2-(4-methoxyphenyl)acetamido)thiophene-2-carboxylic acid

Methyl 3-(2-(4-methoxyphenyl)acetamido)thiophene-2-carboxylate (5.7 g, 18.7 mmol) was dissolved in THF/H$_2$O (40 mL, 4/1, v/v). Sodium hydroxide (2.24 g, 56.1 mmol)

was added and the reaction mixture was stirred at 60° C. for 8 h. The resulting solution was acidified with 10% aqueous HCl and extracted with ethyl acetate. The organic phase was separated, dried (Na$_2$SO$_4$), filtered and concentrated under vacuum to give 3-(2-(4-methoxyphenyl)acetamido)thiophene-2-carboxylic acid. Retention time (min)=1.678, method [1], MS(ESI) 292.1 (M+H).

1.5.3. 3-(2-(4-Methoxyphenyl)acetamido)thiophene-2-carboxamide

The title compound was prepared from 3-(2-(4-methoxyphenyl)acetamido)-thiophene-2-carboxylic acid (1.51 g, 4.95 mmol) according to protocol B (504 mg, 1.73 mmol, 35%). Retention time (min)=1.446, method [1], MS(ESI) 329.1 (M+H).

1.5.4. 2-(4-Methoxyphenyl)-N-(2-(3-methyl-1H-1,2,4-triazol-5-yl)thiophen-3-yl)acetamide The title compound was prepared from 3-(2-(4-methoxyphenyl)acetamido)-thiophene-2-carboxamide (204 mg, 0.703 mmol) according to protocol D. Retention time (min)=3.893, method [7], MS(ESI) 329.1 (M+H); $^1$H NMR (300 MHz, CDCl$_3$) δ 10.33 (s, 1H), 8.10 (d, J=5.4 Hz, 1H), 7.27-7.33 (m, 3H), 6.90 (d, J=9.2 Hz, 2H), 3.81 (s, 3H), 3.71 (s, 2H), 2.54 (s, 3H).

1.6. Synthesis of N-(2-(3-methyl-1H-1,2,4-triazol-5-yl)thiophen-3-yl)-2-(quinolin-5-yl)acetamide (6)

The title compound can be made from 3-(2-(quinolin-5-yl)acetamido)thiophene-2-carboxamide (see Example 1.27.1, below) using protocol D.

1.7. Synthesis of N-(2-(1H-1,2,4-triazol-5-yl)thiophen-3-yl)-2-(4-methoxyphenyl)acetamide (7)

The title compound was prepared from 3-(2-(4-methoxyphenyl)acetamido)-thiophene-2-carboxamide (Example 1.5.3., 271 mg, 0.933 mmol) according to protocol C. Retention time (min)=3.754, method [7], MS(ESI) 315.1 (M+H); $^1$H NMR (300 MHz, CDCl$_3$) δ 10.48 (s, 1H), 8.12-8.16 (m, 2H), 7.28-7.33 (m, 3H), 6.97 (d, J=8.3 Hz, 2H), 3.87 (s, 3H), 3.79 (s, 2H).

1.8. Synthesis of N-(2-(1H-1,2,4-Triazol-1-yl)thiophen-3-yl)-2-(4-methoxyphenyl)acetamide (8)

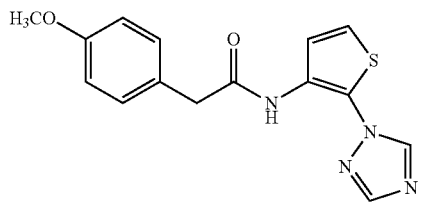 [SMILES: COc1ccc(CC(=O)Nc2ccsc2-n2cncn2)cc1]

1.8.1. 1-(3-Nitrothiophen-2-yl)-1H-1,2,4-triazole 1H-1,2,4-triazole (582 mg, 8.43 mmol), 2-chloro-3-nitrothiophene (1.15 g, 7.03 mmol) and potassium t-butoxide (944 mg, 8.43 mmol) were dissolved in DMF (30 mL). The resulting solution was stirred at 90° C. for 2 h, after which the reaction mixture was cooled to room temperature and diluted with Et$_2$O. The solution was washed with brine and the organic phase was separated, dried (Na$_2$SO$_4$), filtered, concentrated under vacuum to give 1-(3-nitrothiophen-2-yl)-1H-1,2,4-triazole. Retention time (min)=1.073, method [1], MS(ESI) 197.0 (M+H).

1.8.2. 2-(1H-1,2,4-Triazol-1-yl)thiophen-3-amine

A mixture of 1-(3-nitrothiophen-2-yl)-1H-1,2,4-triazole (462 mg, 2.35 mmol), iron (1.31 g, 23.5 mmol) and ammonium chloride (163 mg, 3.06 mmol) in water (5 mL) was stirred at 100° C. for 18 h. The resulting suspension was filtered through a pad of diatomaceous earth and the filtrate was basified with aqueous NaOH. The aqueous solution was extracted with methylene chloride and the organic phase was separated, dried (Na$_2$SO$_4$), filtered and concentrated under vacuum to give 2-(1H-1,2,4-triazol-1-yl)thiophen-3-amine (314 mg, 1.89 mmol, 80%). Retention time (min)=0.454, method [1], MS(ESI) 167.0 (M+H).

1.8.3. N-(2-(1H-1,2,4-Triazol-1-yl)thiophen-3-yl)-2-(4-methoxyphenyl)acetamide The title compound was prepared from 2-(4-methoxyphenyl)acetic acid (233 mg, 1.41 mmol) and 2-(1H-1,2,4-triazol-1-yl)thiophen-3-amine (234 mg, 1.41 mmol) according to protocol B. Retention time (min)=2.847, method [7], MS(ESI) 315.2 (M+H); $^1$H NMR (300 MHz, CDCl$_3$) δ 9.27 (s, 1H), 8.31 (s, 1H), 7.99 (d, J=5.3 Hz, 1H), 7.83 (s, 1H), 7.22 (d, J=8.1 Hz, 2H), 7.09 (d, J=5.3 Hz, 1H), 6.94 (d, J=8.1 Hz, 2H), 3.87 (s, 3H), 3.72 (s, 2H).

1.9. Synthesis of 2-(4-methoxyphenyl)-N-(4-methyl-3-(3-methyl-1H-1,2,4-triazol-5-yl)thiophen-2-yl)acetamide (9)

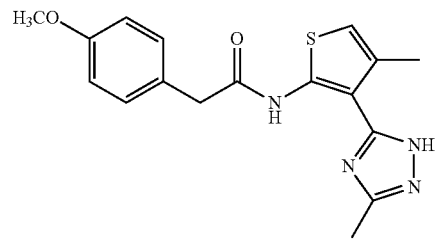 [SMILES: COc1ccc(CC(=O)Nc2scc(C)c2-c2nc(C)n[nH]2)cc1]

1.9.1. 2-(2-(4-Methoxyphenyl)acetamido)-4-methylthiophene-3-carboxamide

The title compound was prepared from 2-(4-methoxyphenyl)acetic acid (1.21 g, 7.22 mmol) and 2-amino-4-methylthiophene-3-carboxamide (1.12 g, 7.22 mmol) according to protocol B. Retention time (min)=1.903, method [1], MS(ESI) 305.0 (M+H).

1.9.2. 2-(4-Methoxyphenyl)-N-(4-methyl-3-(3-methyl-1H-1,2,4-triazol-5-yl)thiophen-2-yl)acetamide The title compound was prepared from 2-(2-(4-methoxyphenyl)acetamido)-4-methylthiophene-3-carboxamide (604 mg, 1.98 mmol) according to protocol D. Retention time (min)=4.530, method [7], MS(ESI) 343.1 (M+H); $^1$H NMR (300 MHz, CDCl₃) δ 11.95 (s, 1H), 7.33 (d, J=9.1 Hz, 2H), 6.95 (d, J=9.1 Hz, 2H), 6.52 (s, 1H), 3.83 (s, 3H), 3.82 (s, 2H), 2.49 (s, 3H), 2.34 (s, 3H).

1.10. Synthesis of N-(2-(2H-1,2,3-triazol-2-yl)thiophen-3-yl)-2-(4-methoxyphenyl)acetamide (10)

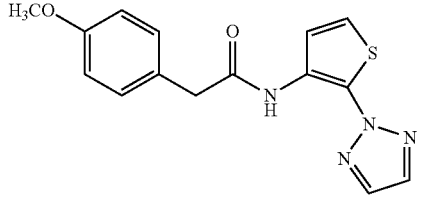 [SMILES: COc1ccc(CC(=O)Nc2ccsc2-n2nccn2)cc1]

1.10.1. 2-(3-Nitrothiophen-2-yl)-2H-1,2,3-triazole

A solution of 1,2,3-triazole (430 mg, 6.23 mmol), 2-chloro-3-nitrothiophene (1.02 g, 6.23 mmol) and potassium t-butoxide (838 mg, 7.48 mmol) in DMF (20 mL) was stirred at 90° C. for 4 h, after which the reaction mixture was cooled to room temperature and diluted with Et₂O. The solution was washed with brine and the organic phase was separated, dried (Na₂SO₄), filtered, concentrated under vacuum and purified by silica gel column chromatography (eluant hexane/ethyl acetate, 8/2 to 1/1) to give a 1:1 mixture of 2-(3-nitrothiophen-2-yl)-2H-1,2,3-triazole and 1-(3-nitrothiophen-2-yl)-1H-1,2,3-triazole (1.08 g, 5.55 mol, 89%). Retention time (min)=1.256 and 1.701, method [1], MS(ESI) 197.0 (M+H).

1.10.2. 2-(2H-1,2,3-Triazol-2-yl)thiophen-3-amine

The title compound was prepared from 2-(3-nitrothiophen-2-yl)-2H-1,2,3-triazole and 1-(3-nitrothiophen-2-yl)-1H-1,2,3-triazole (514 mg, 2.61 mmol) according to protocol F to give a 1/1 mixture of 2-(2H-1,2,3-triazol-2-yl)thiophen-3-amine and 1-(1H-1,2,3-triazol-2-yl)thiophen-3-amine (431 mg, 2.61 mmol, quantitative). Retention time (min)=0.581 and 1.035, method [1], MS(ESI) 167.0 (M+H).

1.10.3. N-(2-(2H-1,2,3-Triazol-2-yl)thiophen-3-yl)-2-(4-methoxyphenyl)-acetamide The title compound was prepared from (2-(4-methoxyphenyl)acetic acid (1.21 g, 7.22 mmol) and a 1:1 mixture of 2-(2H-1,2,3-triazol-2-yl)thiophen-3-amine and 1-(1H-1,2,3-triazol-2-yl)thiophen-3-amine (431 mg, 2.61 mmol) according to protocol B to give N-(2-(2H-1,2,3-triazol-2-yl)thiophen-3-yl)-2-(4-methoxyphenyl)acetamide. Retention time (min)=5.712, method [7], MS(ESI) 315.0 (M+H); ¹H NMR (300 MHz, CDCl₃) δ 9.99 (s, 1H), 8.06 (d, J=6.4 Hz, 1H), 7.67 (s, 2H), 7.28-7.31 (m, 2H), 7.02 (d, J=5.7 Hz, 1H), 6.98 (d, J=9.1 Hz, 2H), 3.88 (s, 3H), 3.76 (s, 2H).

1.11. Synthesis of N-(2-(3-Cyclopropyl-1H-1,2,4-triazol-5-yl)thiophen-3-yl)-2-(4-methoxyphenyl)acetamide (11)

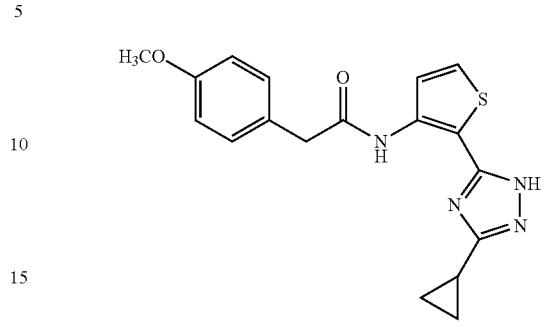

1.11.1. N-(2-(Hydrazinecarbonyl)thiophen-3-yl)-2-(4-methoxyphenyl)-acetamide Hydrazine monohydrate (0.825 mL, 17.1 mmol) was added to a solution of methyl 3-(2-(4-methoxyphenyl)acetamido)thiophene-2-carboxylate (3.48 g, 11.4 mmol) in ethanol (40 mL) and the resulting solution was stirred at room temperature for 24 h. The mixture was diluted with brine and extracted with ethyl acetate. The organic phase was separated, dried (Na₂SO₄), filtered, concentrated under vacuum and purified on a silica gel column (eluant hexane/ethyl acetate, 1/1 to 1/9) to give N-(2-(hydrazine-carbonyl)thiophen-3-yl)-2-(4-methoxyphenyl)acetamide (1.71 g, 5.60 mmol, 49%). Retention time (min)=1.300, method [1], MS(ESI) 306.0 (M+H).

1.11.2. N-(2-(3-Cyclopropyl-1H-1,2,4-triazol-5-yl)thiophen-3-yl)-2-(4-methoxyphenyl)acetamide A mixture of N-(2-(hydrazinecarbonyl)thiophen-3-yl)-2-(4-methoxyphenyl)acetamide (101 mg, 0.30 mmol), cyclopropylcarbamidine hydrochloride (47 mg, 0.39 mmol) and sodium methoxide (39 mg, 0.72 mmol) in ethanol (3 mL) was stirred at 120° C. for 17 h. The mixture was diluted with brine and extracted with ethyl acetate. The organic phase was separated, dried (Na₂SO₄), filtered, concentrated under vacuum and purified by preparative HPLC to give N-(2-(3-cyclopropyl-1H-1,2,4-triazol-5-yl)thiophen-3-yl)-2-(4-methoxyphenyl)acetamide. Retention time (min)=5.578, method [7], MS(ESI) 354.43 (M+H); ¹H NMR (300 MHz, CDCl₃) δ 10.48 (s, 1H), 8.11 (d, J=5.6 Hz, 1H), 7.25-7.32 (m, 3H), 6.94 (d, J=8.8 Hz, 2H), 3.83 (s, 3H), 3.74 (s, 2H), 1.98-2.03 (m, 1H), 1.07-1.17 (m, 4H).

The following compounds were synthesized from N-(2-(hydrazinecarbonyl)-thiophen-3-yl)-2-(4-methoxyphenyl)acetamide (Example 1.11.1) and the appropriate amidine using the procedure described above in Example 1.11.2:

1.12. N-(2-(3-Ethyl-1H-1,2,4-triazol-5-yl)thiophen-3-yl)-2-(4-methoxyphenyl)acetamide (12)

Propionimidamide hydrochloride was used. Retention time (min)=4.404, method [7], MS(ESI) 343.1 (M+H); ¹H NMR (300 MHz, CDCl₃) δ 10.54 (s, 1H), 8.14 (d, J=5.4 Hz, 1H), 7.24-7.34 (m, 3H), 6.92 (d, J=8.3 Hz, 2H), 3.84 (s, 3H), 3.76 (s, 2H), 2.79 (q, J=7.8 Hz, 2H), 1.36 (t, J=7.8 Hz, 3H).

1.13. N-(2-(3-tert-Butyl-1H-1,2,4-triazol-5-yl)thiophen-3-yl)-2-(4-methoxyphenyl)acetamide (13)

Pivalimidamide hydrochloride was used. Retention time (min)=6.103, method [7], MS(ESI) 371.1 (M+H); $^1$H NMR (300 MHz, CDCl$_3$) δ 10.76 (s, 1H), 8.05 (d, J=5.6 Hz, 1H), 7.26-7.31 (m, 3H), 6.88 (d, J=8.8 Hz, 2H), 3.76 (s, 3H), 3.75 (s, 2H), 1.44 (s, 9H).

1.14. 2-(4-Methoxyphenyl)-N-(2-(3-(tetrahydrofuran-2-yl)-1H-1,2,4-triazol-5-yl)thiophen-3-yl)acetamide (14)

Tetrahydrofuran-2-carboximidamide acetate was used. Retention time (min)=4.585, method [7], MS(ESI) 385.1 (M+H); $^1$H NMR (300 MHz, CDCl$_3$) δ 10.37 (s, 1H), 8.14 (d, J=5.4 Hz, 1H), 7.25-7.32 (m, 3H), 6.94 (d, J=8.8 Hz, 2H), 5.08 (dd, J=7.6, 5.8 Hz, 1H), 3.96-4.09 (m, 2H), 3.84 (s, 3H), 3.80 (s, 2H), 2.41-2.45 (m, 1H), 1.95-2.10 (m, 3H).

1.15. 2-(4-Methoxyphenyl)-N-(2-(3-(trifluoromethyl)-1H-1,2,4-triazol-5-yl)thiophen-3-yl)acetamide (15)

2,2,2-Trifluoroacetimidamide was used. Retention time (min)=6.744, method [7], MS(ESI) 383.1 (M+H); $^1$H NMR (300 MHz, CDCl$_3$) δ 10.38 (s, 1H), 8.11 (d, J=5.4 Hz, 1H), 7.28-7.34 (m, 3H), 6.90 (d, J=8.8 Hz, 2H), 3.81 (s, 3H), 3.79 (s, 2H).

1.16. Synthesis of N-(4-methyl-3-(1H-1,2,4-triazol-5-yl)thiophen-2-yl)-2-(2-oxo-3,4-dihydroquinolin-1(2H)-yl)acetamide (16)

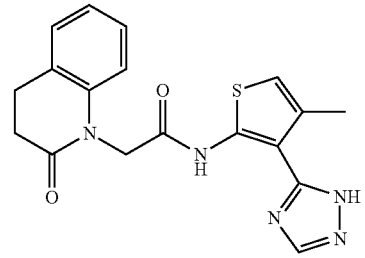 [SMILES: Cc1csc(NC(=O)CN2C(=O)CCc3ccccc32)c1-c1ncn[nH]1]

1.16.1 4-Methyl-2-(2-(2-oxo-3,4-dihydroquinolin-1(2H)-yl)acetamido)-thiophene-3-carboxamide 4-Methyl-2-(2-(2-oxo-3,4-dihydroquinolin-1(2H)-yl)acetamido)thiophene-3-carboxamide was prepared from 2-(2-oxo-3,4-dihydroquinolin-1(2H)-yl)acetic acid (0.49 g, 2.38 mmol) and 2-amino-4-methylthiophene-3-carboxamide (0.37 g, 2.38 mmol) according to protocol B Retention time (min)=3.405, method [1], MS(ESI) 344.0 (M+H).

1.16.2. N-(4-Methyl-3-(1H-1,2,4-triazol-5-yl)thiophen-2-yl)-2-(2-oxo-3,4-dihydroquinolin-1(2H)-yl) acetamide N-(4-Methyl-3-(1H-1,2,4-triazol-5-yl)thiophen-2-yl)-2-(2-oxo-3,4-dihydroquinolin-1(2H)-yl)acetamide was prepared from 4-methyl-2-(2-(2-oxo-3,4-dihydroquinolin-1(2H)-yl)acetamido)thiophene-3-carboxamide (107 mg, 0.315 mmol) according to protocol C. Retention time (min)=4.052, method [7], MS(ESI) 368.1 (M+H); $^1$H NMR (300 MHz, CDCl$_3$) δ 12.40 (s, 1H), 7.95 (s, 1H), 7.21-7.28 (m, 2H), 6.99-7.08 (m, 2H), 6.56 (s, 1H), 4.91 (s, 2H), 3.09 (dd, J=8.2, 6 Hz, 2H), 2.91 (dd, J=8.2, 6 Hz, 2H), 2.51 (s, 3H).

1.17. Synthesis of N-(4-Methyl-3-(3-methyl-1H-1,2,4-triazol-5-yl)thiophen-2-yl)-2-(2-oxo-3,4-dihydroquinolin-1(2H)-yl)acetamide (17)

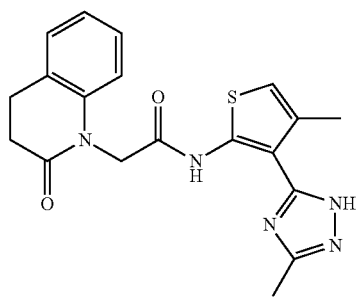 [SMILES: Cc1n[nH]c(-c2c(C)csc2NC(=O)CN2C(=O)CCc3ccccc32)n1]

1.17.1 Methyl 4-methyl-2-(2-(2-oxo-3,4-dihydroquinolin-1(2H)-yl)acetamido)thiophene-3-carboxylate The title compound was prepared from 2-(2-oxo-3,4-dihydroquinolin-1(2H)-yl)acetic acid (0.43 g, 2.09 mmol) and methyl 2-amino-4-methylthiophene-3-carboxylate (0.358 g, 2.09 mmol) according to protocol B. Retention time (min)=6.895, method [7], MS(ESI) 359.1 (M+H).

1.17.2. N-(3-(Hydrazinecarbonyl)-4-methylthiophen-2-yl)-2-(2-oxo-3,4-dihydroquinolin-1(2H)-yl) acetamide Hydrazine monohydrate (0.059 mL, 1.23 mmol) was added to a solution of methyl 4-methyl-2-(2-(2-oxo-3,4-dihydroquinolin-1(2H)-yl)acetamido)thiophene-3-carboxylate (221 mg, 0.616 mmol) in ethanol (2 mL) and the resulting solution was stirred at 50° C. for 24 h. The mixture was diluted with brine and extracted with ethyl acetate. The organic phase was separated, dried (Na$_2$SO$_4$), filtered, concentrated under vacuum to give N-(3-(hydrazinecarbonyl)-4-methylthiophen-2-yl)-2-(2-oxo-3,4-dihydroquinolin-1(2H)-yl)acetamide (174 mg, 0.485 mmol, 79%). Retention time (min)=1.435, method [1], MS(ESI) 359.1 (M+H).

1.17.3. N-(4-Methyl-3-(3-methyl-1H-1,2,4-triazol-5-yl)thiophen-2-yl)-2-(2-oxo-3,4-dihydroquinolin-1(2H)-yl)acetamide The title compound was prepared from acetimidamide hydrochloride (55 mg, 0.590 mmol) and N-(3-(hydrazinecarbonyl)-4-methylthiophen-2-yl)-2-(2-oxo-3,4-dihydroquinolin-1(2H)-yl)acetamide (141 mg, 0.393 mmol) according to the procedure of Example 1.11.2, above. Retention time (min)=4.106, method [7], MS(ESI) 382.1 (M+H); $^1$H NMR (300 MHz, CDCl$_3$) δ 12.07 (s, 1H), 7.23-7.31 (m, 2H), 7.05-7.23 (m, 2H), 6.57 (s, 1H), 4.86 (s, 2H), 3.02-3.07 (m, 2H), 2.84-2.87 (m, 2H), 2.41 (s, 3H), 2.39 (s, 3H).

1.18. Synthesis of 2-(4-methoxyphenyl)-N-(2-(3-(pyridin-4-yl)-1H-1,2,4-triazol-5-yl)thiophen-3-yl) acetamide (18)

The title compound was prepared from pyridine-4-carboximidamide hydrochloride (157 mg, 1.00 mmol) and N-(2-(hydrazinecarbonyl)thiophen-3-yl)-2-(4-methoxyphenyl)acetamide (Example 1.11.1., 204 mg, 0.668 mmol) according to the procedure described in Example 1.11.2., above. Retention time (min)=2.511, method [7], MS(ESI) 392.1 (M+H); $^1$H NMR (300 MHz, DMSO-$d_6$) δ 10.52 (s, 1H), 8.87 (d, J=4.5 Hz, 2H), 8.08-8.16 (m, 2H), 7.94 (d, J=5.0 Hz, 1H), 7.67-7.70 (m, 1H), 7.31 (d, J=8.6 Hz, 2H), 7.88 (d, J=8.6 Hz, 2H), 3.88 (s, 2H), 3.67 (s, 3H).

1.19. Synthesis of N-(2-(3-amino-1H-1,2,4-triazol-5-yl)thiophen-3-yl)-2-(4-methoxyphenyl)acetamide (19)

The title compound was prepared from N-(2-(hydrazinecarbonyl)thiophen-3-yl)-2-(4-methoxyphenyl)acetamide (Example 1.11.1., 152 mg, 0.497 mmol) and S-methylisothiouronium sulfate (276 mg, 0.995 mmol) according to the procedure described in Example 1.11.2 except that sodium hydroxide was used (rather than sodium methoxide). Retention time (min)=2.324, method [7], MS(ESI) 330.0 (M+H); $^1$H NMR (300 MHz, CDCl$_3$) δ 9.95 (s, 1H), 8.07 (d, J=5.7 Hz, 1H), 7.26-7.29 (m, 3H), 6.94 (d, J=7.9 Hz, 2H), 3.83 (s, 3H), 3.74 (s, 2H).

1.20. Synthesis of N-(4-chloro-3-(1H-1,2,4-triazol-5-yl)thiophen-2-yl)-2-(2-oxo-3,4-dihydroquinolin-1(2H)-yl)acetamide (20)

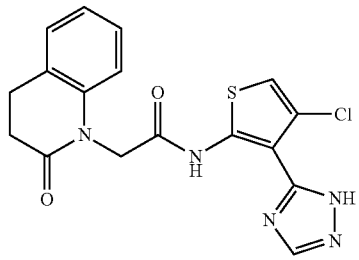 [SMILES: O=C(CN1C(=O)CCc2ccccc21)Nc1scc(Cl)c1-c1ncn[nH]1]

1.20.1. Methyl 4-bromo-2-(2-(2-oxo-3,4-dihydroquinolin-1(2H)-yl)acetamido)thiophene-3-carboxylate The title compound was prepared from 2-(2-oxo-3,4-dihydroquinolin-1(2H)-yl)acetic acid (447 mg, 2.18 mmol) and methyl 2-amino-4-bromothiophene-3-carboxylate (516 mg, 2.18 mmol) according to protocol A. Retention time (min)=2.528, method [1], MS(ESI) 423.0 (M+H).

1.20.2. Methyl 4-chloro-2-(2-(2-oxo-3,4-dihydroquinolin-1(2H)-yl)acetamido)thiophene-3-carboxylate The title compound was prepared from methyl 4-bromo-2-(2-(2-oxo-3,4-dihydroquinolin-1(2H)-yl)acetamido)thiophene-3-carboxylate (148 mg, 0.35 mmol) according to protocol G. Retention time (min)=2.540, method [1], MS(ESI) 379.0 (M+H).

1.20.3. 4-Chloro-2-(2-(2-oxo-3,4-dihydroquinolin-1(2H)-yl)acetamido)-thiophene-3-carboxamide The title compound was prepared from methyl 4-chloro-2-(2-(2-oxo-3,4-dihydroquinolin-1(2H)-yl)acetamido)thiophene-3-carboxylate (254 mg, 0.67 mmol) according to protocol H. Retention time (min)=2.034, method [1], MS(ESI) 364.0 (M+H).

1.20.4. N-(4-Chloro-3-(1H-1,2,4-triazol-5-yl)thiophen-2-yl)-2-(2-oxo-3,4-dihydroquinolin-1(2H)-yl)acetamide The title compound was prepared from 4-chloro-2-(2-(2-oxo-3,4-dihydroquinolin-1(2H)-yl)acetamido)thiophene-3-carboxamide (218 mg, 0.601 mmol) according to protocol C. Retention time (min)=4.171, method [7], MS(ESI) 388.0 (M+H); $^1$H NMR (300 MHz, CDCl$_3$) δ 7.85 (s, 1H), 7.21-7.30 (m, 2H), 7.07 (dd, J=7.4, 7.3 Hz, 1H), 6.94 (d, J=8.3 Hz, 1H), 6.83 (s, 1H), 4.93 (s, 2H), 3.09-3.14 (m, 2H), 2.89-2.94 (m, 2H).

1.21. Synthesis of N-(3-(1H-1,2,4-triazol-5-yl)thiophen-2-yl)-2-(2-oxo-3,4-dihydroquinolin-1(2H)-yl)acetamide (21)

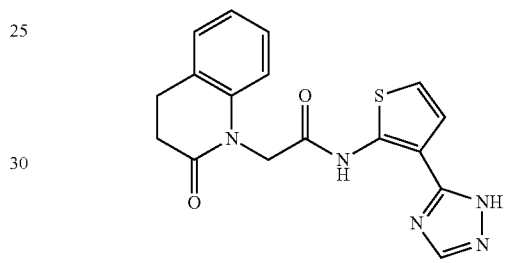

N-(3-(1H-1,2,4-Triazol-5-yl)thiophen-2-yl)-2-(2-oxo-3,4-dihydroquinolin-1(2H)-yl)acetamide was isolated during the purification of N-(4-chloro-3-(1H-1,2,4-triazol-5-yl)thiophen-2-yl)-2-(2-oxo-3,4-dihydroquinolin-1(2H)-yl)acetamide (1.20.4. The des-chlorothiophene was likely formed during the conversion of 4-bromo-2-(2-(2-oxo-3,4-dihydroquinolin-1(2H)-yl)acetamido)thiophene-3-carboxylate to methyl 4-chloro-2-(2-(2-oxo-3,4-dihydroquinolin-1(2H)-yl)acetamido)thiophene-3-carboxylate. Retention time (min)=3.296, method [7], MS(ESI) 354.0 (M+H); $^1$H NMR (300 MHz, CDCl$_3$) δ 7.99 (s, 1H), 7.23-7.29 (m, 3H), 7.06-7.10 (m, 2H), 6.88 (d, J=6.3 Hz, 1H), 4.92 (s, 2H), 3.07-3.10 (m, 2H), 2.92-2.95 (m, 2H).

1.22. Synthesis of N-(4-chloro-3-(1H-1,2,4-triazol-5-yl)thiophen-2-yl)-2-(isoquinolin-5-yl)acetamide (22)

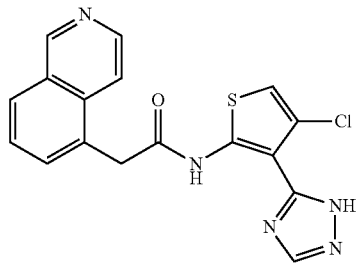 [SMILES: O=C(Cc1cccc2cnccc12)Nc1scc(Cl)c1-c1ncn[nH]1]

1.22.1 Methyl 4-bromo-2-(2-(isoquinolin-5-yl)acetamido)thiophene-3-carboxylate The title compound was prepared from 2-(isoquinolin-5-yl)acetic acid (427 mg, 2.18 mmol) and methyl 2-amino-4-bromothiophene-3-carboxylate (514 mg, 2.18 mmol) according to protocol A. Retention time (min)=1.634, method [1], MS(ESI) 405.0 (M+H).

1.22.2 Methyl 4-chloro-2-(2-(isoquinolin-5-yl)acetamido)thiophene-3-carboxylate The title compound was prepared from methyl 4-bromo-2-(2-(isoquinolin-5-yl)acetamido)thiophene-3-carboxylate (124 mg, 0.306 mmol) according to protocol G. Retention time (min)=1.609, method [1], MS(ESI) 361.0 (M+H).

1.22.3. 4-Chloro-2-(2-(isoquinolin-5-yl)acetamido)thiophene-3-carboxamide

The title compound was prepared from methyl 4-chloro-2-(2-(isoquinolin-5-yl)acetamido)thiophene-3-carboxylate (110 mg, 0.306 mmol) according to protocol H. Retention time (min)=1.139, method [1], MS(ESI) 346.0 (M+H).

1.22.4 N-(4-Chloro-3-(1H-1,2,4-triazol-5-yl)thiophen-2-yl)-2-(isoquinolin-5-yl)acetamide The title compound was prepared from 4-chloro-2-(2-(isoquinolin-5-yl)acetamido)thiophene-3-carboxamide (104 mg, 0.306 mmol) according to protocol C. Retention time (min)=1.570, method [7], MS(ESI) 370.1 (M+H); $^1$H NMR (300 MHz, CD$_3$OD) δ 9.62 (s, 1H), 8.57 (d, J=6.1 Hz, 1H), 8.42 (d, J=8.8 Hz, 1H), 8.35 (d, J=6.1 Hz, 1H), 8.18 (d, J=7.0 Hz, 1H), 8.09 (bs, 1H), 8.00 (dd, J=8.4, 7.3, 1H), 6.95 (s, 1H), 4.51 (s, 2H).

1.23. Synthesis of N-(4-chloro-3-(1H-1,2,4-triazol-5-yl)thiophen-2-yl)-2-(quinolin-5-yl)acetamide (23)

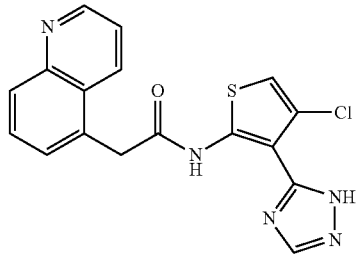 [SMILES: O=C(Cc1cccc2ncccc12)Nc1scc(Cl)c1-c1ncn[nH]1]

1.23.1. Methyl 4-bromo-2-(2-(quinolin-5-yl)acetamido)thiophene-3-carboxylate Methyl 4-bromo-2-(2-(quinolin-5-yl)acetamido)thiophene-3-carboxylate was prepared from 2-(quinolin-5-yl)acetic acid (427 mg, 2.18 mmol) and methyl 2-amino-4-bromothiophene-3-carboxylate (514 mg, 2.18 mmol) according to protocol A. Retention time (min)=1.660, method [1], MS(ESI) 405.0 (M+H).

1.23.2. Methyl 4-chloro-2-(2-(quinolin-5-yl)acetamido)thiophene-3-carboxylate Methyl 4-chloro-2-(2-(quinolin-5-yl)acetamido)thiophene-3-carboxylate was prepared from methyl 4-bromo-2-(2-(quinolin-5-yl)acetamido)thiophene-3-carboxylate (350 mg, 0.86 mmol) according to protocol G. Retention time (min)=1.629, method [1], MS(ESI) 361.0 (M+H).

1.23.3. 4-Chloro-2-(2-(quinolin-5-yl)acetamido)thiophene-3-carboxamide

4-Chloro-2-(2-(quinolin-5-yl)acetamido)thiophene-3-carboxamide was prepared from methyl 4-chloro-2-(2-(quinolin-5-yl)acetamido)thiophene-3-carboxylate (151 mg, 0.418 mmol) according to protocol H. Retention time (min)=1.151, method [1], MS(ESI) 346.0 (M+H).

1.23.4. N-(4-Chloro-3-(1H-1,2,4-triazol-5-yl)thiophen-2-yl)-2-(quinolin-5-yl)acetamide N-(4-Chloro-3-(1H-1,2,4-triazol-5-yl)thiophen-2-yl)-2-(quinolin-5-yl)acetamide was prepared from 4-chloro-2-(2-(quinolin-5-yl)acetamido)thiophene-3-carboxamide (78 mg, 0.225 mmol) according to protocol I. Retention time (min)=1.429, method [7], MS(ESI) 370.0 (M+H); $^1$H NMR (300 MHz, CD$_3$OD) δ 9.15-9.19 (m, 2H), 8.26 (d, J=8.3 Hz, 1H), 8.11-8.17 (m, 2H), 7.95-8.01 (m, 2H), 6.95 (s, 1H), 4.57 (s, 2H).

1.24. Synthesis of N-(2-(1H-1,2,4-triazol-5-yl)thiophen-3-yl)-2-(2,3-dihydrobenzo[b][1,4]dioxin-6-yl)acetamide (24)

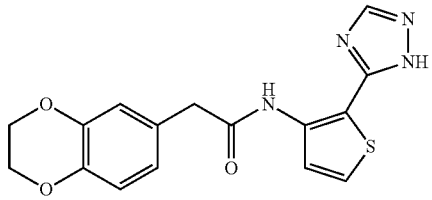 [SMILES: O=C(Cc1ccc2c(c1)OCCO2)Nc1ccsc1-c1ncn[nH]1]

1.24.1. 3-(2-(2,3-Dihydrobenzo[b][1,4]dioxin-6-yl)acetamido)thiophene-2-carboxamide The title compound was prepared from 2-(2,3-dihydrobenzo[b][1,4]dioxin-6-yl)acetic acid (450 mg) and 2-aminothiophene-3-carboxamide (345 mg) according to protocol B. The crude product mixture was taken directly to the next reaction without further purification. Method[1], MS(ESI) 319.2 [M+H], Retention time=1.496 min.

1.24.2. N-(2-(1H-1,2,4-Triazol-5-yl)thiophen-3-yl)-2-(2,3-dihydrobenzo[b][1,4]dioxin-6-yl)acetamide The title compound was prepared from 3-(2-(2,3-dihydrobenzo[b][1,4]dioxin-6-yl)acetamido)thiophene-2-carboxamide according to protocol C. The crude product was purified via preparative HPLC to give N-(2-(1H-1,2,4-triazol-5-yl)thiophen-3-yl)-2-(2,3-dihydrobenzo[b][1,4]dioxin-6-yl)acetamide; Method[7], MS(ESI) 343.0 [M+H], Retention time=3.39 min; $^1$H-NMR (300 MHz, CDCl$_3$) δ 10.51 (s, 1H), 8.21 (s, 1H), 8.11 (d, J=5.5 Hz, 1H), 7.28-7.26 (m, 1H), 7.31 (d, J=5.5 Hz, 1H), 6.93-6.83 (m, 2H), 4.27 (s, 4H), 3.73 (s, 2H).

1.25. Synthesis of N-(4-methyl-3-(1H-1,2,4-triazol-5-yl)thiophen-2-yl)-2-(quinolin-5-yl)acetamide (25)

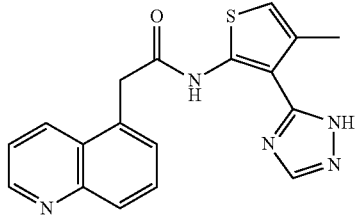 [SMILES: Cc1csc(NC(=O)Cc2cccc3ncccc23)c1-c1ncn[nH]1]

1.25.1. 4-Methyl-2-(2-(quinolin-5-yl)acetamido)thiophene-3-carboxamide

The title compound was prepared from 2-(quinolin-5-yl) acetic acid and 3-amino-4-methylthiophene-2-carboxamide using protocol B. Method[1], MS(ESI) 326.0 [M+H], Retention time=0.767 min.

1.25.2. N-(4-Methyl-3-(1H-1,2,4-triazol-5-yl)thiophen-2-yl)-2-(quinolin-5-yl)acetamide The title compound was prepared from 4-methyl-2-(2-(quinolin-5-yl)acetamido)thiophene-3-carboxamide using protocol C. The crude product was purified via preparative HPLC to give N-(4-methyl-3-(1H-1,2,4-triazol-5-yl)thiophen-2-yl)-2-(quinolin-5-yl)acetamide. Method[7], MS(ESI) 350.1 [M+H], Retention time=1.43 min; $^1$H-NMR (300 MHz, CDCl$_3$) δ 11.16 (s, 1H), 9.02 (d, J=4.94 Hz, 1H), 8.96 (d, J=8.2 Hz, 1H), 8.6 (d, J=8.2 Hz, 1H), 8.13-8.08 (m, 1H), 7.92 (s, 1H), 7.90-7.84 (m, 2H), 6.51 (s, 1H), 4.45 (s, 2H), 2.44 (s, 3H).

1.26. Synthesis of 2-(2,3-dihydrobenzo[b][1,4]dioxin-6-yl)-N-(2-(3-methyl-1H-1,2,4-triazol-5-yl)thiophen-3-yl)acetamide (26)

The title compound was prepared from 2-(2-(2,3-dihydrobenzo[b][1,4]dioxin-6-yl)acetamido)thiophene-3-carboxamide using protocol D except that the DMF was also used in the DMA-DMA step with heating to 95° C. (rather than 110° C.) and the hydrazine step was heated at 95° C. (rather than 90° C.). The product was purified via preparative HPLC to give 2-(2,3-dihydrobenzo[b][1,4]dioxin-6-yl)-N-(2-(3-methyl-1H-1,2,4-triazol-5-yl)thiophen-3-yl)acetamide; Method[7], MS(ESI) 357.1 [M+H], Retention time=3.56 min; $^1$H-NMR (300 MHz, CDCl$_3$) δ 10.33 (s, 1H), 8.06 (d, J=5.5 Hz, 1H), 7.29 (d, J=5.5 Hz, 1H), 7.27-7.26 (m, 1H), 6.88-6.86 (m, 1H), 6.84-6.82 (m, 1H), 4.22 (s, 4H), 3.70 (s, 2H), 2.51 (s, 3H).

1.27. Synthesis of N-(2-(1H-1,2,4-triazol-5-yl)thiophen-3-yl)-2-(quinolin-5-yl)acetamide (27)

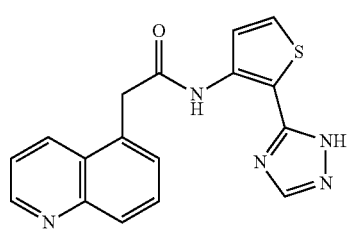 [SMILES: O=C(Cc1cccc2ncccc12)Nc1ccsc1-c1ncn[nH]1]

1.27.1. 3-(2-(Quinolin-5-yl)acetamido)thiophene-2-carboxamide

The title compound was prepared from 2-(quinolin-5-yl) acetic acid and 3-aminothiophene-2-carboxamide using protocol B. Method[1], MS(ESI) 312.1 [M+H], Retention time=0.351 min.

1.27.2. N-(2-(1H-1,2,4-Triazol-5-yl)thiophen-3-yl)-2-(quinolin-5-yl)acetamide This compound was made from 2-(2-(quinolin-5-yl)acetamido)thiophene-3-carboxamide using protocol C and was purified via preparative HPLC. Method[9], MS(ESI) 336.0 [M+H], rt=6.526 min; $^1$H-NMR (300 MHz, CDCl$_3$) δ 9.30 (s, 1H), 9.05 (d, J=8.24 Hz, 1H), 8.98 (d, J=4.95 Hz, 1H), 8.63 (d, J=8.8 Hz, 1H), 8.20-8.15 (m, 1H), 8.06 (s, 1H), 8.04 (s, 1H), 7.99-7.91 (m, 3H), 4.47 (s, 2H).

1.28. Synthesis of N-(4-methyl-3-(3-methyl-1H-1,2,4-triazol-5-yl)thiophen-2-yl)-2-(quinolin-5-yl)acetamide (28)

This compound was made from 4-methyl-2-(2-(quinolin-5-yl)acetamido)-thiophene-3-carboxamide using protocol D. The product was purified via preparative HPLC to give N-(4-methyl-3-(3-methyl-1H-1,2,4-triazol-5-yl)thiophen-2-yl)-2-(quinolin-5-yl)acetamide. Method [9], MS(ESI) 364.1 [M+H], Retention time=8.72 min; $^1$H-NMR (300 MHz, CDCl$_3$l) δ 10.76 (s, 1H), 9.04 (s, 1H), 9.0 (d, J=3.85 Hz, 1H), 8.61 (d, J=8.8 Hz, 1H), 8.14 (dd, J=8.8, 7.7 Hz, 1H), 7.94-7.89 (m, 2H), 6.49 (s, 1H), 4.46 (s, 2H), 2.41 (s, 3H), 2.40 (s, 3H).

1.29. Synthesis of N-(4-methyl-3-(1H-1,2,4-triazol-5-yl)thiophen-2-yl)-2-(quinoxalin-5-yl)acetamide (29)

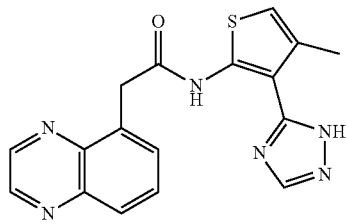 [SMILES: Cc1csc(NC(=O)Cc2cccc3nccnc23)c1-c1ncn[nH]1]

1.29.1. Tert-butyl 2-(quinoxalin-5-yl)acetate

The title compound was prepared 5-bromoquinoxaline (500 mg, 1.0 eq) according to protocol P to give tert-butyl 2-(quinoxalin-5-yl)acetate. Method [1], MS(ESI) 245.1 [M+H], Retention time=2.305 min.

1.29.2. 4-Methyl-2-(2-(quinoxalin-5-yl)acetamido)thiophene-3-carboxamide

To a stirring mixture of tert-butyl 2-(quinoxalin-5-yl) acetate (200 mg) in HOAc (5 mL) was added 6N HCl (5 mL). The reaction mixture was warmed to 80° C. for 2 h. The crude product mixture was concentrated under reduced pressure to give 2-(quinoxalin-5-yl)acetic acid, which was used in the next reaction without further purification. Method[1], MS(ESI) 189.0 [M+H], Retention time=0.722 min.

The title compound was prepared from 2-(quinoxalin-5-yl)acetic acid and 2-amino-4-methylthiophene-3-carboxamide using protocol B. Method[1], MS(ESI) 327.0 [M+H], Retention time=1.644 min.

1.29.3. N-(4-Methyl-3-(1H-1,2,4-triazol-5-yl)thiophen-2-yl)-2-(quinoxalin-5-yl)acetamide This analog was prepared from 4-methyl-2-(2-(quinoxalin-5-yl)acetamido)thiophene-3-carboxamide using protocol C. Method[7], MS(ESI) 351.1 [M+H], Retention time=3.36 min. $^1$H-NMR (300 MHz, CDCl$_3$) δ 11.84 (s, 1H), 8.90-8.87 (m, 2H), 8.21-8.18 (m, 1H), 7.93-7.85 (m, 2H), 7.73 (s, 1H), 6.52 (s, 1H), 4.56 (s, 2H), 2.45 (s, 3H).

1.30. Synthesis of N-(4-methyl-3-(3-methyl-1H-1,2,4-triazol-5-yl)thiophen-2-yl)-2-(quinoxalin-5-yl)acetamide (30)

This analog was made from 4-methyl-2-(2-(quinoxalin-5-yl)acetamido)thiophene-3-carboxamide using protocol D except that the DMF was also used in the DMA-DMA step with heating to 95° C. (rather than 110° C.) and the hydrazine step was heated at 95° C. (rather than 90° C.). Method [7], MS(ESI) 365.1 [M+H], Retention time=3.58 min; $^1$H-NMR (300 MHz, CDCl$_3$) δ 11.9 (s, 1H), 8.87 (s, 2H), 8.17-8.14 (m, 1H), 7.92-7.83 (m, 2H), 6.50 (s, 1H), 4.53 (s, 2H), 2.45 (s, 3H), 2.30 (s, 3H).

1.31. Synthesis of N-(4-methyl-3-(1H-1,2,4-triazol-5-yl)thiophen-2-yl)-2-(4-(3-(piperidin-1-yl)propoxy)phenyl)acetamide (31)

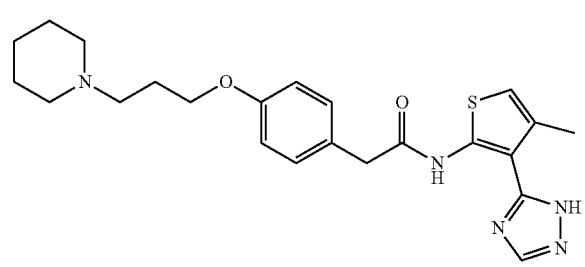 [SMILES: Cc1csc(NC(=O)Cc2ccc(OCCCN3CCCCC3)cc2)c1-c1ncn[nH]1]

1.31.1. Methyl 2-(4-(3-(piperidin-1-yl)propoxy)phenyl)acetate

1) To a stirring mixture of methyl 2-(4-hydroxyphenyl) acetate (1 g) in acetonitrile (12 mL, 0.5M) was added bromo-3-chloropropane (911 mg), K$_2$CO$_3$ (2.4 g). The reaction mixture was heated to 100° C. for 2 h, then quenched with water and extracted with EtOAc. The organic layers were dried over MgSO4, filtered, and concentrated. The crude product was used without further purification in the next reaction step. Method[1], MS(ESI) 243.0 [M+H], Retention time=2.50 min.

2) To a stirring mixture of crude methyl 2-(4-(3-chloropropoxy)phenyl)acetate in acetonitrile (17 mL, 0.35 M) was added KI (192 mg), piperidine (1.5 g), and K$_2$CO$_3$ (2.4 g). The reaction mixture was heated to 100° C. for 2 h. It was then quenched with water and extracted with EtOAc. The organic layers were dried over MgSO$_4$, filtered, and concentrated. The crude product was taken directly to the next reaction. Method[1], MS(ESI) 292.1 [M+H], Retention time=1.330 min.

1.31.2. 2-(4-(3-(Piperidin-1-yl)propoxy)phenyl)acetic acid

To a stirring mixture of methyl 2-(4-(3-(piperidin-1-yl) propoxy)phenyl)acetate (570 mg) in HOAc (5 mL) was added 6N HCl (10 mL). The reaction mixture was warmed to 80° C. for 2 h. The crude product mixture was concentrated under reduced pressure and directly taken to the next reaction without further purification. Method[1], MS(ESI) 278.1 [M+H], Retention time=0.666 min.

1.31.3. 4-Methyl-2-(2-(4-(3-(piperidin-1-yl) propoxy)phenyl)-acetamido)thiophene-3-carboxamide Protocol X:
To a stirring mixture of 2-(4-(3-(piperidin-1-yl)propoxy) phenyl)acetic acid (800 mg) in DMF/DCM (6 mL, 1:1) was added triethylamine (1.2 mL), DMAP (180 mg), 2-amino-4-methylthiophene-3-carboxamide (440 mg), and EDCI (1.1 g). The reaction mixture was stirred at rt overnight, quenched with saturated NaHCO$_3$ solution and extracted with EtOAc. The organic layers were dried over MgSO$_4$, filtered, and concentrated under reduced pressure. The crude product was purified via preparative HPLC to give 4-methyl-2-(2-(4-(3-(piperidin-1-yl)propoxy)phenyl)acetamido)thiophene-3-carboxamide. Method[7], MS(ESI) 416.2 [M+H], Retention time=2.254 min.

1.31.4. N-(4-Methyl-3-(1H-1,2,4-triazol-5-yl)thiophen-2-yl)-2-(4-(3-(piperidin-1-yl)propoxy)phenyl) acetamide This compound was prepared from -methyl-2-(2-(4-(3-(piperidin-1-yl)propoxy)phenyl)-acetamido)thiophene-3-carboxamide using Protocol C. The crude product was purified via preparative HPLC to give N-(4-methyl-3-(1H-1,2,4-triazol-5-yl)thiophen-2-yl)-2-(4-(3-(piperidin-1-yl) propoxy)phenyl)acetamide. Method[7], MS(ESI) 440.2 [M+H], Retention time=2.865 min; $^1$H-NMR (300 MHz, CDCl$_3$) δ 11.64 (s, 1H), 7.96 (s, 1H), 7.31 (s, 1H), 7.29-7.20 (m, 1H), 6.91 (d, J=8.2 Hz, 2H), 6.50 (s, 1H), 4.16-4.12 (m, 2H), 3.81 (s, 2H), 3.69-3.65 (m, 2H), 3.42-3.11 (m, 3H), 2.78-2.60 (m, 2H), 2.43 (s, 3H), 2.33-2.19 (m, 2H), 2.09-1.91 (m, 4H), 1.50-1.42 (m, 1H).

1.32. Synthesis of N-(4-methyl-3-(3-methyl-1H-1,2,4-triazol-5-yl)thiophen-2-yl)-2-(4-(3-(piperidin-1-yl)propoxy)phenyl)acetamide (32)

This compound was prepared from 4-methyl-2-(2-(4-(3-(piperidin-1-yl)propoxy)phenyl)acetamido)thiophene-3-carboxamide (Example 1.31.3) using Protocol D. Method [7], MS(ESI) 454.2 [M+H], Retention time=2.857 min; $^1$H-NMR (300 MHz, CDCl$_3$) δ 11.35 (s, 1H), 7.28-6.92 (m, 2H), 6.87 (d, J=8.8 Hz, 2H), 6.50 (s, 1H), 4.11-4.08 (m, 2H), 3.78 (s, 2H), 3.72-3.68 (m, 2H), 3.35-3.20 (m, 2H), 2.75-2.61 (m, 2H), 2.45 (s, 6H), 2.30-2.21 (m, 2H), 2.02-1.91 (m, 5H), 1.50-1.42 (m, 1H).

1.33. Synthesis of 2-(4-(2-(1H-Imidazol-1-yl)ethoxy)phenyl)-N-(4-methyl-3-(1H-1,2,4-triazol-5-yl)thiophen-2-yl)acetamide (33)

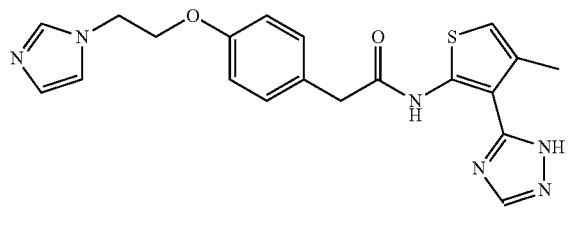 [SMILES: Cc1csc(NC(=O)Cc2ccc(OCCn3ccnc3)cc2)c1-c1ncn[nH]1]

1.33.1. Methyl 2-(4-(2-(1H-imidazol-1-yl)ethoxy)phenyl)acetate

To a stirring mixture of the methyl 2-(4-hydroxyphenyl)acetate (1.4 g, 1 EQ) and 2-(1H-imidazol-1-yl)ethanol (1.0 g) in THF (0.5 mL, 0.5 M) at 0° C. was added PPh$_3$ (2.9 g). To this mixture was added dropwise DIAD (2.2 mL) over 10 min. The reaction mixture was warmed to ambient temperature overnight. A normal aqueous workup with water and EtOAc was followed. The organic layers were dried over MgSO$_4$, filtered, and concentrated under reduced pressure. The crude product was purified via silica gel chromatography to give methyl 2-(4-(2-(1H-imidazol-1-yl)ethoxy)phenyl)acetate. Method[1], MS(ESI) 261.1, Retention time=0.782 min.

1.33.2. 2-(4-(2-(1H-Imidazol-1-yl)ethoxy)phenyl)acetic acid

To a stirring mixture of 2-(4-(2-(1H-imidazol-1-yl)ethoxy)phenyl)acetate (240 mg) in THF/water (3.3 mL, 10:1) was added fine powder KOH (77 mg). The reaction mixture was stirred at rt overnight. The crude product mixture was acidified with 1.0 N HCl and diluted with EtOAc. A normal aqueous workup with EtOAc was followed. The organic layers were dried over MgSO$_4$, filtered, and concentrated under reduce pressure. The crude acid was taken directly to the next reaction without further purification. Method[1], MS(ESI) 247.1, Retention time=0.323 min.

1.33.3. 2-(2-(4-(2-(1H-Imidazol-1-yl)ethoxy)phenyl)acetamido)-4-methylthiophene-3-carboxamide This compound was prepared from 2-(4-(2-(1H-imidazol-1-yl)ethoxy)phenyl)acetic acid and 2-amino-4-methylthiophene-3-carboxamide using protocol B except that triethylamine was also added. The crude product was purified via silica gel column chromatography. Method[1], MS(ESI) 385.1, Retention time=1.254 min.

1.33.4. 2-(4-(2-(1H-Imidazol-1-yl)ethoxy)phenyl)-N-(4-methyl-3-(1H-1,2,4-triazol-5-yl)thiophen-2-yl)acetamide The title compound was prepared from 2-(2-(4-(2-(1H-imidazol-1-yl)ethoxy)phenyl)acetamido)-4-methylthiophene-3-carboxamide using protocol C. Method[7], MS(EI) 409.1 [M+H], Retention time=2.352 min; $^1$H-NMR (300 MHz, CD$_3$OD) δ 9.08 (s, 1H), 8.24 (b s, 1H), 7.79 (t, J=1.65 Hz, 1H), 7.62 (t, J=1.65 Hz, 1H), 7.36-7.33 (m, 2H), 7.02-7.0 (m, 2H), 6.62 (s, 1H), 4.72 (t, J=4.94 Hz, 2H), 4.45-4.42 (m, 2H), 3.80 (s, 2H), 2.48 (s, 3H).

1.34. Synthesis of N-(4-Bromo-3-(1H-1,2,4-triazol-5-yl)thiophen-2-yl)-2-(isoquinolin-5-yl)acetamide (34)

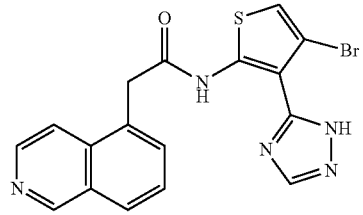 [SMILES: O=C(Cc1cccc2cnccc12)Nc1scc(Br)c1-c1ncn[nH]1]

1.34.1. Methyl 2-amino-4-bromothiophene-3-carboxylate

Methyl 2-(((9H-fluoren-9-yl)methoxy)carbonylamino)-4-bromothiophene-3-carboxylate (1 g) was stirred in DCM/morpholine (12 mL, 1:1) at rt until all the ester was consumed. The crude mixture was concentrated under reduced pressure. The residue was dissolved in ethyl ether. The white solid was removed. The mother liquid was concentrated under reduced pressure and a 1:1 mixture of ethyl ether/pentane (20 mL) was added. An additional white solid was removed. The organic layer was concentrated under reduced pressure and the crude mixture was placed under high vacuum to remove the excess of morpholine. The crude amine was taken directly to the next reaction step without further purification. Method[1], MS(ESI) 235.9 [M+H], Retention time=1.919 min.

1.34.2. Methyl 4-bromo-2-(2-(isoquinolin-5-yl)acetamido)thiophene-3-carboxylate This compound was prepared from methyl 2-amino-4-bromothiophene-3-carboxylate and 2-(isoquinolin-5-yl)acetic acid using protocol A. Method[1], MS(ESI) 404.9 [M+H], Retention time=1.678 min.

1.34.3. 4-Bromo-2-(2-(isoquinolin-5-yl)acetamido)thiophene-3-carboxamide

The title compound was prepared from methyl 4-bromo-2-(2-(isoquinolin-5-yl)acetamido)thiophene-3-carboxylate using protocol H. The crude product was purified by preparative HPLC. Method[1], MS(ESI) 389.9, Retention time=1.166 min.

1.34.4. N-(4-Bromo-3-(1H-1,2,4-triazol-5-yl)thiophen-2-yl)-2-(isoquinolin-5-yl)acetamide The title compound was prepared from 4-bromo-2-(2-(isoquinolin-5-yl)acetamido)thiophene-3-carboxamide (28 mg) using protocol C and was purified by preparative HPLC. Method[7], MS(ESI) 413.9 [M+H], Retention time=1.50 min; $^1$H-NMR (300 MHz, CD$_3$OD) δ 9.72 (b s, 1H), 8.60 (b s, 1H), 8.48 (d, J=7.7 Hz, 2H), 8.24 (d, J=6.6 Hz, 2H), 8.09-8.04 (m, 1H), 7.11 (s, 1H), 4.55 (s, 2H).

1.35. Synthesis of N-(4-Bromo-3-(1H-1,2,4-triazol-5-yl)thiophen-2-yl)-2-(quinolin-5-yl)acetamide (35)

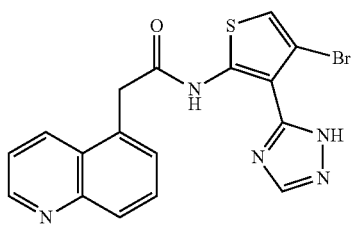 [SMILES: O=C(Cc1cccc2ncccc12)Nc1scc(Br)c1-c1ncn[nH]1]

1.35.1. Methyl 4-bromo-2-(2-(quinolin-5-yl)acetamido)thiophene-3-carboxylate This compound was prepared from methyl 2-amino-4-bromothiophene-3-carboxylate and 2-(quinolin-5-yl)acetic acid using protocol A. Method[1], MS(ESI) 405.0 [M+H], Retention time=1.650 min.

1.35.2. 4-Bromo-2-(2-(quinolin-5-yl)acetamido)thiophene-3-carboxamide

This compound was synthesized from methyl 4-bromo-2-(2-(quinolin-5-yl)acetamido)thiophene-3-carboxylate using protocol H. Method[1], MS(ESI) 390.0 [M+H], Retention time=1.174 min.

1.35.3. N-(4-Bromo-3-(1H-1,2,4-triazol-5-yl)thiophen-2-yl)-2-(quinolin-5-yl)acetamide This analog was made from 4-bromo-2-(2-(quinolin-5-yl)acetamido)thiophene-3-carboxamide using protocol C. The crude product was purified via prep. HPLC to give N-(4-bromo-3-(1H-1,2,4-triazol-5-yl)thiophen-2-yl)-2-(quinolin-5-yl)acetamide. Method[9], MS {ESI} 413.9 [M+H], Retention time=9.42 min; $^1$H-NMR (300 MHz, CD$_3$OD) δ 9.15-9.14 (m, 1H), 9.12 (s, 1H), 8.25-8.21 (m, 2H), 8.16-8.10 (m, 1H), 8.0-7.97 (m, 1H), 7.96-7.94 (m, 1H), 7.10 (s, 1H), 4.56 (s, 2H).

1.36. Synthesis of N-(4-Bromo-3-(1H-1,2,4-triazol-5-yl)thiophen-2-yl)-2-(2-oxo-3,4-dihydroquinolin-1(2H)-yl)acetamide (36)

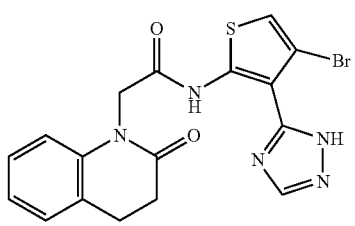 [SMILES: O=C(CN1C(=O)CCc2ccccc21)Nc1scc(Br)c1-c1ncn[nH]1]

1.36.1. 4-Bromo-2-(2-(2-oxo-3,4-dihydroquinolin-1(2H)-yl)acetamido)thiophene-3-carboxamide This compound was prepared from methyl 4-bromo-2-(2-(2-oxo-3,4-dihydroquinolin-1(2H)-yl)acetamido)thiophene-3-carboxylate using protocol H. Method[1], MS(ESI) 407.9 [M+H], Retention time=2.043 min.

1.36.2. N-(4-Bromo-3-(1H-1,2,4-triazol-5-yl)thiophen-2-yl)-2-(2-oxo-3,4-dihydroquinolin-1(2H)-yl)acetamide This analog was synthesized from 4-bromo-2-(2-(2-oxo-3,4-dihydroquinolin-1(2H)-yl)acetamido)thiophene-3-carboxamide using protocol C. Method[7], MS(ESI) 432.0 [M+H], Retention time=4.311 min; $^1$H-NMR (300 MHz, CD$_3$Cl) δ 7.89 (b s, 1H), 7.30-7.20 (m, 3H), 7.09-7.04 (m, 1H), 6.95-6.93 (m, 2H), 4.92 (s, 2H), 3.11-3.07 (m, 2H), 2.93-2.88 (m, 2H).

1.37. Synthesis of N-(4-Cyano-3-(1H-1,2,4-triazol-5-yl)thiophen-2-yl)-2-(isoquinolin-5-yl)acetamide (37)

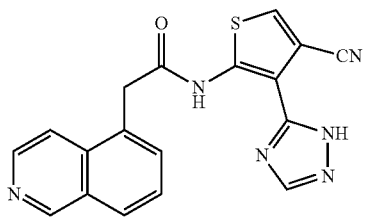 [SMILES: N#Cc1csc(NC(=O)Cc2cccc3cnccc23)c1-c1ncn[nH]1]

1.37.1. Methyl 4-cyano-2-(2-(isoquinolin-5-yl)acetamido)thiophene-3-carboxylate

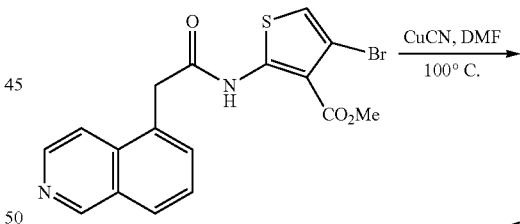

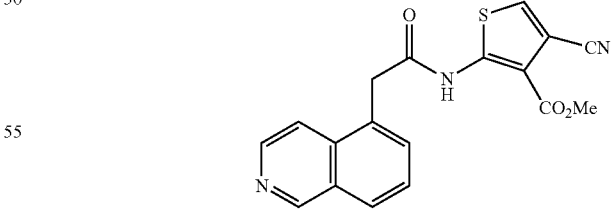

Protocol Y:

To a stirring mixture of methyl 4-bromo-2-(2-(isoquinolin-5-yl)acetamido)thiophene-3-carboxylate (100 mg) in DMF (0.5 mL) was added CuCN (150 mg). The resulting mixture was heated to 100° C. overnight. The reaction mixture was cooled to room temperature. To this mixture was added a 10% NH$_4$OH solution and ethyl ether. The crude mixture was stirred at rt for 1 h. A normal aqueous workup with ethyl ether was followed. The organic layers were dried over MgSO$_4$, filtered and concentrated under reduce pressure. The crude product mixture was purified by silica gel column chromatography to give methyl 4-cyano-2-(2-(isoquinolin-5-yl)acetamido)thiophene-3-carboxylate. Method[1], MS(ESI) 352.0 [M+H], Retention time=1.343 min.

1.37.2. 4-Cyano-2-(2-(isoquinolin-5-yl)acetamido)thiophene-3-carboxamide

This compound was prepared from methyl 4-cyano-2-(2-(isoquinolin-5-yl)acetamido)-thiophene-3-carboxylate using protocol H. Method[1], MS(ESI) 337.0 [M+H], Retention time=0.673 min.

1.37.3. N-(4-Cyano-3-(1H-1,2,4-triazol-5-yl)thiophen-2-yl)-2-(isoquinolin-5-yl)acetamide The title compound was prepared from 4-cyano-2-(2-(isoquinolin-5-yl)acetamido)thiophene-3-carboxamide (15 mg) according to protocol C except that DCM was added to the DMF-DMA step and refluxed while the hydrazine step was heated at 90° C. (rather than 95° C.). The product was purified via prep. HPLC to give N-(4-cyano-3-(1H-1,2,4-triazol-5-yl)thiophen-2-yl)-2-(isoquinolin-5-yl)acetamide. Method[7], MS(ESI) 361.1 [M+H], rt=1.273 min; $^1$H-NMR (300 MHz, CD$_3$OD) δ 9.62 (b s, 1H), 8.60-8.57 (m, 1H), 8.44-8.37 (m, 2H), 8.34 (s, 1H), 8.29-8.20 (m, 1H), 8.04-8.0 (m, 1H), 7.86 (s, 1H), 4.56 (s, 2H).

1.38. Synthesis of N-(4-Cyano-3-(1H-1,2,4-triazol-5-yl)thiophen-2-yl)-2-(2-oxo-3,4-dihydroquinolin-1(2H)-yl)acetamide (38)

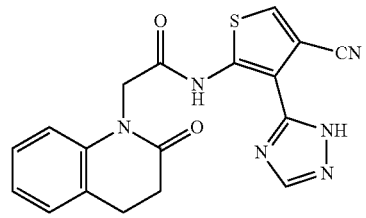 [SMILES: N#Cc1csc(NC(=O)CN2C(=O)CCc3ccccc32)c1-c1ncn[nH]1]

1.38.1. Methyl 4-cyano-2-(2-(2-oxo-3,4-dihydroquinolin-1(2H)-yl)acetamido)thiophene-3-carboxylate This compound was prepared from methyl 4-bromo-2-(2-(2-oxo-3,4-dihydroquinolin-1(2H)-yl)acetamido)thiophene-3-carboxylate using protocol Y. Method[1], MS(ESI) 370.0 [M+H], Retention time=2.237 min.

1.38.2. 4-Cyano-2-(2-(2-oxo-3,4-dihydroquinolin-1(2H)-yl)acetamido)thiophene-3-carboxamide This compound was prepared from methyl 4-cyano-2-(2-(2-oxo-3,4-dihydroquinolin-1(2H)-yl)acetamido)thiophene-3-carboxylate using protocol H. Method[1], MS(ESI) 355.0 [M+H], Retention time=3.392 min.

1.38.3. N-(4-Cyano-3-(1H-1,2,4-triazol-5-yl)thiophen-2-yl)-2-(2-oxo-3,4-dihydroquinolin-1(2H)-yl)acetamide This analog was synthesized from 4-cyano-2-(2-(2-oxo-3,4-dihydroquinolin-1(2H)-yl)acetamido)thiophene-3-carboxamide using protocol C. The crude product was purified via preparative HPLC to give N-(4-cyano-3-(1H-1,2,4-triazol-5-yl)thiophen-2-yl)-2-(2-oxo-3,4-dihydroquinolin-1(2H)-yl)acetamide. Method[7], MS(ESI) 379.1 [M+H], Retention time=3.91 min; $^1$H-NMR (300 MHz, CDCl$_3$) δ 12.34 (s, 1H), 8.13 (s, 1H), 7.62 (s, 1H), 7.28-7.10 (m, 2H), 7.06-7.01 (m, 1H), 6.94 (d, J=7.7 Hz, 1H), 4.92 (s, 2H), 3.12-3.06 (m, 2H), 2.91-2.86 (m, 2H).

1.39. Synthesis of N-(2-(3-methyl-1H-1,2,4-triazol-5-yl)thiophen-3-yl)-2-(4-(2-oxopyrrolidin-1-yl)phenyl)acetamide (39)

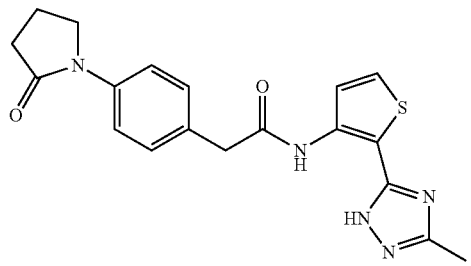 [SMILES: Cc1n[nH]c(-c2sccc2NC(=O)Cc2ccc(N3CCCC3=O)cc2)n1]

1.39.1. 3-(2-(4-iodophenyl)acetamido)thiophene-2-carboxamide

This compound was prepared from 2-(4-iodophenyl)acetic acid and 3-aminothiophene-2-carboxamide using protocol B. Method[1], MS(ESI) 387.0, Retention time=1.777 min.

1.39.2. 3-(2-(4-(2-Oxopyrrolidin-1-yl)phenyl)acetamido)thiophene-2-carboxamide To a stirring mixture of 3-(2-(4-iodophenyl)acetamido)thiophene-2-carboxamide (300 mg) in dioxane (2 mL) at rt was added CuI (103 mg), K$_2$CO$_3$ (325 mg), pyrrolidin-2-one (80 mg), and rac-dimethylcyclohexane-1,2-diamine (92 mg). The resulting mixture was heated to 90° C. overnight. The crude product mixture was diluted with saturated NaHCO$_3$ solution and extracted with EtOAc. The organic layers were dried over MgSO$_4$, filtered, and concentrated under reduced pressure. The product was purified via silica gel chromatography to give 2-(2-(4-(2-oxopyrrolidin-1-yl)phenyl)acetamido)thiophene-3-carboxamide. Method[1], MS(ESI) 344.1, Retention time=1.476 min.

1.39.3. N-(2-(3-methyl-1H-1,2,4-triazol-5-yl)thiophen-3-yl)-2-(4-(2-oxopyrrolidin-1-yl)phenyl)acetamide This analog was prepared from 3-(2-(4-(2-oxopyrrolidin-1-yl)phenyl)-acetamido)thiophene-2-carboxamide using protocol C. Method[7], MS(ESI) 382.1 [M+H], Retention time=3.46 min; $^1$H-NMR (300 MHz, CDCl$_3$) δ 10.02 (s, 1H), 8.13 (d, J=5.5 Hz, 1H), 7.46-7.38 (m, 4H), 7.30 (d, J=5.5 Hz, 1H), 3.97-3.93 (m, 2H), 3.87 (s, 2H), 2.78-2.72 (m, 2H), 2.52 (s, 3H), 2.40-2.25 (m, 2H).

1.40. Synthesis of N-(4-methyl-3-(5-methyl-4H-1,2,4-triazol-3-yl)thiophen-2-yl)-2-(4-(pyridin-4-yl)phenyl)acetamide (40)

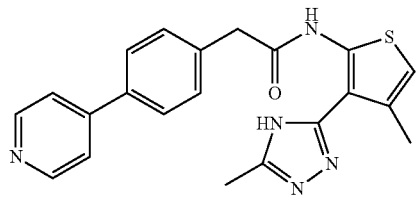 [SMILES: Cc1nnc(-c2c(C)csc2NC(=O)Cc2ccc(-c3ccncc3)cc2)[nH]1]

1.40.1. 2-(2-(4-Iodophenyl)acetamido)-4-methylthiophene-3-carboxamide

To a solution of 2-amino-4-methylthiophene-3-carboxamide (1 g, 6.4 mmol) and 2-(4-iodophenyl)acetic acid (1.83 g, 7.0 mmol) in methylene chloride (10 mL) was added Hunig's base (i.e., N,N-diisopropylethylamine) (3.1 mL, 18 mmol) and HATU (2.66 g, 7.0 mmol). The heterogeneous mixture was stirred for 18 h. The reaction was quenched by addition of saturated aqueous ammonium chloride solution and the biphasic mixture was extracted with additional methylene chloride. The organic layer was washed with brine, dried over sodium sulfate and concentrated under reduced pressure to provide a pale brown solid. LCMS method [2]: rt=2.02 min; M+Na 423.0. Material was used without further purification.

1.40.2. 2-(4-Iodophenyl)-N-(4-methyl-3-(5-methyl-4H-1,2,4-triazol-3-yl)thiophen-2-yl)acetamide The title compound was prepared from 2-(2-(4-iodophenyl)acetamido)-4-methylthiophene-3-carboxamide (277 mg, 0.69 mmol) using protocol D and was purified by column chromatography using 3% MeOH/methylene chloride (140 mg, 46% yield). Method [1]: rt=2.11 min; MH+ 438.9.

1.40.3. N-(4-Methyl-3-(5-methyl-4H-1,2,4-triazol-3-yl)thiophen-2-yl)-2-(4-(pyridin-4-yl)phenyl)acetamide A 30 mL reaction vial was charged with 2-(4-iodophenyl)-N-(4-methyl-3-(5-methyl-4H-1,2,4-triazol-3-yl)thiophen-2-yl)acetamide (140 mg, 0.32 mmol), pyridin-4-ylboronic acid (60 mg, 0.48 mmol), sodium bicarbonate (100 mg, 1.2 mmol), DME (2 mL), and water (2 mL). The heterogeneous mixture was stirred vigorously under a stream of nitrogen for 5 minutes before Pd(PPh$_3$)$_4$ was added and the vial was sealed under its Teflon cap. The reaction mixture was heated to 90° C. for 3.25 h before being transferred to a microwave vial and being microwaved to 150° C. for 5 minutes. The reaction mix was concentrated under reduced pressure and the residue was partitioned between methylene chloride and a saturated aqueous solution of ammonium chloride. The organic solution was washed with brine and dried over sodium sulfate. The solution was concentrated under reduced pressure and the crude product was purified by column chromatography (3.5% MeOH/methylene chloride) Yield: 10.0 mg (8%). Method [1]: rt=1.136 min; MH+ 390.2. $^1$H-NMR (300 MHz, CD$_3$OD) δ 8.71 (d, J=6.3 Hz, 1H), 8.60 (dd, J=4.6, 1.6 Hz, 2H), 7.84 (d, J=8.0 Hz, 2H), 7.77 (dd, J=4.6, 1.6 Hz, 2H), 7.57 (d, J=8.2 Hz, 2H), 6.58 (s, 1H), 3.94 (s, 2H), 2.45 (s, 3H), 2.31 (s, 3H).

1.41. Synthesis of N-(4-cyano-3-(4H-1,2,4-triazol-3-yl)thiophen-2-yl)-2-(quinolin-5-yl)acetamide (41)

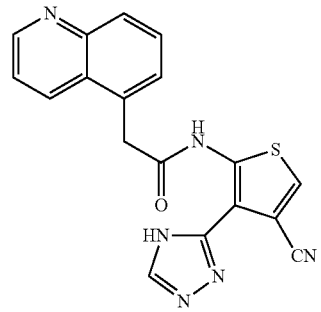 [SMILES: N#Cc1csc(NC(=O)Cc2cccc3ncccc23)c1-c1nnc[nH]1]

1.41.1. Methyl 4-bromo-2-(2-(quinolin-5-yl)acetamido)thiophene-3-carboxylate The title compound was prepared from methyl 2-amino-4-bromothiophene-3-carboxylate (660 mg, 2.8 mmol) and 2-(quinolin-5-yl)acetic acid using protocol A. 560 mg (49% yield). Method [1]: rt=1.666 min; MH+ 405/407.

1.41.2. Methyl 4-cyano-2-(2-(quinolin-5-yl)acetamido)thiophene-3-carboxylate A 20 mL microwave vessel was charged with methyl 4-bromo-2-(2-(quinolin-5-yl)acetamido)thiophene-3-carboxylate (560 mg, 1.38 mmol), CuCN (540 mg, 6 mmol), DMF (8 mL), and (1R,2R)—N$^1$,N$^2$-dimethylcyclohexane-1,2-diamine (300 uL). The reaction mixture was flushed with nitrogen and sealed under a teflon cap before being heated to 150° C. using microwave radiation for 0.5 h. The reaction mixture was concentrated under reduced pressure to give an oil that was partitioned between an organic layer of 10% iPrOH/chloroform and an aqueous layer saturated with sodium bicarbonate. The heterogeneous organic layer was filtered and concentrated under reduced pressure to give a green oil. The crude product was purified by column chromatography with 60-70% ethyl acetate/hexanes. Yield: 40 mg (8%). Method [1]: rt=1.401 min; MH+ 352.0.

1.41.3. 4-Cyano-2-(2-(quinolin-5-yl)acetamido)thiophene-3-carboxamide

The title compound was prepared from methyl 4-cyano-2-(2-(quinolin-5-yl)acetamido)thiophene-3-carboxylate using protocol H (8 mg, 80% yield). Method [1]: rt=0.665 min; MH+ 337.0.

1.41.4. (Z)-4-Cyano-N-((dimethylamino)methylene)-2-(2-(quinolin-5-yl)acetamido)-thiophene-3-carboxamide The title compound was prepared from 4-cyano-2-(2-(quinolin-5-yl)acetamido)thiophene-3-carboxamide (37 mg, 0.11 mmol) according to protocol C and was used without further purification. Method [1]: rt=1.291 min; MH+ 392.1.

1.41.5. N-(4-Cyano-3-(4H-1,2,4-triazol-3-yl)thiophen-2-yl)-2-(quinolin-5-yl)acetamide To a mixture of 4-cyano-N-((dimethylamino)methylene)-2-(2-(quinolin-5-yl)acetamido)thiophene-3-carboxamide (0.11 mmol) in HOAc (2 mL) was added hydrazine (19 uL of 65% aqueous solution). The reaction mixture was heated to 87° C. for 12 hours and was then cooled to 23° C. and concentrated. The residue was taken up in a 10% isopropanol/chloroform solution and washed with a saturated, aqueous solution of sodium bicarbonate. The organic solution was dried over sodium sulfate and concentrated to give a solid, which was purified by column chromatography (using 5 to 10% methanol/methylene chloride) and prep-HPLC (5-40% MeCN gradient). 5 mgs (13% for the final 2 steps). Method [8]: rt=8.1 min; MH+ 361.1. $^1$H-NMR (300 MHz, CDCl$_3$) δ 8.86 (s, 1H), 8.48 (d, J=8.6 Hz, 1H), 8.14 (d, J=8.5 Hz, 1H), 7.85 (m, 2H), 7.69 (d, J=6.6 Hz, 1H), 7.54 (m, 2H), 4.34 (s, 2H), 3.30 (s, 3H). $^{13}$C-NMR (75 MHz, DMSO-d$_6$) δ 168.7, 158.9, 158.4, 149.5, 139.5, 132.3, 131.3, 131.2, 130.5, 127.9, 127.2, 122.3, 118.3, 115.7, 112.5, 105.7, 105.6.

Compounds of Examples 1.42 through 1.48, below, were synthesized by activation of the corresponding carboxylic acids and condensation with 4-bromo-3-(4H-1,2,4-triazol-3-yl)thiophen-2-amine, which was prepared according to the scheme, below.

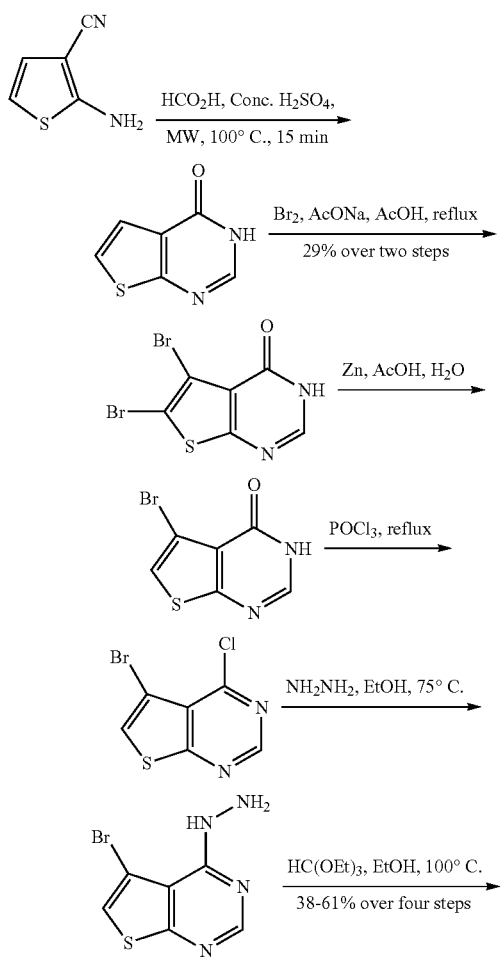

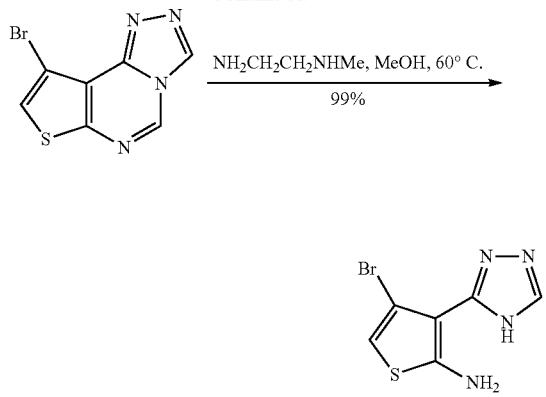

1.42. N-(4-Bromo-3-(1H-1,2,4-triazol-5-yl)thiophen-2-yl)-2-(2-oxo-7-(trifluoromethyl)quinolin-1(2H)-yl)acetamide

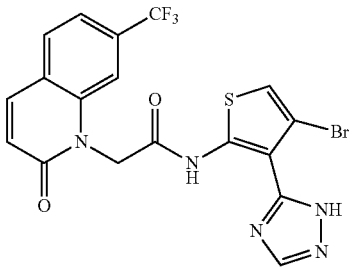 [SMILES: O=C(Cn1c(=O)ccc2ccc(C(F)(F)F)cc21)Nc1scc(Br)c1-c1ncn[nH]1]

Retention time (min)=5.456, method [7], MS(ESI) 497.9 (M+H); $^1$H NMR (300 MHz, CD$_3$OD) δ 7.92 (d, J=9.8 Hz, 1H), 7.79 (d, J=8.2 Hz, 1H), 7.73 (s, 1H), 7.52-7.55 (m, 2H), 6.96-7.01 (m, 2H), 5.34 (s, 2H).

1.43. N-(4-Bromo-3-(1H-1,2,4-triazol-5-yl)thiophen-2-yl)-2-(6-fluoro-2-oxo-3,4-dihydroquinolin-1(2H)-yl)acetamide

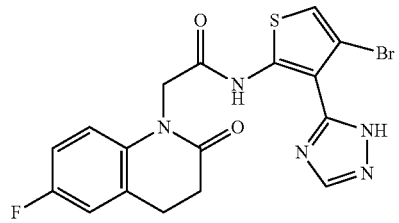 [SMILES: O=C(CN1C(=O)CCc2cc(F)ccc21)Nc1scc(Br)c1-c1ncn[nH]1]

Method[7], MS(ESI) 450.0 [M+H], Retention time=4.428 min; $^1$H-NMR (300 MHz, CDCl$_3$) δ 7.80 (s, 1H), 7.28 (s, 1H), 7.10-7.0 (m, 2H), 6.94 (s, 1H), 4.86 (d, J=3.84 Hz, 2H), 3.12-3.06 (m, 2H), 2.86-2.81 (m, 2H).

1.44. N-(4-Bromo-3-(1H-1,2,4-triazol-5-yl)thiophen-2-yl)-2-(7-fluoro-2-oxoquinolin-1(2H)-yl)acetamide

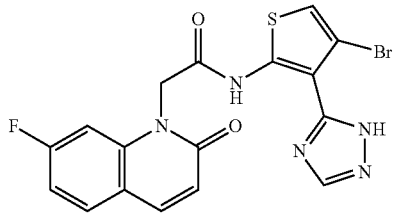 [SMILES: O=C(Cn1c(=O)ccc2ccc(F)cc21)Nc1scc(Br)c1-c1ncn[nH]1]

Method[7], MS(ESI) 448.0 [M+H], Retention time=4.417 min; $^1$H-NMR (300 MHz, CDCl$_3$) δ 7.86 (d, J=8.9 Hz, 1H), 7.70 (s, 1H), 7.66-7.60 (m, 1H), 7.04-6.90 (m, 2H), 6.95 (s, 1H), 6.85 (d, J=9.34 Hz, 1H), 5.26 (s, 2H).

1.45. N-(4-Bromo-3-(1H-1,2,4-triazol-5-yl)thiophen-2-yl)-2-(7-chloro-2-oxo-3,4-dihydroquinolin-1(2H)-yl)acetamide

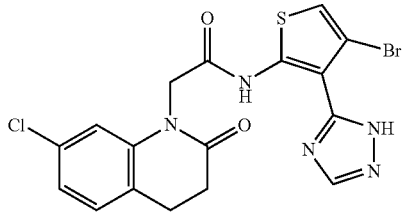 [SMILES: O=C(CN1C(=O)CCc2ccc(Cl)cc21)Nc1scc(Br)c1-c1ncn[nH]1]

Method[7], MS(ESI) 466.0 [M+H], Retention time=5.594 min; $^1$H-NMR (300 MHz, CDCl$_3$) δ 7.93 (s, 1H), 7.17 (d, J=7.7 Hz, 1H), 7.04 (dd, J=8.24, 1.65 Hz, 1H), 6.98 (s, 1H), 6.94 (d, J=1.65 Hz, 1H), 4.88 (s, 2H), 3.08-3.03 (m, 2H), 2.93-2.85 (m, 2H).

1.46. N-(4-Bromo-3-(1H-1,2,4-triazol-5-yl)thiophen-2-yl)-2-(6,7-difluoro-2-oxoquinolin-1(2H)-yl)acetamide

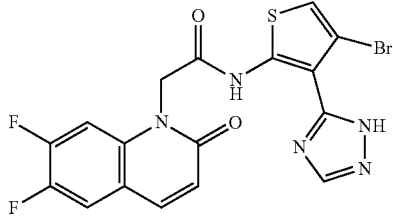 [SMILES: O=C(Cn1c(=O)ccc2cc(F)c(F)cc21)Nc1scc(Br)c1-c1ncn[nH]1]

Method[7], MS(ESI) 465.9 [M+H], Retention time=4.516 min; $^1$H-NMR (300 MHz, CDCl$_3$) δ 8.58 (b s, 1H), 8.07 (d, J=9.8 Hz, 1H), 8.02 (dd, J=10.44, 8.8 Hz, 1H), 7.91-7.84 (m, 1H), 7.33 (s, 1H), 6.79 (d, J=9.9 Hz, 1H), 5.27 (s, 2H).

1.47. N-(4-Bromo-3-(1H-1,2,4-triazol-5-yl)thiophen-2-yl)-2-(2-oxo-6-(trifluoromethyl)quinolin-1(2H)-yl)acetamide

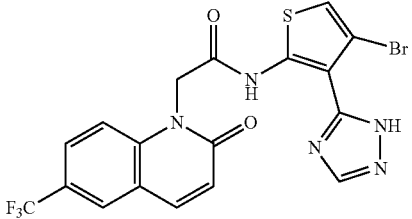 [SMILES: O=C(Cn1c(=O)ccc2cc(C(F)(F)F)ccc21)Nc1scc(Br)c1-c1ncn[nH]1]

Method[7], MS(ESI) 497.9 [M+H], Retention time=5.696 min; $^1$H-NMR (300 MHz, CDCl$_3$) δ 12.87 (b s, 1H), 7.92 (d, J=6.6 Hz, 1H), 7.73 (s, 1H), 7.77 (d, J=8.24 Hz, 1H), 7.73 (s, 1H), 7.42 (d, J=9.34 Hz, 1H), 6.98 (d, J=9.9 Hz, 1H), 6.95 (s, 1H), 5.33 (s, 2H).

1.48. N-(4-Bromo-3-(1H-1,2,4-triazol-5-yl)thiophen-2-yl)-2-(6-fluoro-2-oxoquinolin-1(2H)-yl)acetamide

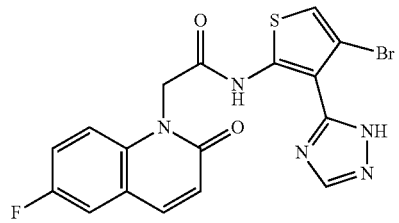 [SMILES: O=C(Cn1c(=O)ccc2cc(F)ccc21)Nc1scc(Br)c1-c1ncn[nH]1]

Method[7], MS(ESI) 448.0 [M+H], Retention time=4.347 min; $^1$H-NMR (300 MHz, CDCl$_3$) δ 7.82 (d, J=9.9 Hz, 1H), 7.68 (s, 1H), 7.37-7.33 (m, 1H), 7.28 (s, 1H), 7.26-7.23 (m, 1H), 6.95-6.92 (m, 2H), 5.30 (s, 2H).

1.49. Synthesis of N-(4-bromo-3-(1H-1,2,4-triazol-5-yl)thiophen-2-yl)-2-(2-oxo-1,6-naphthyridin-1(2H)-yl)acetamide

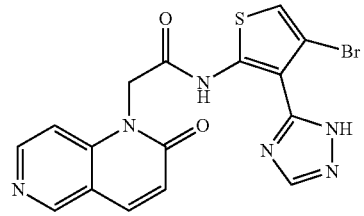 [SMILES: O=C(Cn1c(=O)ccc2cnccc21)Nc1scc(Br)c1-c1ncn[nH]1]

1.49.1. Methyl 2-(2-oxo-1,6-naphthyridin-1(2H)-yl)acetate

The title compound was prepared from 1,6-naphthyridin-2(1H)-one according to protocol K. Retention time (min)=0.949, method [3], MS(ESI) 219.1 (M+H).

1.49.2. 2-(2-Oxo-1,6-naphthyridin-1(2H)-yl)acetic acid

To a solution of methyl 2-(2-oxo-1,6-naphthyridin-1(2H)-yl)acetate (1.51 g, 6.92 mmol) in THF (10 mL) was added sodium hydroxide (4 mL of a 3 N aqueous solution, 13.8 mmol) and the reaction mixture was stirred at room temperature for 18 h. The resulting solution was diluted with ethyl acetate and washed with water. The aqueous phase was separated, adjusted to pH 2 with aqueous HCl and extracted with ethyl acetate. The organic phase was separated, dried ($Na_2SO_4$), filtered and concentrated under vacuum to give 2-(2-oxo-1,6-naphthyridin-1(2H)-yl)acetic acid. Retention time (min)=0.368, method [3], MS(ESI) 205.0 (M+H).

1.49.3. N-(4-Bromo-3-(1H-1,2,4-triazol-5-yl)thiophen-2-yl)-2-(2-oxo-1,6-naphthyridin-1(2H)-yl)acetamide The title compound was prepared from 2-(2-oxo-1,6-naphthyridin-1(2H)-yl)acetic acid (62 mg, 0.306 mmol) and 4-bromo-3-(1H-1,2,4-triazol-5-yl)thiophen-2-amine (25 mg, 0.101 mmol) according to Protocol L. Retention time (min)=1.258, method [7], MS(ESI) 431.0 (M+H); $^1$H NMR (300 MHz, $CD_3OD$) δ 9.10 (s, 1H), 8.65 (d, J=6.5 Hz, 1H), 8.33 (s, 1H), 8.23 (d, J=9.7 Hz, 1H), 7.75 (d, J=6.5 Hz, 1H), 7.15 (s, 1H), 7.01 (d, J=9.7 Hz, 1H), 5.39 (s, 2H).

1.50. Synthesis of N-(4-bromo-3-(1H-1,2,4-triazol-5-yl)thiophen-2-yl)-2-(2-oxo-1,5-naphthyridin-1(2H)-yl)acetamide

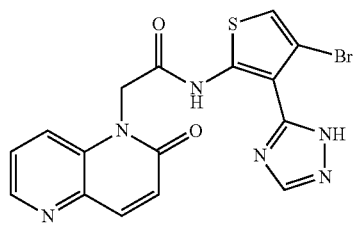 [SMILES: O=C(Cn1c(=O)ccc2ncccc21)Nc1scc(Br)c1-c1ncn[nH]1]

1.50.1. Methyl 2-(2-oxo-1,5-naphthyridin-1(2H)-yl)acetate 1,5-naphthyridin-2(1H)-one (2.05 g, 14.0 mmol) was treated with lithium hexamethyldisilazide instead of sodium hydride according to protocol K to give methyl 2-(2-oxo-1,5-naphthyridin-1(2H)-yl)acetate (224 mg). Retention time (min)=2.084, method [3], MS(ESI) 219.0 (M+H).

1.50.2. 2-(2-Oxo-1,5-naphthyridin-1(2H)-yl)acetic acid

To a solution of methyl 2-(2-oxo-1,5-naphthyridin-1(2H)-yl)acetate (0.205 g, 0.939 mmol) in THF (5 mL) was added sodium hydroxide (0.939 mL of a 3 N aqueous solution, 2.818 mmol) and the reaction mixture was stirred at 70° C. for 0.5 h. The resulting solution was concentrated under vacuum and co-evaporated from toluene to give 2-(2-oxo-1,5-naphthyridin-1(2H)-yl)acetic acid. Retention time (min)=1.033, method [3], MS(ESI) 205.1 (M+H).

1.50.3. N-(4-Bromo-3-(1H-1,2,4-triazol-5-yl)thiophen-2-yl)-2-(2-oxo-1,5-naphthyridin-1(2H)-yl)acetamide The title compound was prepared from 2-(2-oxo-1,5-naphthyridin-1(2H)-yl)acetic acid (42 mg, 0.204 mmol) and 4-bromo-3-(1H-1,2,4-triazol-5-yl)thiophen-2-amine (25 mg, 0.101 mmol) according to protocol A. Retention time (min)=2.295, method [7], MS(ESI) 431.0 (M+H); $^1$H NMR (300 MHz, $CD_3OD$) δ 8.57 (dd, J=4.6, 1.7 Hz, 1H), 8.16 (d, J=9.9 Hz, 1H), 8.11 (s, 1H), 7.98 (d, J=9.1 Hz, 1H), 7.62 (dd, J=8.8, 5.1 Hz, 1H), 7.01 (d, J=4.3 Hz, 1H), 7.05 (s, 1H), 5.33 (s, 2H).

1.51. Synthesis of N-(4-bromo-3-(1H-1,2,4-triazol-5-yl)thiophen-2-yl)-2-(2-oxo-3,4-dihydro-1,6-naphthyridin-1(2H)-yl)acetamide

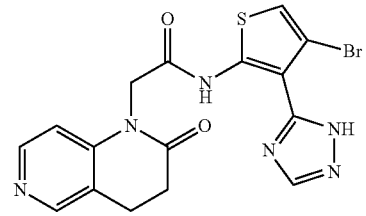 [SMILES: O=C(CN1C(=O)CCc2cnccc21)Nc1scc(Br)c1-c1ncn[nH]1]

1.51.1. 2-(2-Oxo-3,4-dihydro-1,6-naphthyridin-1(2H)-yl)acetic acid

A suspension of 2-(2-oxo-1,6-naphthyridin-1(2H)-yl)acetic acid (150 mg, 0.734 mmol) and Pd/C (20 mg) in methanol was shaken under a 40 psi atmosphere of $H_2$ for 18 h. The suspension was filtered through Celite and the filtrate was concentrated under vacuum to give 2-(2-oxo-3,4-dihydro-1,6-naphthyridin-1(2H)-yl)acetic acid. Retention time (min)=0.343, method [3], MS(ESI) 207.1 (M+H).

1.51.2. N-(4-Bromo-3-(1H-1,2,4-triazol-5-yl)thiophen-2-yl)-2-(2-oxo-3,4-dihydro-1,6-naphthyridin-1(2H)-yl)acetamide The title compound was prepared from 2-(2-oxo-3,4-dihydro-1,6-naphthyridin-1(2H)-yl)acetic acid (40 mg, 0.195 mmol) and 4-bromo-3-(1H-1,2,4-triazol-5-yl)thiophen-2-amine (24 mg, 0.0979 mmol) according to protocol A. Retention time (min)=8.108, method [6], MS(ESI) 433.0 (M+H); $^1$H NMR (300 MHz, $CD_3OD$) δ 8.61-8.48 (m, 3H), 7.51 (d, J=6.8 Hz, 1H), 7.16 (s, 1H), 5.08 (s, 2H) 3.29-3.25 (m, 2H), 2.98-2.93 (m, 2H).

1.52. Synthesis of N-(4-bromo-3-(1H-1,2,4-triazol-5-yl)thiophen-2-yl)-2-(2-oxo-3,4-dihydro-1,5-naphthyridin-1(2H)-yl)acetamide

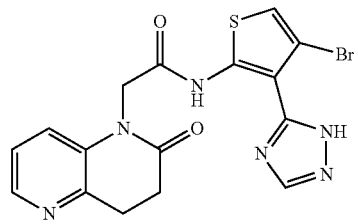 [SMILES: O=C(CN1C(=O)CCc2ncccc21)Nc1scc(Br)c1-c1ncn[nH]1]

1.52.1. 2-(2-Oxo-3,4-dihydro-1,5-naphthyridin-1 (2H)-yl)acetic acid 2-(2-oxo-1,5-naphthyridin-1(2H)-yl)acetic acid (90 mg, 0.441 mmol) was treated according to Example 1.51.1 to give 2-(2-oxo-3,4-dihydro-1,5-naphthyridin-1(2H)-yl)acetic acid. Retention time (min)=0.262, method [3], MS(ESI) 207.0 (M+H).

1.52.2. N-(4-Bromo-3-(1H-1,2,4-triazol-5-yl)thiophen-2-yl)-2-(2-oxo-3,4-dihydro-1,5-naphthyridin-1 (2H)-yl)acetamide N-(4-Bromo-3-(1H-1,2,4-triazol-5-yl)thiophen-2-yl)-2-(2-oxo-3,4-dihydro-1,5-naphthyridin-1(2H)-yl)acetamide was prepared from 2-(2-oxo-3,4-dihydro-1,5-naphthyridin-1(2H)-yl)acetic acid (42 mg, 0.203 mmol) and 4-bromo-3-(1H-1,2,4-triazol-5-yl)thiophen-2-amine (25 mg, 0.102 mmol) according to protocol A. Retention time (min)=1.274, method [7], MS(ESI) 433.0 (M+H); $^1$H NMR (300 MHz, CD$_3$OD) δ 8.35 (s, 1H), 8.23 (d, J=4.5 Hz, 1H), 7.65 (d, J=9.2 Hz, 1H), 7.45 (dd, J=9.2, 4.5 Hz, 1H), 7.12 (s, 1H), 4.91 (s, 2H) 3.34-3.33 (m, 2H), 2.98-2.93 (m, 2H).

1.53. Synthesis of N-(4-bromo-3-(1H-1,2,4-triazol-5-yl)thiophen-2-yl)-2-(2-oxo-7-(trifluoromethoxy) quinolin-1(2H)-yl)acetamide

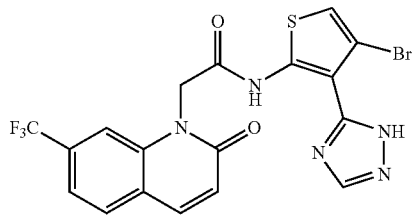

1.53.1. Ethyl 3-(2-amino-4-(trifluoromethoxy)phenyl)acrylate

The title compound was prepared from 2-bromo-5-(trifluoromethoxy)aniline according to protocol M. Retention time (min)=2.693, method [1], MS(ESI) 276.1 (M+H).

1.53.2. 7-(Trifluoromethoxy)quinolin-2(1H)-one 7-(Trifluoromethoxy)quinolin-2(1H)-one was prepared from ethyl 3-(2-amino-4-(trifluoromethoxy)phenyl)acrylate according to protocol N. Retention time (min)=1.803, method [1], MS(ESI) 230.1 (M+H).

1.53.3. Methyl 2-(2-oxo-7-(trifluoromethoxy)quinolin-1(2H)-yl)acetate

The title compound was prepared from 7-(trifluoromethoxy)quinolin-2(1H)-one according to protocol K. Retention time (min)=2.226, method [1], MS(ESI) 302.0 (M+H).

1.53.4. 2-(2-Oxo-7-(trifluoromethoxy)quinolin-1 (2H)-yl)acetic acid

Methyl 2-(2-oxo-7-(trifluoromethoxy)quinolin-1(2H)-yl) acetate (0.49 g, 1.62 mmol) was dissolved in THF (4 mL). Sodium hydroxide (1.08 mL of a 3 N aqueous solution, 3.25 mmol) was added and the reaction mixture was stirred 60° C. for 2 h. The resulting solution was diluted with ethyl acetate and washed with water. The aqueous phase was separated, adjusted to pH 2 with aqueous HCl and extracted with ethyl acetate. The organic phase was separated, dried (Na$_2$SO$_4$), filtered and concentrated under vacuum to give 2-(2-oxo-7-(trifluoromethoxy)quinolin-1(2H)-yl)acetic acid. Retention time (min)=1.75, method [1], MS(ESI) 288.1 (M+H).

1.53.5. N-(4-Bromo-3-(1H-1,2,4-triazol-5-yl)thiophen-2-yl)-2-(2-oxo-7-(trifluoromethoxy)quinolin-1 (2H)-yl)acetamide The title compound was prepared from 2-(2-oxo-7-(trifluoromethoxy)quinolin-1(2H)-yl)acetic acid (79 mg, 0.275 mmol) and 4-bromo-3-(1H-1,2,4-triazol-5-yl)thiophen-2-amine (35 mg, 0.137 mmol) according to protocol A. Retention time (min)=6.037, method [7], MS(ESI) 514.0 (M+H); $^1$H NMR (300 MHz, CD$_3$OD) δ 8.15 (s, 1H), 8.11 (d, J=9.9 Hz, 1H), 7.88 (d, J=9.1 Hz, 1H), 7.41 (s, 1H), 7.26 (m, 1H), 7.10 (s, 1H), 6.81 (d, J=9.9 Hz, 1H), 5.31 (s, 2H).

1.54 Synthesis of N-(4-bromo-3-(1H-1,2,4-triazol-5-yl)thiophen-2-yl)-2-(7-cyano-2-oxoquinolin-1 (2H)-yl)acetamide

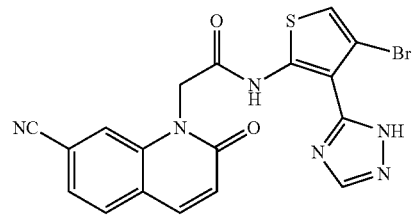 [SMILES: N#Cc1ccc2ccc(=O)n(CC(=O)Nc3scc(Br)c3-c3ncn[nH]3)c2c1]

1.54.1. Methyl 2-(7-bromo-2-oxoquinolin-1(2H)-yl)acetate

The title compound was prepared from 7-bromoquinolin-2(1H)-one according to protocol K. Retention time (min)=1.89, method [1], MS(ESI) 296.0 (M+H).

1.54.2. Methyl 2-(7-cyano-2-oxoquinolin-1(2H)-yl)acetate

CuCN (0.211 g, 2.36 mmol) and Pd(PPh$_3$)$_4$ (0.136 g, 0.118 mmol) were added to a solution of methyl 2-(7-bromo-2-oxoquinolin-1(2H)-yl)acetate (0.35 g, 1.18 mmol) in DMF (1 mL) in a screw cap vial. The vial was sealed and placed into a oil bath at 120° C. and the reaction mixture was stirred for 18 h. The resulting mixture was diluted with Et$_2$O and washed with brine. The organic phase was separated, dried (Na$_2$SO$_4$), filtered, concentrated under vacuum and the residue was purified on a silica gel column to give methyl 2-(7-cyano-2-oxoquinolin-1(2H)-yl)acetate (0.204 g, 71%). Retention time (min)=1.464, method [1], MS(ESI) 243.1 (M+H).

1.54.3. 2-(7-Cyano-2-oxoquinolin-1(2H)-yl)acetic acid

Trimethyl tin hydroxide (0.388 g, 2.14 mmol) was added to a solution of methyl 2-(7-cyano-2-oxoquinolin-1(2H)-yl)

acetate (0.104 g, 0.429 mmol) in 1,2-dichloroethane (5 mL) and the resulting suspension was stirred at reflux for 4 h. The reaction mixture was diluted with dichloromethane and washed with 1N aqueous HCl. Filtration of the organic phase provided 87 mg (89%) of 2-(7-cyano-2-oxoquinolin-1(2H)-yl)acetic acid. Retention time (min)=0.987, method [1], MS(ESI) 229.1 (M+H).

1.54.4. N-(4-Bromo-3-(1H-1,2,4-triazol-5-yl)thiophen-2-yl)-2-(7-cyano-2-oxoquinolin-1(2H)-yl)acetamide N-(4-Bromo-3-(1H-1,2,4-triazol-5-yl)thiophen-2-yl)-2-(7-cyano-2-oxoquinolin-1(2H)-yl)acetamide was prepared from 2-(7-cyano-2-oxoquinolin-1(2H)-yl)acetic acid (65 mg, 0.286 mmol) and 4-bromo-3-(1H-1,2,4-triazol-5-yl)thiophen-2-amine (21 mg, 0.143 mmol) according to protocol A. Retention time (min)=4.143, method [7], MS(ESI) 454.9 (M+H); $^1$H NMR (300 MHz, DMSO-$d_6$) δ 12.18 (s, 1H), 8.56 (s, 1H), 8.24 (s, 1H), 8.16 (d, J=9.0 Hz, 1H), 8.01 (d, J=8.0 Hz, 1H), 7.70 (d, J=8.01 Hz, 1H), 7.28 (s, 1H), 6.90 (d, J=9.0 Hz, 1H), 5.31 (s, 2H).

1.55. Synthesis of N-(4-bromo-3-(1H-1,2,4-triazol-5-yl)thiophen-2-yl)-2-(isoquinolin-8-yl)acetamide N-(4-Bromo-3-(1H-1,2,4-triazol-5-yl)thiophen-2-yl)-2-(isoquinolin-8-yl)acetamide was prepared from 2-(isoquinolin-8-yl)acetic acid (53 mg, 0.286 mmol) and 4-bromo-3-(1H-1,2,4-triazol-5-yl)thiophen-2-amine (35 mg, 0.143 mmol) according to protocol A. Retention time (min)=1.769, method [7], MS(ESI) 414.0 (M+H); $^1$H NMR (300 MHz, CD$_3$OD) δ 9.84 (bs, 1H), 8.55 (bs, 1H), 8.41 (d, J=6.0 Hz, 1H), 8.26-8.23 (m, 2H), 8.18 (dd, J=8.1, 7.2 Hz, 1H), 7.99 (d, J=4.0 Hz, 1H), 7.09 (s, 1H), 4.61 (s, 2H).

1.56. Synthesis of N-(4-bromo-3-(1H-1,2,4-triazol-5-yl)thiophen-2-yl)-2-(6-fluoroquinolin-5-yl)acetamide N-(4-bromo-3-(1H-1,2,4-triazol-5-yl)thiophen-2-yl)-2-(6-fluoroquinolin-5-yl)acetamide was prepared from 2-(6-fluoroquinolin-5-yl)acetic acid (42 mg, 0.203 mmol) and 4-bromo-3-(1H-1,2,4-triazol-5-yl)thiophen-2-amine (25 mg, 0.102 mmol) according to protocol A. Retention time (min)=2.499, method [7], MS(ESI) 432.0 (M+H); $^1$H NMR (300 MHz, CD$_3$OD) δ 8.99 (dd, J=4.2, 1.1 Hz, 1H), 8.86 (d, J=7.9 Hz, 1H), 8.23 (dd, J=8.9, 4.5 Hz, 1H), 8.08 (s, 1H), 7.85 (dd, J=9.4, 9.2 Hz, 1H), 7.81 (dd, J=9.2, 4.5 Hz, 1H), 7.07 (s, 1H), 4.48 (s, 2H).

1.57 Synthesis of N-(4-bromo-3-(1H-1,2,4-triazol-5-yl)thiophen-2-yl)-2-(6-fluoroquinolin-7-yl)acetamide N-(4-Bromo-3-(1H-1,2,4-triazol-5-yl)thiophen-2-yl)-2-(6-fluoroquinolin-7-yl)acetamide was prepared from 2-(6-fluoroquinolin-7-yl)acetic acid (42 mg, 0.203 mmol) and 4-bromo-3-(1H-1,2,4-triazol-5-yl)thiophen-2-amine (25 mg, 0.102 mmol) according to protocol A. Retention time (min)=2.338, method [7], MS(ESI) 432.0 (M+H); $^1$H NMR (300 MHz, CD$_3$OD) δ 9.02 (d, J=4.2 Hz, 1H), 8.73 (d, J=8.0 Hz, 1H), 8.24 (d, J=7.2 Hz, 1H), 7.93 (s, 1H), 7.88 (d, J=10.0 Hz, 1H), 7.82 (dd, J=9.0, 4.2 Hz, 1H), 7.09 (s, 1H), 4.42 (s, 2H).

1.58. Synthesis of N-(4-Bromo-3-(1H-1,2,4-triazol-5-yl)thiophen-2-yl)-2-(2-oxo-7-(trifluoromethyl)-1,6-naphthyridin-1(2H)-yl)acetamide

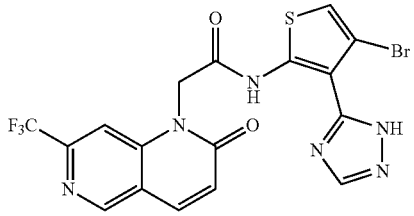

1.58.1. 5-Iodo-2-(trifluoromethyl)pyridin-4-ol

Iodine (8.16 g, 32.1 mmol) was added in five portions to a solution of 2-(trifluoromethyl)pyridin-4-ol (5 g, 30.65 mmol) and K$_2$CO$_3$ (4.66 g, 33.7 mmol) in methanol (34 mL) at 0° C. and the resulting mixture was stirred at room temperature for 20 h. The solution was washed with saturated aqueous sodium sulfite then acetic acid (10 mL) was added and the solution was extracted with ethyl acetate, dried (Na$_2$SO$_4$), filtered, concentrated under vacuum and the residue was purified on a silica gel column to give 5-iodo-2-(trifluoromethyl)pyridin-4-ol (5.1 g, 57%). Retention time (min)=1.761, method [1], MS(ESI) 290.9 (M+H).

1.58.2. 4-Chloro-5-iodo-2-(trifluoromethyl)pyridine

A solution of 5-iodo-2-(trifluoromethyl)pyridin-4-ol (4.8 g, 16.6 mmol) in POCl$_3$ (30 mL) was heated to 100° C. for 30 minutes. The resulting solution was concentrated under vacuum and the residue was neutralized by the addition of ice and aqueous potassium carbonate. The solution was extracted with ethyl acetate, dried (Na$_2$SO$_4$), filtered and concentrated under vacuum to give 4-chloro-5-iodo-2-(trifluoromethyl)pyridine. Retention time (min)=2.594, method [1], MS(ESI) 307.9 (M+H).

1.58.3. 5-Iodo-2-(trifluoromethyl)pyridin-4-amine

Concentrated aqueous ammonium hydroxide (10 mL) was added to a solution of 4-chloro-5-iodo-2-(trifluoromethyl)pyridine (4.11 g, 13.3 mmol) in DMSO in a glass pressure tube. The tube was sealed and placed in an oil bath pre-heated to 110° C. for 48 h. The resulting solution was diluted with brine, extracted with ethyl acetate, dried (Na$_2$SO$_4$), filtered and concentrated under vacuum to give 5-iodo-2-(trifluoromethyl)pyridin-4-amine. Retention time (min)=1.584, method [1], MS(ESI) 289.0 (M+H).

1.58.4. Ethyl 3-(4-amino-6-(trifluoromethyl)pyridin-3-yl)acrylate

Ethyl 3-(4-amino-6-(trifluoromethyl)pyridin-3-yl)acrylate was prepared from 5-iodo-2-(trifluoromethyl)pyridin-4-amine according to protocol M. Retention time (min)=1.064, method [1], MS(ESI) 215.1 (M+H).

158.5. 7-(Trifluoromethyl)-1,6-naphthyridin-2(1H)-one 7-(Trifluoromethyl)-1,6-naphthyridin-2(1H)-one was prepared from ethyl 3-(4-amino-6-(trifluoromethyl)pyridine-3- yl)acrylate according to protocol N. Retention time (min)=1.064, method [1], MS(ESI) 215.1 (M+H).

1.58.6. Methyl 2-(2-oxo-7-(trifluoromethyl)-1,6-naphthyridin-1(2H)-yl)acetate Methyl 2-(2-oxo-7-(trifluoromethyl)-1,6-naphthyridin-1(2H)-yl)acetate was prepared from 7-(trifluoromethyl)-1,6-naphthyridin-2(1H)-one according to Protocol K. Retention time (min)=1.621, method [1], MS(ESI) 287.1 (M+H).

1.58.7. 2-(2-Oxo-7-(trifluoromethyl)-1,6-naphthyridin-1(2H)-yl)acetic acid

Methyl 2-(2-oxo-7-(trifluoromethyl)-1,6-naphthyridin-1(2H)-yl)acetate (0.069 g, 0.10 mmol) was treated according to Example 1.53.4 to give 2-(2-oxo-7-(trifluoromethyl)-1,6-naphthyridin-1(2H)-yl)acetic acid. Retention time (min)=1.081, method [1], MS(ESI) 273.1 (M+H).

1.58.8. N-(4-Bromo-3-(1H-1,2,4-triazol-5-yl)thiophen-2-yl)-2-(2-oxo-7-(trifluoromethyl)-1,6-naphthyridin-1(2H)-yl)acetamide The title compound was prepared from 2-(2-oxo-7-(trifluoromethyl)-1,6-naphthyridin-1(2H)-yl)acetic acid (55 mg, 0.203 mmol) and 4-bromo-3-(1H-1,2,4-triazol-5-yl)thiophen-2-amine (25 mg, 0.102 mmol) according to protocol A. Retention time (min)=4.505, method [7], MS(ESI) 499.0 (M+H); $^1$H NMR (300 MHz, CD$_3$OD) δ 9.06 (s, 1H), 8.31 (s, 1H), 8.24 (d, J=9.4 Hz, 1H), 7.94 (s, 1H), 7.14 (s, 1H), 6.99 (d, J=9.4 Hz, 1H), 5.39 (s, 2H).

1.59. Synthesis of N-(4-bromo-3-(1H-1,2,4-triazol-5-yl)thiophen-2-yl)-2-(5-oxopyrazolo[1,5-a]pyrimidin-4(5H)-yl)acetamide

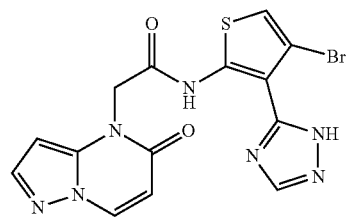 [SMILES: O=C(Cn1c(=O)ccn2nccc12)Nc1scc(Br)c1-c1ncn[nH]1]

1.59.1. Pyrazolo[1,5-a]pyrimidin-5(4H)-one 1,3-Dimethyl uracil (3.15 g, 22.5 mmol) and sodium ethoxide (23 mL of a 21% solution in ethanol) were added to a solution of 1H-pyrazol-5-amine (1.7 g, 20.4 mmol) in ethanol (50 mL). The resulting mixture was heated to 60° C. for 2 h and was then cooled to room temperature. The pale brown solid was isolated by filtration to give pyrazolo[1,5-a]pyrimidin-5(4H)-one (1.6 g, 58%). Retention time (min)=0.820, method [3], MS(ESI) 136.1 (M+H).

1.59.2. Methyl 2-(5-oxopyrazolo[1,5-a]pyrimidin-4(5H)-yl)acetate

Methyl 2-(5-oxopyrazolo[1,5-a]pyrimidin-4(5H)-yl)acetate was prepared from pyrazolo[1,5-a]pyrimidin-5(4H)-one according to Protocol K. Retention time (min)=1.951, method [3], MS(ESI) 208.1 (M+H).

1.59.3. 2-(5-Oxopyrazolo[1,5-a]pyrimidin-4(5H)-yl)acetic acid

Methyl 2-(5-oxopyrazolo[1,5-a]pyrimidin-4(5H)-yl)acetate (0.26 g, 1.25 mmol) was treated according to Example 1.54.3 to give 2-(5-oxopyrazolo[1,5-a]pyrimidin-4(5H)-yl) acetic acid. Retention time (min)=1.00, method [3], MS(ESI) 194.1 (M+H).

1.59.4. N-(4-Bromo-3-(1H-1,2,4-triazol-5-yl)thiophen-2-yl)-2-(5-oxopyrazolo[1,5-a]pyrimidin-4(5H)-yl)acetamide The title compound was prepared from 2-(5-oxopyrazolo[1,5-a]pyrimidin-4(5H)-yl)acetic acid (39 mg, 0.203 mmol) and 4-bromo-3-(1H-1,2,4-triazol-5-yl)thiophen-2-amine (25 mg, 0.102 mmol) according to protocol A. Retention time (min)=2.451, method [7], MS(ESI) 420.0 (M+H); $^1$H NMR (300 MHz, CDCl$_3$) δ 8.28 (d, J=8.5 Hz, 1H), 7.83 (s, 1H), 7.77 (d, J=2.6 Hz, 1H), 6.97 (s, 1H), 6.25 (d, J=7.9 Hz, 1H), 5.94 (d, J=2.6 Hz, 1H), 4.98 (s, 2H).

1.60. Synthesis of 2-(2-oxo-1,6-naphthyridin-1(2H)-yl)-N-(2-(thiazol-4-yl)thiophen-3-yl)acetamide The title compound was prepared from 2-(2-oxo-1,6-naphthyridin-1(2H)-yl)acetic acid (83 mg, 0.307 mmol) and 3-(1H-1,2,4-triazol-5-yl)thiophen-2-amine (28 mg, 0.154 mmol) according to protocol A. Retention time (min)=1.460, method [7], MS(ESI) 369.1 (M+H); $^1$H NMR (300 MHz, CD$_3$OD) δ 9.09 (s, 1H), 8.89 (d, J=2.3 Hz, 1H), 8.62 (d, J=6.6 Hz, 1H), 8.23 (d, J=9.7 Hz, 1H), 7.81-7.76 (m, 2H), 7.65 (d, J=2.3 Hz, 1H), 7.35 (d, J=5.5 Hz, 1H), 7.01 (d, J=9.0 Hz, 1H), 5.30 (s, 2H).

1.61. Synthesis of N-(4-bromo-3-(1H-1,2,4-triazol-5-yl)thiophen-2-yl)-2-(2-oxo-6-(trifluoromethyl)-1,5-naphthyridin-1(2H)-yl)acetamide

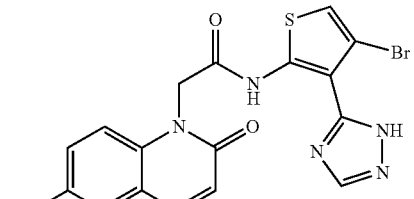

1.61.1. 2-Iodo-6-(trifluoromethyl)pyridin-3-amine

Iodine (7.83 g, 30.84 mmol) and silver sulfate (9.6 g, 30.84 mmol) were added to a solution of 6-(trifluoromethyl)pyridin-3-amine (5 g, 30.84 mmol) in ethanol (200 ml) and the resulting suspension was stirred at room temperature for 18 h. the solution was filtered and the filtrate was concentrated under vacuum. The residue was re-dissolved in methylene chloride and washed with aqueous NaOH (1 N), dried (Na$_2$SO$_4$), filtered and concentrated under vacuum to give 2-iodo-6-(trifluoromethyl)pyridin-3-amine. Retention time (min)=2.136, method [1], MS(ESI) 289.01 (M+H).

1.61.2. Ethyl 3-(3-amino-6-(trifluoromethyl)pyridin-2-yl)acrylate

Ethyl 3-(3-amino-6-(trifluoromethyl)pyridin-2-yl)acrylate was prepared from 2-iodo-6-(trifluoromethyl)pyridin-3-amine according to protocol M. Retention time (min)=2.350, method [1], MS(ESI) 261.1 (M+H).

1.61.3. 6-(Trifluoromethyl)-1,5-naphthyridin-2(1H)-one 6-(Trifluoromethyl)-1,5-naphthyridin-2(1H)-one was prepared from ethyl 3-(3-amino-6-(trifluoromethyl)pyridin-2-yl)acrylate according to protocol N. Retention time (min)=1.401, method [1], MS(ESI) 215.0 (M+H).

1.61.4. Methyl 2-(2-oxo-6-(trifluoromethyl)-1,5-naphthyridin-1(2H)-yl)acetate Methyl 2-(2-oxo-6-(trifluoromethyl)-1,5-naphthyridin-1(2H)-yl)acetate was prepared from 6-(trifluoromethyl)-1,5-naphthyridin-2(1H)-one according to Protocol K. Retention time (min)=1.822, method [1], MS(ESI) 287.1 (M+H).

1.61.5. 2-(2-Oxo-6-(trifluoromethyl)-1,5-naphthyridin-1(2H)-yl)acetic acid

Methyl 2-(2-oxo-6-(trifluoromethyl)-1,5-naphthyridin-1(2H)-yl)acetate (0.15 g, 0.524 mmol) was treated according to Ex. 1.53.4 to give 2-(2-oxo-6-(trifluoromethyl)-1,5-naphthyridin-1(2H)-yl)acetic acid. Retention time (min)=1.535, method [1], MS(ESI) 273.0 (M+H).

1.61.6. N-(4-Bromo-3-(1H-1,2,4-triazol-5-yl)thiophen-2-yl)-2-(2-oxo-6-(trifluoromethyl)-1,5-naphthyridin-1(2H)-yl)acetamide The title compound was prepared from 2-(2-oxo-6-(trifluoromethyl)-1,5-naphthyridin-1(2H)-yl)acetic acid (66 mg, 0.245 mmol) and 4-bromo-3-(1H-1,2,4-triazol-5-yl)thiophen-2-amine (30 mg, 0.122 mmol) according to protocol A. Retention time (min)=5.195, method [7], MS(ESI) 499.0 (M+H); $^1$H NMR (300 MHz, CD$_3$OD) δ 8.26-8.21 (m, 3H), 7.96 (d, J=8.9 Hz, 1H), 7.17-7.13 (m, 2H), 5.37 (s, 2H).

1.62. Synthesis of N-(4-bromo-3-(1H-1,2,4-triazol-5-yl)thiophen-2-yl)-2-(5-oxo-2-(trifluoromethyl)pyrazolo[1,5-a]pyrimidin-4(5H)-yl)acetamide

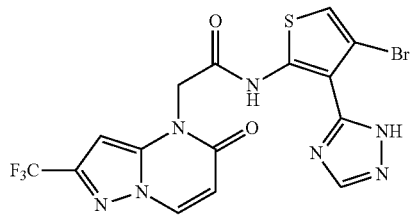 [SMILES: O=C(Cn1c(=O)ccn2nc(C(F)(F)F)cc12)Nc1scc(Br)c1-c1ncn[nH]1]

1.62.1. 2-(Trifluoromethyl)pyrazolo[1,5-a]pyrimidin-5(4H)-one 3-(Trifluoromethyl)-1H-pyrazol-5-amine (4.8 g, 31.7 mmol) was subjected to the protocol in Example 1.59.1 to give 2-(trifluoromethyl)pyrazolo[1,5-a]pyrimidin-5(4H)-one. Retention time (min)=1.220, method [1], MS(ESI) 204.0 (M+H).

1.62.2. Methyl 2-(5-oxo-2-(trifluoromethyl)pyrazolo[1,5-a]pyrimidin-4(5H)-yl)acetate Methyl 2-(5-oxo-2-(trifluoromethyl)pyrazolo[1,5-a]pyrimidin-4(5H)-yl)acetate was prepared from 2-(trifluoromethyl)pyrazolo[1,5-a]pyrimidin-5(4H)-one according to protocol K. Retention time (min)=1.846, method [1], MS(ESI) 276.0 (M+H).

1.62.3. 2-(5-Oxo-2-(trifluoromethyl)pyrazolo[1,5-a]pyrimidin-4(5H)-yl)acetic acid Methyl 2-(5-oxo-2-(trifluoromethyl)pyrazolo[1,5-a]pyrimidin-4(5H)-yl)acetate (0.129 g, 0.469 mmol) was subjected to the conditions in Example 1.54.3 to give 2-(5-oxo-2-(trifluoromethyl)pyrazolo[1,5-a]pyrimidin-4(5H)-yl) acetic acid. Retention time (min)=1.448, method [1], MS(ESI) 262.2 (M+H).

1.62.4. N-(4-Bromo-3-(1H-1,2,4-triazol-5-yl)thiophen-2-yl)-2-(5-oxo-2-(trifluoromethyl)pyrazolo[1,5-a]pyrimidin-4(5H)-yl)acetamide The title compound was prepared from 2-(5-oxo-2-(trifluoromethyl)pyrazolo[1,5-a]pyrimidin-4(5H)-yl)acetic acid (63 mg, 0.244 mmol) and 4-bromo-3-(1H-1,2,4-triazol-5-yl)thiophen-2-amine (30 mg, 0.122 mmol) according to protocol A. Retention time (min)=4.975, method [7], MS(ESI) 488.0 (M+H); $^1$H NMR (300 MHz, DMSO-d$_6$) δ 8.79 (d, J=7.4 Hz, 1H), 8.61 (bs, 1H), 7.32 (s, 1H), 6.96 (s, 1H), 6.45 (d, J=7.4 Hz, 1H), 5.01 (s, 2H).

1.63. Synthesis of N-(4-bromo-3-(1-methyl-1H-1,2,4-triazol-3-yl)thiophen-2-yl)-2-(2-oxo-3,4-dihydro-1,5-naphthyridin-1(2H)-yl)acetamide Sodium hydride (4.2 mg of a 60% dispersion in mineral oil, 0.107 mmol) was added to a solution of N-(4-bromo-3-(1H-1,2,4-triazol-3-yl)thiophen-2-yl)-2-(2-oxo-3,4-dihydro-1,5-naphthyridin-1(2H)-yl)acetamide (31 mg, 0.0715 mmol) in DMF (0.1 mL) at 0° C. The suspension was stirred for 5 minutes after which iodomethane (12 mg, 0.058 mmol) was added. The reaction mixture was stirred at room temperature for 20 minutes then diluted with water, extracted with ethyl acetate, dried (Na$_2$SO$_4$), filtered, concentrated under vacuum and purified by preparative HPLC to give N-(4-bromo-3-(1-methyl-1H-1,2,4-triazol-3-yl)thiophen-2-yl)-2-(2-oxo-3,4-dihydro-1,5-naphthyridin-1(2H)-yl)acetamide. Retention time (min)=1.740, method [7], MS(ESI) 447.0 (M+H); $^1$H NMR (300 MHz, CD$_3$OD) δ 8.47 (s, 1H), 8.33 (d, J=5.2 Hz, 1H), 7.85 (bs, 1H), 7.61 (bs, 1H), 7.11 (s, 1H), 4.94 (s, 2H), 4.02 (s, 3H), 3.41-3.36 (m, 2H), 3.01-2.97 (m, 2H).

1.64. Synthesis of N-(4-Chloro-3-(1H-1,2,4-triazol-5-yl)thiophen-2-yl)-2-(5-oxopyrazolo[1,5-a]pyrimidin-4(5H)-yl)acetamide The title compound was prepared from 2-(5-oxopyrazolo[1,5-a]pyrimidin-4(5H)-yl)acetic acid (94 mg, 0.488 mmol) and 4-chloro-3-(1H-1,2,4-triazol-5-yl)thiophen-2-amine (49 mg, 0.244 mmol) according to protocol A. Retention time (min)=2.161, method [7], MS(ESI) 376.0 (M+H); $^1$H NMR (300 MHz, CDCl₃) δ 8.31 (d, J=8.1 Hz, 1H), 7.83 (s, 1H), 7.76 (s, 1H), 6.85 (s, 1H), 6.27 (d, J=8.1 Hz, 1H), 5.94 (s, 1H), 4.98 (s, 2H).

1.65. Synthesis of N-(4-Chloro-3-(1-methyl-1H-1,2,4-triazol-3-yl)thiophen-2-yl)-2-(5-oxopyrazolo[1,5-a]pyrimidin-4(5H)-yl)acetamide Iodomethane (36 mg, 0.255 mmol) and K₂CO₃ (44 mg, 0.319 mmol) were added to a solution of N-(4-chloro-3-(1H-1,2,4-triazol-3-yl)thiophen-2-yl)-2-(5-oxopyrazolo[1,5-a]pyrimidin-4(5H)-yl)acetamide (80 mg, 0.212 mmol) in DMF (1 mL). The reaction mixture was stirred at room temperature for 30 minutes and was subsequently diluted with ethyl acetate and washed with brine. The organic phase was dried (Na₂SO₄), filtered, concentrated under vacuum and purified by preparative HPLC to give N-(4-chloro-3-(1-methyl-1H-1,2,4-triazol-3-yl)thiophen-2-yl)-2-(5-oxopyrazolo[1,5-a]pyrimidin-4(5H)-yl)acetamide. Retention time (min)=3.00, method [7], MS(ESI) 390.1 (M+H); ¹H NMR (300 MHz, CD₃Cl) δ 8.25 (d, J=8.2 Hz, 1H), 7.90 (s, 1H), 7.76 (d, J=2.1 Hz, 1H), 6.79 (s, 1H), 6.22 (d, J=8.2 Hz, 1H), 5.97 (d, J=2.1 Hz, 1H), 5.36 (s, 2H), 3.99 (s, 3H).

1.66. Synthesis of N-(4-Chloro-3-(1-methyl-1H-1,2,4-triazol-3-yl)thiophen-2-yl)-2-(2-oxo-6-(trifluoromethyl)-1,5-naphthyridin-1(2H)-yl)acetamide The title compound was prepared from N-(4-chloro-3-(1H-1,2,4-triazol-3-yl)thiophen-2-yl)-2-(2-oxo-6-(trifluoromethyl)-1,5-naphthyridin-1(2H)-yl)acetamide (51 mg, 0.112 mmol) using the conditions in Example 1.65, and was purified by preparative HPLC. Retention time (min)=5.927, method [7], MS(ESI) 469.1 (M+H); ¹H NMR (300 MHz, DMSO-d₆) δ 8.51 (s, 1H), 8.31 (d, J=8.9 Hz, 1H), 8.20 (d, J=9.8 Hz, 1H), 8.10 (d, J=8.9 Hz, 1H), 7.18 (s, 1H), 7.13 (d, J=9.8 Hz, 1H), 5.35 (s, 2H), 3.92 (s, 3H).

1.67. Synthesis of N-(4-chloro-3-(1H-1,2,4-triazol-3-yl)thiophen-2-yl)-2-(2-oxo-6-(trifluoromethyl)-1,5-naphthyridin-1(2H)-yl)acetamide The title compound was prepared from 2-(2-oxo-6-(trifluoromethyl)-1,5-naphthyridin-1(2H)-yl)acetic acid (160 mg, 0.588 mmol) and 4-chloro-3-(1H-1,2,4-triazol-3-yl)thiophen-2-amine (59 mg, 0.294 mmol) according to protocol A. Retention time (min)=5.046, method [7], MS(ESI) 455.1 (M+H); ¹H NMR (300 MHz, DMSO-d₆) δ 8.62 (s, 1H), 8.30 (d, J=8.9 Hz, 1H), 8.21 (d, J=9.8 Hz, 1H), 8.09 (d, J=8.9 Hz, 1H), 7.20 (s, 1H), 7.13 (d, J=9.8 Hz, 1H), 5.36 (s, 2H).

1.68. Synthesis of N-(4-bromo-3-(1H-1,2,4-triazol-3-yl)thiophen-2-yl)-2-(3-fluoroquinolin-8-yl)acetamide

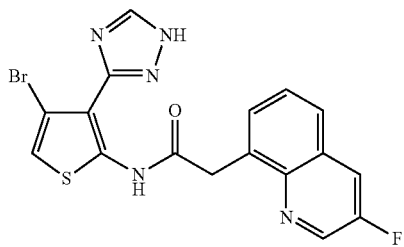 [SMILES: O=C(Cc1cccc2cc(F)cnc12)Nc1scc(Br)c1-c1nc[nH]n1]

1.68.1. 3-Fluoroquinoline

Tert-butylnitrite (4.6 ml, 38.7 mmol) was added dropwise over 15 min to a solution of quinolin-3-amine (4.61 g, 32.0 mmol) and borontrifluoride-etherate (6 ml, 47.3 mmol) in dichlorobenzene (100 ml). The solution was heated to 100° C. After stirring for 1 h, the solution was cooled to ambient temperature and the dichlorobenzene was decanted leaving 3-fluoroquinoline as a black residue. Method [8] retention time 3.28 min by HPLC (M+ 148).

1.68.2. 3-Fluoro-8-nitroquinoline and 3-fluoro-5-nitroquinoline

A solution of 3:1 concentrated sulfuric acid/concentrated nitric acid (32 ml) was added dropwise to 3-fluoroquinoline (13.04 g, 88.6 mmol) in concentrated sulfuric acid (100 ml) at 0° C. After stirring for 2 h, the solution was made alkaline with 10 N aq. NaOH and extracted with diethyl ether. The combined organic extracts were dried over magnesium sulfate, filtered, and concentrated under reduced pressure to yield 3-fluoro-8-nitroquinoline and 3-fluoro-5-nitroquinoline as a yellow solid. Method [7] retention time 3.50 and 3.92 min by HPLC (M+ 193) and (M+ 193).

1.68.3. 3-Fluoroquinolin-8-amine and 3-fluoroquinolin-5-amine

3-Fluoro-8-nitroquinoline, 3-fluoro-5-nitroquinoline, and tin(II)chloride-dihydrate (68.23 g, 302 mmol) in ethyl acetate (200 ml) was placed into a preheated oil bath at 60° C. After heating for 4 h, the solution was cooled to ambient temperature, diluted with 3 N aq. NaOH, and filtered through a pad of celite. The filtrate was extracted with ethyl acetate, the combined organic extracts were dried over magnesium sulfate, filtered, and concentrated under reduced pressure. The residue was flash chromatographed with 19:1, 9:1, 17:3, 4:1, 3:1, 7:3, and 3:2 hexane:ethyl acetate as the eluant to afford 2.14 g (11% yield over two steps) 3-fluoroquinolin-8-amine and 7.02 g (37% yield over two steps) of 3-fluoroquinolin-5-amine. Method [6] retention time 1.57 and 4.02 min by HPLC (M+ 163) and (M+ 163).

1.68.4. 8-Bromo-3-fluoroquinoline

3-Fluoroquinolin-8-amine (900 mg, 5.55 mmol) was added to tert-butylnitrite (1.3 ml, 10.9 mmol) and cupric bromide (1.37 g, 6.13 mmol) in acetonitrile (10 ml). The heterogenous mixture was heated to 70° C. After stirring for 18 h, the solution was diluted with water and extracted with methylene chloride. The combined organic extracts were dried over magnesium sulfate, filtered, and concentrated. The residue was purified by flash chromatography (hexane:ethyl acetate) to afford 568 mg (45% yield) of 8-bromo-3-fluoroquinoline. Method [7] retention time 4.76 min by HPLC (M+ 226 and 228).

1.68.5. 2-(3-Fluoroquinolin-8-yl)acetic acid

The title compound was prepared from 8-bromo-3-fluoroquinoline (568 mg, 2.51 mmol) and 0.5 M (2-Tert-butoxy-2-oxoethyl)zinc(II) chloride according to Protocol P, accept that the ester was converted to the acid using NaOH and MeOH in dioxane. Method [7] retention time 2.39 min by HPLC (M+=206).

1.68.6. N-(4-Bromo-3-(1H-1,2,4-triazol-3-yl)thiophen-2-yl)-2-(3-fluoroquinolin-8-yl)acetamide 4-Bromo-3-(4H-1,2,4-triazol-3-yl)thiophen-2-amine (17 mg, 69.4 umol), 2-(3-fluoroquinolin-8-yl)acetic acid hydrogen chloride (22 mg, 91.0 umol), 2-chloro-1-methylpyridinium iodide (101 mg, 395 umol) and triethylamine (0.2 ml) in methylene chloride (1 ml) was heated to reflux. After stirring for 1 h, the solution was concentrated and the residue was purified by HPLC to yield N-(4-bromo-3-(1H-1,2,4-triazol-3-yl)thiophen-2-yl)-2-(3-fluoroquinolin-8-yl)acetamide. Method [7] retention time 5.67 min by HPLC (M+ 432 and 434) and (M+Na 454 and 456). $^1$H NMR (300 MHz, CDCl$_3$) δ 12.25 (s, 1H), 8.83 (d, J=3.3 Hz, 1H), 7.87 (m, 2H), 7.80 (d, J=6.0 Hz, 1H), 7.73 (s, 1H), 7.66 (t, J=7.8 Hz, 1H), 6.90 (s, 1H), 6.70 (broad s, 2H), 4.56 (s, 2H).

1.69. Synthesis of N-(4-bromo-3-(1H-1,2,4-triazol-3-yl)thiophen-2-yl)-2-(3-fluoroquinolin-5-yl)acetamide

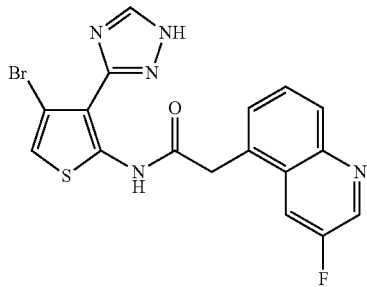 [SMILES: O=C(Cc1cccc2ncc(F)cc12)Nc1scc(Br)c1-c1nc[nH]n1]

The title compound was prepared by converting 3-fluoroquinolin-5-amine (850 mg, 5.24 mmol) into 2-(3-fluoroquinolin-5-yl)acetic acid hydrogen chloride (76 mg, 315 umol) and reaction with 4-bromo-3-(4H-1,2,4-triazol-3-yl)thiophen-2-amine (34 mg, 139 umol) as outlined in Example 1.68., above. Method [8] retention time 2.46 min by HPLC (M+ 206). $^1$H NMR (300 MHz, CDCl$_3$) δ 12.35 (s, 1H), 8.89 (d, J=2.7 Hz, 1H), 8.26 (d, J=8.7 Hz, 1H), 8.07 (dd, J=9.3 and 2.7 Hz, 1H), 7.83 (m, 1H), 7.74 (d, J=6.9 Hz, 1H), 7.59 (s, 1H), 6.93 (s, 1H), 4.33 (s, 2H).

1.70. Synthesis of N-(4-bromo-3-(1H-1,2,4-triazol-3-yl)thiophen-2-yl)-2-(3-(trifluoromethyl)quinolin-5-yl)acetamide

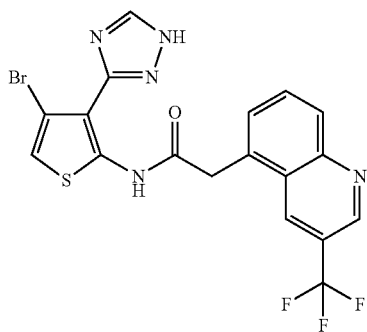 [SMILES: O=C(Cc1cccc2ncc(C(F)(F)F)cc12)Nc1scc(Br)c1-c1nc[nH]n1]

1.70.1. 3-Iodoquinoline

3-Bromoquinoline (64.00 g, 308 mmol), N,N'-dimethylethylenediamine (13.5 ml, 127 mmol), cuprous iodide (12.00 g, 63.0 mmol) and sodium iodide (112 g, 747 mmol) in dioxane (300 ml) was placed into a preheated oil bath at 100° C. After stirring for 18 h, the heterogeneous mixture was diluted water and extracted with methylene chloride. The combined organic extracts were dried over magnesium sulfate, filtered, and concentrated under reduced pressure. The residue was flash chromatographed with methylene chloride as the eluant to afford 68.47 g (87% yield) of 3-iodoquinoline as a yellow solid. Method [8] retention time 6.47 min by HPLC (M+=256).

1.70.2. 3-(Trifluoromethyl)quinoline

3-Iodoquinoline (13.65 g, 53.5 mmol), cuprous iodide (21.12, 111 mmol), potassium fluoride (7.11 g, 122 mmol), and methyl 2-chloro-2,2-difluoroacetate (23 ml, 216 mmol) in dimethylformamide (200 ml) was placed into a preheated oil bath at 120° C. After stirring for 6 h, the solution was diluted water and extracted with diethyl ether. The combined organic extracts were dried over magnesium sulfate, filtered, and concentrated under reduced pressure. The residue was flash chromatographed with 99:1, 49:1, 24:1, 23:2, 9:1, and 4:1 hexane:ethyl acetate as the eluant to afford 3.89 g (37% yield) of 3-(trifluoromethyl)quinoline. Method [7] retention time 4.67 min by HPLC (M+ 198).

1.70.3. 8-Bromo-3-(trifluoromethyl)quinoline and 5-bromo-3-(trifluoromethyl)quinoline 3-(Trifluoromethyl)quinoline (7.00 g, 35.5 mmol) and N-bromosuccinimide (9.00 g, 50.6 mmol) in concentrated sulfuric acid (50 ml) was heated to 50° C. After stirring for 1.5 h, the solution was cooled to ambient temperature, diluted with saturated aq. sodium sulfite, made alkaline with 3 N aq. sodium hydroxide, and extracted with methylene chloride. The combined organic extracts were dried over magnesium sulfate, filtered, and concentrated under reduced pressure. The residue was flash chromatographed with 99:1, 49:1, 24:1, and 23:2 hexane:ethyl acetate as the eluant to afford 4.55 g of impure 8-bromo-3-(trifluoromethyl)quinoline and 3.89 g (37% yield) of 5-bromo-3-(trifluoromethyl)quinoline. Method [8] Retention time 6.75 and 7.47 min by HPLC (M+=276 and 278) and (M+=276 and 278).

1.70.4. 2-(3-(Trifluoromethyl)quinolin-5-yl)acetic acid

The title compound was prepared from 5-bromo-3-(trifluoromethyl)quinoline (3.59 g, 13.0 mmol) according to the procedures outlined in Protocol P. Method [7] retention time 2.80 min by HPLC (M+=256).

1.70.5. N-(4-bromo-3-(1H-1,2,4-triazol-3-yl)thiophen-2-yl)-2-(3-(trifluoromethyl)quinolin-5-yl)acetamide The title compound was prepared from 4-bromo-3-(4H-1,2,4-triazol-3-yl)thiophen-2-amine (56 mg, 228 umol) and 2-(3-trifluoromethylquinolin-5-yl)acetic acid hydrogen chloride (200 mg, 784 umol) according to the procedures outlined in Example 1.68.6., above. Method [7] retention time 5.93 min by HPLC (M+ 482 and 484) and (M+Na 504 and 506). $^1$H NMR (300 MHz, CDCl$_3$) δ 12.45 (s, 1H), 9.23

(s, 1H), 8.84 (s, 1H), 8.37 (d, J=8.4 Hz, 1H), 8.03 (m, 1H), 7.85 (d, J=6.9 Hz, 1H), 7.74 (s, 1H), 6.95 (s, 1H), 4.38 (s, 2H).

Synthesis of N-(4-bromo-3-(1H-1,2,4-triazol-3-yl)thiophen-2-yl)-2-(3-(trifluoromethyl)quinolin-8-yl)acetamide

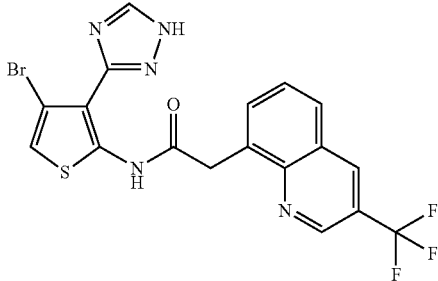 [SMILES: O=C(Cc1cccc2cc(C(F)(F)F)cnc12)Nc1scc(Br)c1-c1nc[nH]n1]

1.71.1. 2-(3-(Trifluoromethyl)quinolin-8-yl)acetic acid

The title compound was synthesized from 2-tert-butoxy-2-oxoethyl)zinc(II) chloride and 8-bromo-3-(trifluoromethyl)quinoline (4.55 g) according to protocol P. Method [7] retention time 3.78 min by HPLC (M+ 256).

1.71.2. N-(4-bromo-3-(1H-1,2,4-triazol-3-yl)thiophen-2-yl)-2-(3-(trifluoromethyl)quinolin-8-yl)acetamide The title compound was synthesized from 4-bromo-3-(4H-1,2,4-triazol-3-yl)thiophen-2-amine (40 mg, 163 umol) and 2-(3-fluoroquinolin-8-yl)acetic acid hydrogen chloride (284 mg, 1.11 mmol) according to the procedure outlined in Example 1.68., above. Method [7] retention time 7.10 min by HPLC (M+ 482 and 484) and (M+Na 504 and 506). $^1$H NMR (300 MHz, DMSO-$d_6$) δ 11.80 (s, 1H), 9.20 (d, J=2.7 Hz, 1H), 9.01 (s, 1H), 8.39 (broad s, 1H), 8.25 (d, J=8.1 Hz, 1H), 8.08 (d, J=6.6 Hz, 1H), 7.79 (t, J=7.2 Hz, 1H), 7.21 (s, 1H), 4.38 (s, 2H).

1.72. Synthesis of N-(4-chloro-3-(3-isopropyl-1H-1,2,4-triazol-5-yl)thiophen-2-yl)-2-(2-oxo-3,4-dihydro-1,5-naphthyridin-1(2H)-yl)acetamide

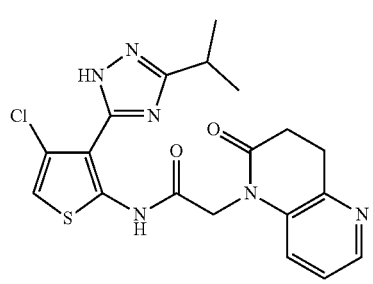 [SMILES: CC(C)c1n[nH]c(-c2c(Cl)csc2NC(=O)CN2C(=O)CCc3ncccc32)n1]

1.72.1. 5-Chloro-4-hydrazinylthieno[2,3-d]pyrimidine

5-Chloro-4-chlorothieno[2,3-d]pyrimidine (1.38 g, 6.73 mmol) and hydrazine monohydrate (5.0 ml, 103 mmol) in absolute ethanol (20 ml) were heated at 75° C. After stirring for 24 h, the solution was concentrated to yield 5-chloro-4-hydrazinylthieno[2,3-d]pyrimidine. Method [6] Retention time 0.35 min by HPLC (M+=201 and 203).

1.72.2. 9-Chloro-3-isopropylthieno[3,2-e][1,2,4]triazolo[4,3-c]pyrimidine

5-Chloro-4-hydrazinylthieno[2,3-d]pyrimidine and 1,1,1-triethoxy-2-methylpropane (10 ml) in ethanol (10 ml) were heated at 100° C. for 2 h. The solution was concentrated and the residue was flash chromatographed with 9:1, 4:1, 7:3, and 3:2 hexane:ethyl acetate as the eluant to afford 300 mg (24% yield over 2 steps) of 9-chloro-3-isopropylthieno[3,2-e][1,2,4]triazolo[4,3-c]pyrimidine as a brown solid. Method [8] Retention time 4.62 min by HPLC (M+=253 and 255).

1.72.3. 4-Chloro-3-(3-isopropyl-1H-1,2,4-triazol-5-yl)thiophen-2-amine 9-chloro-3-isopropylthieno[3,2-e][1,2,4]triazolo[4,3-c]pyrimidine (300 mg, 1.19 mmol) and N-methylethane-1,2-diamine (0.50 ml, 5.67 mmol) in methanol (10 ml) was placed into a preheated oil bath at 60° C. After stirring for 15 min, the solution was diluted with saturated ammonium chloride and extracted with methylene chloride. The combined organic extracts were dried over magnesium sulfate, filtered, and concentrated under reduced pressure to yield 4-chloro-3-(3-isopropyl-1H-1,2,4-triazol-5-yl)thiophen-2-amine. Method [7] Retention time 1.39 min by HPLC (M+=243 and 245).

1.72.4. N-(4-chloro-3-(3-isopropyl-1H-1,2,4-triazol-5-yl)thiophen-2-yl)-2-(2-oxo-3,4-dihydro-1,5-naphthyridin-1(2H)-yl)acetamide The title compound was prepared from 4-chloro-3-(3-isopropyl-1H-1,2,4-triazol-5-yl)thiophen-2-amine (117 mg, 482 umol) and 2-(2-oxo-3,4-dihydro-1,5-naphthyridin-1(2H)-yl)acetic acid (155 mg, 752 umol) using protocol A and was purified by HPLC to yield N-(4-chloro-3-(3-isopropyl-1H-1,2,4-triazol-5-yl)thiophen-2-yl)-2-(2-oxo-3,4-dihydro-1,5-naphthyridin-1(2H)-yl)acetamide. Method [7] Retention time 0.35 min by HPLC (M+=431 and 433) and (M+Na=453 and 455). $^1$H NMR (300 MHz, DMSO-$d_6$) δ 12.28 (s, 1H), 8.30 (d, J=5.1 Hz, 1H), 7.76 (d, J=8.7 Hz, 1H), 7.51 (m, 1H), 7.16 (d, J=1.8 Hz, 1H), 4.89 (s, 2H) 3.17 (m, 2H), 2.98 (m, 1H), 2.81 (m, 2H), 1.28 (d, J=7.2 Hz, 6H).

1.73. Synthesis of N-(4-chloro-3-(3-ethyl-1H-1,2,4-triazol-5-yl)thiophen-2-yl)-2-(2-oxo-3,4-dihydro-1,5-naphthyridin-1(2H)-yl)acetamide

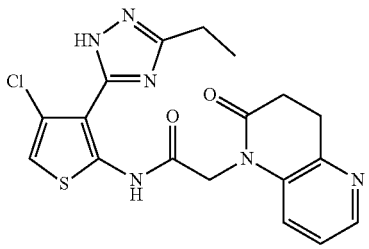 [SMILES: CCc1n[nH]c(-c2c(Cl)csc2NC(=O)CN2C(=O)CCc3ncccc32)n1]

1.73.1. 9-Chloro-3-ethylthieno[3,2-e][1,2,4]triazolo [4,3-c]pyrimidine

5-Chloro-4-hydrazinylthieno[2,3-d]pyrimidine and 1,1,1-triethoxypropane (5 ml) in ethanol (5 ml) was placed into a preheated oil bath at 100° C. for 2 h. The solution was concentrated and the residue was flash chromatographed with 9:1, 4:1, 7:3, and 3:2 hexane:ethyl acetate as the eluant to afford 20 mg of 9-chloro-3-ethylthieno[3,2-e][1,2,4]triazolo[4,3-c]pyrimidine. Method [8] Retention time 6.31 min by HPLC (M+=239 and 241).

1.73.2. 4-Chloro-3-(3-ethyl-1H-1,2,4-triazol-5-yl)thiophen-2-amine

9-Chloro-3-ethylthieno[3,2-e][1,2,4]triazolo[4,3-c]pyrimidine (20 mg, 83.8 umol) and N-methylethane-1,2-diamine (0.05 ml, 5.67 umol) in methanol (2 ml) was placed into a preheated oil bath at 60° C. After stirring for 15 min, the solution was diluted with saturated ammonium chloride and extracted with methylene chloride. The combined organic extracts were dried over magnesium sulfate, filtered, and concentrated under reduced pressure to afford 18 mg (94% yield) of 4-chloro-3-(3-ethyl-1H-1,2,4-triazol-5-yl)thiophen-2-amine as a brown solid. Method [8] Retention time 2.63 min by HPLC (M+ 229 and 231).

1.73.3. N-(4-chloro-3-(3-ethyl-1H-1,2,4-triazol-5-yl)thiophen-2-yl)-2-(2-oxo-3,4-dihydro-1,5-naphthyridin-1(2H)-yl)acetamide The title compound was prepared from 4-chloro-3-(3-ethyl-1H-1,2,4-triazol-5-yl)thiophen-2-amine (18 mg, 78.7 umol) and 2-(2-oxo-3,4-dihydro-1,5-naphthyridin-1(2H)-yl)acetic acid (20 mg, 97.0 umol) using protocol A. The residue was purified by HPLC to yield N-(4-chloro-3-(3-ethyl-1H-1,2,4-triazol-5-yl)thiophen-2-yl)-2-(2-oxo-3,4-dihydro-1,5-naphthyridin-1(2H)-yl)acetamide. Method [8] Retention time 4.47 min by HPLC (M+=417 and 419) and (M+Na=439 and 441). $^1$H NMR (300 MHz, CDCl$_3$) δ 8.39 (dd, J=5.4 and 1.2 Hz, 1H), 7.67 (dd, J=8.1 and 1.2 Hz, 1H), 7.49 (dd, J=8.1 and 5.4 Hz, 1H), 6.85 (s, 1H), 4.93 (s, 2H), 3.49 (m, 2H), 3.01 (m, 2H), 2.84 (q, J=7.8 Hz, 2H), 1.39 (t, J=7.8 Hz, 3H).

1.74. Synthesis of N-(4-chloro-3-(3-methyl-1H-1,2,4-triazol-5-yl)thiophen-2-yl)-2-(2-oxo-3,4-dihydro-1,5-naphthyridin-1(2H)-yl)acetamide

1.74.1. 9-Chloro-3-methylthieno[3,2-e][1,2,4]triazolo[4,3-c]pyrimidine

5-Chloro-4-hydrazinylthieno[2,3-d]pyrimidine and 1,1,1-triethoxyethane (10 ml) in ethanol (10 ml) was placed into a preheated oil bath at 100° C. for 2 h. The solution was concentrated and the residue was flash chromatographed with 9:1, 4:1, 7:3, and 3:2 hexane:ethyl acetate as the eluant to afford 92 mg of 9-chloro-3-methylthieno[3,2-e][1,2,4]triazolo[4,3-c]pyrimidine white-pink solid. Method [7] Retention time 3.77 min by HPLC (M+=225 and 227).

1.74.2. 4-Chloro-3-(3-methyl-1H-1,2,4-triazol-5-yl)thiophen-2-amine

9-Chloro-3-methylthieno[3,2-e][1,2,4]triazolo[4,3-c]pyrimidine (82 mg, 365 umol) and N-methylethane-1,2-diamine (0.30 ml, 3.40 mmol) in methanol (2 ml) was placed into a preheated oil bath at 60° C. After stirring for 15 min, the solution was diluted with saturated ammonium chloride and extracted with methylene chloride. The combined organic extracts were dried over magnesium sulfate, filtered, and concentrated under reduced pressure to afford 69 mg (88% yield) of 4-chloro-3-(3-methyl-1H-1,2,4-triazol-5-yl)thiophen-2-amine as a yellow solid. Method [1] Retention time 0.61 min by HPLC (M+=215 and 217).

1.74.3. N-(4-chloro-3-(3-methyl-1H-1,2,4-triazol-5-yl)thiophen-2-yl)-2-(2-oxo-3,4-dihydro-1,5-naphthyridin-1(2H)-yl)acetamide The title compound was prepared from 4-chloro-3-(3-methyl-1H-1,2,4-triazol-5-yl)thiophen-2-amine (69 mg, 321 umol) and 2-(2-oxo-3,4-dihydro-1,5-naphthyridin-1(2H)-yl)acetic acid (82 mg, 397 umol) using protocol A. The residue was purified by HPLC. Method [8] Retention time 3.40 min by HPLC (M+=403 and 405) and (M+Na=425 and 427). $^1$H NMR (300 MHz, CDCl$_3$) δ 8.39 (d, J=5.4 Hz, 1H), 7.67 (d, J=8.4 Hz, 1H), 7.49 (dd, J=8.4 and 5.4 Hz, 1H), 6.86 (s, 1H), 5.46 (broad s, 2H), 4.95 (s, 2H), 3.49 (m, 2H), 3.01 (m, 2H), 2.50 (s, 3H).

1.75. Synthesis of N-(4-chloro-3-(1H-1,2,4-triazol-3-yl)thiophen-2-yl)-2-(2-oxo-6-(trifluoromethyl)quinolin-1(2H)-yl)acetamide The title compound was prepared from 4-chloro-3-(1H-1,2,4-triazol-3-yl)thiophen-2-amine (502 mg, 2.50 mmol) and 2-(2-oxo-6-(trifluoromethyl)quinolin-1(2H)-yl)acetic acid (675 mg, 2.49 mmol) using protocol A (626 mg, 55% yield). Method [7] Retention time 5.59 min by HPLC (M+=454 and 456) and (M+Na=476 and 478). $^1$H NMR (300 MHz, DMSO-d$_6$) δ 12.23 (s, 1H), 8.38 (broad s, 1H), 8.27 (s, 1H), 8.22 (d, J=9.3 Hz, 1H), 7.89 (d, J=9.3 Hz, 1H), 7.70 (d, J=9.3, 1H), 7.17 (s, 1H), 6.87 (d, J=9.9 Hz, 1H), 5.31 (s, 2H).

1.76. Synthesis of N-(4-chloro-3-(1-(3-(dimethylamino)propyl)-1H-1,2,4-triazol-3-yl)thiophen-2-yl)-2-(2-oxo-6-(trifluoromethyl)quinolin-1(2H)-yl)acetamide Diisopropyl azodicarboxylate (0.30 ml, 1.52 mmol) was added dropwise to a heterogeneous mixture of N-(4-chloro-3-(1H-1,2,4-triazol-3-yl)thiophen-2-yl)-2-(2-oxo-6-(trifluoromethyl)quinolin-1(2H)-yl)acetamide (111 mg, 245 umol), polymer supported triphenylphosphine (500 mg, 1.50 mmol), and 3-(dimethylamino)propan-1-ol (300 mg, 2.91 mmol) in tetrahydrofuran (5 ml) at 0° C. After stirring for 2 h, the heterogeneous mixture was filtered through a pad of celite and concentrated under reduced pressure. The residue was purified by HPLC to yield N-(4-chloro-3-(1-(3-(dimethylamino)propyl)-1H-1,2,4-triazol-3-yl)thiophen-2-yl)-2-(2-oxo-6-(trifluoromethyl)quinolin-1(2H)-yl)acetamide. Method [7] Retention time 4.33 min by HPLC (M+=539 and 541). $^1$H NMR (300 MHz, DMSO-d$_6$) δ 12.10 (s, 1H), 8.52 (s, 1H), 8.29 (s, 1H), 8.22 (d, J=9.6 Hz, 1H), 7.92 (d, J=8.7 Hz, 1H), 7.72 (d, J=8.7, 1H), 7.18 (s, 1H), 6.87 (d, J=9.6 Hz, 1H), 5.32 (s, 2H), 4.31 (t, J=6.6 Hz, 2H), 3.09 (t, J=6.6 Hz, 2H), 2.75 (s, 6H), 2.17 (m, 2H).

1.77. Synthesis of N-(4-chloro-3-(1-(2-(dimethylamino)ethyl)-1H-1,2,4-triazol-3-yl)thiophen-2-yl)-2-(2-oxo-6-(trifluoromethyl)quinolin-1(2H)-yl)acetamide The title compound was prepared from N-(4-chloro-3-(1H-1,2,4-triazol-3-yl)thiophen-2-yl)-2-(2-oxo-6-(trifluoromethyl)quinolin-1(2H)-yl)acetamide (125 mg, 275 umol)

and 2-(dimethylamino)ethanol (311 mg, 3.49 mmol) using the procedures described in Example 1.76 except that the reaction was run at 60° C. (rather than 0° C.). The residue was purified by HPLC to yield N-(4-chloro-3-(1-(2-(dimethylamino)ethyl)-1H-1,2,4-triazol-3-yl)thiophen-2-yl)-2-(2-oxo-6-(trifluoromethyl)quinolin-1(2H)-yl)acetamide. Method [7] Retention time 4.40 min by HPLC (M+=525 and 527) and (M+Na=547 and 549). $^1$H NMR (300 MHz, DMSO-d$_6$) δ 8.41 (s, 1H), 8.28 (s, 1H), 8.22 (d, J=9.3 Hz, 1H), 7.90 (d, J=8.7 Hz, 1H), 7.72 (d, J=8.7, 1H), 7.16 (s, 1H), 6.87 (d, J=9.3 Hz, 1H), 5.32 (s, 2H), 4.28 (t, J=6.0 Hz, 2H), 2.64 (t, J=6.0 Hz, 2H), 2.15 (s, 6H).

1.78. Synthesis of N-(4-chloro-3-(1-(3-(4-methylpiperazin-1-yl)propyl)-1H-1,2,4-triazol-3-yl)thiophen-2-yl)-2-(2-oxo-6-(trifluoromethyl)quinolin-1(2H)-yl)acetamide The title compound was prepared from N-(4-chloro-3-(1H-1,2,4-triazol-3-yl)thiophen-2-yl)-2-(2-oxo-6-(trifluoromethyl)quinolin-1(2H)-yl)acetamide (108 mg, 248 umol) and 3-(4-methylpiperazin-1-yl)propan-1-ol (350 mg, 2.21 mmol) using the procedures described in Example 1.76. HPLC purification gave N-(4-chloro-3-(1-(3-(4-methylpiperazin-1-yl)propyl)-1H-1,2,4-triazol-3-yl)thiophen-2-yl)-2-(2-oxo-6-(trifluoromethyl)quinolin-1(2H)-yl)acetamide. Method [7] retention time 4.27 min by HPLC (M+=594 and 596). $^1$H NMR (300 MHz, DMSO-d$_6$) δ 12.13 (s, 1H), 8.47 (s, 1H), 8.29 (s, 1H), 8.22 (d, J=9.9 Hz, 1H), 7.92 (d, J=7.2 Hz, 1H), 7.72 (d, J=8.7 Hz, 1H), 7.17 (s, 1H), 6.87 (d, J=9.3 Hz, 1H), 5.32 (s, 2H), 4.25 (t, J=6.6 Hz, 2H), 2.95 (broad m, 10H), 2.73 (s, 3H), 1.97 (m, 2H).

1.79. Synthesis of N-(4-chloro-3-(1-(3-morpholinopropyl)-1H-1,2,4-triazol-3-yl)thiophen-2-yl)-2-(2-oxo-6-(trifluoromethyl)quinolin-1(2H)-yl)acetamide The title compound was prepared from N-(4-chloro-3-(1H-1,2,4-triazol-3-yl)thiophen-2-yl)-2-(2-oxo-6-(trifluoromethyl)quinolin-1(2H)-yl)acetamide (110 mg, 242 umol) and 3-morpholinopropan-1-ol (350 mg, 2.41 mmol) using the procedure described in Example 1.76. HPLC purification gave N-(4-chloro-3-(1-(3-morpholinopropyl)-1H-1,2,4-triazol-3-yl)thiophen-2-yl)-2-(2-oxo-6-(trifluoromethyl)quinolin-1(2H)-yl)acetamide. Method [7] Retention time 4.58 min by HPLC (M+=581 and 583) and (M+Na=603 and 605). $^1$H NMR (300 MHz, DMSO-d$_6$) δ 12.10 (s, 1H), 8.47 (s, 1H), 8.26 (s, 1H), 8.20 (d, J=9.3 Hz, 1H), 7.91 (d, J=7.2 Hz, 1H), 7.70 (d, J=9.3 Hz, 1H), 7.16 (s, 1H), 6.86 (d, J=9.3 Hz, 1H), 5.30 (s, 2H), 4.30 (t, J=7.2 Hz, 2H), 3.20 (broad m, 10H), 1.20 (m, 2H).

1.80. Synthesis of N-(4-chloro-3-(1-(3-(pyrrolidin-1-yl)propyl)-1H-1,2,4-triazol-3-yl)thiophen-2-yl)-2-(2-oxo-6-(trifluoromethyl)quinolin-1(2H)-yl)acetamide The title compound was prepared from N-(4-chloro-3-(1H-1,2,4-triazol-3-yl)thiophen-2-yl)-2-(2-oxo-6-(trifluoromethyl)quinolin-1(2H)-yl)acetamide (110 mg, 242 umol) and 3-(pyrrolidin-1-yl)propan-1-ol (325 mg, 2.52 mmol) using the procedures described in Example 1.76. HPLC purification gave N-(4-chloro-3-(1-(3-(pyrrolidin-1-yl)propyl)-1H-1,2,4-triazol-3-yl)thiophen-2-yl)-2-(2-oxo-6-(trifluoromethyl)quinolin-1(2H)-yl)acetamide. Method [7] Retention time 4.65 min by HPLC (M+=565 and 567). $^1$H NMR (300 MHz, DMSO-d$_6$) δ 12.10 (s, 1H), 8.50 (s, 1H), 8.28 (s, 1H), 8.21 (d, J=9.3 Hz, 1H), 7.91 (d, J=9.3 Hz, 1H), 7.70 (d, J=9.3 Hz, 1H), 7.17 (s, 1H), 6.86 (d, J=9.3 Hz, 1H), 5.31 (s, 2H), 4.31 (t, J=6.6 Hz, 2H), 3.20 (broad m, 6H), 2.18 (m, 2H), 1.99 (m, 2H), 1.83 (m, 2H).

1.81. Synthesis of 2-(6-bromo-2-oxoquinolin-1(2H)-yl)-N-(4-bromo-3-(1H-1,2,4-triazol-3-yl)thiophen-2-yl)acetamide

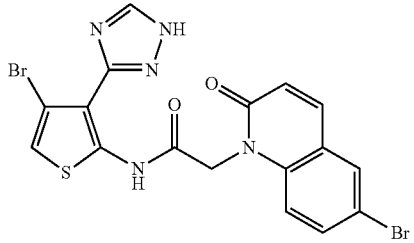 [SMILES: O=C(Cn1c(=O)ccc2cc(Br)ccc21)Nc1scc(Br)c1-c1nc[nH]n1]

1.81.1. 2-(6-Bromo-2-oxoquinolin-1(2H)-yl)acetic acid

6-Bromoquinolin-2(1H)-one (5.03 g, 22.5 mmol) was subjected to protocol K with ethyl bromoacetate instead of methyl bromoacetate to afford 6.96 g (100% yield) of ethyl 2-(6-bromo-2-oxoquinolin-1(2H)-yl)acetate as a white solid. Method [7] Retention time 4.79 min by HPLC (M+=310 and 312) and (M+Na=332 and 334). The acetate (318 mg, 1.03 mmol) was subjected to the protocol in Example 1.53.4 to afford 228 mg (83% yield) of 2-(6-bromo-2-oxoquinolin-1(2H)-yl)acetic acid as a white solid. Method [8] Retention time 4.79 min by HPLC (M+=282 and 282) and (M+Na=304 and 306).

1.81.2. 2-(6-Bromo-2-oxoquinolin-1(2H)-yl)-N-(4-bromo-3-(1H-1,2,4-triazol-3-yl)thiophen-2-yl)acetamide The title compound was prepared from 4-bromo-3-(1H-1,2,4-triazol-3-yl)thiophen-2-amine (55 mg, 224 umol) and 2-(6-bromo-2-oxoquinolin-1(2H)-yl)acetic acid (85 mg, 301 umol) according to protocol A. HPLC purification gave 2-(6-bromo-2-oxoquinolin-1(2H)-yl)-N-(4-bromo-3-(1H-1,2,4-triazol-3-yl)thiophen-2-yl)acetamide. Method [7] retention time 5.41 min by HPLC (M+=508, 510, and 512). $^1$H NMR (300 MHz, CDCl$_3$) δ 7.80 (m, 2H), 7.70 (s, 1H), 7.63 (dd, J=9.0 and 2.4 Hz, 1H), 7.19 (d, J=9.0 Hz, 1H), 6.94 (m, 2H), 5.31 (s, 2H).

1.82. Synthesis of 2-(6-bromo-2-oxoquinolin-1(2H)-yl)-N-(4-chloro-3-(1H-1,2,4-triazol-3-yl)thiophen-2-yl)acetamide The title compound was prepared from 4-chloro-3-(1H-1,2,4-triazol-3-yl)thiophen-2-amine (115 mg, 573 umol) and 2-(6-bromo-2-oxoquinolin-1(2H)-yl)acetic acid (135 mg, 479 umol) according to protocol A. HPLC purification gave 2-(6-bromo-2-oxoquinolin-1(2H)-yl)-N-(4-chloro-3-(1H-1,2,4-triazol-3-yl)thiophen-2-yl)acetamide. Method [7] Retention time 5.30 min by HPLC (M+=464, 466, and 468) are the major peak intensities. $^1$H NMR (300 MHz, CDCl$_3$)

δ 7.80 (m, 2H), 7.70 (s, 1H), 7.64 (dd, J=9.0 and 2.4 Hz, 1H), 7.19 (d, J=9.0 Hz, 1H), 6.94 (d, J=9.3 Hz, 1H), 6.82 (s, 1H), 5.30 (s, 2H).

Synthesis of N-(4-bromo-3-(1H-1,2,4-triazol-3-yl)thiophen-2-yl)-2-(6-cyano-2-oxoquinolin-1(2H)-yl)acetamide

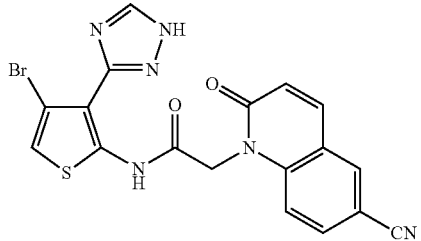 [SMILES: N#Cc1ccc2c(ccc(=O)n2CC(=O)Nc2scc(Br)c2-c2nc[nH]n2)c1]

1.83.1. Ethyl 2-(6-cyano-2-oxoquinolin-1(2H)-yl)acetate

Ethyl 2-(6-bromo-2-oxoquinolin-1(2H)-yl)acetate (2.37 g, 7.64 mmol) cuprous cyanide (8.87 g, 99.0 mmol), and tetrakis(triphenylphosphine)palladium(0) (3.50 g, 3.03 mmol) in dimethylformamide (100 ml) was placed into a preheated oil bath at 140° C. After stirring for 24 h, the solution was diluted with water and extracted with ethyl acetate. The combined organic extracts were dried over magnesium sulfate, filtered, and concentrated under reduced pressure. The residue was flash chromatographed with 9:1, 4:1, 7:3, and 3:2 methylene chloride:ethyl acetate as the eluant to afford 0.74 g (38% yield) of ethyl 2-(6-cyano-2-oxoquinolin-1(2H)-yl)acetate. Method [7] retention time 2.87 min by HPLC (M+ 257).

1.83.2. 2-(6-Cyano-2-oxoquinolin-1(2H)-yl)acetic acid

Ethyl 2-(6-cyano-2-oxoquinolin-1(2H)-yl)acetate was subjected to the protocol in Example 1.53.4 to afford 550 mg (83% yield) of 2-(6-cyano-2-oxoquinolin-1(2H)-yl)acetic acid as a yellow solid. Method [7] retention time 2.44 min by HPLC (M+ 229).

1.83.3. N-(4-bromo-3-(1H-1,2,4-triazol-3-yl)thiophen-2-yl)-2-(6-cyano-2-oxoquinolin-1(2H)-yl)acetamide The title compound was prepared from 4-bromo-3-(1H-1,2,4-triazol-3-yl)thiophen-2-amine (253 mg, 1.03 mmol) and 2-(6-cyano-2-oxoquinolin-1(2H)-yl)acetic acid (325 mg, 1.42 mmol) according to protocol A. HPLC purification gave N-(4-bromo-3-(1H-1,2,4-triazol-3-yl)thiophen-2-yl)-2-(6-cyano-2-oxoquinolin-1(2H)-yl)acetamide. Method [7] Retention time 4.00 min by HPLC (M+=455 and 457). $^1$H NMR (300 MHz, DMSO-$d_6$) δ 8.42 (broad s, 1H), 8.37 (s, 1H), 8.13 (d, J=9.9 Hz, 1H), 7.98 (d, J=9.0 Hz, 1H), 7.70 (d, J=9.0 Hz, 1H), 7.27 (s, 1H), 6.87 (d, J=9.3 Hz, 1H), 5.30 (s, 2H).

1.84. Synthesis of N-(4-chloro-3-(1H-1,2,4-triazol-3-yl)thiophen-2-yl)-2-(6-cyano-2-oxoquinolin-1(2H)-yl)acetamide The title compound was prepared from 4-chloro-3-(1H-1,2,4-triazol-3-yl)thiophen-2-amine (215 mg, 1.07 mmol) and 2-(6-cyano-2-oxoquinolin-1(2H)-yl)acetic acid (325 mg, 1.42 mmol) using protocol A. HPLC purification gave N-(4-chloro-3-(1H-1,2,4-triazol-3-yl)thiophen-2-yl)-2-(6-cyano-2-oxoquinolin-1(2H)-yl)acetamide. Method [7] Retention time 3.83 min by HPLC (M+=411 and 413). $^1$H NMR (300 MHz, DMSO-$d_6$) δ 8.37 (s, 2H), 8.13 (d, J=9.9 Hz, 1H), 7.98 (d, J=8.7 Hz, 1H), 7.70 (d, J=9.3 Hz, 1H), 7.17 (s, 1H), 6.86 (d, J=9.9 Hz, 1H), 5.31 (s, 2H).

1.85. Synthesis of N-(4-bromo-3-(4H-1,2,4-triazol-3-yl)thiophen-2-yl)-2-(isoquinolin-4-yl)acetamide To a solution of 4-bromo-3-(4H-1,2,4-triazol-3-yl)thiophen-2-amine (50 mg, 0.2 mmol) and 2-(isoquinolin-4-yl)acetic acid (56 mg, 0.3 mmol) in methylene chloride (2 mL) were added Hunig's base (i.e., N,N-diisopropylethylamine) (71 uL, 0.4 mmol) and HBTU (133 mg, 0.35 mmol). The heterogeneous reaction mixture was homogenous after 3 h. The reaction was quenched with saturated aqueous ammonium chloride and the aqueous was extracted with methylene chloride. The organic phase was washed with brine and dried over sodium sulfate. The resulting solution was concentrated to provide a pale red solid, which was purified by column chromatography using 3.5% MeOH/CH$_2$Cl$_2$. LCMS: retention time 1.955 min using analytical method [7] with an M+Na of 414.0. 19.0 mg (15% yield): white solid. $^1$H-NMR (300 MHz, CDCl$_3$) δ 9.34 (s, 1H), 8.66 (s, 1H), 8.07 (d, J=8.0 Hz, 1H), 8.01 (d, J=8.0 Hz, 1H), 7.75 (m, 1H), 7.65 (m, 2H), 6.88 (d, J=0.5 Hz, 1H), 4.30 (s, 2H). $^{13}$C-NMR (75 MHz, CDCl$_3$) δ 168.3, 153.2, 144.8, 142.8, 135.0, 131.5, 128.7, 128.4, 127.8, 123.5, 122.9, 116.2, 104.7, 38.7.

1.86. Synthesis of N-(4-bromo-3-(4H-1,2,4-triazol-3-yl)thiophen-2-yl)-2-(3,3-difluoro-2-oxoindolin-1-yl)acetamide

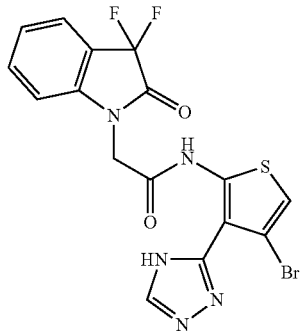 [SMILES: O=C(CN1C(=O)C(F)(F)c2ccccc21)Nc1scc(Br)c1-c1nnc[nH]1]

1.86.1. 3,3-Difluoroindolin-2-one

A 100 mL reaction flask was charged with indoline-2,3-dione (0.88 g, 6.0 mmol). DCM (40 mL) was added, followed by DAST (2.4 g, 15.0 mmol). The reaction was stirred for 16 h before being quenched by the addition of 2 mL MeOH. The organic reaction mixture was rinsed with water and the organic layer was dried over sodium sulfate. The solution was concentrated under reduced pressure to give 3,3-difluoroindolin-2-one (1.0 g, 98%). LC-MS of this crude showed the desired m/z of 170.0 at a method [1] retention time of 1.673 min in.

1.86.2. tert-Butyl 2-(3,3-difluoro-2-oxoindolin-1-yl)acetate

The title compound was prepared from 3,3-difluoroindolin-2-one using protocol K except using tert-butyl 2-bromoacetate to give crude tert-butyl 2-(3,3-difluoro-2-oxoindolin-1-yl)acetate as a yellow oil. LCMS method [1] showed an M+Na peak of 306.1 with a retention time of 2.502 min.

1.86.3. 2-(3,3-Difluoro-2-oxoindolin-1-yl)acetic acid

A 30 mL reaction vial was charged with tert-butyl 2-(3,3-difluoro-2-oxoindolin-1-yl)acetate (275 mg, 1 mmol) as a yellow oil. DCM (3 mL) was added, followed by an equal volume of formic acid. The reaction was stirred for 16 h. The reaction mixture was concentrated under reduced pressure to give 2-(3,3-difluoro-2-oxoindolin-1-yl)acetic acid as a yellow solid. The desired M+H (228) was observed in the LCMS using the method [1] with a retention time of 1.652 min.

1.86.4. N-(4-Bromo-3-(4H-1,2,4-triazol-3-yl)thiophen-2-yl)-2-(3,3-difluoro-2-oxoindolin-1-yl)acetamide The title compound was prepared from 2-(3,3-difluoro-2-oxoindolin-1-yl)acetic acid (50 mg, 0.22 mmol), 4-bromo-3-(4H-1,2,4-triazol-3-yl)thiophen-2-amine (45 mg, 0.18 mmol) using protocol A. HPLC purification gave N-(4-bromo-3-(4H-1,2,4-triazol-3-yl)thiophen-2-yl)-2-(3,3-difluoro-2-oxoindolin-1-yl)acetamide (12 mg) as a white solid (m/z 454.0, retention of 5.696 min in [7]). $^1$H-NMR (300 MHz, CDCl$_3$) δ 13.1 (s, 1H), 7.82 (s, 1H), 7.70 (dd, J=7.5, 1.5 Hz, 1H), 7.50 (td, J=7.9, 1.2 Hz, 1H), 6.99 (s, 1H), 6.92 (d, J=7.9 Hz, 1H), 4.71 (s, 2H).

1.87. Synthesis of N-(4-bromo-3-(4H-1,2,4-triazol-3-yl)thiophen-2-yl)-2-(7-(trifluoromethyl)quinolin-5-yl)acetamide and N-(4-bromo-3-(4H-1,2,4-triazol-3-yl)thiophen-2-yl)-2-(5-(trifluoromethyl)quinolin-7-yl)acetamide

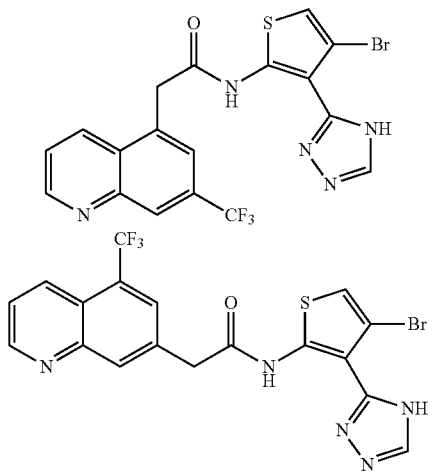

1.87.1. 7-Bromo-5-(trifluoromethyl)quinoline and 5-bromo-7-(trifluoromethyl)quinoline 3-bromo-5-(trifluoromethyl)aniline (11.7 g, 48.5 mmol) was taken up in glycerol (7.2 mL) and conc. H$_2$SO$_4$ (13 mL).

Nitrobenzene (5.0 mL) and FeSO$_4$.7H$_2$O (800 mg, 2.88 mmol) were added, and the mixture was slowly warmed to 130° C. for 4 h. Isolation led to a 3:2 mixture of regioisomers, which was used without further purification in the subsequent reaction. HPLC method [4], retention time 2.53 and 2.59 min; MS(ESI) 278.0 (MH+, $^{81}$Br).

1.87.2. tert-Butyl 2-(5-(trifluoromethyl)quinolin-7-yl)acetate and tert-butyl 2-(7-(trifluoromethyl)quinolin-5-yl)acetate The title compounds were prepared from 7-bromo-5-(trifluoromethyl)quinoline and 5-bromo-7-(trifluoromethyl)quinoline (550 mg, 2.0 mmol) using protocol P. Flash chromatography (10-30% EtOAc/hexanes elution) afforded the product as a brown oil (400 mg, 64%). HPLC method [7], retention time 5.61 and 5.74 min; MS(ESI) 312.0 (MH+).

1.87.3. 2-(5-(Trifluoromethyl)quinolin-7-yl)acetic acid and 2-(7-(trifluoromethyl)quinolin-5-yl)acetic acid A mixture of tert-butyl 2-(5-(trifluoromethyl)quinolin-7-yl)acetate and tert-butyl 2-(7-(trifluoromethyl)quinolin-5-yl)acetate (400 mg, 1.3 mmol) was dissolved in glacial AcOH (8 mL) and 6 N HCl (8 mL). The mixture was heated to 70° C. for 1 h, then 80° C. for an additional hr. The reaction mixture was concentrated in vacuo to afford the crude title compounds, which were used without further purification. HPLC method [4], retention time 1.29 min; MS(ESI) 256.0 (MH+).

1.87.4. N-(4-Bromo-3-(4H-1,2,4-triazol-3-yl)thiophen-2-yl)-2-(7-(trifluoromethyl)quinolin-5-yl)acetamide and N-(4-bromo-3-(4H-1,2,4-triazol-3-yl)thiophen-2-yl)-2-(5-(trifluoromethyl)quinolin-7-yl)acetamide 2-(5-(trifluoromethyl)quinolin-7-yl)acetic acid and the mixture of 2-(7-(trifluoromethyl)quinolin-5-yl)acetic acid (28.3 mg, 0.11 mmol) and 4-bromo-3-(4H-1,2,4-triazol-3-yl)thiophen-2-amine (23 mg, 0.094 mmol) were treated according to protocol A. The crude product mixture was purified by HPLC to afford N-(4-bromo-3-(4H-1,2,4-triazol-3-yl)thiophen-2-yl)-2-(5-(trifluoromethyl)quinolin-7-yl)acetamide and N-(4-bromo-3-(4H-1,2,4-triazol-3-yl)thiophen-2-yl)-2-(7-(trifluoromethyl)quinolin-5-yl)acetamide. LCMS method [13], retention time (min) 10.100 and 10.386; MS(ESI) 482.0 (MH+, $^{79}$Br); $^1$H NMR (300 MHz, CD$_3$OD) δ 9.01 (dd, J=4.3, 1.6 Hz, 1H), 8.62 (d, J=8.4 Hz, 1H), 8.41 (s, 1H), 7.98 (s, 1H), 7.70 (dd, J=8.7, 4.3 Hz, 1H), 4.50 (s, 2H).

1.88. Synthesis of N-(4-bromo-3-(4H-1,2,4-triazol-3-yl)thiophen-2-yl)-2-(2-(trifluoromethyl)quinolin-7-yl)acetamide

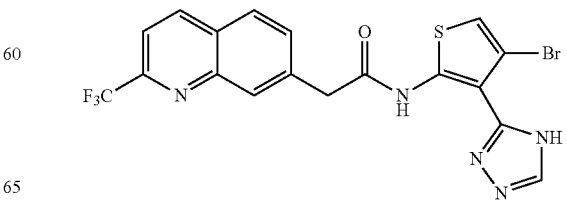

1.88.1. tert-Butyl 2-(2-(trifluoromethyl)quinolin-7-yl)acetate

The title compound was prepared from 7-bromo-2-(trifluoromethyl)quinoline (Keller, H. and Schlosser, M. *Tetrahedron* 1996, 52: 4637-4644) (45 mg, 0.163 mmol) using protocol P and was purified by flash chromatography (10-30% EtOAc/hexanes elution) to afforded a brown oil. HPLC method [5], retention time 1.875 min; MS(ESI) 312.0 (MH+).

1.88.2. 2-(2-(Trifluoromethyl)quinolin-7-yl)acetic acid tert-Butyl 2-(2-(trifluoromethyl)quinolin-7-yl)acetate was dissolved in glacial AcOH (0.8 mL) and 6 N HCl (0.8 mL) and heated to 80° C. for 2 hr. The reaction mixture was concentrated in vacuo to afford the crude product, which was used without further purification. HPLC method [4], retention time=1.874 min; MS(ESI) 256.1 (MH+).

1.88.3. N-(4-Bromo-3-(4H-1,2,4-triazol-3-yl)thiophen-2-yl)-2-(2-(trifluoromethyl)quinolin-7-yl)acetamide The title compound was synthesized via protocol B from 2-(2-(trifluoromethyl)quinolin-7-yl)acetic acid and 4-bromo-3-(4H-1,2,4-triazol-3-yl)thiophen-2-amine, using HOAt instead of HOBt. HPLC purification afforded the product as a white solid. HPLC method [7], retention time 8.68 min; MS(ESI) 484.2 (MH+, $^{81}$Br); $^1$H NMR (300 MHz, CD$_3$OD) δ 8.76 (d, J=9.5 Hz, 1H), 8.25 (d, J=9.0 Hz, 1H), 7.96 (dd, J=8.7, 7.3 Hz, 1H), 7.92-7.81 (m, 1H), 7.11-6.97 (m, 1H), 4.45 (s, 2H).

1.89. Synthesis of N-(4-cyano-3-(1H-1,2,4-triazol-3-yl)thiophen-2-yl)-2-(2-oxo-3,4-dihydro-1,5-naphthyridin-1(2H)-yl)acetamide

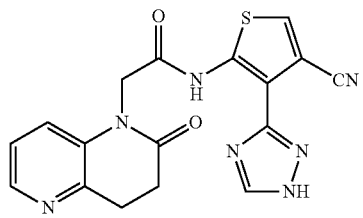 [SMILES: N#Cc1csc(NC(=O)CN2C(=O)CCc3ncccc32)c1-c1nc[nH]n1]

1.89.1. Thieno[3,2-e][1,2,4]triazolo[1,5-c]pyrimidine-9-carbonitrile

9-Bromothieno[3,2-e][1,2,4]triazolo[1,5-c]pyrimidine (1.16 g, 4.55 mmol) was dissolved in DMF (23 mL), and copper(I) cyanide (817 mg, 9.1 mmol) was added. This mixture was heated to 150° C. for 23 h, whereupon the reaction mixture was concentrated under reduced pressure, and the residue purified by flash chromatography. LCMS method [4], retention time=0.890 min; MS(ESI) 202.0 (MH+); $^1$H NMR (300 MHz, CDCl$_3$) δ 9.36 (s, 1H), 8.57 (s, 1H), 8.32 (s, 1H).

1.89.2. 5-Amino-4-(4H-1,2,4-triazol-3-yl)thiophene-3-carbonitrile

Thieno[3,2-e][1,2,4]triazolo[1,5-c]pyrimidine-9-carbonitrile (251 mg, 1.25 mmol) was dissolved in MeOH (6.2 mL), and N$^1$-methylethane-1,2-diamine (0.22 mL, 2.5 mmol) was added. This was heated to 60° C. for 20 min, then immediately cooled in an ice bath. Saturated NH$_4$Cl (30 mL) was added, then the aqueous mixture was extracted with 10% iPrOH/CHCl$_3$ (3×). The organic layers were combined, dried (MgSO$_4$), filtered and concentrated under reduced pressure to give the titled compound as a single peak on LC/MS: method [4], retention time=0.658 min; MS(ESI) 192.0 (MH+).

1.89.3. N-(4-Cyano-3-(1H-1,2,4-triazol-3-yl)thiophen-2-yl)-2-(2-oxo-3,4-dihydro-1,5-naphthyridin-1(2H)-yl)acetamide The title compound was synthesized according to protocol A from 5-amino-4-(4H-1,2,4-triazol-3-yl)thiophene-3-carbonitrile (69 mg, 0.364 mmol) and 2-(2-oxo-3,4-dihydro-1,5-naphthyridin-1(2H)-yl)acetic acid hydrochloride (89 mg, 0.367 mmol). HPLC purification afforded desired product as a white solid. LCMS method [11], retention time=6.22 min; MS(ESI) 380.1 (MH+); $^1$H NMR (300 MHz, CD$_3$OD) δ 8.52 (s, 1H), 8.28 (d, J=5.2 Hz, 1H), 7.88 (s, 1H), 7.82 (d, J=8.4 Hz, 1H), 7.55 (dd, J=8.4, 5.3 Hz, 1H), 5.01 (s, 2H), 3.37 (t, J=7.6 Hz, 2H), 2.99 (t, J=7.6 Hz, 2H).

1.90. Synthesis of N-(4-cyano-3-(1-methyl-1H-1,2,4-triazol-3-yl)thiophen-2-yl)-2-(2-oxo-3,4-dihydro-1,5-naphthyridin-1(2H)-yl)acetamide N-(4-cyano-3-(1H-1,2,4-triazol-3-yl)thiophen-2-yl)-2-(2-oxo-3,4-dihydro-1,5-naphthyridin-1(2H)-yl)acetamide (180 mg, 0.475 mmol) was dissolved in MeOH/CH$_2$Cl$_2$ (1:1, 4 mL total), and TMSCHN$_2$ (Aldrich, 2.0 M in diethyl ether, 8 mL, 16 mmol) was added at rt. This was stirred for 4 h, whereupon the reaction mixture was concentrated under reduced pressure. The crude residue was purified by HPLC to give a white solid as a trifluoroacetic acid salt: method [11], retention time=7.56 min; MS(ESI) 394.2 (MH+); $^1$H NMR (300 MHz, CD$_3$OD) 8.41 (s, 1H), 8.25 (d, J=5.0 Hz, 1H), 7.87 (s, 1H), 7.72 (d, J=8.7 Hz, 1H), 7.52-7.42 (m, 1H), 4.98 (s, 2H), 3.97 (s, 3H), 3.40-3.20 (m, 2H), 2.96 (t, J=8.3 Hz, 2H).

1.91. Synthesis of N-(4-chloro-3-(1-methyl-1H-1,2,4-triazol-3-yl)thiophen-2-yl)-2-(2-oxo-3,4-dihydro-1,5-naphthyridin-1(2H)-yl)acetamide

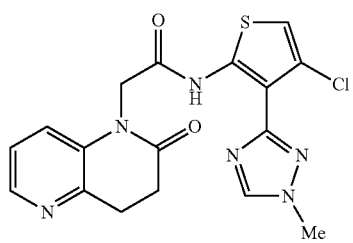 [SMILES: Cn1cnc(-c2c(Cl)csc2NC(=O)CN2C(=O)CCc3ncccc32)n1]

1.91.1. 4-Chloro-3-(4H-1,2,4-triazol-3-yl)thiophen-2-amine

This compound was made via a sequence analogous to the synthesis of 4-bromo-3-(4H-1,2,4-triazol-3-yl)thiophen-2-amine: method [11], retention time=3.73 min; MS(ESI)

201.0 (MH+, ³⁵Cl); ¹H NMR (300 MHz, DMSO-d₆) δ 13.68 (br s, 1H), 8.35 (br s, 1H), 7.14 (br s, 2H), 6.48 (s, 1H).

1.91.2. N-(4-Chloro-3-(1H-1,2,4-triazol-3-yl)thiophen-2-yl)-2-(2-oxo-3,4-dihydro-1,5-naphthyridin-1(2H)-yl)acetamide The titled compound was synthesized from 4-chloro-3-(4H-1,2,4-triazol-3-yl)thiophen-2-amine and 2-(2-oxo-3,4-dihydro-1,5-naphthyridin-1(2H)-yl)acetic acid via protocol A. LCMS method [4], retention time=1.035; MS(ESI) 389.1 (MH+, ³⁵Cl).

1.91.3. N-(4-Chloro-3-(1-methyl-1H-1,2,4-triazol-3-yl)thiophen-2-yl)-2-(2-oxo-3,4-dihydro-1,5-naphthyridin-1(2H)-yl)acetamide The titled compound was synthesized from N-(4-chloro-3-(1H-1,2,4-triazol-3-yl)thiophen-2-yl)-2-(2-oxo-3,4-dihydro-1,5-naphthyridin-1(2H)-yl)acetamide and TMSCHN₂. HPLC purification afforded a white solid. LCMS method [11], retention time=7.322 min; MS(ESI) 403.2 (MH+, ³⁵Cl); ¹H NMR (300 MHz, CD₃OD) δ 8.43 (s, 1H), 8.29 (d, J=5.3 Hz, 1H), 7.85 (d, J=8.0 Hz, 1H), 7.59 (t, J=7.1 Hz, 1H), 6.94 (s, 1H), 4.98 (s, 2H), 3.98 (s, 3H), 3.36 (t, J=7.5 Hz, 2H), 2.97 (dd, J=8.2, 6.3 Hz, 2H).

1.92. Synthesis of N-(4-bromo-3-(1H-1,2,4-triazol-5-yl)thiophen-2-yl)-2-(quinolin-8-1)acetamide To a mixture of 2-(quinolin-8-yl)acetic acid (35.6 mg, 0.19 mmol) and 4-bromo-3-(1H-1,2,4-triazol-5-yl)thiophen-2-amine (27.6 mg, 0.11 mmol) in methylene chloride (1.0 mL) and triethylamine (0.1 mL) was added 2-chloro-1-methylpyridinium iodide (46.5 mg, 0.18 mmol) at rt. After stirring for 15 min, the reaction mixture was concentrated under reduced pressure. Purification by flash chromatography (silica, 40:60 ethyl acetate/hexane) gave N-(5-bromo-3-(1H-1,2,4-triazol-5-yl)thiophen-2-yl)-2-(quinolin-8-1)acetamide (12 mgs, 26%). The desired product was submitted to prep HPLC for further purification. Retention time (min)=3.486, method [7], MS(ESI) 415.9 (M+H). ¹H NMR (CDCl₃) δ 12.42 (s, 1H), 9.09 (d, J=1.7 Hz, 1H), 8.40 (d, J=8.5 Hz, 1H), 7.96 (d, J=8.6 Hz, 1H), 7.89 (d, J=8.6 Hz, 1H), 7.73 (s, 1H), 7.71 (d, J=8.0 Hz, 1H), 7.66 (d, J=8.0 Hz, 1H), 7.58 (d, J=4.5 Hz, 1H), 6.86 (s, 1H), 4.62 (s, 2H).

1.93. Synthesis of 2-(benzo[d]thiazol-7-yl)-N-(4-bromo-3-(1H-1,2,4-triazol-5-yl)thiophen-2-yl)acetamide The title compound was prepared from 2-(benzo[d]thiazol-7-yl)acetic acid (25.5 mg, 0.13 mmol) and 4-bromo-3-(1H-1,2,4-triazol-5-yl)thiophen-2-amine (22.3 mg, 0.093 mmol) according to protocol A. The crude product was purified by prep HPLC. LCMS Retention time (min)=4.075, method [7], MS(ESI) 421.9 (M+H). ¹H NMR (CDCl₃) δ 12.39 (s, 1H), 9.02 (s, 1H), 8.22, (d, J=6.6 Hz, 1H), 7.65-7.61 (m, 1H), 7.54 (s, 1H), 7.55-7.49 (m, 1H), 6.90 (s, 1H), 4.19 (s, 2H).

1.94. Synthesis of N-(4-bromo-3-(1H-1,2,4-triazol-5-yl)thiophen-2-yl)-2-(7-fluoroquinolin-5-yl)acetamide

1.94.1. N-(3-Bromo-5-fluorophenyl)acetamide

To a mixture of tris(dibenzylideneacetone)dipalladium (0.20 g, 0.22 mmol), 9,9-dimethyl-4,5-bis(diphenylphosphine)xanthene (0.13, 0.22 mmol) and cesium carbonate (5.0 g, 15.41 mmol) under N₂ gas was added acetamide (0.90, 14.73 mmol), 1,3-dibromo-5-fluorobenzene (2.8 g, 10.83 mmol) and dioxane (22 mL). The reaction mixture was heated at 80° C. overnight and concentrated under reduced pressure. Purification by flash chromatography (silica, 50:50 ethyl acetate/hexane) gave N-(3-bromo-5-fluorophenyl)acetamide (3.51 g, quantitative). Retention time (min)=1.945, method [4], MS(ESI) 232.0 (M+H).

1.94.2. 3-Bromo-5-fluoroaniline hydrochloride

To a solution of N-(3-bromo-5-fluorophenyl)acetamide (3.5 g, 15.13 mmole) in absolute ethanol (40 mL) was added HCl (50 mL of a 11% aqueous solution). The reaction mixture was stirred while refluxing in an oil bath set at 110° C. overnight. Conc hydrochloric acid (5 mL) was added and stirred for an additional 5 h prior to concentrating under reduce pressure. The resulting 3-bromo-5-fluoroaniline hydrochloride (2.9 g, 85% yield) was used in the next reaction without further purification. Retention time (min)=2.077, method [4], MS(ESI) 192.0 (M+H).

1.94.3. 5-Bromo-7-fluoroquinoline and 7-bromo-5-fluoroquinoline

To 3-bromo-5-fluoroaniline hydrochloride (2.9 g, 12.89 mmol) was added glycerol (1.9 mL, 25.99 mmol), nitrobenzene (1.3 mL), sulfuric acid (3.5 mL) and iron (II) sulfate heptahydrate (0.23 g, 0.82 mmol). The reaction mixture was placed in an oil bath set at 80° C. and stirred overnight followed by basification with 12N NaOH and extraction with dichloromethane. The organic phase was collected, dried (sodium sulfate), filtered and concentrated under reduced pressure. Purification by flash chromatography (silica, 50:50 ethyl acetate/hexane) gave 5-bromo-7-fluoroquinoline and 7-bromo-5-fluoroquinoline (1.03 g, 30%) Retention time (min)=1.877 and 1.967, method [4], MS(ESI) 227.9 (M+H).

1.94.4. tert-Butyl 2-(7-fluoroquinolin-5-yl)acetate and tert-Butyl 2-(5-fluoroquinolin-7-yl)acetate The title compounds were prepared from 5-bromo-7-fluoroquinoline and 7-bromo-5-fluoroquinoline (1.0 g, 4.356 mmol) using protocol P. Purification by flash chromatography (silica, 30:70 ethyl acetate/hexane) gave a mixture of tert-butyl 2-(7-fluoroquinolin-5-yl)acetate and tert-butyl 2-(5-fluoroquinolin-7-yl)acetate (0.500 g, 42%) Retention time (min)=1.559 and 1.725, method [4], MS(ESI) 262.1 (M+H).

1.94.5. 2-(7-Fluoroquinolin-5-yl)acetic acid

To a solution of tert-butyl 2-(7-fluoroquinolin-5-yl)acetate and tert-butyl 2-(5-fluoroquinolin-7-yl)acetate (0.50 g, 1.91 mmol) in acetic acid (5 mL) was added 4M hydrochloric acid in 1,4-dioxane (10 mL). The reaction mixture was heated in an oil bath set at 60° C. under condenser with N₂ (g) inlet overnight. The mixture was concentrated under reduced pressure and purified by flash chromatography (silica, 60:40 ethyl acetate/hexane followed by 20:80 methanol/dichloromethane). Further purification and separation by prep HPLC yielded the single regio-isomer 2-(7-fluoroquinolin-5-yl)acetic acid (0.025 g, 6%). Retention time (min)=0.337, method [4], MS(ESI) 206.1 (M+H).

1.94.6. N-(4-Bromo-3-(1H-1,2,4-triazol-5-yl)thiophen-2-yl)-2-(7-fluoroquinolin-5-yl)acetamide The title compound was prepared from 2-(7-fluoroquinolin-5-yl)acetic acid (0.025 g, 0.122 mmol) and 4-bromo-3-(1H-1,2,4-triazol-5-yl)thiophen-2-yl-amine (0.20 g, 0.083 mmol) according to protocol A. The desired product was submitted to prep HPLC for further purification. Retention time (min)=2.33, method [7], MS(ESI) 434.0 (M+H). $^1$H NMR (CDCl$_3$) δ 11.79 (s, 1H), 8.94 (d, J=4.0 Hz, 1H), 8.54 (d, J=8.1 Hz, 1H) 8.38 (s, 1H broad), 7.80 (d, J=10.1 Hz, 1H), 7.70 (d, J=10.1 Hz, 1H), 7.59-7.55 (m 1H), 7.22 (s, 1H), 4.47 (s, 2H).

1.95. Synthesis of N-(4-cyano-3-(1H-1,2,3-triazol-1-yl)thiophen-2-yl)-2-(2-oxo-6-(trifluoromethyl)quinolin-1(2H)-yl)acetamide

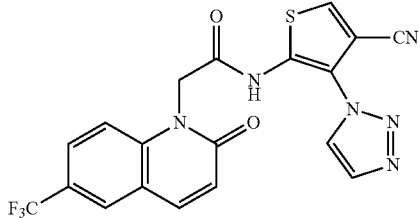 [SMILES: N#Cc1csc(NC(=O)Cn2c(=O)ccc3cc(C(F)(F)F)ccc32)c1-n1ccnn1]

1.95.1. 5-Nitro-4-(1H-1,2,3-triazol-1-yl)thiophene-3-carbonitrile and 5-nitro-4-(2H-1,2,3-triazol-2-yl)thiophene-3-carbonitrile A mixture of 4-bromo-5-nitrothiophene-3-carbonitrile (0.53 g, 2.26 mmol), 1H-1,2,3-triazole (20 μL, 0.35 mmol) and sodium bicarbonate (0.050 g, 0.60 mmol) in DMF (0.6 mL) were stirred in an oil bath set at 110° C. under condenser with N$_2$ (g) inlet for 2 h. The reaction mixture was quenched with H$_2$O and extracted with ethyl acetate. The organic phase was collected, dried (sodium sulfate), filtered and concentrated under reduced pressure. Purification by flash chromatography (silica, 30:70 ethyl acetate/hexane) gave the regio-isomer of each nitro intermediate (0.138 g and 0.116 g, 67% of 1:1 mixture). Retention time (min)=1.260 and 1.692, method [4], MS(ESI) 222.0 (M+H).

1.95.2. 5-Amino-4-(1H-1,2,3-triazol-1-yl)thiophene-3-carbonitrile 5-amino-4-(1H-1,2,3-triazol-1-yl)thiophene-3-carbonitrile was prepared from 5-nitro-4-(1H-1,2,3-triazol-1-yl)thiophene-3-carbonitrile (0.12 g, 0.52 mmol) according to protocol P. Retention time (min)=2.114, method [4], MS(ESI) 192.0 (M+H).

1.95.3. N-(4-Cyano-3-(1H-1,2,3-triazol-1-yl)thiophen-2-yl)-2-(2-oxo-6-(trifluoromethyl)quinolin-1(2H)-yl)acetamide The title compound was prepared from 2-(2-oxo-6-(trifluoromethyl)quinolin-1(2H)-yl)acetic acid (0.072 g, 0.27 mmol) and 5-amino-4-(1H-1,2,3-triazol-1-yl)thiophene-3-carbonitrile (0.025 g, 0.13 mmol) according to protocol A. The crude product was purified by prep HPLC. LCMS retention time (min)=5.505, method [7], MS(ESI) 445.1 (M+H). $^1$H NMR (CDCl$_3$) δ 11.17 (s, 1H), 8.41 (s, 1H), 7.91-7.87 (m, 3H), 7.79 (d, J=9.0 Hz, 1H), 7.67 (s, 1H), 7.48 (d, J=9.0 Hz, 1H), 5.26 (s, 2H).

1.96. Synthesis of N-(4-cyano-3-(2H-1,2,3-triazol-2-yl)thiophen-2-yl)-2-(2-oxo-6-(trifluoromethyl)quinolin-1(2H)-yl)acetamide

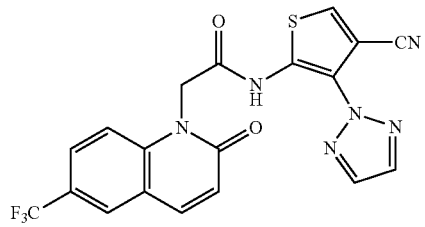 [SMILES: N#Cc1csc(NC(=O)Cn2c(=O)ccc3cc(C(F)(F)F)ccc32)c1-n1nccn1]

1.96.1. 5-Amino-4-(2H-1,2,3-triazol-2-yl)thiophene-3-carbonitrile 5-amino-4-(2H-1,2,3-triazol-2-yl)thiophene-3-carbonitrile was prepared from 5-nitro-4-(2H-1,2,3-triazol-2-yl)thiophene-3-carbonitrile (0.11 g, 0.62 mmole) according to protocol P. Retention time (min)=1.304, method [4], MS(ESI) 192.1 (M+H).

1.96.2. N-(4-Cyano-3-(2H-1,2,3-triazol-2-yl)thiophen-2-yl)-2-(2-oxo-6-(trifluoromethyl)quinolin-1(2H)-yl)acetamide N-(4-cyano-3-(2H-1,2,3-triazol-2-yl)thiophen-2-yl)-2-(2-oxo-6-(trifluoromethyl)quinolin-1(2H)-yl)acetamide was prepared from 2-(2-oxo-6-(trifluoromethyl)quinolin-1(2H)-yl)acetic acid (0.15 g, 0.56 mmol) and 5-amino-4-(2H-1,2,3-triazol-2-yl)thiophene-3-carbonitrile (0.070 g, 0.37 mmol) according to protocol A. The crude product was purified by prep HPLC. Retention time (min)=6.5, method [7], MS(ESI) 467.1 (M+Na). $^1$H NMR (CDCl$_3$) δ 11.50 (s, 1H), 7.93-7.85 (m, 4H), 7.83 (s, 1H), 7.64 (s, 1H), 7.60 (d, J=8.5 Hz, 1H), 6.95 (d, J=9.7 Hz, 1H), 5.29 (s, 2H).

1.97. Synthesis of N-(4-bromo-3-(2H-1,2,3-triazol-2-yl)thiophen-2-yl)-2-(2-oxo-6-(trifluoromethyl)quinolin-1(2H)-yl)acetamide

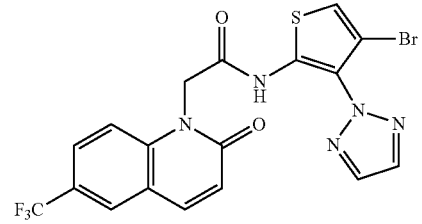 [SMILES: O=C(Cn1c(=O)ccc2cc(C(F)(F)F)ccc21)Nc1scc(Br)c1-n1nccn1]

1.97.1. 2-(4-Bromo-2-nitrothiophen-3-yl)-2H-1,2,3-triazole

A mixture of 3,4-dibromo-2-nitrothiophene (1.5 g, 5.23 mmol), 1H-1,2,3-triazole (0.30 mL, 5.18 mmol) and potassium bicarbonate (0.54 g, 5.36 mmol) in DMF (13 mL) were stirred in an oil bath set at 110° C. under condenser with N₂ (g) inlet for 1 h. The reaction mixture was quenched with H₂O and extracted with ethyl acetate. The organic phase was collected, dried (sodium sulfate), filtered and concentrated under reduced pressure. Purification by flash chromatography (silica, 30:70 ethyl acetate/hexane) gave the regioisomer nitro intermediate of interest (0.518 g, 36%). Retention time (min)=1.950, method [4], MS(ESI) 276.9 (M+H).

1.97.2. 4-Bromo-3-(2H-1,2,3-triazol-2-yl)thiophene-2-amine

A mixture of 2-(4-bromo-2-nitrothiophen-3-yl)-2H-1,2,3-triazole (0.59 g, 2.15 mmol), iron powder (0.75 g, 13.38 mmol), glacial acetic acid (8.4 mL) and H₂O (1.2 mL) was heated in an oil bath set at 70° C. under condenser with N₂ (g) inlet for 1 h. Purification by flash chromatography (silica, 40:60 ethyl acetate/hexane) gave 4-bromo-3-(2H-1,2,3-triazol-2-yl)thiophene-2-amine (0.35 g, 66%). Retention time (min)=1.540, method [4], MS(ESI) 246.9 (M+H).

1.97.3. N-(4-Bromo-3-(2H-1,2,3-triazol-2-yl)thiophen-2-yl)-2-(2-oxo-6-(trifluoromethyl)quinolin-1(2H)-yl)acetamide The title compound was prepared from 2-(2-oxo-6-(trifluoromethyl)quinolin-1(2H)-yl)acetic acid (0.31 g, 1.14 mmol) and 4-bromo-3-(2H-1,2,3-triazol-2-yl)thiophene-2-amine (0.35 g, 1.42 mmol) according to protocol A. The desired product was submitted to prep HPLC for further purification. Retention time (min)=6.9, method [7], MS(ESI) 498.0 (M+H). ¹H NMR (CDCl₃) δ 10.56 (s, 1H), 7.90-7.89 (m, 2H), 7.86 (s, 1H), 7.83 (d, J=8.9 Hz, 1H), 7.66 (d, J=8.9 Hz, 1H), 6.97 (s, 1H), 6.92 (d, J=8.9 Hz, 2H), 5.16 (s, 2H).

1.98. Synthesis of N-(4-chloro-3-(1-methyl-1H-1,2,4-triazol-3-yl)thiophen-2-yl)-2-(2-oxo-1,5-naphthyridin-1(2H)-yl)acetamide

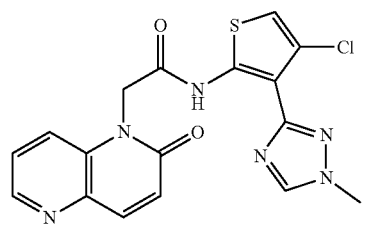 [SMILES: Cn1cnc(-c2c(Cl)csc2NC(=O)Cn2c(=O)ccc3ncccc32)n1]

1.98.1. N-(4-Chloro-3-(1H-1,2,4-triazol-3-yl)thiophen-2-yl)-2-(2-oxo-1,5-naphthyridin-1(2H)-yl)acetamide The title compound was prepared from 2-(2-oxo-1,5-naphthyridin-1(2H)-yl)acetic acid (0.13 g, 0.62 mmol) and 4-chloro-3-(1H-1,2,4-triazol-3-yl)thiophen-2-amine (0.22 g, 1.12 mmol) according to protocol A and purified by prep HPLC. Retention time (min)=1.010, method [4], MS(ESI) 389.0 (M+H).

1.98.2. N-(4-Chloro-3-(1-methyl-1H-1,2,4-triazol-3-yl)thiophen-2-yl)-2-(2-oxo-1,5-naphthyridin-1(2H)-yl)acetamide To a solution of N-(4-chloro-3-(1H-1,2,4-triazol-3-yl)thiophen-2-yl)-2-(2-oxo-1,5-naphthyridin-1(2H)-yl)acetamide (0.047, 0.12 mmol) in DMF (0.4 mL) was added potassium carbonate (0.041 g, 0.30 mmol) and iodomethane (17 uL, 0.27 mmol). After 2 h the reaction mixture was partitioned between H₂O and ethyl acetate. The organic phase was collected, dried (sodium sulfate), filtered and concentrated under reduced pressure. The desired product was submitted to prep HPLC for further purification. Retention time (min)=4.407, method [8], MS(ESI) 403.1 (M+H). ¹H NMR (CDCl₃) δ 12.40 (s, 1H), 8.32 (d, J=5.1 Hz, 1H), 8.07 (s, 1H), 7.56 (d, J=8.1 Hz, 1H) 7.41 (d, J=5.1 Hz, 1H), 7.39 (d, J=5.1 Hz, 1H) 6.81 (s, 1H), 4.89 (s, 2H), 4.02 (s, 3H), 3.47-3.42 (m, 2H), 3.03-2.98 (m, 2H).

Synthesis of N-(4-bromo-3-(1H-1,2,4-triazol-5-yl) thiophen-2-yl)-2-(8-fluoroisoquinolin-5-yl)acetamide

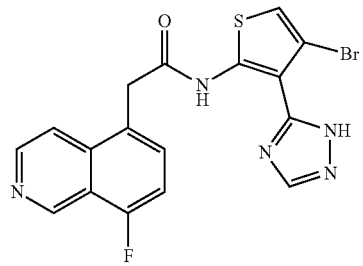 [SMILES: O=C(Cc1ccc(F)c2cnccc12)Nc1scc(Br)c1-c1ncn[nH]1]

1.99.1. 5-Bromo-8-nitroisoquinoline

KNO₃ (5.1 g, 50 mmol) was suspended in sulfuric acid (40 mL) and chilled to 0° C. 5-bromoisoquinoline (4 g, 19.2 mmol) was added slowly over the course of 20 minutes. The yellow, heterogeneous solution was brought to pH 8 by slow addition of ammonium hydroxide. Yellow solid was filtered off and recrystallized from methanol to give 7.5 g of 5-bromo-8-nitroisoquinoline. LCMS showed an m/z of 253.0/255.0 with a retention time of 1.797 min, method [1].

1.99.2. 5-Bromoisoquinolin-8-amine

A 3-neck flask was charged with 5-bromo-8-nitroisoquinoline (4 g, 15.8 mmol) and dissolved in MeOH (50 mL). A condenser was affixed and the mixture was heated to 100° C. Aqueous (20 mL) solution of ammonium chloride (4.12 g, 79 mmol) was added slowly, followed by iron powder (3 g, 53.7 mmol). The heterogeneous mixture was stirred at 100° C. for 3 h. LCMS confirmed complete reduction to the amine. The mixture was filtered and the solution was concentrated under reduced pressure to give a brown solid as crude product (2.4 g, 68%). LCMS showed an m/z of 225.0/223.0 with a retention time of 0.767 min, method [1].

1.99.3. 5-Bromo-8-fluoroisoquinoline

To a solution of 8-amino-5-bromoisoquinoline in 48% HBF₄ (30 mL) at 0° C. was slowly added an aqueous (10 mL) solution of NaNO₂ (172 mg, 2.5 mmol). The reaction mixture was stirred at 0° C. for 1 h and was then concentrated under reduced pressure to give a dark residue. The dark residue was heated to 150° C. for 16 h. The resulting dark oil was cooled to 23° C., quenched with ammonium hydroxide and extracted with DCM. The organic solution was concentrated and the resulting dark solid was recrystallized from EtOAc/Hexanes. The desired product (100 mg)

was in the mother liquor while the by-product was filtered away as a solid. LCMS showed an m/z of 228.0/226.0 with a retention time of 1.318 min, method [1].

1.99.4. 2-(8-Fluoroisoquinolin-5-yl)acetic acid

A 30 mL reaction vial was flame dried and charged with isopropylamine (0.67 mL, 4.8 mmol) in toluene (3 mL). The solution was chilled to 0° C. before a 1.5M solution of nBuLi (4.8 mmol, 3.2 mL) was added. $Pd_2(dba)_3$ catalyst (184 mg, 0.2 mmol) was added, followed by ligand 2'-(dicyclohexylphosphino)-N,N-dimethylbiphenyl-2-amine (160 mg, 0.4 mmol), and t-butylacetate (464 mg, 4 mmol). After 15 min, a toluene (3 mL) solution of 5-bromo-8-fluoroisoquinoline (200 mg, 0.9 mmol) was added. The reaction was stirred for 16 h while warming to 23° C. The crude mixture was purified by column chromatography (3% MeOH/DCM) to give tert-butyl 2-(8-fluoroisoquinolin-5-yl) acetate (140 mg). LCMS showed an m/z of 262.1 with a retention time of 1.469 min, method [1].

To a solution of the above ester (200 mg) in DCM (2 mL) was added formic acid (3 mL). The reaction was sealed with a Teflon cap and heater to 50° C. for 16 h. The solvent was removed and the crude product was used without further purification. LCMS showed an m/z of 206.1 with a retention time of 0.437 min, method [1].

1.99.5. N-(4-Bromo-3-(1H-1,2,4-triazol-5-yl)thiophen-2-yl)-2-(8-fluoroisoquinolin-5-yl)acetamide The title compound was prepared from 2-(8-fluoroisoquinolin-5-yl)acetic acid and 4-bromo-3-(1H-1,2,4-triazol-5-yl)thiophen-2-amine using protocol B. Retention time (min)=1.987, method [7], MS(ESI) 432.0 (M+H); $^1$H NMR (300 MHz, $CD_3OD$) δ 9.74 (s, 1H), 8.66 (d, J=6.6 Hz, 1H), 8.30 (d, J=6.1 Hz, 1H), 8.20 (b s, 1H), 8.1 (dd, J=8.24, 5.5 Hz, 1H), 7.67 (dd, J=9.9, 7.7 Hz, 1H), 7.1 (s, 1H), 4.46 (s, 2H).

Synthesis of N-(4-bromo-3-(1H-1,2,4-triazol-5-yl)thiophen-2-yl)-2-(2-oxo-6-(trifluoromethoxy)quinolin-1(2H)-yl)acetamide

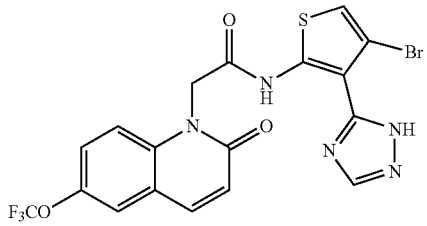 [SMILES: O=C(Cn1c(=O)ccc2cc(OC(F)(F)F)ccc21)Nc1scc(Br)c1-c1ncn[nH]1]

1.100.1 (E)-Ethyl 3-(2-amino-5-(trifluoromethoxy)phenyl)acrylate

To a mixture of 2-bromo-4-(trifluoromethoxy)aniline (1.00 mmol), triethylamine (1.5 mmol) and $P(o-tol)_3$ (0.40 mmol) in DMF (0.5 M) in a glass pressure tube under nitrogen gas were added ethyl acrylate (1.0 mmol) and palladium acetate (0.20 mmol). The tube was sealed and heated to 120° C. for 18 h. The resulting solution was concentrated under vacuum and purified by column chromatography. Retention time (min)=2.467, method [1], MS(ESI) 276.1 (M+H).

1.100.2. 6-(Trifluoromethoxy)quinolin-2(1H)-one

To a stirring mixture of (E)-ethyl 3-(2-amino-5-(trifluoromethoxy)phenyl)acrylate (2.2 mmol) in 4N HCl in dioxane (25 mL) was added concentrated HCl (2 mL). The resulting mixture was warmed to 100° C. overnight. The reaction mixture was cooled to rt and then slowly quenched with a cold saturated $NaHCO_3$ solution until pH>7. The product was extracted with EtOAc and used without further purification. Retention time (min)=1.804, method [1], MS(ESI) 230.1 (M+H).

1.100.3. Methyl 2-(2-oxo-6-(trifluoromethoxy)quinolin-1(2H)-yl)acetate

Methyl 2-(2-oxo-6-(trifluoromethoxy)quinolin-1(2H)-yl)acetate was prepared from 6-(trifluoromethoxy)quinolin-2(1H)-one according to Protocol K. Retention time (min) =2.083, method [1], MS(ESI) 302.1 (M+H).

1.100.4. 2-(2-Oxo-6-(trifluoromethoxy)quinolin-1(2H)-yl)acetic acid

To a stirring solution of methyl 2-(2-oxo-6-(trifluoromethoxy)quinolin-1(2H)-yl)acetate (1.2 mmol) in THF/water (2:1) was added LiOH. $H_2O$ (8.1 mmol). The resulting mixture was stirred overnight. The crude product mixture was slowly acidified with 1N HCl solution and then extracted with EtOAc. The organic phase was separated, dried ($MgSO_4$), filtered and concentrated under vacuum to give 2-(2-oxo-6-(trifluoromethoxy)quinolin-1(2H)-yl)acetic acid. Retention time (min)=1.783, method [1], MS(ESI) 288.1 (M+H).

1.100.5. N-(4-Bromo-3-(1H-1,2,4-triazol-5-yl)thiophen-2-yl)-2-(2-oxo-6-(trifluoromethoxy)quinolin-1(2H)-yl)acetamide The title compound was prepared from 2-(2-oxo-6-(trifluoromethoxy)quinolin-1(2H)-yl)acetic acid (40 mg, 0.14 mmol) and 4-bromo-3-(1H-1,2,4-triazol-5-yl)thiophen-2-amine (28 mg, 0.11 mmol) according to protocol A. Retention time (min)=6.06, method [7], MS(ESI) 514.0 (M+H); $^1$H NMR (300 MHz, $CD_3Cl$) δ 7.85 (d, J=9.35 Hz, 1H), 7.73 (s, 1H), 7.50 (s, 1H), 7.44-7.41 (m, 1H), 7.35-7.33 (m, 1H), 6.97 (d, J=9.9 Hz, 1H), 6.95 (s, 1H), 5.31 (s, 2H).

1.101. Synthesis of N-(5-chloro-3-(1H-1,2,4-triazol-5-yl)thiophen-2-yl)-2-(2-oxo-6-(trifluoromethyl)quinolin-1(2H)-yl)acetamide

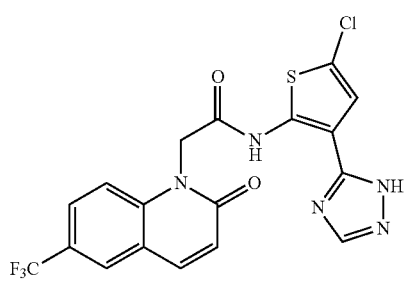 [SMILES: O=C(Cn1c(=O)ccc2cc(C(F)(F)F)ccc21)Nc1sc(Cl)cc1-c1ncn[nH]1]

1.101.1. 8-Chlorothieno[3,2-e][1,2,4]triazolo[4,3-c]pyrimidine

To a stirring mixture of thieno[3,2-e][1,2,4]triazolo[4,3-c]pyrimidine (123 mg, 0.7 mmol) in HOAc (1 mL) was added NCS (200 mg, 1.5 mmol), Pd(OAc)$_2$ (48 mg, 0.21 mmol). The reaction mixture was stirred at 120° C. overnight. The reaction was neutralized with a saturated NaHCO$_3$ solution and extracted with DCM. This product was purified via an isco column to give 8-chlorothieno[3,2-e][1,2,4]triazolo[4,3-c]pyrimidine as the major product. Retention time (min)=1.663, method [1], MS(ESI) 211.0 (M+H).

1.101.2. 5-Chloro-3-(4H-1,2,4-triazol-3-yl)thiophen-2-amine

To a stirring mixture of 8-chlorothieno[3,2-e][1,2,4]triazolo[4,3-c]pyrimidine (60 mg, 0.285 mmol) in MeOH (10 mL) was added N-methylethyl 1,2-diamine (106 mg, 1.4 mmol). The resulting mixture was warmed to 60° C. for 1 hr. The reaction mixture was cooled to rt and then diluted with DCM. This mixture was then washed several times with a saturated NH$_4$Cl solution. The organic layer was dried over MgSO$_4$, filtered, and concentrated under reduced pressure to give 5-chloro-3-(4H-1,2,4-triazol-3-yl)thiophen-2-amine. This amine was taken directly to the next coupling reaction without further purification. Retention time (min)=1.227, method [1], MS(ESI) 201.1 (M+H).

1.101.3. N-(5-chloro-3-(1H-1,2,4-triazol-5-yl)thiophen-2-yl)-2-(2-oxo-6-(trifluoromethyl)quinolin-1(2H)-yl)acetamide The title compound was synthesized from 2-(2-oxo-6-(trifluoromethyl)quinolin-1(2H)-yl)acetic acid and 5-chloro-3-(4H-1,2,4-triazol-3-yl)thiophen-2-amine according to protocol A. Retention time (min)=6.178, method [7], MS(ESI) 454.1 (M+H); $^1$H NMR (300 MHz, CD$_3$Cl) δ 11.93 (b s, 1H), 8.0 (s, 1H), 7.92-7.86 (m, 2H), 7.84-7.81 (m, 1H), 7.58 (d, J=8.8 Hz, 1H), 7.17 (s, 1H), 6.97 (d, J=9.34 Hz, 1H), 5.30 (s, 2H).

1.102. Synthesis of N-(4-bromo-3-(1H-1,2,4-triazol-5-yl)thiophen-2-yl)-2-(2-oxo-5-(trifluoromethyl)quinolin-1(2H)-yl)acetamide

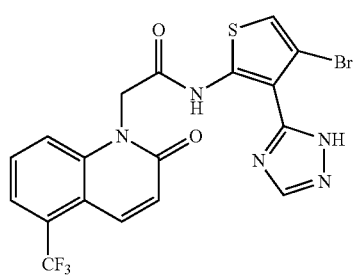 [SMILES: O=C(Cn1c(=O)ccc2c(C(F)(F)F)cccc21)Nc1scc(Br)c1-c1ncn[nH]1]

1.102.1. (E)-Ethyl 3-(2-amino-6-(trifluoromethyl)phenyl)acrylate

The aryl halide (2.1 mmol) and P(PPh)$_3$ (0.82 mmol) were dissolved in triethylamine (3.15 mmol) in a glass pressure tube and nitrogen gas was bubbled through the solution via a gas dispersion tube for 10 minutes. Ethyl acrylate (2.3 mmol) and palladium acetate (0.41 mmol) were added to the reaction mixture and the tube was sealed and placed into an oil bath pre-heated to 120° C. for 18 h. The resulting solution was concentrated under vacuum and purified via an isco column. Retention time (min)=2.416, method [1], MS(ESI) 260.1 (M+H).

1.102.2. 5-(Trifluoromethyl)quinolin-2(1H)-one

To a stirring mixture of (E)-ethyl 3-(2-amino-6-(trifluoromethyl)phenyl)acrylate in 4N HCl in dioxane (25 mL) was added concentrated HCl (2 mL). The resulting mixture was warmed to 100° C. overnight. The reaction mixture was cooled to rt and then slowly quenched with a cold saturated NaHCO$_3$ solution until pH>7. A normal aqueous extraction with EtOAc was followed. The crude mixture was taken directly to the next reaction without further purification. Retention time (min)=1.892, method [1], MS(ESI) 214.0 (M+H).

1.102.3. Methyl 2-(2-oxo-5-(trifluoromethyl)quinolin-1(2H)-yl)acetate

Methyl 2-(2-oxo-5-(trifluoromethyl)quinolin-1(2H)-yl)acetate was prepared from 5-(trifluoromethoxy)quinolin-2(1H)-one (T. Sakamoto, Y. Kondo, H, Yamanaka, *Chem. Phar. Bull.*, 33, 1985, 4764) according to protocol K. Retention time (min)=2.02, method [1], MS(ESI) 286.1 (M+H). To a stirring solution of the acetate (0.33 mmol) in THF/water (10:1) was added LiOH.H$_2$O (2.33 mmol). The resulting mixture was stirred overnight. The crude product mixture was slowly acidified with 1N HCl solution and then extracted with EtOAc. The organic phase was separated, dried (MgSO$_4$), filtered, and concentrated under vacuum to give 2-(2-oxo-5-(trifluoromethoxy)quinolin-1(2H)-yl)acetic acid. Retention time (min)=1.710, method [1], MS(ESI) 272.1 (M+H).

1.102.4. N-(4-bromo-3-(1H-1,2,4-triazol-5-yl)thiophen-2-yl)-2-(2-oxo-5-(trifluoromethyl)quinolin-1(2H)-yl)acetamide The title compound was synthesized from 2-(2-oxo-5-(trifluoromethoxy)quinolin-1(2H)-yl)acetic acid and 4-bromo-3-(1H-1,2,4-triazol-5-yl)thiophen-2-amine according to protocol A. Retention time (min)=5.810, method [7], MS(ESI) 498.0 (M+H). $^1$H NMR (300 MHz, CD$_3$Cl) δ 8.30-8.23 (m, 1H), 7.67 (s, 1H), 7.65-7.62 (m, 1H), 7.63 (s, 1H), 7.57-7.53 (m, 1H), 7.05 (d, J=9.9 Hz, 1H), 6.95 (s, 1H), 5.37 (s, 2H).

1.103. Synthesis of N-(4-bromo-3-(1H-1,2,4-triazol-5-yl)thiophen-2-yl)-2-(2-oxo-6-(trifluoromethyl)-3,4-dihydroquinolin-1(2H)-yl)acetamide

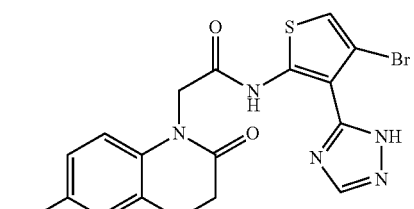

1.103.1. 2-(2-Oxo-6-(trifluoromethyl)-3,4-dihydroquinolin-1(2H)-yl)acetic acid To a stirring mixture of 2-(2-oxo-6-(trifluoromethyl)quinolin-1(2H)-yl)acetic acid in Pd/C was added MeOH. The reaction mixture was placed under an atmosphere of hydrogen (balloon) for several hours. The product mixture was filtered through a plug of celite. The plug was washed several times with EtOAc. The mixture was concentrated under reduced pressure and the crude amine was taken directly to the next reaction without further purification. Retention time (min)=1.841, method [1], MS(ESI) 274.1 (M+H).

1.103.2. N-(4-bromo-3-(1H-1,2,4-triazol-5-yl)thiophen-2-yl)-2-(2-oxo-6-(trifluoromethyl)-3,4-dihydroquinolin-1(2H)-yl)acetamide The title compound was synthesized from 2-(2-oxo-6-(trifluoromethyl)-3,4-dihydroquinolin-1(2H)-yl)acetic acid and 4-bromo-3-(1H-1,2,4-triazol-5-yl)thiophen-2-amine according to protocol A. Retention time (min)=6.373, method [7], MS(ESI) 500.0 (M+H); $^1$H NMR (300 MHz, CD$_3$Cl) δ 7.90 (s, 1H), 7.50 (s, 1H), 7.48 (d, J=6.6 Hz, 1H), 7.03 (d, J=9.34, 1H), 6.90 (s, 1H), 4.92 (s, 2H), 3.20-3.14 (m, 2H), 2.93-2.90 (m, 2H).

1.104. Synthesis of N-(4-bromo-3-(1H-1,2,4-triazol-5-yl)thiophen-2-yl)-2-(6-ethynyl-2-oxoquinolin-1(2H)-yl)acetamide

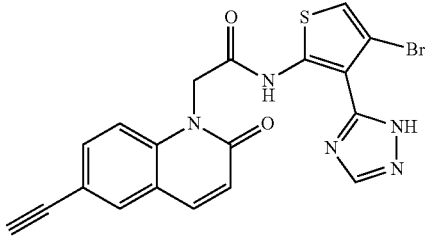 [SMILES: C#Cc1ccc2c(ccc(=O)n2CC(=O)Nc2scc(Br)c2-c2ncn[nH]2)c1]

1.104.1. Methyl 2-(2-oxo-6-((trimethylsilyl)ethynyl)quinolin-1(2H)-yl)acetate Methyl 2-(6-bromo-2-oxoquinolin-1(2H)-yl)acetate (0.67 mmol), CuI (0.67 mmol) and PdCl$_2$(PPh$_3$)$_2$ (0.40 mmol) were dissolved in triethylamine (3 mL) in a glass pressure tube and nitrogen gas was bubbled through the solution via a gas dispersion tube for 5 minutes. Ethynyltrimethylsilane (3.5 mmol) was added to the reaction mixture and the tube was sealed and placed into an oil bath pre-heated to 80° C. for 8 h. The resulting solution was concentrated under vacuum and purified via an isco column. Retention time (min)=2.759, method [1], MS(ESI) 314.1 (M+H).

1.104.2. 2-(6-Ethynyl-2-oxoquinolin-1(2H)-yl)acetic acid

Methyl 2-(2-oxo-6-((trimethylsilyl)ethynyl)quinolin-1(2H)-yl)acetate (0.128 mmol) was subjected to the protocol in Example 1.53.4, except with LiOH.H$_2$O instead of NaOH. Retention time (min)=1.435, method [1], MS(ESI) 228.1 (M+H).

1.104.3. N-(4-Bromo-3-(1H-1,2,4-triazol-5-yl)thiophen-2-yl)-2-(6-ethynyl-2-oxoquinolin-1(2H)-yl)acetamide The title compound was synthesized from 2-(6-ethynyl-2-oxoquinolin-1(2H)-yl)acetic acid and 4-bromo-3-(1H-1,2,4-triazol-5-yl)thiophen-2-amine according to protocol A. Retention time (min)=6.563, method [7], MS(ESI) 454.0 (M+H); $^1$H NMR (300 MHz, DMSO-d$_6$) δ 8.51 (s, 1H), 8.07 (d, J=9.35 Hz, 1H), 8.01-7.97 (m, 1H), 7.68-7.63 (m, 1H), 7.50 (d, J=8.80 Hz, 1H), 7.30 (s, 1H), 6.80 (d, J=9.9 Hz, 1H), 5.27 (s, 2H), 4.23 (s, 1H).

1.105. Synthesis of N-(4-bromo-3-(1H-1,2,4-triazol-5-yl)thiophen-2-yl)-2-(6-methylimidazo[2,1-b]thiazol-3-yl)acetamide The title compound was synthesized from 2-(6-methylimidazo[2,1-b]thiazol-3-yl)acetic acid and 4-bromo-3-(1H-1,2,4-triazol-5-yl)thiophen-2-amine according to protocol A. Retention time (min)=8.520, method [6], MS(ESI) 423.0 (M+H); $^1$H NMR (300 MHz, CD$_3$Cl) δ 8.12 (s, 1H), 7.35 (s, 1H), 7.22 (s, 1H), 7.0 (s, 1H), 4.15 (s, 2H), 2.50 (s, 3H).

1.106. Synthesis of N-(4-bromo-3-(1H-1,2,4-triazol-5-yl)thiophen-2-yl)-2-(imidazo[1,2-a]pyridin-5-yl)acetamide

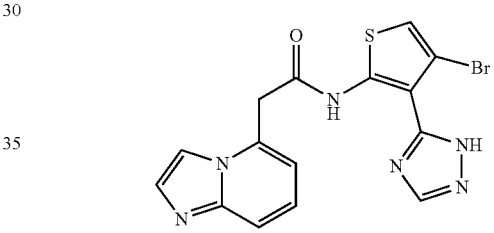

1.106.1 tert-Butyl 2-(imidazo[1,2-a]pyridin-5-yl)acetate

The title compound was prepared from 5-bromoimidazo[1,2-a]pyridine (1.0 g) according to protocol P. The crude product mixture was purified via normal phase chromatography to give tert-butyl 2-(imidazo[1,2-a]pyridin-5-yl)acetate. Method[1], MS(ESI) 233.1 [M+H], Retention time=0.951 min.

1.106.2. 2-(Imidazo[1,2-a]pyridin-5-yl)acetic acid

To a stirring mixture of tert-butyl 2-(imidazo[1,2-a]pyridin-5-yl)acetate (200 mg) in HOAc (5 mL) was added 6N HCl (5 mL). The reaction mixture was warmed to 80° C. for 2 h. The crude product mixture was concentrated under reduced pressure and directly taken to the next reaction without further purification. Method[1], MS(ESI) 177.1 [M+H], Retention time=0.303 min.

1.106.3. N-(4-Bromo-3-(1H-1,2,4-triazol-5-yl)thiophen-2-yl)-2-(imidazo[1,2-a]pyridin-5-yl)acetamide N-(4-bromo-3-(1H-1,2,4-triazol-5-yl)thiophen-2-yl)-2-(imidazo[1,2-a]pyridin-5-yl)acetamide was synthesized from 2-(imidazo[1,2-a]pyridin-5-yl)acetic acid and 4-bromo-3-(1H-1,2,4-triazol-5-yl)thiophen-2-amine according to protocol A. Retention time (min)=7.958, method [6], MS(ESI) 403.0 (M+H); $^1$H NMR (300 MHz, CD$_3$OD) δ 8.46 (b s, 1H), 8.35 (d, J=2.2 Hz, 1H), 8.12 (d, J=2.2 Hz, 1H), 8.08-7.96 (m, 2H), 7.58 (d, J=7.2 Hz, 1H), 7.16 (s, 1H), 4.64 (s, 2H).

1.107. Synthesis of N-(4-bromo-3-(1H-1,2,4-triazol-5-yl)thiophen-2-yl)-2-(7-fluoro-2-oxo-6-(trifluoromethyl)quinolin-1(2H)-yl)acetamide

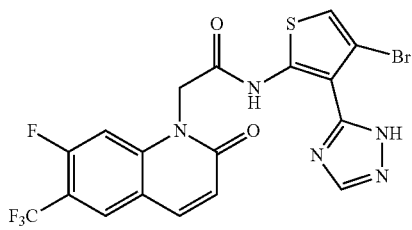 [SMILES: O=C(Cn1c(=O)ccc2cc(C(F)(F)F)c(F)cc21)Nc1scc(Br)c1-c1ncn[nH]1]

1.107.1. 2-Bromo-5-fluoro-4-(trifluoromethyl)aniline

To a stirring mixture of 3-fluoro-4-(trifluoromethyl)aniline (1.5 g) in DCM (12 mL) at room temperature was added dropwise a solution of NBS (1.5 g) in DCM (24 mL) over 15 min. The reaction mixture was stirred at rt for 1.5 h. The product mixture was concentrated under reduced pressure to one half of its original volume. The white solid was filtered off and the crude product mixture was further purified via column chromatography. Retention time (min)=2.490, method [1], MS(ESI) 257.9 (M+H).

1.107.2. (E)-Ethyl 3-(2-amino-4-fluoro-5-(trifluoromethyl)phenyl)acrylate

2-Bromo-5-fluoro-4-(trifluoromethyl)aniline (0.97 mmol) and P(o-tol)$_3$ (0.40 mmol) were dissolved in triethylamine (2.0 mL) in a glass pressure tube and nitrogen gas was bubbled through the solution via a gas dispersion tube for 10 minutes. Ethyl acrylate (1.0 mmol) and palladium acetate (0.20 mmol) were added to the reaction mixture and the tube was sealed and placed into an oil bath pre-heated to 85° C. for 18 h. The resulting solution was concentrated under vacuum and purified via an isco column. Retention time (min)=2.504, method [1], MS(ESI) 278.0 (M+H).

1.107.3. 7-Fluoro-6-(trifluoromethyl)quinolin-2(1H)-one

To a stirring mixture of (E)-ethyl 3-(2-amino-4-fluoro-5-(trifluoromethyl)phenyl)acrylate in 4N HCl in dioxane (10 mL) was added concentrated HCl (2 mL). The resulting mixture was warmed to 100° C. overnight. The reaction mixture was cooled to rt and then slowly quenched with a cold saturated NaHCO$_3$ solution until pH>7. A normal aqueous extraction with EtOAc was followed. The crude mixture was taken directly to the next reaction without further purification. Retention time (min)=1.887, method [1], MS(ESI) 232.0 (M+H).

1.107.4. Methyl 2-(7-fluoro-2-oxo-6-(trifluoromethyl)quinolin-1(2H)-yl)acetate The title compound was prepared from 7-fluoro-6-(trifluoromethyl)quinolin-2(1H)-one (T. Sakamoto, Y. Kondo, H, Yamanaka, *Chem. Phar. Bull.*, 33, 1985, 4764) according to protocol K. Retention time (min)=2.224, method [1], MS(ESI) 304.0 (M+H).

1.107.5 2-(7-Fluoro-2-oxo-6-(trifluoromethyl)quinolin-1(2H)-yl)acetic acid

To a stirring solution of methyl methyl 2-(7-fluoro-2-oxo-6-(trifluoromethyl)quinolin-1(2H)-yl)acetate (0.59 mmol) in THF/water (5:1) was added LiOH.H$_2$O (3.0 mmol). The resulting mixture was stirred overnight. The crude product mixture was slowly acidified with 1N HCl solution and then extracted with EtOAc. The organic phase was separated, dried (MgSO$_4$), filtered, and concentrated under vacuum to give 2-(7-fluoro-2-oxo-6-(trifluoromethyl)quinolin-1(2H)-yl)acetic acid. Retention time (min)=1.90, method [1], MS(ESI) 290.1 (M+H).

1.107.6 N-(4-Bromo-3-(1H-1,2,4-triazol-5-yl)thiophen-2-yl)-2-(7-fluoro-2-oxo-6-(trifluoromethyl)quinolin-1(2H)-yl)acetamide N-(4-bromo-3-(1H-1,2,4-triazol-5-yl)thiophen-2-yl)-2-(7-fluoro-2-oxo-6-(trifluoromethyl)quinolin-1(2H)-yl)acetamide was synthesized from 2-(7-fluoro-2-oxo-6-(trifluoromethyl)quinolin-1(2H)-yl)acetic acid and 4-bromo-3-(1H-1,2,4-triazol-5-yl)thiophen-2-amine according to protocol A. Retention time (min)=6.276, method [7], MS(ESI) 516.0 (M+H); $^1$H NMR (300 MHz, DMSO-d$_6$) δ 8.54 (b s, 1H), 8.37 (d, J=8.24 Hz, 1H), 8.20 (d, J=9.34 Hz, 1H), 7.89 (d, J=13.72 Hz, 1H), 7.31 (s, 1H), 6.81 (d, J=9.34 Hz, 1H), 5.28 (s, 2H).

1.108. Synthesis of N-(4-bromo-3-(1H-1,2,4-triazol-5-yl)thiophen-2-yl)-2-(6-fluoroisoquinolin-5-yl)acetamide

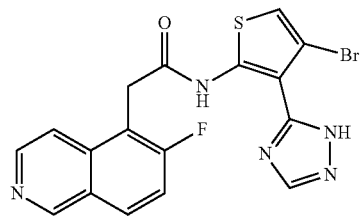 [SMILES: O=C(Cc1c(F)ccc2cnccc12)Nc1scc(Br)c1-c1ncn[nH]1]

1.108.1 5-Bromo-6-fluoroisoquinoline

To a stirring mixture of 6-fluoroisoquinoline in H$_2$SO$_4$ (5 mL) at 0° C. was added solid NBS (1.5 EQ) slowly over 5 min. The reaction mixture was reacted at 0° C. for 1 h. To this reaction mixture was added NBS (0.5 EQ). The cold bath was then removed. The reaction mixture was reacted until all the starting material was consumed. To this reaction mixture was neutralized with a cold solution of NaOH (5N) until the pH of this mixture>10. The white solid was filtered off and dissolved in DCM and washed with a solution of NaOH (1N). The organic layer was dried over MgSO$_4$, filtered, and concentrated under reduced pressure. The crude product was purified via a column to give 5-bromo-6-fluoroisoquinoline. Retention time (min)=2.810, method [3], MS(ESI) 226.0 (M+H).

1.108.2. tert-Butyl 2-(6-fluoroisoquinolin-5-yl)acetate

The title compound was prepared from 5-bromo-6-fluoroisoquinoline (290 mg) using protocol P. The crude product was purified via normal phase chromatography to give tert-butyl 2-(6-fluoroisoquinolin-5-yl)acetate. Method[1], MS(ESI) 262.1 [M+H], Retention time=1.503 min.

1.108.3 2-(6-Fluoroisoquinolin-5-yl)acetic acid

To a stirring mixture tert-butyl 2-(6-fluoroisoquinolin-5-yl)acetate (150 mg) in HOAc (5 mL) was added 6N HCl (5 mL). The reaction mixture was warmed to 100° C. for 3 h. The crude product mixture was concentrated under reduced pressure and directly taken to the next reaction without further purification. Method[1], MS(ESI) 206.1 [M+H], Retention time=0.313 min.

1.108.4. N-(4-Bromo-3-(1H-1,2,4-triazol-5-yl)thiophen-2-yl)-2-(6-fluoroisoquinolin-5-yl)acetamide N-(4-bromo-3-(1H-1,2,4-triazol-5-yl)thiophen-2-yl)-2-(6-fluoroisoquinolin-5-yl)acetamide was prepared from 2-(6-fluoroisoquinolin-5-yl)acetic acid and 4-bromo-3-(1H-1,2,4-triazol-5-yl)thiophen-2-amine according to protocol A. Retention time (min)=1.901, method [7], MS(ESI) 432.0 (M+H); $^1$H NMR (300 MHz, DMSO-$d_6$) 11.96 (b s, 1H), 9.58 (s, 1H), 8.64 (d, J=6.05 Hz, 1H), 8.46-8.41 (m, 1H), 8.24 (d, J=6.05 Hz, 1H), 7.84 (t, J=9.34 Hz, 1H), 7.27 (s, 1H), 4.46 (s, 2H).

Example 2

Thiophene Thiazole Analogs

2.1. Synthesis of 2-(Isoquinolin-5-yl)-N-(2-(4-methylthiazol-2-yl)thiophen-3-yl)acetamide (42)

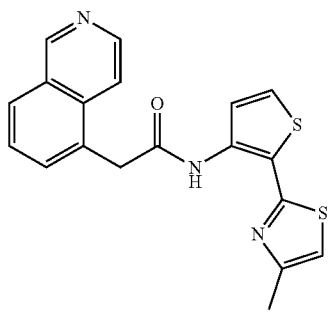 [SMILES: Cc1csc(-c2sccc2NC(=O)Cc2cccc3cnccc23)n1]

2.1.1. 4-Methyl-2-(3-nitrothiophen-2-yl)thiazole

4-Methyl-2-(3-nitrothiophen-2-yl)thiazole was prepared from 2-chloro-3-nitrothiophene (219 mg, 1.34 mmol) and 4-methyl-2-(tributylstannyl)thiazole (520 mg, 1.34 mmol) according to protocol E. Retention time (min)=2.462, method [1], MS(ESI) 227.0 (M+H).

2.1.2. 2-(4-Methylthiazol-2-yl)thiophen-3-amine 2-(4-Methylthiazol-2-yl)thiophen-3-amine was prepared from 4-methyl-2-(3-nitrothiophen-2-yl)thiazole (69 mg, 0.305 mmol) according to protocol F. Retention time (min)=1.828, method [1], MS(ESI) 197.0 (M+H).

2.1.3. 2-(Isoquinolin-5-yl)-N-(2-(4-methylthiazol-2-yl)thiophen-3-yl)acetamide 2-(Isoquinolin-5-yl)-N-(2-(4-methylthiazol-2-yl)thiophen-3-yl)acetamide was prepared from 2-(isoquinolin-5-yl)acetic acid (63 mg, 0.341 mmol) and 2-(4-methylthiazol-2-yl)thiophen-3-amine (67 mg, 0.341 mmol) according to protocol A. Retention time (min)=3.130, method [7], MS(ESI) 366.0 (M+H); $^1$H NMR (300 MHz, CDCl$_3$) δ 11.55 (s, 1H), 9.64 (s, 1H), 8.60 (d, J=6.8 Hz, 1H), 8.39 (d, J=6.6 Hz, 1H), 8.20 (d, J=8.4 Hz, 1H), 8.05-8.08 (m, 2H), 7.88-7.91 (m, 1H), 7.24 (d, J=5.5 Hz, 1H), 6.74 (s, 1H), 4.31 (s, 2H), 2.45 (s, 3H).

2.2. Synthesis of 2-(isoquinolin-5-yl)-N-(2-(thiazol-4-yl)thiophen-3-yl)acetamide (43)

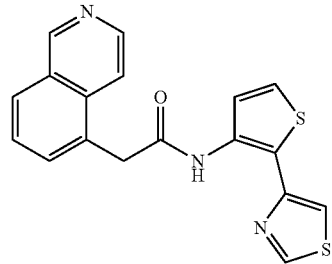 [SMILES: O=C(Cc1cccc2cnccc12)Nc1ccsc1-c1cscn1]

2.2.1. 4-(3-Nitrothiophen-2-yl)thiazole 4-(3-Nitrothiophen-2-yl)thiazole was prepared from 4-(tributylstannyl)thiazole (0.51 g, 1.31 mmol) and 2-chloro-3-nitrothiophene (0.21 g, 1.31 mmol) according to protocol E. Retention time (min)=2.012, method [1], MS(ESI) 212.9 (M+H).

2.2.2. 2-(Thiazol-4-yl)thiophen-3-amine 2-(Thiazol-4-yl)thiophen-3-amine was prepared from 4-(3-nitrothiophen-2-yl)thiazole (151 mg, 0.828 mmol)) according to protocol F. Retention time (min)=0.544, method [1], MS(ESI) 183.0 (M+H).

2.2.3. 2-(Isoquinolin-5-yl)-N-(2-(thiazol-4-yl)thiophen-3-yl)acetamide 2-(Isoquinolin-5-yl)-N-(2-(thiazol-4-yl)thiophen-3-yl)acetamide was prepared from 2-(isoquinolin-5-yl)acetic acid (120 mg, 0.641 mmol) and 2-(thiazol-4-yl)thiophen-3-amine (117 mg, 0.641 mmol) according to protocol A. Retention time (min)=2.147, method [7], MS(ESI) 352.0 (M+H); $^1$H NMR (300 MHz, CDCl$_3$) δ 10.99 (s, 1H), 9.63 (s, 1H), 8.59 (d, J=5.9 Hz, 1H), 8.43 (d, J=1.6 Hz, 1H), 8.23-8.42 (m, 2H), 8.04-8.08 (m, 2H), 7.90 (dd, J=8.1, 7.2 Hz, 1H), 7.18-7.23 (m, 2H), 4.31 (s, 2H).

2.3. Synthesis of 2-(2-Oxo-3,4-dihydro-1,6-naphthyridin-1(2H)-yl)-N-(2-(thiazol-4-yl)thiophen-3-yl)acetamide (44)

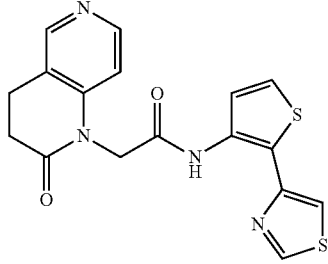 [SMILES: O=C(CN1C(=O)CCc2cnccc21)Nc1ccsc1-c1cscn1]

2.3.1. Methyl 2-(2-oxo-3,4-dihydro-1,6-naphthyridin-1(2H)-yl)acetate

The title compound was prepared from 3,4-dihydro-1,6-naphthyridin-2(1H)-one (0.84 g, 5.67 mmol) using protocol K to give methyl 2-(2-oxo-3,4-dihydro-1,6-naphthyridin-1(2H)-yl)acetate. Retention time (min)=0.341, method [1], MS(ESI) 221.0 (M+H).

2.3.2. 2-(2-Oxo-3,4-dihydro-1,6-naphthyridin-1(2H)-yl)acetic acid

Aqueous 1N HCl (2 mL) was added to a solution of methyl 2-(2-oxo-3,4-dihydro-1,6-naphthyridin-1(2H)-yl)acetate (1.24 g, 5.67 mmol) in acetic acid (5 mL) and the resulting mixture was heated to 60° C. for 4 h. The solution was concentrated under vacuum to give 2-(2-Oxo-3,4-dihydro-1,6-naphthyridin-1(2H)-yl)acetic acid. Retention time (min)=0.275, method [1], MS(ESI) 207.0 (M+H).

2.3.3. 2-(2-Oxo-3,4-dihydro-1,6-naphthyridin-1(2H)-yl)-N-(2-(thiazol-4-yl)thiophen-3-yl)acetamide The title compound was prepared from 2-(2-oxo-3,4-dihydro-1,6-naphthyridin-1(2H)-yl)acetic acid (65 mg, 0.32 mmol) and 2-(thiazol-4-yl)thiophen-3-amine (57 mg, 0.32 mmol) according to protocol A. Retention time (min)=1.471, method [7], MS(ESI) 371.1 (M+H); $^1$H NMR (300 MHz, CDCl$_3$) δ 11.48 (s, 1H), 8.87 (d, J=1.8 Hz, 1H), 8.48-8.76 (m, 1H), 7.99 (d, J=5.4 Hz, 1H), 7.37 (d, J=1.8 Hz, 1H), 7.27-2.28 (m, 2H), 7.23 (d, J=5.4 Hz, 1H), 4.91 (s, 2H), 3.20-3.25 (m, 2H), 2.96-3.01 (m, 2H).

2.4. Synthesis of 2-(2-oxo-3,4-dihydroquinolin-1(2H)-yl)-N-(2-(thiazol-4-yl)thiophen-3-yl)acetamide (45)

The title compound was prepared from 2-(2-oxo-3,4-dihydroquinolin-1(2H)-yl)acetic acid (88 mg, 0.43 mmol) and 2-(thiazol-4-yl)thiophen-3-amine (79 mg, 0.43 mmol) according to protocol A. Retention time (min)=5.703, method [7], MS(ESI) 370.0 (M+H); $^1$H NMR (300 MHz, CDCl$_3$) δ 11.2 (s, 1H), 8.49 9d, J=2.7 Hz, 1H), 8.13 (d, J=5.4 Hz, 1H), 7.19-7.25 (m, 4H), 7.02-7.08 (m, 2H), 4.81 (s, 2H), 3.05-3.09 (m, 2H), 3.2.85-2.89 (m, 2H).

2.5. Synthesis of 2-(isoquinolin-5-yl)-N-(2-(2-methoxythiazol-4-yl)thiophen-3-yl)acetamide (46)

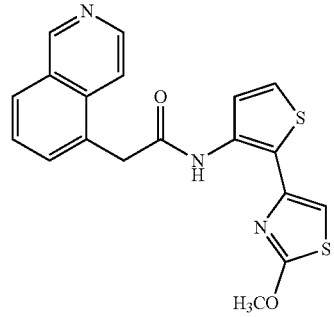

2.5.1. 2-Methoxy-4-(3-nitrothiophen-2-yl)thiazole

2-Methoxy-4-(3-nitrothiophen-2-yl)thiazole was prepared from 2-methoxy-4-(tributylstannyl)thiazole (1.0 g, 2.47 mmol) and 2-chloro-3-nitrothiophene (0.404 g, 2.47 mmol) according to protocol E. Retention time (min)=2.516, method [1], MS(ESI) 242.9 (M+H).

2.5.2. 2-(2-Methoxythiazol-4-yl)thiophen-3-amine 2-(2-Methoxythiazol-4-yl)thiophen-3-amine was prepared from 2-methoxy-4-(3-nitrothiophen-2-yl)thiazole (209 mg, 0.862 mmol) according to protocol F. Retention time (min)=1.17, method [1], MS(ESI) 213.0 (M+H).

2.5.3. 2-(Isoquinolin-5-yl)-N-(2-(2-methoxythiazol-4-yl)thiophen-3-yl)acetamide The title compound was prepared from 2-(isoquinolin-5-yl)acetic acid (72 mg, 0.36 mmol) and 2-(2-methoxythiazol-4-yl)thiophen-3-amine (78 mg, 0.36 mmol) according to protocol A. Retention time (min)=3.237, method [7], MS(ESI) 382.0 (M+H); $^1$H NMR (300 MHz, CDCl$_3$) δ 10.99 (s, 1H), 9.69 (s, 1H), 8.60 (d, J=6.5 Hz, 1H), 8.39 (d, J=6.5 Hz, 1H), 8.23 (d, J=8.4 Hz, 1H), 8.06 (d, J=7.3 Hz, 1H), 7.96 (d, J=5.5 Hz, 1H), 7.89 (dd, J=8.4, 7.3, 1H), 7.15 (d, J=5.5 Hz, 1H), 6.70 (s, 1H), 4.26 (s, 2H), 4.17 (s, 3H).

2.6. Synthesis of N-(2-(2-chlorothiazol-4-yl)thiophen-3-yl)-2-(isoquinolin-5-yl)acetamide (47)

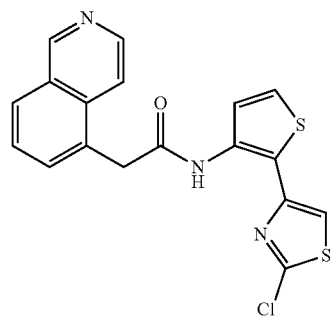 [SMILES: O=C(Cc1cccc2cnccc12)Nc1ccsc1-c1csc(Cl)n1]

2.6.1. 2-Chloro-4-(3-nitrothiophen-2-yl)thiazole

A solution of 2-methoxy-4-(3-nitrothiophen-2-yl)thiazole (403 mg, 1.66 mmol) in POCl$_3$ (2 mL) was heated at 60° C. for 1 h then to 100° C. for a further 2 h. The resulting solution was cooled to room temperature and diluted with cold H$_2$O then saturated aqueous sodium bicarbonate. The mixture was extracted with methylene chloride and the combined organic phases were dried (Na$_2$SO$_4$), filtered and concentrated under vacuum to give 2-chloro-4-(3-nitrothiophen-2-yl)thiazole. Retention time (min)=2.550, method [1], MS(ESI) 246.9 (M+H).

2.6.2. 2-(2-Chlorothiazol-4-yl)thiophen-3-amine 2-(2-Chlorothiazol-4-yl)thiophen-3-amine was prepared from 2-chloro-4-(3-nitrothiophen-2-yl)thiazole (307 mg, 1.24 mmol) according to protocol F. Retention time (min) =1.579, method [1], MS(ESI) 216.9 (M+H).

2.6.3. N-(2-(2-chlorothiazol-4-yl)thiophen-3-yl)-2-(isoquinolin-5-yl)acetamide The title compound was prepared from 2-(isoquinolin-5-yl)acetic acid (218 mg, 1.11 mmol) and 2-(2-chlorothiazol-4-yl)thiophen-3-amine (241 mg, 1.11 mmol) according to protocol A. Retention time (min)=3.049, method [7], MS(ESI) 385.89 (M+H); $^1$H NMR (300 MHz, CD$_3$OD) δ 9.54 (s, 1H), 8.56 (d, J=6.4 Hz, 1H), 8.39 (d, J=6.4 Hz, 1H), 8.31 (d, J=8.1 Hz, 1H), 8.16 (d, J=6.8 Hz, 1H), 7.94 (dd, J=8.1, 7.2 Hz, 1H), 7.73 (d, J=5.5 Hz, 1H), 7.45 (s, 1H), 7.37 (d, J=5.5 Hz, 1H), 4.39 (s, 2H).

2.7. Synthesis of 2-(Isoquinolin-5-yl)-N-(2-(thiazol-2-yl)thiophen-3-yl)acetamide (48)

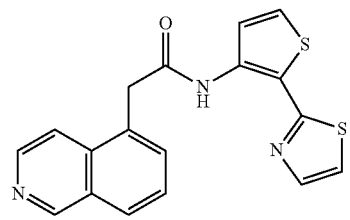 [SMILES: O=C(Cc1cccc2cnccc12)Nc1ccsc1-c1nccs1]

2.7.1. 2-(Thiazol-2-yl)thiophen-3-amine 2-(3-Nitrothiophen-2-yl)thiazole was synthesized from 2-chloro-3-nitrothiophene according to protocol E except that 2-(tributylstannyl)thiazole was used. Method[1], MS(ESI) 212.9 [M+H], Retention time=2.163 min. 2-(Thiazol-2-yl)thiophen-3-amine was synthesized from 2-(3-nitrothiophen-2-yl)thiazole according to protocol F. Method [1], MS(ESI) 183 [M+H], Retention time=1.718 min.

2.7.2. 2-(Isoquinolin-5-yl)-N-(2-(thiazol-2-yl)thiophen-3-yl)acetamide

The title compound was prepared from 2-(thiazol-2-yl)thiophen-3-amine and 2-(isoquinolin-5-yl)acetic acid according to protocol A. Preparative HPLC gave 2-(isoquinolin-5-yl)-N-(2-(thiazol-2-yl)thiophen-3-yl)acetamide. Method[7], MS(ESI) 352.1 [M+H], Retention time=2.59 min; $^1$H-NMR (300 MHz, CDCl$_3$) δ 11.32 (s, 1H), 8.26 (d, J=8.2 Hz, 1H), 8.10-8.09 (m, 1H), 8.07 (s, 1H), 7.94 (t, J=7.7 Hz, 1H), 7.35 (d, J=3.3 Hz, 1H), 7.31-7.24 (m, 4H), 7.10 (d, J=3.3 Hz, 1H), 4.33 (s, 2H).

2.8. Synthesis of 2-(isoquinolin-5-yl)-N-(2-(5-methylthiazol-2-yl)thiophen-3-yl)acetamide (49)

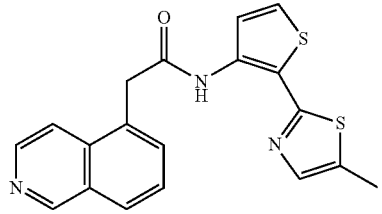 [SMILES: Cc1cnc(-c2sccc2NC(=O)Cc2cccc3cnccc23)s1]

2.8.1. 2-(5-Methylthiazol-2-yl)thiophen-3-amine

This amine was prepared from 2-chloro-3-nitrothiophene using protocols E and F. Method[1], MS(ESI) 227.0 [M+H], Retention time=2.538 min.

2.8.2. 2-(Isoquinolin-5-yl)-N-(2-(5-methylthiazol-2-yl)thiophen-3-yl)acetamide The title compound was prepared from 2-(isoquinolin-5-yl)acetic acid and 2-(5-methylthiazol-2-yl)thiophen-3-amine using Protocol A. Method[7], MS(ESI) 366.0 [M+H], Retention time=3.157 min; $^1$H-NMR (300 MHz, CDCl$_3$) δ 11.24 (s, 1H), 9.67 (s, 1H), 8.57 (d, J=6.6 Hz, 1H), 8.30 (d, J=6.6 Hz, 1H), 8.26 (d, J=8.24 Hz, 1H), 8.08-8.04 (m, 2H), 7.96-7.91 (m, 1H), 7.20 (d, J=5.5 Hz, 1H), 6.97 (d, J=1.1 Hz, 1H), 4.31 (s, 2H), 2.43 (d, J=1.1 Hz, 3H).

2.9. Synthesis of 2-(4-(3-(piperidin-1-yl)propoxy)phenyl)-N-(2-(thiazol-4-yl)thiophen-3-yl)acetamide (50)

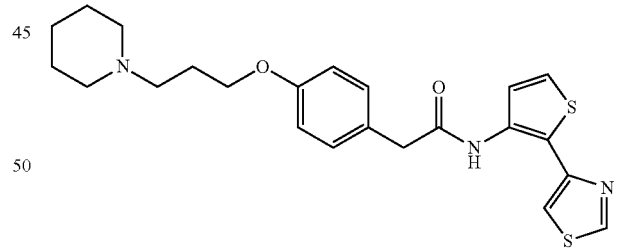

2.9.1. 2-(Thiazol-4-yl)thiophen-3-amine

This amine was prepared from 2-chloro-3-nitrothiophene using Protocols E and F except that 4-(tributylstannyl)thiazole was used. Method[1], MS(ESI) 183.0 [M+H], Retention time=0.518 min.

2.9.2. 2-(4-(3-(Piperidin-1-yl)propoxy)phenyl)-N-(2-(thiazol-4-yl)thiophen-3-yl)acetamide The title compound was prepared from 2-(thiazol-4-yl)thiophen-3-amine and 2-(4-(3-(piperidin-1-yl)propoxy)phenyl)acetic acid using protocol X. Method[7], MS(ESI) 442.1 [M+H], Retention time=3.586 min; $^1$H-NMR (300 MHz, CDCl$_3$) δ 10.8 (s, 1H), 8.54-8.53 (m, 1H), 8.13-8.11 (m, 1H), 7.33-7.30 (m, 2H), 7.25-7.17 (m, 2H), 6.90 (d, J=8.8 Hz, 2H), 4.08 (t, J=4.95 Hz, 2H), 3.74 (m, 3H), 3.28-3.21 (m, 2H), 2.72-2.61 (m, 2H), 2.40-2.20 (m, 6H), 2.05-1.91 (m, 3H).

2.10. Synthesis of N-(3-(benzo[d]thiazol-2-yl)-4-methylthiophen-2-yl)-2-(isoquinolin-5-yl)acetamide (51)

The title compound was prepared from 2-(isoquinolin-5-yl)acetic acid and 3-(benzo[d]thiazol-2-yl)-4-methylthiophen-2-amine using Protocol B except that triethylamine was also added. MS(ESI) 416.0 [M+H], Retention time=2.86 min; $^1$H-NMR (300 MHz, CDCl$_3$) δ 9.40 (s, 1H), 8.57 (d, J=6.04 Hz, 1H), 8.10-8.07 (m, 2H), 8.0 (d, J=6.6 Hz, 1H), 7.90-7.88 (m, 1H), 7.83-7.77 (m, 1H), 7.71-7.68 (m, 1H), 7.55-7.51 (m, 1H), 7.42-7.37 (m, 1H), 6.56 (s, 1H), 4.39 (s, 2H), 2.56 (s, 3H).

2.11. Synthesis of N-(4-cyano-3-(thiazol-2-yl)thiophen-2-yl)-2-(2-oxo-6-(trifluoromethyl)quinolin-1(2H)-yl)acetamide

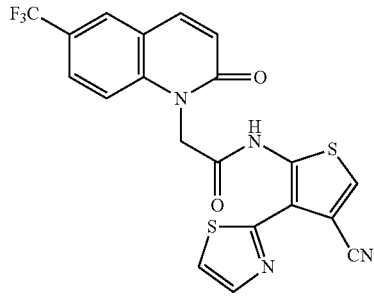 [SMILES: N#Cc1csc(NC(=O)Cn2c(=O)ccc3cc(C(F)(F)F)ccc32)c1-c1nccs1]

2.11.1. (E)-Ethyl 3-(2-amino-5-(trifluoromethyl)phenyl)acrylate

To a mixture of 2-bromo-4-(trifluoromethyl)aniline (5 g, 20.83 mmol), triethylamine (4.4 mL, 31.2 mmol) and P(o-tol)$_3$ (2.5 g, 8.33 mmol) in DMF (42 mL, 0.5 M) in a glass pressure tube under nitrogen gas were added ethyl acrylate (2.3 g, 23 mmol) and palladium acetate (940 mg, 4.167 mmol). The tube was sealed and heated to 120° C. for 18 h. The resulting solution was concentrated under vacuum and purified by column chromatography. Retention time (min)=2.532, method [1], MS(ESI) 260.1 (M+H).

2.11.2. 6-(Trifluoromethyl)quinolin-2(1H)-one

To a stirring mixture of (E)-ethyl 3-(2-amino-5-(trifluoromethyl)phenyl)acrylate (4 g, 15.4 mmol) in 4N HCl in dioxane (20 mL) was added concentrated HCl (3 mL). The resulting mixture was warmed to 100° C. overnight. The reaction mixture was cooled to rt and then slowly quenched with a cold saturated NaHCO$_3$ solution until pH>7. A normal aqueous extraction with EtOAc was followed. The crude mixture was taken directly to the next reaction without further purification. Retention time (min)=1.849, method [1], MS(ESI) 214.0 (M+H).

2.11.3. Ethyl 2-(2-oxo-6-(trifluoromethyl)quinolin-1(2H)-yl)acetate

To a stirring mixture of the above crude 6-(trifluoromethyl)quinolin-2(1H)-one in DMF/THF (0.5 M, 1:1) at rt was added NaH portionwise (1.2 g, 30.88 mmol) over 15 min. The reaction mixture was stirred at rt for additional 20 min before a solution of bromo methyl acetate (4.73 g, 30.88 mmol) in THF was added. The resulting mixture was stirred at rt until the starting material was consumed. The mixture was slowly quenched with brine and extracted with EtOAc. The crude product mixture was purified by column chromatography (3.6 g, 82% in two steps). Retention time (min)=2.042, method [1], MS(ESI) 286.1 (M+H).

2.11.4. 2-(2-Oxo-6-(trifluoromethyl)quinolin-1(2H)-yl)acetic acid

To a stirring solution of methyl 2-(2-oxo-6-(trifluoromethyl)quinolin-1(2H)-yl)acetate (4.8 g, 16.8 mmol) in THF/water (25 mL/5 mL, 5:1) was added LiOH.H$_2$O (3.52 g, 84.2 mmol). The resulting mixture was stirred overnight. The crude mixture was slowly acidified with 1N HCl and then extracted with EtOAc. The organic phase was dried (MgSO$_4$), filtered and concentrated under vacuum to give 2-(2-oxo-6-(trifluoromethyl)quinolin-1(2H)-yl)acetic acid (4.3 g). Retention time (min)=3.005, method [7], MS(ESI) 272.1 (M+H).

2.11.5. 5-Nitro-4-(thiazol-2-yl)thiophene-3-carbonitrile

A mixture of 4-bromo-5-nitrothiophene-3-carbonitrile (0.5 g, 2.1 mmol), 2-(tributylstannyl)thiazole (1.2 g, 3.2 mmol), dioxane (3.5 mL), and tetrakis(triphenylphosphine)palladium(0) (0.23 g, 0.21 mmol) was heated by microwave to 130° C. for 30 min under nitrogen. The reaction mix was concentrated under reduced pressure, and the resulting dark oil was purified by column chromatography using a mobile phase of 20% EtOAc/hexanes to give 5-nitro-4-(thiazol-2-yl)thiophene-3-carbonitrile (180 mg) as an oil. LCMS of this material revealed an m/z of 238.0 with a retention time of 1.807 min method [1].

2.11.6. 5-Amino-4-(thiazol-2-yl)thiophene-3-carbonitrile

A 30 mL reaction vial was charged with 5-nitro-4-(thiazol-2-yl)thiophene-3-carbonitrile (180 mg, 0.76 mmol) and AcOH (3 mL). A spatula tip of iron dust was added and the reaction vial was heated to 60° C. for 20 min. The reaction mixture was cooled to 23° C. and partitioned between methylene chloride and sodium bicarbonate solution. The organic solution was dried over sodium sulfate and concentrated to give 5-amino-4-(thiazol-2-yl)thiophene-3-carbonitrile as a red solid. LCMS showed an m/z of 208.0 with a retention time of 2.016 min using method [1].

2.11.7. N-(4-Cyano-3-(thiazol-2-yl)thiophen-2-yl)-2-(2-oxo-6-(trifluoromethyl)quinolin-1(2H)-yl)acetamide The title compound was prepared from 5-amino-4-(thiazol-2-yl)thiophene-3-carbonitrile (271 mg, 1 mmol) and 2-(2-oxo-6-(trifluoromethyl)quinolin-1(2H)-yl)acetic acid (0.76 mmol) according to protocol A. The crude product was purified by column chromatography (35% EtOAc/hexanes)

and HPLC to give N-(4-cyano-3-(thiazol-2-yl)thiophen-2-yl)-2-(2-oxo-6-(trifluoromethyl)quinolin-1(2H)-yl)acetamide (24. mg) as a white solid with an m/z of 461.1 and retention of 7.348 min using the [7] LCMS method. $^1$H-NMR (300 MHz, CDCl$_3$) δ 13.21 (s, 1H), 7.93 (m, 2H), 7.86 (dd, J=8.9, 1.8 Hz, 1H), 7.58 (s, 1H), 7.54 (d, J=3.4 Hz, 1H), 7.46 (d, J=8.8 Hz, 1H), 7.31 (d, J=3.3 Hz, 1H), 7.00 (d, J=9.6 Hz, 1H), 5.35 (s, 2H). $^{13}$C-NMR (75 MHz, CDCl$_3$) δ 165.3, 161.7, 161.0, 140.8, 140.0, 139.9, 129.4, 128.0, 126.5, 122.7, 120.4, 117.8, 115.9, 115.0, 114.7, 106.0, 46.3.

2.12. Synthesis of N-(4-cyano-3-(thiazol-2-yl)thiophen-2-yl)-2-(2-oxo-3,4-dihydro-1,5-naphthyridin-1(2H)-yl)acetamide

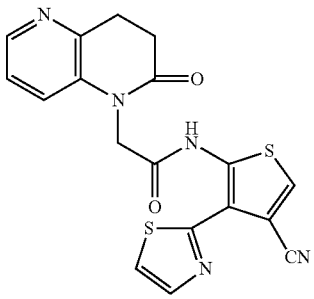 [SMILES: N#Cc1csc(NC(=O)CN2C(=O)CCc3ncccc32)c1-c1nccs1]

The title compound was prepared from 5-amino-4-(thiazol-2-yl)thiophene-3-carbonitrile (67 mg, 0.32 mmol) and 2-(2-oxo-3,4-dihydro-1,5-naphthyridin-1(2H)-yl)acetic acid (100 mg, 0.48 mmol) according to protocol A. The crude product was purified by column chromatography (2% methanol/methylene chloride) and HPLC to give N-(4-cyano-3-(thiazol-2-yl)thiophen-2-yl)-2-(2-oxo-3,4-dihydro-1,5-naphthyridin-1(2H)-yl)acetamide (5.4 mg) as a white solid. LCMS m/z 396.1, method [7] retention time 2.611 min. $^1$H-NMR (300 MHz, CDCl$_3$) δ 8.39 (d, J=4.1 Hz, 1H), 7.76 (d, J=3.3 Hz, 2H), 7.62 (s, 1H), 7.58 (d, J=7.4 Hz, 1H), 7.44 (m, 2H), 3.46 (t, J=7.1 Hz, 2H), 3.02 (t, J=7.2 Hz, 2H).

Synthesis of N-(4-bromo-3-(thiazol-2-yl)thiophen-2-yl)-2-(2-oxo-3,4-dihydro-1,5-naphthyridin-1(2H)-yl)acetamide

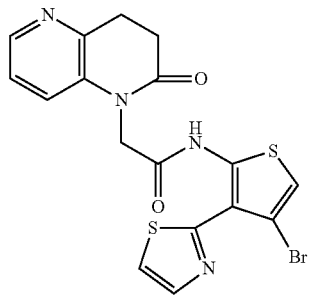 [SMILES: O=C(CN1C(=O)CCc2ncccc21)Nc1scc(Br)c1-c1nccs1]

2.13.1. 2-(4-Bromo-2-nitrothiophen-3-yl)thiazole

A mixture of 3,4-dibromo-2-nitrothiophene (242 mg, 0.85 mmol), 2-(tributylstannyl)thiazole (315 mg, 0.84 mmol), Pd(Ph$_3$P)$_4$ catalyst (194 mg, 0.17 mmol) and dioxane (0.9 mL) was heated in the microwave to 130° C. for 25 min. The reaction mixture was diluted with EtOAc and filtered to remove solids. The remaining organic solution was washed with saturated, aqueous solutions of sodium bicarbonate and salt before drying over sodium sulfate. The organic was concentrated under reduced pressure to give a dark oil. The crude product was purified by column chromatography (30% EtOAc/hexanes) to give 2-(4-bromo-2-nitrothiophen-3-yl)thiazole (210 mg). LCMS m/z of 289.1/291.1 with a retention time of 2.043 min on the [1] method.

2.13.2. 4-Bromo-3-(thiazol-2-yl)thiophen-2-amine

The title compound was prepared from 2-(4-bromo-2-nitrothiophen-3-yl)thiazole (120 mg, 0.41 mmol) according to the procedures of Example 2.11.6 to give 4-bromo-3-(thiazol-2-yl)thiophen-2-amine as a dark residue (90 mg). LCMS m/z of 260.9/292.9 with a retention time of 6.003 min in the [7] method.

2.13.3. N-(4-Bromo-3-(thiazol-2-yl)thiophen-2-yl)-2-(2-oxo-3,4-dihydro-1,5-naphthyridin-1(2H)-yl)acetamide The title compound was prepared from 4-bromo-3-(thiazol-2-yl)thiophen-2-amine (90 mg, 0.35 mmol) and 2-(2-oxo-3,4-dihydro-1,5-naphthyridin-1(2H)-yl)acetic acid (105 mg, 0.52 mmol) according to protocol A. The crude product was purified by HPLC to give N-(4-bromo-3-(thiazol-2-yl)thiophen-2-yl)-2-(2-oxo-3,4-dihydro-1,5-naphthyridin-1(2H)-yl)acetamide (24 mg) as a white solid. LCMS m/z 449.0/451.0 and retention of 4.019 min using method [7]. $^1$H-NMR (300 MHz, CDCl$_3$) δ 8.39 (d, J=5.2 Hz, 1H), 7.76 (d, J=3.3 Hz, 1H), 7.70 (d, J=8.3 Hz, 1H), 7.51 (dd, J=8.4, 5.3 Hz, 1H), 7.34 (d, J=3.4, 1H), 6.94 (s, 1H), 4.09 (s, 2H), 3.49 (t, J=7.2 Hz, 2H), 3.00 (t, J=7.2 Hz, 2H).

2.14. Synthesis of N-(4-chloro-3-(thiazol-2-yl)thiophen-2-yl)-2-(2-oxo-3,4-dihydro-1,5-naphthyridin-1(2H)-yl)acetamide

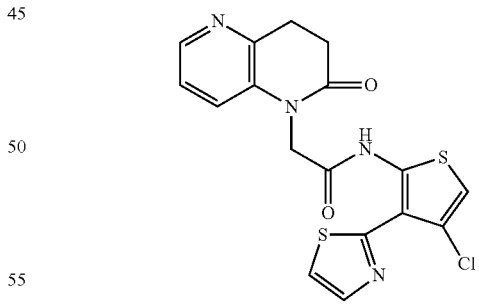

2.14.1. 2-(4-Chloro-2-nitrothiophen-3-yl)thiazole

A mixture of 2-(4-bromo-2-nitrothiophen-3-yl)thiazole (120 mg, 0.41 mmol), CuCl (240 mg) in dioxane (1.5 mL) and 5 drops of DMF was heated to 110° C. for 1 h by microwave. The reaction mixture was diluted with EtOAc and washed with saturated, aqueous sodium bicarbonate and brine before drying over sodium sulfate. It was concentrated under reduced pressure to give 2-(4-chloro-2-nitrothiophen- 3-yl)thiazole as a yellow residue (100 mg). LCMS m/z of 246.9/249.0 with a retention time of 3.994 min on the [7] method.

2.14.2. 4-Chloro-3-(thiazol-2-yl)thiophen-2-amine

The title compound was prepared from 2-(4-chloro-2-nitrothiophen-3-yl)thiazole (100 mg, 0.4 mmol) according to the procedures of Example 2.11.6 to give 4-chloro-3-(thiazol-2-yl)thiophen-2-amine as a dark residue (90 mg). LCMS m/z of 217.0/218.9 with a retention time of 2.426 min in the [1] method.

2.14.3. N-(4-Chloro-3-(thiazol-2-yl)thiophen-2-yl)-2-(2-oxo-3,4-dihydro-1,5-naphthyridin-1(2H)-yl)acetamide The title compound was prepared from 4-chloro-3-(thiazol-2-yl)thiophen-2-amine (0.4 mmol) and 2-(2-oxo-3,4-dihydro-1,5-naphthyridin-1(2H)-yl)acetic acid (165 mg, 0.8 mmol) according to protocol A. The crude product was purified by column chromatography (4% methanol/methylene chloride) and HPLC to afford N-(4-chloro-3-(thiazol-2-yl)thiophen-2-yl)-2-(2-oxo-3,4-dihydro-1,5-naphthyridin-1(2H)-yl)acetamide (2.1 mg) as a white solid. LCMS m/z of 405.1/407.1 and retention of 3.670 min using the [7] LCMS method. $^1$H-NMR (300 MHz, CDCl$_3$) δ 8.36 (d, J=4.9 Hz, 1H), 7.71 (d, J=3.4 Hz, 1H), 7.57 (d, J=8.1 Hz, 1H), 7.42 (dd, J=8.1, 5.1 Hz, 1H), 7.36 (d, J=3.4, 1H), 6.82 (s, 1H), 4.92 (s, 2H), 3.44 (t, J=7.1 Hz, 2H), 3.01 (t, J=7.1 Hz, 2H).

2.15. Synthesis of N-(4-chloro-3-(thiazol-2-yl)thiophen-2-yl)-2-(8-(trifluoromethyl)quinolin-5-yl)acetamide The title compound was prepared from 4-chloro-3-(1H-1,2,4-triazol-5-yl)thiophen-2-amine (150 mg, 0.75 mmol) and 2-(8-(trifluoromethyl)quinolin-5-yl)acetic acid (148 mg, 0.58 mmol) according to protocol A. The crude product was purified by column chromatography (35% EtOAc/hexanes) to give N-(4-chloro-3-(thiazol-2-yl)thiophen-2-yl)-2-(8-(trifluoromethyl)quinolin-5-yl)acetamide (35 mg) as a white solid. LCMS m/z of 438.1/440.1 and retention of 5.789 min using the [7] LCMS method. $^1$H-NMR (300 MHz, DMSO-d6) δ 9.06 (dd, J=4.2, 1.6 Hz, 1H), 8.64 (dd, J=8.7, 1.6 Hz, 1H), 8.26 (d, J=7.6 Hz, 1H), 7.83 (d, J=7.5 Hz, 1H), 7.72 (dd, J=8.6, 4.2 Hz, 1H), 7.13 (s, 1H), 4.56 (s, 2H).

2.16. Synthesis of N-(4-cyano-3-(thiazol-4-yl)thiophen-2-yl)-2-(2-oxo-6-(trifluoromethyl)quinolin-1(2H)-yl)acetamide

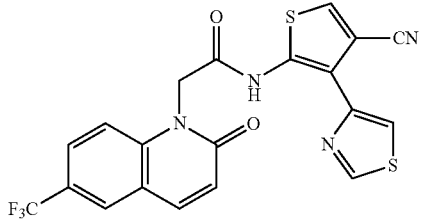 [SMILES: N#Cc1csc(NC(=O)Cn2c(=O)ccc3cc(C(F)(F)F)ccc32)c1-c1cscn1]

2.16.1. 5-Nitro-4-(thiazol-4-yl)thiophene-3-carbonitrile

A microwave vial equipped with a stir bar was added 4-bromo-5-nitrothiophene-3-carbonitrile (0.15 g, 0.66 mmole) and tetrakis(triphenylphosphine)palladium (0) (0.077 g, 0.066 mmol) and then purged with N$_2$ (g) inlet prior to addition of 4-(tributylstannyl)thiazole (0.42 g, 1.13 mmol), dioxane (1.2 mL) and few drops of DMF. The reaction mixture was heated at 110° C. for 30 min and then concentrated under reduced pressure. Purification by flash chromatography (silica, 50:50 ethyl acetate/hexane) gave 5-nitro-4-(thiazol-4-yl)thiophene-3-carbonitrile (71 mgs, 45%) Retention time (min)=1.656, method [4], MS(ESI) 238.0 (M+H).

2.16.2. 5-amino-4-(thiazol-4-yl)thiophene-3-carbonitrile

Protocol Q:

To a solution of 5-nitro-4-(thiazol-4-yl)thiophene-3-carbonitrile (0.071 g, 0.31 mmol) in ethyl acetate (3 mL) was added tin (II) chloride dihydrate (0.29 g, 1.27 mmol). The reaction mixture was heated in an oil bath set at 70° C. under condenser. After 20 min. the mixture was cooled to RT and concentrated under reduced pressure. Purification by flash chromatography (silica, 40:60 ethyl acetate/hexane) gave 5-amino-4-(thiazol-4-yl)thiophene-3-carbonitrile (24 mgs, 38%) Retention time (min)=1.837, method [4], MS(ESI) 208.0 (M+H).

2.16.3. N-(4-Cyano-3-(thiazol-4-yl)thiophen-2-yl)-2-(2-oxo-6-(trifluoromethyl)quinolin-1(2H)yl)acetamide The title compound was prepared from 2-(2-oxo-6-(trifluoromethyl)quinolin-1(2H)-yl)acetic acid (0.047 g, 0.17 mmol) and 5-amino-4-(thiazol-4-yl)thiophene-3-carbonitrile (0.024 g, 0.12 mmol) according to protocol A. The desired product was submitted to prep HPLC for further purification. Retention time (min)=7.57, method [7], MS(ESI) 461.1 (M+H). $^1$H NMR (CDCl$_3$) δ 12.73 (s, 1H), 8.60 (d, J=2.4 Hz, 1H), 8.14 (d, J=2.4 Hz, 1H), 7.92-7.89 (m, 2H), 7.89 (d, J=9.3 Hz, 1H), 7.59 (s, 1H), 7.48 (d, J=8.9 Hz, 1H), 6.96 (d, J=9.3 Hz, 1H), 5.30 (s, 2H).

2.17. Synthesis of N-(4-cyano-3-(thiazol-5-yl)thiophen-2-yl)-2-(2-oxo-6-(trifluoromethyl)quinolin-1(2H)-yl)acetamide

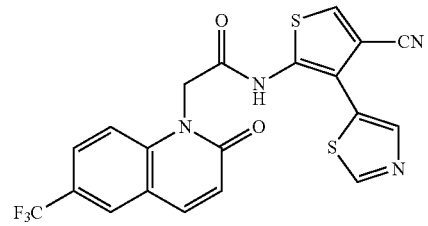 [SMILES: N#Cc1csc(NC(=O)Cn2c(=O)ccc3cc(C(F)(F)F)ccc32)c1-c1cncs1]

2.17.1. 5-Nitro-4-(thiazol-5-yl)thiophene-3-carbonitrile

Protocol R:

A microwave vial equipped with a stir bar was added 4-bromo-5-nitrothiophene-3-carbonitrile (0.24 g, 1.05 mmole) and tetrakis(triphenylphosphine)palladium (0) (0.14 g, 0.12 mmol), copper iodide (0.028 g, 0.15 mmol) and then purged with N$_2$ (g) inlet prior to addition of 5-(tributylstannyl)thiazole (0.63 g, 1.67 mmol), dioxane (2.3 mL) and few drops of DMF. The reaction mixture was heated at 110° C. for 30 min and then concentrated under reduced pressure. Purification by flash chromatography (silica, 40:60 ethyl acetate/hexane) gave 5-nitro-4-(thiazol-5-yl)thiophene-3-carbonitrile (153 mgs, 61%) Retention time (min)=1.715, method [4], MS(ESI) 238.0 (M+H).

2.17.2. 5-Amino-4-(thiazol-5-yl)thiophene-3-carbonitrile

5-Amino-4-(thiazol-5-yl)thiophene-3-carbonitrile was prepared from 5-nitro-4-(thiazol-5-yl)thiophene-3-carbonitrile (0.15 g, 0.65 mmol) according to protocol Q. Retention time (min)=1.520, method [7], MS(ESI) 208.0 (M+H).

2.17.3. N-(4-Cyano-3-(thiazol-5-yl)thiophen-2-yl)-2-(2-oxo-6-(trifluoromethyl)quinolin-1(2H)-yl)acetamide The title compound was prepared from 2-(2-oxo-6-(trifluoromethyl)quinolin-1(2H)-yl)acetic acid (0.047 g, 0.17 mmol) and 5-amino-4-(thiazol-5-yl)thiophene-3-carbonitrile (0.055, 0.26 mmol) according to protocol A. The crude product was purified by prep HPLC. Retention time (min)=5.989, method [7], MS(ESI) 461.1 (M+H). $^1$H NMR (CDCl$_3$) δ 9.95 (s, 1H), 7.91-7.85 (m, 4H) 7.78 (d, J=8.7 Hz, 1H), 7.63 (s, 1H), 6.84 (d, J=8.7 Hz, 1H), 5.06 (s, 2H).

2.18. Synthesis of N-(3-(benzo[d]thiazol-2-yl)-4-cyanothiophen-2-yl)-2-(2-oxo-1,5-naphthyridin-1(2H)-yl)acetamide

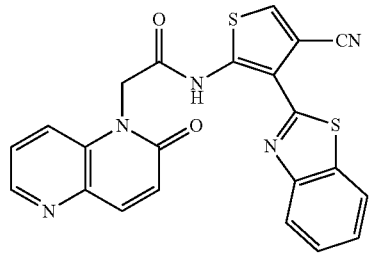 [SMILES: N#Cc1csc(NC(=O)Cn2c(=O)ccc3ncccc32)c1-c1nc2ccccc2s1]

2.18.1. 5-Nitro-4-(benzo[d]thiazol-2-yl)thiophene-3-carbonitrile 5-nitro-4-(benzo[d]thiazol-2-yl)thiophene-3-carbonitrile was prepared from 4-bromo-5-nitrothiophene-3-carbonitrile (0.16 g, 0.67 mmol) and 2-(tributylstannyl)benzo[d]thiazole (0.45 g, 1.07 mmol) according to protocol R. Retention time (min)=0.381, method [4], MS(ESI) 288.0 (M+H).

2.18.2. 5-Amino-4-(benzo[d]thiazol-2-yl)thiophene-3-carbonitrile 5-amino-4-(benzo[d]thiazol-2-yl)thiophene-3-carbonitrile was prepared from 5-nitro-4-(benzo[d]thiazol-2-yl) thiophene-3-carbonitrile (0.27 g, 0.92 mmol) according to protocol Q. Retention time (min)=2.579 method [4], MS(ESI) 258.0 (M+H).

2.18.3. N-(3-(benzo[d]thiazol-2-yl)-4-cyanothiophen-2-yl)-2-(2-oxo-1,5-naphthyridin-1(2H)-yl)acetamide The title compound was prepared from 2-(2-oxo-1,5-naphthyridin-1(2H)-yl)acetic acid (0.040 g, 0.19 mmol) and 5-amino-4-(benzo[d]thiazol-2-yl)thiophene-3-carbonitrile (0.073 g, 0.28 mmol) according to protocol A. The crude product was purified by prep HPLC. LCMS retention time (min)=5.122, method [12], MS(ESI) 446.1 (M+H). $^1$H NMR (CDCl$_3$) δ 13.38 (s, 1H), 8.32 (d, J=5.6 Hz, 1H), 7.99 (d, J=7.5 Hz, 1H), 7.94 (d, J=7.5 Hz, 1H), 7.62 (s, 1H), 7.58 (d, J=8.4 Hz, 1H), 7.54 (d, J=8.4 Hz, 1H), 7.47-7.42 (m, 1H), 7.35-7.30 (m, 1H), 4.95 (s, 2H), 3.33-3.28 (m, 2H), 2.99-2.94 (m, 2H).

2.19. Synthesis of 2-(2-oxo-6-(trifluoromethyl)quinolin-1(2H)-yl)-N-(2-(thiazol-4-yl)thiophen-3-yl)acetamide The title compound was prepared from 2-(thiazol-4-yl) thiophen-3-amine and 2-(2-oxo-6-(trifluoromethyl)quinolin-1(2H)-yl)acetic acid according to protocol A. Retention time (min)=6.485, method [7], MS(ESI) 436.1 (M+H); $^1$H NMR (300 MHz, CD$_3$Cl) δ 11.32 (s, 1H), 8.51 (d, J=1.5 Hz, 1H), 8.04 (d, J=5.5 Hz, 1H), 7.92 (d, J=10.2 Hz, 1H), 7.90 (s, 1H), 7.80 (d, J=8.9 Hz, 1H), 7.50 (d, J=8.9 Hz, 1H), 7.22 (d, J=1.4 Hz, 1H), 7.20 (d, J=5.5 Hz, 1H), 7.03 (d, J=9.7 Hz, 1H), 5.23 (s, 2H).

Example 3

Synthesis of Thiophene Oxazoles

3.1. Synthesis of 2-(4-methoxyphenyl)-N-(2-(oxazol-2-yl)thiophen-3-yl)acetamide (52)

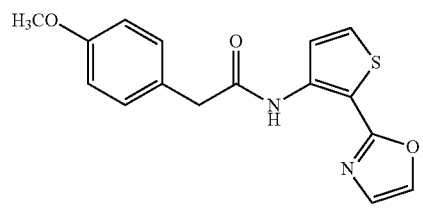 [SMILES: COc1ccc(CC(=O)Nc2ccsc2-c2ncco2)cc1]

3.1.1. 2-(3-Nitrothiophen-2-yl)oxazole 2-(3-nitrothiophen-2-yl)oxazole was prepared from 2-(tributylstannyl)oxazole (0.94 g, 2.62 mmol) and 2-chloro-3-nitrothiophene (0.429 g, 2.62 mmol) according to protocol E. Retention time (min)=1.794, method [1], MS(ESI) 197.0 (M+H).

3.1.2. 2-(Oxazol-2-yl)thiophen-3-amine 2-(Oxazol-2-yl)thiophen-3-amine was prepared from 2-(3-nitrothiophen-2-yl)oxazole (250 mg, 1.27 mmol)) according to protocol F. Retention time (min)=1.388, method [1], MS(ESI) 167.0 (M+H).

3.1.3. 2-(4-Methoxyphenyl)-N-(2-(oxazol-2-yl)thiophen-3-yl)acetamide 2-(4-methoxyphenyl)-N-(2-(oxazol-2-yl)thiophen-3-yl) acetamide was prepared from 2-(4-methoxyphenyl)acetic acid 64 mg, 0.385 mmol) and 2-(oxazol-2-yl)thiophen-3-amine (64 mg, 0.385 mmol) according to protocol A. Retention time (min)=6.845, method [7], MS(ESI) 315.1 (M+H); $^1$H NMR (300 MHz, CDCl$_3$) δ 10.59 (s, 1H), 8.17 (d, J=5.2 Hz, 1H), 7.52 (s, 1H), 7.28-7.37 (m, 3H), 6.94-6.99 (m, 3H), 3.85 (s, 3H), 3.66 (s, 2H).

3.2. Synthesis of 2-(isoquinolin-5-yl)-N-(2-(oxazol-2-yl)thiophen-3-yl)acetamide (53)

2-(Isoquinolin-5-yl)-N-(2-(oxazol-2-yl)thiophen-3-yl)acetamide was prepared from 2-(isoquinolin-5-yl)acetic acid (48 mg, 0.246 mmol) and 2-(oxazol-2-yl)thiophen-3-amine (41 mg, 0.246 mmol) according to protocol A. Retention time (min)=2.206, method [7], MS(ESI) 336.1 (M+H); $^1$H NMR (300 MHz, CDCl$_3$) δ 10.79 (s, 1H), 9.71 (s, 1H), 8.59 (d, J=6.5 Hz, 1H), 8.36 (d, J=6.5 Hz, 1H), 8.28 (d, J=8.2 Hz, 1H), 8.07-8.13 (m, 2H), 7.95 (dd, J=8.3, 7.3 Hz, 1H), 7.55 (s, 1H), 7.36 (d, J=5.3 Hz, 1H), 6.95 (s, 1H), 4.36 (s, 2H).

3.3. Synthesis of N-(4-bromo-3-(oxazol-2-yl)thiophen-2-yl)-2-(2-oxo-3,4-dihydro-1,5-naphthyridin-1(2H)-yl)acetamide

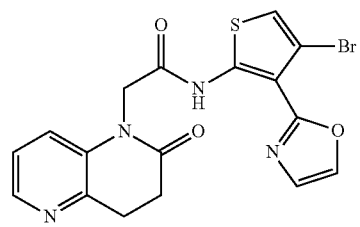 [SMILES: O=C(CN1C(=O)CCc2ncccc21)Nc1scc(Br)c1-c1ncco1]

3.3.1. 2-(4-Bromo-2-nitrothiophen-3-yl)oxazole

A mixture of 3,4-dibromo-2-nitrothiophene (0.166 mg, 0.581 mmol), Pd(PPh$_3$)$_4$ (67 mg, 0.0581 mmol) and 2-(tributylstannyl)oxazole (250 mg, 0.698 mmol) in DMF (1.1 mL) was evacuated and purged with nitrogen three times. The reaction mixture was heated to 90° C. for 18 h and the resulting solution was cooled to room temperature and diluted with Et$_2$O. The solution was washed with brine and the organic phase was separated, dried (Na$_2$SO$_4$), filtered, concentrated under vacuum and purified on a silica gel column (eluant hexane/ethyl acetate, 20/1 to 1/1, v/v) to give 2-(4-bromo-2-nitrothiophen-3-yl)oxazole (107 mg, 67%). Retention time (min)=1.948, method [1], MS(ESI) 274.9 (M+H).

3.3.2. 4-Bromo-3-(oxazol-2-yl)thiophen-2-amine

The title compound was prepared from 2-(4-bromo-2-nitrothiophen-3-yl)oxazole (224 mg, 0.814 mmol) using the procedures of Example 2.11.6 to give 4-bromo-3-(oxazol-2-yl)thiophen-2-amine which was used without further purification. Retention time (min)=2.131, method [1], MS(ESI) 244.9 (M+H).

3.3.3. N-(4-Bromo-3-(oxazol-2-yl)thiophen-2-yl)-2-(2-oxo-3,4-dihydro-1,5-naphthyridin-1(2H)-yl)acetamide The title compound was prepared from 2-(2-oxo-3,4-dihydro-1,5-naphthyridin-1(2H)-yl)acetic acid (85 mg, 0.416 mmol) and 4-bromo-3-(oxazol-2-yl)thiophen-2-amine (51 mg, 0.208) mmol) according to protocol A. Retention time (min)=3.245, method [7], MS(ESI) 433.0 (M+H); $^1$H NMR (300 MHz, CDCl$_3$) δ 8.39 (dd, J=5.1, 1.0 Hz, 1H), 7.72 (s, 1H), 7.55 (d, J=7.0 Hz, 1H), 7.45 (dd, J=8.4, 5.5 Hz, 1H), 7.17 (s, 1H), 6.94 (s, 1H), 4.93 (s, 2H), 3.51-3.46 (m, 2H), 3.05-3.00 (m, 2H).

3.4. Synthesis of N-(4-cyano-3-(oxazol-2-yl)thiophen-2-yl)-2-(2-oxo-6-(trifluoromethyl)quinolin-1(2H)-yl)acetamide

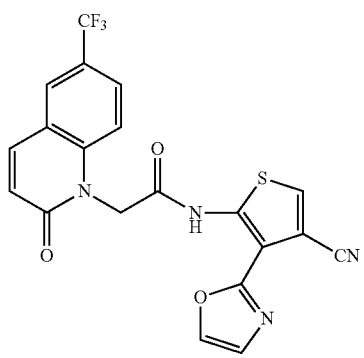 [SMILES: N#Cc1csc(NC(=O)Cn2c(=O)ccc3cc(C(F)(F)F)ccc32)c1-c1ncco1]

3.4.1. 5-Nitro-4-(oxazol-2-yl)thiophene-3-carbonitrile

The above titled compound (34 mg, 18%) was synthesized from 4-bromo-5-nitrothiophene-3-carbonitrile (203 mg, 0.87 mmol) and 2-tributylstannyloxazole (0.27 mL, 1.29 mmol), tetrakis(triphenylphosphine)palladium(0) (103 mg, 0.089 mmol) and copper(I) iodide (16 mg, 0.084 mmol) according to methods described herein. LCMS method [4], retention time=1.62 min; MS(ESI) 222.0 (MH+).

3.4.2. 5-Amino-4-(oxazol-2-yl)thiophene-3-carbonitrile

The title compound was prepared from 5-nitro-4-(oxazol-2-yl)thiophene-3-carbonitrile (34 mg, 0.15 mmol) using protocol Q. Flash chromatography (EtOAc/hexanes elution) gave desired product (20.8 mg, 71%): R$_f$=0.84 (60% EtOAc/hexanes, silica); HPLC method [4], retention time=1.673 min; MS(ESI) 192.0 (MH+).

3.4.3. N-(4-Cyano-3-(oxazol-2-yl)thiophen-2-yl)-2-(2-oxo-6-(trifluoromethyl)quinolin-1(2H)-yl)acetamide The title compound was synthesized from 5-amino-4-(oxazol-2-yl)thiophene-3-carbonitrile (21 mg, 0.11 mmol) and 2-(2-oxo-6-(trifluoromethyl)quinolin-1(2H)-yl)acetic acid (30 mg, 0.11 mmol) according to protocol A. The product was purified by HPLC. LCMS method [7], retention time=6.70 min; MS(ESI) 445.0 (MH+); $^1$H NMR (300 MHz, CD$_3$OD) δ 8.19 (d, J=9.8 Hz, 2H), 7.95-7.80 (m, 3H), 7.85 (d, J=1.8 Hz, 1H), 7.08 (d, J=0.8 Hz, 1H), 6.90 (d, J=9.6 Hz, 1H), 5.45 (s, 2H).

Example 4

Synthesis of Thiophene Oxadiazoles

4.1. Synthesis of 2-(4-methoxyphenyl)-N-(3-(5-methyl-1,2,4-oxadiazol-3-yl)thiophen-2-yl)acetamide (54)

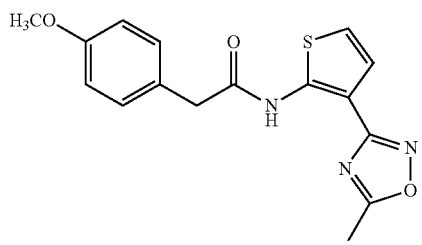 [SMILES: COc1ccc(CC(=O)Nc2sccc2-c2noc(C)n2)cc1]

4.1.1. N-(3-Cyanothiophen-2-yl)-2-(4-methoxyphenyl)acetamide

N-(3-cyanothiophen-2-yl)-2-(4-methoxyphenyl)acetamide was prepared from 2-(4-methoxyphenyl)acetic acid (1.37 g, 8.29 mmol) and 2-aminothiophene-3-carbonitrile (1.03 g, 8.29 mmol) according to protocol B. Retention time (min)=2.150, method [1], MS(ESI) 273.0 (M+H).

4.1.2. N-(3-(N'-Hydroxycarbamimidoyl)thiophen-2-yl)-2-(4-methoxyphenyl)-acetamide To a solution of N-(3-cyanothiophen-2-yl)-2-(4-methoxyphenyl)acetamide (234 mg, 0.859 mmol) in a mixture of ethanol (5 mL), methylene chloride (0.5 mL) and triethylamine (202 μL, 1.46 mmol) was added hydroxylamine hydrochloride (90 mg, 1.29 mmol). The resulting solution was stirred at room temperature for 18 h and was subsequently diluted with saturated aqueous sodium bicarbonate and extracted with ethyl acetate. The organic phases were combined, dried ($Na_2SO_4$), filtered, concentrated under vacuum and purified on a silica gel column (eluant hexane/ethyl acetate, 7/3 to 2/8) to give N-(3-(N-hydroxycarbamimidoyl)thiophen-2-yl)-2-(4-methoxyphenyl)acetamide. Retention time (min)=1.161, method [1], MS(ESI) 306.1 (M+H).

4.1.3. 2-(4-Methoxyphenyl)-N-(3-(5-methyl-1,2,4-oxadiazol-3-yl)thiophen-2-yl)acetamide To a solution of N-(3-(N-hydroxycarbamimidoyl)thiophen-2-yl)-2-(4-methoxyphenyl)-acetamide (104 mg, 0.341 mmol) in acetonitrile (2 mL) was added DIPEA (127 mg, 0.987 mmol) and acetyl chloride (48 μL, 0.681 mmol). The resulting solution was stirred at 60° C. for 18 h and was subsequently diluted with saturated aqueous sodium bicarbonate and extracted with ethyl acetate. The organic phases were combined, dried ($Na_2SO_4$), filtered, concentrated under vacuum and purified by preparative HPLC to give 2-(4-methoxyphenyl)-N-(3-(5-methyl-1,2,4-oxadiazol-3-yl)thiophen-2-yl)acetamide. Retention time (min)=6.733, method [7], MS(ESI) 330.1 (M+H); $^1$H NMR (300 MHz, $CDCl_3$) δ 10.63 (s, 1H), 7.30-7.35 (m, 3H), 7.00 (d, J=9.2 Hz, 2H), 6.89 (d, J=6.2 Hz, 1H), 3.86 (s, 3H), 3.80 (s, 2H), 2.50 (s, 3H).

4.2. Synthesis of N-(2-(1,3,4-oxadiazol-2-yl)thiophen-3-yl)-2-(naphthalen-1-yl)acetamide (55)

To a solution of (isocyanoimino)triphenylphosphorane (978 mg, 3.24 mmol) in anhydrous $CH_2Cl_2$ (30 mL) was added dropwise a solution of 3-(2-(naphthalen-1-yl)acetamido)thiophene-2-carboxylic acid (340 mg, 1.09 mmol) in anhydrous $CH_2Cl_2$ (27 mL). The resulting mixture was stirred at room temperature under nitrogen overnight and evaporated under reduced pressure. Purification by flash chromatography (silica, 30:70 ethyl acetate/hexane) gave N-(2-(1,3,4-oxadiazol-2-yl)thiophen-3-yl)-2-(naphthalen-1-yl)acetamide (45 mg, 12%). Method [7] m/z 357.9 (M+Na); retention time=5.919. $^1$H-NMR ($CDCl_3$) δ 8.18 (d, J=1.1 Hz, 1H), 8.16 (d, J=1.4 Hz, 1H), 8.05 (d, J=8.3 Hz, 1H), 7.88 (d, J=8.0 Hz, 2H), 7.61-7.41 (m, 5H), 4.27 (s, 2H).

4.3. Synthesis of 2-(4-methoxyphenyl)-N-(2-(5-methyl-1,3,4-oxadiazol-2-yl)thiophen-3-yl)acetamide (56)

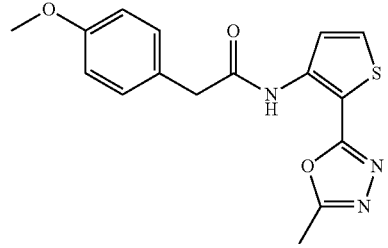 [SMILES: COc1ccc(CC(=O)Nc2ccsc2-c2nnc(C)o2)cc1]

4.3.1. Methyl 3-(2-(4-methoxyphenyl)acetamido)thiophene-2-carboxylate

The title compound was prepared from 4-methoxyphenyl acetic acid (6.65 g, 40.2 mmol) and methyl-3-amino-2-thiophene carboxylate (6.30 g, 40.08 mmol) using protocol A to afford the coupled intermediate (7.40 g, 60%). Method [7] m/z 306.0 (M+H); retention time=5.907. $^1$H-NMR ($CDCl_3$) δ 10.04, (broad s, 1H), 8.07 (d, J=5.5 Hz, 1H), 7.38 (d, J=5.5 Hz, 1H), 7.22 (d, J=8.3 Hz, 2H), 6.88 (d, J=8.3 Hz, 2H), 3.76 (s, 3H), 3.75 (s, 3H), 3.65 (s, 2H).

4.3.2. 3-(2-(4-Methoxyphenyl)acetamido)thiophene-2-carboxylic acid

A 3M lithium hydroxide solution (80 mL) was added to methyl-3-(2-(4-methoxyphenyl)acetamido)thiophene-2-carboxylate (7.30 g, 23.91 mmol) dissolved in methanol. The reaction mixture was refluxed for 2 h, cooled to room temperature and then partitioned between ethyl acetate and $H_2O$. The aqueous layer with acidified with conc HCl, filtered and washed with $H_2O$. The precipitate that formed was collected by filtration (8.55 g, quantitative) and used in the next step without further purification. Method [7] m/z 291.9 (M+H); retention time=3.827. $^1$H-NMR ($CD_3OD$) δ 8.0 (d, J=5.3 Hz, 1H), 7.61 (d, J=5.3 Hz, 1H), 7.26 (d, J=8.3 Hz, 2H), 6.91 (d, J=8.3 Hz, 2H), 3.76 (s, 3H), 3.70 (s, 2H).

4.3.3. N-(2-(2-Acetylhydrazinecarbonyl)thiophen-3-yl)-2-(4-methoxyphenyl)-acetamide The title compound was prepared from 3-(2-(4-methoxyphenyl)acetamido)-thiophene-2-carboxylic acid (500 mg, 1.72 mmol) and acetylhydrazide (1.0 g, 13.50 mmol) according to protocol B to give N-(2-(2-acetylhydrazinecarbonyl)thiophen-3-yl)-2-(4-methoxyphenyl)acetamide which was used without further purification (300 mg, 50%). Method [4] m/z 370.0 (M+Na); retention time=1.186.

4.3.4. 2-(4-Methoxyphenyl)-N-(2-(5-methyl-1,3,4-oxadiazol-2-yl)thiophen-3-yl)acetamide To a solution of N-(2-(2-acetylhydrazinecarbonyl)thiophen-3-yl)-2-(4-methoxyphenyl)acetamide (300 mg, 0.86 mmol) in anh. acetonitrile (6 mL) was added diisopropylethylamine (0.8 mL, 4.84 mmol) and triphenylphosphine (396 mg, 1.51 mmol). After 5 min, hexachloroethane (292 mg, 1.23 mmol) was added to the reaction mixture and then stirred at room temperature overnight under $N_2$(g) inlet. The reaction mixture was evaporated under reduced pressure, partitioned between ethyl acetate and $H_2O$, dried (sodium sulfate), filtered and concentrated under reduced pressure. Purification by flash column chromatography (silica, 40:60 ethyl acetate/hexane) gave 2-(4-methoxyphenyl)-N-(2-(5-methyl-1,3,4-oxadiazol-2-yl)thiophen-3-yl)acetamide (25 mg, 9%). See James, C. A. et al., *Tet. Lett.* 47 (2006) 511-514. Method [7] m/z 330.0 (M+H); retention time=4.805. $^1$H-NMR (CDCl$_3$) δ 10.15 (broad s, 1H), 8.18 (d, J=5.4 Hz, 1H), 7.43 (d, J=5.4 Hz, 1H), 7.31 (d, J=7.6 Hz, 2H), 6.92 (d, J=7.6 Hz, 2H), 3.81 (s, 3H), 3.75 (s, 2H), 2.75 (s, 3H).

4.4. Synthesis of N-(2-(5-isopropyl-1,3,4-oxadiazol-2-yl)thiophen-3-yl)-2-(4-methoxyphenyl)acetamide (57)

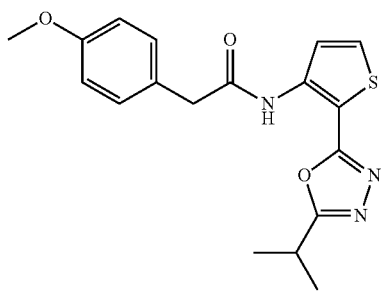 [SMILES: COc1ccc(CC(=O)Nc2ccsc2-c2nnc(C(C)C)o2)cc1]

4.4.1. N-(2-(2-Isobutyrylhydrazinecarbonyl)thiophen-3-yl)-2-(4-methoxyphenyl)-acetamide N-(2-(2-isobutyrylhydrazinecarbonyl)thiophen-3-yl)-2-(4-methoxyphenyl)acetamide (443 mg, 34%) was prepared from 3-(2-(4-methoxyphenyl)acetamido)thiophene-2-carboxylic acid and isobutyrohydrazine according to essentially the same procedure as described above in Example 4.3.3. and was purified by flash column chromatography (silica, 50:50 ethyl acetate/hexane). Method [4] m/z 398.0 (M+Na); retention time=1.453.

4.4.2. N-(2-(5-Isopropyl-1,3,4-oxadiazol-2-yl)thiophen-3-yl)-2-(4-methoxyphenyl)-acetamide N-(2-(5-isopropyl-1,3,4-oxadiazol-2-yl)thiophen-3-yl)-2-(4-methoxyphenyl)acetamide (339 mgs, 81%) was prepared from N-(2-(2-isobutyrylhydrazinecarbonyl)thiophen-3-yl)-2-(4-methoxyphenyl)acetamide according to essentially the same procedure as described for Example 4.3.4 and was purified by flash column chromatography (silica, 50:50 ethyl acetate/hexane). Method [7] m/z 358.0 (M+H); retention time=6.683. $^1$H-NMR (CDCl$_3$) δ 10.21 (broad s, 1H), 8.15 (d, J=5.2 Hz, 1H), 7.40 (d, J=5.2 Hz, 1H), 7.29 (d, J=8.2 Hz, 2H), 6.89 (d, J=8.2 Hz, 2H), 3.79 (s, 3H), 3.71 (s, 2H), 3.24-3.14 (m, 1H). 1.42 (s, 3H). 1.40 (s, 3H).

4.5. Synthesis of N-(2-(5-methyl-1,3,4-oxadiazol-2-yl)thiophen-3-yl)-2-(naphthalen-1-yl)acetamide (58)

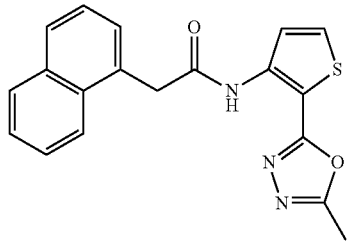 [SMILES: Cc1nnc(-c2sccc2NC(=O)Cc2cccc3ccccc23)o1]

4.5.1. N-(2-(2-Acetylhydrazinecarbonyl)thiophen-3-yl)-2-(naphthalen-1-yl)acetamide The title compound was prepared from 3-(2-(naphthalene-1-yl)acetamido)thiophene-2-carboxylic acid (321 mg, 1.03 mmol) and methyl keto hydrazine (609 mg, 8.22 mmol) using protocol B to give the desired N-(2-(2-acetylhydrazinecarbonyl)thiophen-3-yl)-2-(naphthalen-1-yl)acetamide, which was used without further purification (250 mg, 66%).

4.5.2. N-(2-(5-Methyl-1,3,4-oxadiazol-2-yl)thiophen-3-yl)-2-(naphthalen-1-yl)acetamide N-(2-(5-methyl-1,3,4-oxadiazol-2-yl)thiophen-3-yl)-2-(naphthalen-1-yl)acetamide (105 mgs, 44%) was prepared from N-(2-(2-acetylhydrazinecarbonyl)thiophen-3-yl)-2-(naphthalen-1-yl)acetamide (250 mg, 0.68 mmol) according to essentially the same procedure as described in Example 4.3.4. Method [7] m/z 371.9 (M+Na); retention time=6.243. $^1$H-NMR (CDCl$_3$) δ 10.08 (s, 1H), 8.12 (d, J=5.4 Hz, 1H), 8.03 (d, J=8.1 Hz, 1H), 7.83 (d, J=8.1 Hz, 2H), 7.57-7.40 (m, 4H), 7.33 (d, J=5.4 Hz, 1H), 4.21 (s, 2H), 2.45 (s, 3H).

4.6. Synthesis of N-(4-methyl-3-(3-methyl-1,2,4-oxadiazol-5-yl)thiophen-2-yl)-2-(naphthalen-1-yl)acetamide (59)

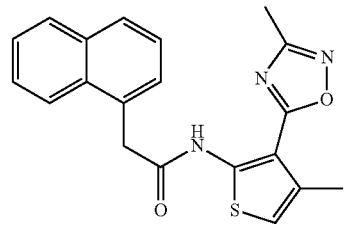 [SMILES: Cc1noc(-c2c(C)csc2NC(=O)Cc2cccc3ccccc23)n1]

4.6.1. Methyl 4-methyl-2-(2-(naphthalen-1-yl)acetamido)thiophene-3-carboxylate The title compound was prepared from 2-(naphthalen-1-yl)acetic acid (10 g, 54 mmol) and methyl 2-amino-4- methylthiophene-3-carboxylate (9.2 g, 54 mmol) according to protocol A (15.4 g, 85%) as a white solid. $^1$H NMR (CDCl$_3$) δ 11.0 (s, 1H), 8.05-7.85 (m, 3H), 7.63-7.50 (m, 4H), 6.36 (s, 1H), 4.29 (s, 2H), 3.57 (s, 3H), 2.28 (s, 3H); $^{13}$C NMR (CDCl$_3$) δ 168.3, 165.6, 149.3, 135.0, 134.0, 132.1, 129.8, 128.9, 128.6, 127.0, 126.2, 125.7, 123.7, 112.9, 112.2, 51.1, 41.9, 17.7; MH+ 340.

4.6.2. N-(4-methyl-3-(3-methyl-1,2,4-oxadiazol-5-yl)thiophen-2-yl)-2-(naphthalen-1-yl)acetamide Sodium hydride (60% dispersion in mineral oil, 106 mg, 2.65 mmol) was added to a solution of acetamide oxime (218 mg, 2.94 mmol) in dry THF (5 mL) at rt. Methyl 4-methyl-2-(2-(naphthalen-1-yl)acetamido)thiophene-3-carboxylate (Aldrich, 500 mg, 1.47 mmol) was added, and the reaction mixture was allowed to stir over 3 days. The mixture was concentrated under reduced pressure, then partitioned between ethyl acetate and water. The organic layer was separated, and washed with saturated NaCl solution. The organic layer was dried (MgSO$_4$), filtered and concentrated. The residue was purified by flash chromatography (EtOAc/hexanes elution), and then triturated from acetonitrile to afford the desired product (58 mg) as a white solid. Method [7]: rt=9.42 min; $^1$H NMR (CDCl$_3$) δ 11.3 (s, 1H), 8.02-7.89 (m, 3H), 7.63-7.50 (m, 4H), 6.48 (s, 1H), 4.35 (s, 2H), 2.42 (s, 3H), 2.08 (s, 3H); $^{13}$C NMR (CDCl$_3$) δ 172.1, 168.9, 165.2, 146.4, 134.0, 133.4, 132.4, 129.4, 129.1, 129.0, 128.8, 127.2, 126.4, 125.7, 123.7, 114.0, 106.9, 42.1, 16.9, 11.4; MH+ 364.1.

4.7. Synthesis of N-(4-methyl-3-(3-methyl-1,2,4-oxadiazol-5-yl)thiophen-2-yl)-2-(4-(pyridin-4-yl)phenyl)acetamide (60)

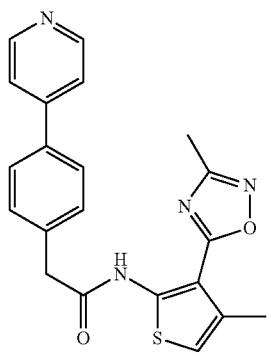 [SMILES: Cc1noc(-c2c(C)csc2NC(=O)Cc2ccc(-c3ccncc3)cc2)n1]

4.7.1. Methyl 2-(2-(4-iodophenyl)acetamido)-4-methylthiophene-3-carboxylate The title compound was synthesized in 87% yield according to protocol A from 2-(4-iodophenyl)acetic acid and methyl 2-amino-4-methylthiophene-3-carboxylate. $^{13}$C NMR (CDCl$_3$) δ 167.5, 166.6, 149.8, 138.1, 134.8, 133.1, 131.4, 113.0, 112.3, 93.2, 51.5, 43.3, 17.8; MH+ 416.0.

4.7.2. Methyl 4-methyl-2-(2-(4-(pyridin-4-yl)phenyl)acetamido)thiophene-3-carboxylate Methyl 2-(2-(4-iodophenyl)acetamido)-4-methylthiophene-3-carboxylate (420.4 mg, 1.01 mmol), 4-pyridylboronic acid (Aldrich, 167 mg, 1.36 mmol), tetrakis(triphenylphosphine)palladium(0) (123 mg, 0.11 mmol), and potassium carbonate (565 mg, 4.1 mmol) were combined in DME (2 mL) and water (1 mL) in a sealed tube, and heated to 80° C. over 17 h. The reaction mixture was cooled to rt, then partitioned between EtOAc and water. The organic layer was separated, washed (brine), dried (Na$_2$SO$_4$), filtered and concentrated under reduced pressure. Flash chromatography (EtOAc/hexanes) afforded the titled compound. $^1$H NMR (CDCl$_3$) δ 11.3 (s, 1H), 8.67 (dd, J=4.7, 1.4H, 2H), 7.67 (d, J=8.2 Hz, 2H), 7.60-7.40 (m, 4H), 6.38 (s, 1H), 3.88 (s, 2H), 3.80 (s, 3H), 2.33 (s, 3H); $^{13}$C NMR (CDCl$_3$) δ 167.7, 166.6, 150.3, 149.9, 147.8, 137.4, 134.8, 134.6, 130.3, 127.7, 121.5, 113.0, 112.3, 51.5, 43.5, 17.8; MH+ 367.1.

4.7.3. N-(4-methyl-3-(3-methyl-1,2,4-oxadiazol-5-yl)thiophen-2-yl)-2-(4-(pyridin-4-yl)phenyl)acetamide Acetamide oxime (66 mg, 0.89 mmol) was taken up in dry THF (1 mL) at rt, and sodium hydride (60% dispersion in mineral oil, 55 mg, 1.4 mmol) was added. After hydrogen evolution ceased, methyl 4-methyl-2-(2-(4-(pyridin-4-yl)phenyl)acetamido)thiophene-3-carboxylate (82 mg, 0.22 mmol) was added in one portion. The reaction was stirred at rt for 90 min, then at 50° C. for 21 h. The mixture was concentrated under reduced pressure, then partitioned between ethyl acetate and water. The organic layer was separated, and washed with saturated NaCl solution. The organic layer was dried (MgSO$_4$), filtered and concentrated. HPLC purification of the crude residue afforded the title compound as a trifluoroacetic acid salt. $^1$H NMR (CDCl$_3$) δ 11.6 (s, 1H), 8.86 (dd, J=5.3, 1.4H, 2H), 7.94 (dd, J=5.3, 1.4H, 2H), 7.77 (d, J=8.2 Hz, 2H), 7.61 (d, J=8.2 Hz, 2H), 6.54 (s, 1H), 3.99 (s, 2H), 2.51 (s, 3H), 2.34 (s, 3H); MH+ 407.1.

4.8. Synthesis of N-(2-(3-methyl-1,2,4-oxadiazol-5-yl)thiophen-3-yl)-2-(naphthalen-1-yl)acetamide (61)

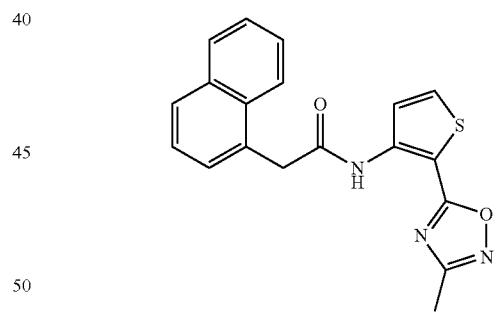

4.8.1. Methyl 3-(2-(naphthalen-1-yl)acetamido)thiophene-2-carboxylate

Methyl 3-(2-(naphthalen-1-yl)acetamido)thiophene-2-carboxylate was prepared from methyl 3-aminothiophene-2-carboxylate (4.30 g, 27.3 mmol) and 2-(naphthalen-1-yl)acetic acid (3.10 g, 27.3 mmol) according to protocol A. Retention time (min)=8.738, method [7], MS(ESI) 326.1 (M+H).

4.8.2. N-(2-(3-Methyl-1,2,4-oxadiazol-5-yl)thiophen-3-yl)-2-(naphthalen-1-yl)acetamide Sodium hydride (60% dispersion, 15 mg, 0.39 mmol) was added to a solution of acetamide oxime (29 mg, 0.39 mmol)

in THF (1 mL). The resulting mixture was stirred at room temperature for 10 minutes after which a solution of methyl 3-(2-(naphthalen-1-yl)acetamido)thiophene-2-carboxylate (107 mg, 0.33 mmol) in THF (1 mL) was added. The reaction mixture was stirred for 1 h and was subsequently diluted with ethyl acetate (10 mL). The resulting solution was washed with brine (5 mL) and the organic phase was then dried (Na$_2$SO$_4$), filtered and concentrated under vacuum. The residue was dissolved in THF (1 mL) and HCl (1 mL of a 10% aqueous solution) was added. The mixture was stirred for 20 minutes after which ethyl acetate (10 mL) was added. The resulting solution was washed with brine (5 mL) and the organic phase was then dried (Na$_2$SO$_4$), filtered, concentrated under vacuum and the residue was purified by preparative HPLC to give N-(2-(3-methyl-1,2,4-oxadiazol-5-yl)thiophen-3-yl)-2-(naphthalen-1-yl)acetamide. Retention time (min)=9.533, method [7], MS(ESI) 350.1 (M+H). $^1$H NMR (300 MHz, CDCl$_3$) δ 10.10 (s, 1H), 8.26 (d, J=5.4 Hz, 1H), 8.03 (d, J=9.3 Hz, 2H), 7.59-7.49 (m, 5H), 4.27 (s, 2H), 2.14 (s, 3H).

Synthesis of N-(3-(1,2,4-oxadiazol-3-yl)thiophen-2-yl)-2-(6,7-difluoro-2-oxoquinolin-1(2H)-yl)acetamide

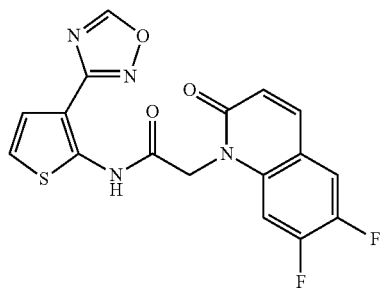 [SMILES: O=C(Cn1c(=O)ccc2cc(F)c(F)cc21)Nc1sccc1-c1ncon1]

4.9.1. N-(Thieno[2,3-d]pyrimidin-4-yl)hydroxylamine 4-chlorothieno[2,3-d]pyrimidine (340 mg, 1.99 mmol), hydroxylamine-hydrogen chloride (550 mg, 7.91 mmol), and diisopropylethylamine (1 ml) in absolute ethanol (5 ml) was placed into a preheated oil bath at 75° C. After stirring for 6 h, the solution was concentrated under reduced pressure.

4.9.2. (E)-Ethyl N-3-(1,2,4-oxadiazol-3-yl)thiophen-2-ylformimidate

N-(thieno[2,3-d]pyrimidin-4-yl)hydroxylamine and triethylorthoformate (10 ml) in ethanol (10 ml) was placed into a preheated oil bath at 100° C. for 4 h. The solution was concentrated to yield (E)-ethyl N-3-(1,2,4-oxadiazol-3-yl)thiophen-2-ylformimidate. Method [8] retention time 4.08 min by HPLC (M+=224).

4.9.3. 3-(1,2,4-Oxadiazol-3-yl)thiophen-2-amine (E)-Ethyl N-3-(1,2,4-oxadiazol-3-yl)thiophen-2-ylformimidate (82 mg, 365 umol) and N-methylethane-1,2-diamine (0.30 ml, 3.40 mmol) in methanol (2 ml) was placed into a preheated oil bath at 60° C. After stirring for 15 min, the solution was concentrated under reduced pressure and the residue was flash chromatographed with 9:1, 4:1, 7:3, and 3:2 hexane:ethyl acetate as the eluant to afford 18 mg (5.4% yield over three steps) of 3-(1,2,4-oxadiazol-3-yl)thiophen-2-amine. Method [6] retention time 4.08 min by HPLC (M+ 168). $^1$H NMR (300 MHz, CDCl$_3$) δ 8.70 (s, 1H), 7.22 (d, J=5.4 Hz, 1H), 6.45 (d, J=5.4 Hz, 1H).

4.9.4. N-(3-(1,2,4-oxadiazol-3-yl)thiophen-2-yl)-2-(6,7-difluoro-2-oxoquinolin-1(2H)-yl)acetamide The title compound was prepared from 3-(1,2,4-oxadiazol-3-yl)thiophen-2-amine (18 mg, 108 umol) and 2-(6,7-difluoro-2-oxoquinolin-1(2H)-yl)acetic acid (32 mg, 134 umol) using protocol A. The crude product was purified by HPLC to yield N-(3-(1,2,4-oxadiazol-3-yl)thiophen-2-yl)-2-(6,7-difluoro-2-oxoquinolin-1(2H)-yl)acetamide. Method [7] retention time 5.34 min by HPLC (M+=389) and (M+Na=411). $^1$H NMR (300 MHz, CDCl$_3$) δ 11.06 (s, 1H), 8.69 (s, 1H), 7.74 (d, J=9.9 Hz, 1H), 7.42 (m, 2H), 7.35 (m, 1H), 6.98 (d, J=5.4 Hz, 1H), 6.86 (d, J=9.3 Hz, 1H), 5.22 (s, 2H).

Example 5

Synthesis of Thiazole Triazoles

5.1. Synthesis of N-(4-(1H-1,2,4-triazol-5-yl)thiazol-5-yl)-2-(isoquinolin-5-yl)acetamide (62)

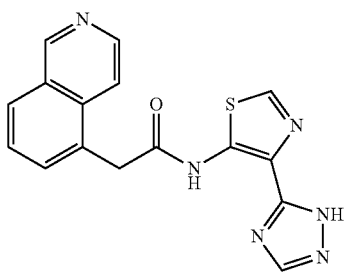 [SMILES: O=C(Cc1cccc2cnccc12)Nc1scnc1-c1ncn[nH]1]

5.1.1. Methyl 5-(diphenylmethyleneamino)thiazole-4-carboxylate

A mixture of methyl 5-bromothiazole-4-carboxylate (3.51 g, 15.8 mmol), diphenylmethanimine (4.0 ml, 23.9 mmol), cesium carbonate (10.98 g, 33.7 mmol), Pd$_2$(dba)$_3$-CHCl$_3$ (876 mg, 957 umol), and 4,5-bis(diphenylphosphino)-9,9-dimethylxanthene (Xantphos, 1.67 g, 2.89 mmol) in toluene (30 ml) was heated at 80° C. for 18 h. The heterogeneous mixture was directly flash chromatographed with 9:1, 4:1, 7:3, 3:2 and 1:1 hexane:ethyl acetate as the eluant to yield 4.30 g (84% yield) of methyl 5-(diphenylmethyleneamino)thiazole-4-carboxylate as a yellow oil. Retention time (min)=6.41, method [7], MS(ESI) 323.0 (M+H).

5.1.2. Methyl 5-aminothiazole-4-carboxylate

Aqueous 3N HCl (1 mL) was added to a solution of methyl 5-(diphenylmethyleneamino)thiazole-4-carboxylate (1.22 g, 3.81 mmol) in THF (5 mL). The reaction mixture was stirred for 1 h and the white solid which had formed was isolated by filtration to give methyl 5-aminothiazole-4-carboxylate (0.527 g, 2.72 mmol, 71%). Retention time (min)=0.422, method [7], MS(ESI) 159.0 (M+H).

5.1.3. Methyl 5-(2-(isoquinolin-5-yl)acetamido)thiazole-4-carboxylate

Methyl 5-(2-(isoquinolin-5-yl)acetamido)thiazole-4-carboxylate was prepared from methyl 5-aminothiazole-4-carboxylate (0.132 g, 0.834 mmol) and 2-(isoquinolin-5-yl)acetic acid (0.163 g, 0.834 mmol) according to protocol A. Retention time (min)=2.400, method [3], MS(ESI) 328.0 (M+H).

5.1.4. 5-(2-(Isoquinolin-5-yl)acetamido)thiazole-4-carboxamide 5-(2-(Isoquinolin-5-yl)acetamido)thiazole-4-carboxamide was prepared from methyl 5-(2-(isoquinolin-5-yl)acetamido)thiazole-4-carboxylate (210 mg, 0.64 mmol) according to protocol H. Retention time (min)=2.507, method [3], MS(ESI) 313.0 (M+H).

5.1.5. N-(4-(1H-1,2,4-triazol-5-yl)thiazol-5-yl)-2-(isoquinolin-5-yl)acetamide N-(4-(1H-1,2,4-triazol-5-yl)thiazol-5-yl)-2-(isoquinolin-5-yl)acetamide was prepared from 5-(2-(isoquinolin-5-yl)acetamido)thiazole-4-carboxamide (124 mg, 0.396 mmol) according to protocol I. Retention time (min)=4.890, method [8], MS(ESI) 337.1 (M+H); $^1$H NMR (300 MHz, CD$_3$OD) δ 9.75 (s, 1H), 8.45-8.59 (m, 4H), 8.29-8.31 (m, 1H), 8.05-8.14 (m, 2H), 4.63 (s, 2H).

5.2. Synthesis of 2-(isoquinolin-5-yl)-N-(4-(1-methyl-1H-1,2,4-triazol-5-yl)thiazol-5-yl)acetamide (63)

2-(Isoquinolin-5-yl)-N-(4-(1-methyl-1H-1,2,4-triazol-5-yl)thiazol-5-yl)acetamide was prepared from 5-(2-(Isoquinolin-5-yl)acetamido)thiazole-4-carboxamide (Example 5.1.4., 197 mg, 0.631 mmol) according to protocol J. Retention time (min)=1.196, method [7], MS(ESI) 351.1 (M+H); $^1$H NMR (300 MHz, CD$_3$OD) δ 9.75 (s, 1H), 8.45-8.60 (m, 4H), 8.28 (d, J=7.6 Hz, 1H), 8.07 (dd, J=8.8, 7.6 Hz, 1H), 7.73 (s, 1H), 4.61 (s, 2H), 4.27 (s, 3H).

Example 6

Synthesis of 2-(2-pyridyl)-3-(1-naphthylacetylamino)thiophene (64)

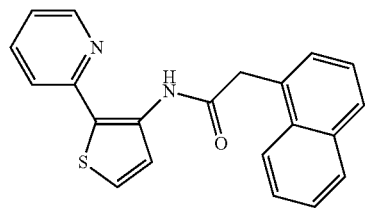 [SMILES: O=C(Cc1cccc2ccccc12)Nc1ccsc1-c1ccccn1]

6.1. 2-Iodo-3-(tert-butoxycarbonylamino)thiophene

A vial was charged with 199 mg (1.0 mmol) 3-(tert-butoxycarbonylamino)thiophene, 164 mg (2.0 mmol) NaOAc, 4.0 mL HOAc, and a stir bar. The mixture was stirred at room temperature, giving a homogeneous solution "A". A second vial was charged with 162 mg (1.0 mmol) iodine monochloride and 2.0 mL glacial acetic acid. The second mixture was swirled at room temperature. This second homogeneous solution "B" was added to solution "A" dropwise over three minutes. A white solid began to precipitate immediately. After the addition, the mixture was allowed to stand overnight, at which time the white solid had separated from the brown supernatant. With stirring, 200 uL sat. Na$_2$S$_2$O$_3$/H$_2$O was added, decolorizing the mixture from brown to yellow. 10 mL water was added, and then the mixture was evaporated, affording a semi-solid light brown residue. The residue was partitioned between EtOAc and H$_2$O, and the separated EtOAc phase was washed (sat. NaHCO$_3$, then sat. NaCl). The EtOAc phase was filtered, and concentrated to give 262 mg (81%) of the title compound as light brown crystals. $^1$H NMR (CDCl$_3$, 300 MHz) δ 7.49 (bs, 1H), 7.45 (d, J=5.4 Hz, 1H), 6.50 (bs, 1H), 1.54 (s, 9H). Method [5]: rt=1.40 min; m/z=269.9 (MH+ minus isobutylene).

6.2. 2-(2-Pyridyl)-3-(1-naphthylacetylamino)thiophene

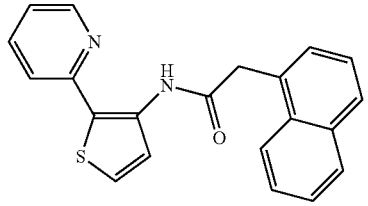 [SMILES: O=C(Cc1cccc2ccccc12)Nc1ccsc1-c1ccccn1]

A vial was charged with 255 mg (0.783 mmol) 2-iodo-3-(tert-butoxycarbonylamino)-thiophene, 467 mg (1.27 mmol) 2-(tributylstannyl)pyridine, 18 mg (0.015 mmol) Pd(PPh$_3$)$_4$, and 2 mL toluene. The vial was flushed with nitrogen. The vial was shaken at 95 C for 24 h. The cooled vial was opened, and TLC indicated consumption of 2-iodo-3-(tert-butoxycarbonylamino)thiophene and formation of a complex product mixture. The toluene was evaporated, and the residue was treated with 3 mL CF$_3$CO$_2$H. After 5 h at rt, the CF$_3$CO$_2$H was evaporated, and the residue was partitioned between 1 M H$_2$SO$_4$ and toluene. The aqueous phase was made basic by adding solid NaHCO$_3$, and then the mixture was extracted with EtOAc. Evaporation of the EtOAc extracts provided 75 mg of a 2:1 mixture of 2-(2-pyridinyl)-3-aminothiophene and 2-(3-aminothiophene-2-yl)-3-aminothiophene, as determined by HPLCMS.

The title compound was prepared from the above mixture and 1-naphthylacetic acid (230 mg, 1.23 mmol) according to protocol A. The residue was purified by flash chromatography using EtOAc/hexanes on silica gel, affording 40 mg (15%) of the title compound as a white solid. $^1$H NMR (CDCl$_3$, 300 MHz) δ 11.92 (bs, 1H), 8.26 (d, J=5.4 Hz, 1H), 8.08 (dd, J=1.8 Hz, J=6.9 Hz, 1H), 7.93-7.88 (m, 2H), 7.59-7.46 (m, 6H), 7.27 (d, J=8.1 Hz, 1H), 7.20 (d, J=6.3 Hz, 1H), 6.84 (dd, J=4.8 Hz, J=7.2 Hz, 1H), 4.24 (s, 2H). $^{13}$C NMR (CDCl$_3$, 75 MHz) δ 153.5, 147.1, 138.3, 136.7, 134.0, 132.6, 130.9, 128.9, 128.6, 128.4, 126.8, 126.1, 125.6, 124.4, 124.1, 123.9, 120.1, 119.8, 116.9, 43.2. Method [5]: rt=1.67 min; MH+ 345.2.

Example 7

Synthesis of Thiophene Pyrazoles

7.1. Synthesis of N-(2-(1H-pyrazol-1-yl)thiophen-3-yl)-2-(4-methoxyphenyl)-acetamide (65)

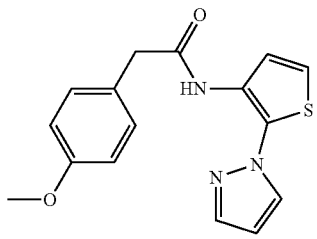 [SMILES: COc1ccc(CC(=O)Nc2ccsc2-n2cccn2)cc1]

7.1.1. 1-(3-Nitrothiophen-2-yl)-1H-pyrazole

Potassium tert-butoxide (2.28 g, 20.3 mmol) and 1H-pyrazole (2.02 g, 29.7 mmol) in DMF (50 ml) was stirred for 30 min. 2-chloro-3-nitrothiophene (2.56 g, 15.6 mmol) was added and the solution was placed into a preheated oil bath at 100° C. After stirring for 1 h, the solution was diluted with brine and extracted with diethyl ether. The combined organic extracts were dried over magnesium sulfate, filtered and concentrated under reduced pressure. The residue was flash chromatographed with 9:1, 4:1, 7:3, 3:2, and 1:1 hexane:ethyl acetate as the eluant to yield impure 1-(3-nitrothiophen-2-yl)-1H-pyrazole. Method [1] Retention time 1.52 min by HPLC (MH+196).

7.1.2. 2-(1H-Pyrazol-1-yl)thiophen-3-amine

The title compound was prepared from 1-(3-nitrothiophen-2-yl)-1H-pyrazole using protocol Q to yield impure 2-(1H-pyrazol-1-yl)thiophen-3-amine. Method [3] Retention time 1.55 min by HPLC (MH+ 166).

7.1.3. N-(2-(1H-Pyrazol-1-yl)thiophen-3-yl)-2-(4-methoxyphenyl)acetamide

The title compound was prepared from 2-(1H-pyrazol-1-yl)thiophen-3-amine and 2-(4-methoxyphenyl)acetic acid using protocol B. The solution was directly purified by HPLC to yield N-(2-(1H-pyrazol-1-yl)thiophen-3-yl)-2-(4-methoxyphenyl)acetamide. Method [7] Retention time 5.22 min by HPLC (MH+ 314). $^1$H NMR (300 MHz, CDCl$_3$) δ 9.94 (broad s, 1H), 8.00 (d, J=5.7 Hz, 1H), 7.61 (d, J=2.7 Hz, 1H), 7.39 (d, J=1.8 Hz, 1H), 7.27 (m, 2H), 6.94 (m, 3H), 6.35 (t, J=2.4 Hz, 1H), 3.87 (s, 3H), 3.71 (s, 2H).

7.2. Synthesis of 2-(4-methoxyphenyl)-N-(2-(4-methyl-1H-pyrazol-1-yl)thiophen-3-yl)acetamide (66)

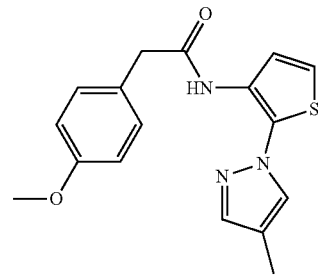 [SMILES: COc1ccc(CC(=O)Nc2ccsc2-n2cc(C)cn2)cc1]

7.2.1. 4-Methyl-1-(3-nitrothiophen-2-yl)-1H-pyrazole

Potassium tert-butoxide (2.78 g, 24.8 mmol) and 4-methyl-1H-pyrazole (3.0 ml g, 37.3 mmol) in DMF (50 ml) was stirred for 30 min. 2-chloro-3-nitrothiophene (3.08 g, 18.7 mmol) was added and the solution was placed into a preheated oil bath at 100° C. After stirring for 1 h, the solution was diluted with brine and extracted with diethyl ether. The combined organic extracts were dried over magnesium sulfate, filtered and concentrated under reduced pressure. The residue was flash chromatographed with 9:1, 4:1, 7:3, 3:2, and 1:1 hexane:ethyl acetate as the eluant to yield 4-methyl-1-(3-nitrothiophen-2-yl)-1H-pyrazole. Method [1] Retention time 1.80 min by HPLC (MH+210).

7.2.2. 2-(4-Methyl-1H-pyrazol-1-yl)thiophen-3-amine

4-Methyl-1-(3-nitrothiophen-2-yl)-1H-pyrazole was treated with protocol Q to yield impure 2-(4-methyl-1H-pyrazol-1-yl)thiophen-3-amine. Method [3] Retention time 2.61 min by HPLC (MH+ 180).

7.2.3. 2-(4-Methoxyphenyl)-N-(2-(4-methyl-1H-pyrazol-1-yl)thiophen-3-yl)acetamide The title compound was prepared from 2-(4-methyl-1H-pyrazol-1-yl)thiophen-3-amine and 2-(4-methoxyphenyl)acetic acid using protocol B and purified by HPLC. Method [7] Retention time 6.16 min by HPLC (MH+ 328). $^1$H NMR (300 MHz, CDCl$_3$) δ 9.93 (broad s, 1H), 7.97 (d, J=6.0 Hz, 1H), 7.38 (s, 1H), 7.19 (s, 1H), 7.27 (d, J=8.7 Hz, 2H), 6.96 (d, J=8.7 Hz, 2H), 6.90 (d, J=6.0 Hz, 1H), 3.87 (s, 3H), 3.70 (s, 2H), 2.11 (s, 3H).

7.3. Synthesis of N-(2-(1H-pyrazol-3-yl)thiophen-3-yl)-2-(naphthalen-1-yl)acetamide (67)

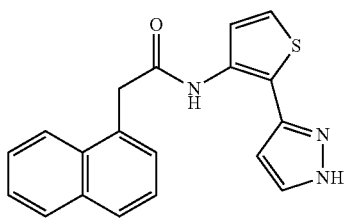 [SMILES: O=C(Cc1cccc2ccccc12)Nc1ccsc1-c1cc[nH]n1]

7.3.1. (E)-N-(2-(3-(Dimethylamino)acryloyl)thiophen-3-yl)-2-(naphthalen-1-yl)acetamide A solution of N-(2-acetylthiophen-3-yl)-2-(naphthalen-1-yl)acetamide (165 mg, 0.53 mmol) in N,N-dimethylformamide dimethyl acetal (0.2 mL, 1.50 mmol) was heated at 80° C. for 2 h. The reaction mixture was partitioned between ethyl acetate and H$_2$O. The organic layer was washed with H$_2$O, dried (sodium sulfate), filtered and concentrated under reduced pressure to give the desired N-(2-(3-(dimethylamino)acryloyl)thiophen-3-yl)-2-(naphthalen-1-yl)acetamide (185 mg, 95%) which was used without further purification. Method [4] m/z 387.0 (M+Na); rt=2.199 min.

7.3.2. N-(2-(1H-Pyrazol-3-yl)thiophen-3-yl)-2-(naphthalen-1-yl)acetamide

To a solution of (E)-N-(2-(3-(dimethylamino)acryloyl)thiophene-3-yl)-2-(naphthalen-1-yl)acetamide (185 mg, 0.51 mmol) in abs. ethanol (2 mL) was added hydrazine hydrate (0.2 ml, 4.11 mmol) and acetic acid (0.5 mL, 8.73 mmol). The reaction mixture was stirred at room temperature overnight under N$_2$ (g) inlet and then concentrated under reduced pressure. The resulting residue was partitioned between ethyl acetate and H$_2$O. The organic layer was dried (sodium sulfate), filtered and concentrated under reduced pressure. The precipitate that formed was washed with methanol and collected filtration to afford N-(2-(1H-pyrazol-3-yl)thiophen-3-yl)-2-(naphthalen-1-yl)acetamide (50 mg, 30%). Method [7] m/z 334.0 (M+H); retention time=5.887. $^1$H-NMR (DMSO-d$_6$) δ 12.92 (broad s, 1H), 10.37 (s, 1H), 8.09 (d, J=7.7 Hz, 1H), 7.92 (d, J=6.9 Hz, 2H), 7.86 (d, J=7.7 Hz, 1H), 7.77 (s, 1H), 7.66 (d, J=5.3 Hz, 1H), 7.61-7.47 (m, 4H), 7.36 (d, J=5.3 Hz, 1H), 6.36 (d, J=2.4 Hz, 1H), 4.19 (s, 2H).

7.4. Synthesis of N-(2-(1-methyl-1H-pyrazol-3-yl)thiophen-3-yl)-2-(naphthalen-1-yl)acetamide (68)

To a solution of (E)-N-(2-(3-(dimethylamino)acryloyl)thiophen-3-yl)-2-(naphthalen-1-yl)acetamide (Example 7.3.1., 143 mg, 0.39 mmol) in abs. ethanol (2 mL) was added methyl hydrazine (0.2 mL, 3.80 mmol) and acetic acid (0.5 mL, 8.73 mmol). The reaction mixture was stirred at room temperature overnight under N$_2$(g) inlet and then concentrated under reduced pressure. The resulting residue was partitioned between ethyl acetate and H$_2$O. The organic layer was dried (sodium sulfate), filtered and concentrated under reduced pressure. Purification by flash column chromatography (silica, 20:80 ethyl acetate/hexane) yielded N-(2-(1-methyl-1H-pyrazol-3-yl)thiophen-3-yl)-2-(naphthalen-1-yl)acetamide (27 mgs, 20%). Method [7] m/z 348.0 (M+H); retention time=5.328. $^1$H-NMR (CDCl$_3$) δ 7.96 (d, J=5.2 Hz, 2H), 7.94-7.91 (m, 1H), 7.86 (d, J=7.8 Hz, 1H), 7.56-7.53 (m, 2H), 7.41 (d, J=7.8 Hz, 1H), 7.36 (d, J=9.1 Hz, 1H), 7.32 (d, J=5.2 Hz, 1H), 7.15 (s, 1H), 7.09 (d, J=1.9 Hz, 1H), 5.17 (d, J=1.9 Hz, 1H), 4.13 (s, 2H), 3.45 (s, 3H).

7.5. Synthesis of N-(2-(5-methyl-1H-pyrazol-3-yl)thiophen-3-yl)-2-(naphthalen-1-yl)acetamide (69)

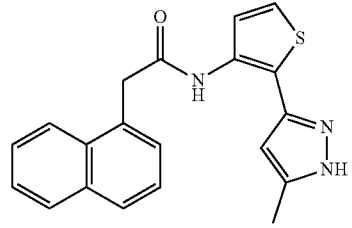 [SMILES: Cc1cc(-c2sccc2NC(=O)Cc2cccc3ccccc23)n[nH]1]

7.5.1. (E)-N-(2-(3-(Dimethylamino)but-2-enoyl)thiophen-3-yl)-2-(naphthalen-1-yl)acetamide A solution of N-(2-acetylthiophen-3-yl)-2-(naphthalen-1-yl)acetamide (197 mg, 0.64 mmol) in N,N-dimethylacetamide dimethyl acetal (0.3 mL, 2.05 mmol) was heated at 80° C. for 2 h. The reaction mixture was partitioned between ethyl acetate and H$_2$O. The organic layer was washed with H$_2$O, dried (sodium sulfate), filtered and concentrated to give the desired N-(2-(3-(dimethylamino)but-2-enoyl)thiophen-3-yl)-2-(naphthalen-1-yl)acetamide (139 mg, 58%) which was used without further purification.

7.5.2. N-(2-(5-methyl-1H-pyrazol-3-yl)thiophen-3-yl)-2-(naphthalen-1-yl)acetamide To a solution of (E)-N-(2-(3-(dimethylamino)but-2-enoyl)thiophen-3-yl)-2-(naphthalen-1-yl)acetamide (139 mg, 0.37 mmol) in abs. ethanol (2 mL) was added hydrazine hydrate (1 mL, 62.91 mmol) and acetic acid (0.5 mL, 8.73 mmol). The reaction mixture was stirred at room temperature overnight under N$_2$ (g) inlet and then concentrated under reduced pressure. The resulting residue was partitioned between ethyl acetate and H$_2$O. The organic layer was dried (sodium sulfate), filtered and concentrated under reduced pressure. Purification by flash column chromatography (silica, 20:80 ethyl acetate/hexane) yielded N-(2-(5-methyl-1H-pyrazol-3-yl)thiophen-3-yl)-2-(naphthalen-1-yl)acetamide (20 mgs, 16%). Method [7] m/z 348.1 (M+Na); retention time=6.791. $^1$H-NMR (CDCl$_3$) δ 10.28 (broad s, 1H), 8.07 (d, J=5.8 Hz, 2H), 7.91 (d, J=4.5 Hz, 2H), 7.53 (d, J=5.8 Hz, 2H), 7.53 (s, 1H), 7.50 (d, J=4.5 Hz, 2H), 7.08 (d, J=5.2 Hz, 1H), 5.88 (s, 1H), 4.23 (s, 2H), 2.19 (s, 3H).

Example 8

Thiophene Tetrazole Analogs

8.1. Synthesis of N-(3-(2H-tetrazol-5-yl)thiophen-2-yl)-2-(4-methoxyphenyl)-acetamide (70)

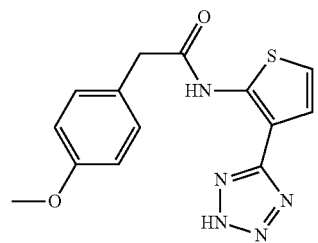 [SMILES: COc1ccc(CC(=O)Nc2sccc2-c2nn[nH]n2)cc1]

8.1.1. 2-(4-Methoxyphenyl)-N-(2-(4-methyl-1H-pyrazol-1-yl)thiophen-3-yl)acetamide The title compound was synthesized from 2-(4-methoxyphenyl)acetic acid and 2-aminothiophene-3-carbonitrile using protocol B. The crude product was purified using normal phase chromatography with 9:1, 4:1, 7:3, and 3:2 hexane:ethyl acetate as the eluant to yield N-(3-cyanothiophen-2-yl)-2-(4-methoxyphenyl)acetamide. Method [1] Retention time 1.81 min by HPLC (MH+ 307).

8.1.2. N-(3-(2H-Tetrazol-5-yl)thiophen-2-yl)-2-(4-methoxyphenyl)-acetamide

N-(3-cyanothiophen-2-yl)-2-(4-methoxyphenyl)acetamide (285 mg, 1.05 mmol), and azidotributylstannane (614 mg, 1.85 mmol) in toluene (10 ml) was placed into a preheated oil bath at 100° C. After stirring for 6 h, The solution was concentrated and directly purified by HPLC to yield N-(3-(2H-tetrazol-5-yl)thiophen-2-yl)-2-(4-methoxyphenyl)acetamide. Method [7] Retention time 4.92 min by HPLC (MH+ 316). $^1$H NMR (300 MHz, DMSO) δ 11.05 (s, 1H), 7.37 (d, J=6.0 Hz, 1H), 7.30 (d, J=8.4 Hz, 2H), 7.23 (d, J=6.0 Hz, 1H), 6.94 (d, J=8.4 Hz, 2H), 3.88 (s, 2H), 3.76 (s, 3H).

8.2. Synthesis of 2-(4-methoxyphenyl)-N-(3-(2-methyl-2H-tetrazol-5-yl)thiophen-2-yl)acetamide (71)

Iodomethane (0.20 ml, 3.21 mmol) was added to a heterogeneous mixture of N-(3-(2H-tetrazol-5-yl)thiophen-2-yl)-2-(4-methoxyphenyl)acetamide (Example 8.1., 620 mg, 1.97 mmol) and potassium carbonate (1.36 g, 9.84 mmol) in DMF (10 ml). After stirring for 72 h, the solution was diluted with water and extracted with methylene chloride. The combined organic extracts were dried over magnesium sulfate, filtered and concentrated under reduced pressure. The residue was directly purified by HPLC to yield 2-(4-methoxyphenyl)-N-(3-(2-methyl-2H-tetrazol-5-yl)thiophen-2-yl)acetamide. Method [7] Retention time 6.03 min by HPLC (MH+ 330). $^1$H NMR (300 MHz, CDCl$_3$) δ 10.59 (s, 1H), 7.34 (d, J=6.0 Hz, 1H), 7.33 (d, J=8.7 Hz, 2H), 7.00 (d, J=8.7 Hz, 2H), 6.91 (d, J=6.0 Hz, 1H), 4.28 (s, 3H), 3.89 (s, 3H), 3.86 (s, 2H).

8.3. Synthesis of N-(3-(2-(methoxymethyl)-2H-tetrazol-5-yl)thiophen-2-yl)-2-(4-methoxyphenyl)acetamide (72)

Chloromethyl methyl ether (0.20 ml, 2.63 mmol) was added to a heterogeneous mixture of N-(3-(2H-tetrazol-5-yl)thiophen-2-yl)-2-(4-methoxyphenyl)acetamide (Example 8.1., 580 mg, 1.84 mmol) and potassium carbonate (1.36 g, 9.84 mmol) in DMF (10 ml). After stirring for 72 h, the solution was diluted with water and extracted with methylene chloride. The combined organic extracts were dried over magnesium sulfate, filtered and concentrated under reduced pressure. The residue was directly purified by HPLC to yield N-(3-(2-(methoxymethyl)-2H-tetrazol-5-yl)thiophen-2-yl)-2-(4-methoxyphenyl)-acetamide. Method [7] Retention time 6.60 min by HPLC (MH+ 360). $^1$H NMR (300 MHz, CDCl$_3$) δ 10.58 (s, 1H), 7.47 (d, J=5.7 Hz, 1H), 7.33 (d, J=8.4 Hz, 2H), 7.00 (d, J=8.4 Hz, 2H), 6.93 (d, J=5.7 Hz, 1H), 5.77 (s, 2H), 3.87 (s, 3H), 3.86 (s, 2H), 3.37 (s, 3H).

8.4. Synthesis of N-(3-(1-(methoxymethyl)-1H-tetrazol-5-yl)thiophen-2-yl)-2-(4-methoxyphenyl)acetamide (72a)

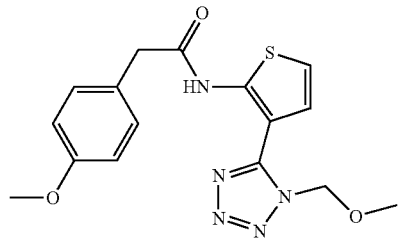

The title compound was isolated during the purification of N-(3-(2-(methoxymethyl)-2H-tetrazol-5-yl)thiophen-2-yl)-2-(4-methoxyphenyl)acetamide, above. Method [7] Retention time 6.60 min by HPLC (MH+ 660).

Example 9

Synthesis of Thiophene Imidazoles

9.1. Synthesis of N-(2-(1-methyl-1H-imidazol-2-yl)thiophen-3-yl)-2-(naphthalen-1-yl)acetamide (73)

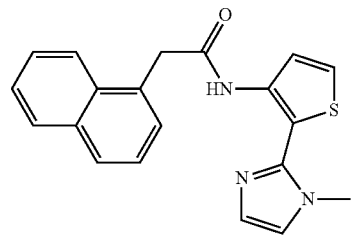 [SMILES: Cn1ccnc1-c1sccc1NC(=O)Cc1cccc2ccccc12]

9.1.1. 2-(Naphthalen-1-yl)-N-(thiophen-3-yl)acetamide 2-(naphthalen-1-yl)acetamide (14.00 g, 75.6 mmol), 3-iodothiophene (10.15 g, 48.3 mmol), trans-1,2diaminocyclohexane (3.0 ml, 25.0 mmol), cuprous iodide (1.97 g, 10.3 mmol), and potassium carbonate (13.66 g, 98.8 mmol) in dioxane (50 ml) was placed into a preheated oil bath at 95° C. After stirring for 18 h, the heterogenous mixture was diluted with water and extracted with methylene chloride. The combined organic extracts were dried over magnesium sulfate, filtered and concentrated under reduced pressure. The residue was flash chromatographed with 19:1, 9:1, 17:3, and 4:1 methylene chloride:ethyl acetate as the eluant to yield 12.26 g (95% yield) of 2-(naphthalen-1-yl)-N-(thiophen-3-yl)acetamide as a brown solid. Method [7] Retention time 2.07 min by HPLC (MH+ 268).

9.1.2. N-(2-Iodothiophen-3-yl)-2-(naphthalen-1-yl)acetamide 2-(naphthalen-1-yl)-N-(thiophen-3-yl)acetamide (7.50 g, 28.1 mmol) and N-iodosuccinimide (7.12 g, 31.6 mmol) in acetonitrile (100 ml) was placed into a preheated oil bath at 75° C. After stirring for 18 h, the solution was concentrated under reduced pressure. The residue was flash chromatographed with 99:1, 49:1, 24:1, and 23:2 methylene chloride: ethyl acetate as the eluant to yield impure N-(2-iodothiophen-3-yl)-2-(naphthalen-1-yl)acetamide. Method [1] Retention time 2.32 min by HPLC (MH+394).

9.1.3. N-(2-(1-Methyl-1H-imidazol-2-yl)thiophen-3-yl)-2-(naphthalen-1-yl)acetamide This molecule was synthesized from N-(2-iodothiophen-3-yl)-2-(naphthalen-1-yl)acetamide and 1-methyl-2-(tributylstannyl)-1H-imidazole according to protocol E. The residue was directly purified by HPLC to yield N-(2-(1-methyl-1H-imidazol-2-yl)thiophen-3-yl)-2-(naphthalen-1-yl)acetamide. Method [7] Retention time 3.41 min by HPLC (MH+ 348). $^1$H NMR (300 MHz, CDCl$_3$) δ 10.27 (s, 1H), 7.87 (m, 3H), 7.51 (m, 6H), 6.91 (d, J=1.5 hz, 1H), 6.82 (d, J=1.5 Hz, 1H), 4.15 (s, 3H), 3.68 (s, 2H).

9.2. Synthesis of 2-(4-methoxyphenyl)-N-(2-(1-methyl-1H-imidazol-4-yl)thiophen-3-yl)acetamide (74)

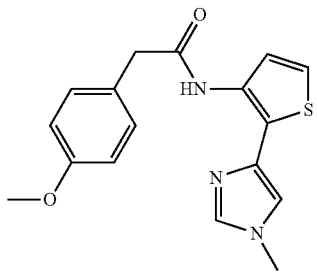 [SMILES: COc1ccc(CC(=O)Nc2ccsc2-c2cn(C)cn2)cc1]

9.2.1. 1-Methyl-4-(tributylstannyl)-1H-imidazole

3 M Ethyl magnesium bromide in THF (11.0 ml, 33.0 mmol) was added dropwise to a solution of 4-iodo-1-methyl-1H-imidazole (5.61 g, 27.0 mmol) in THF (50 ml) at −78° C. After stirring for 2 h, tributyltin chloride (8.0 ml, 29.5 mmol) was added. After stirring for an additional 2 h, the solution was concentrated under reduced pressure. The residue was flash chromatographed (hexane:ethyl acetate) to yield 1-methyl-4-(tributylstannyl)-1H-imidazole. Method [7] Retention time 7.34 min by HPLC (MH+ 373).

9.2.2. 1-Methyl-4-(3-nitrothiophen-2-yl)-1H-imidazole

The title compound was prepared from 2-chloro-3-nitrothiophene (2.57 g, 15.7 mmol) and 1-methyl-4-(tributylstannyl)-1H-imidazole (8.64 g, 23.3 mmol) using protocol E except the reaction was heated to 90° C. (rather than 95° C.) and was purified by flash chromatography (hexane:ethyl acetate). Method [1] Retention time 0.57 min by HPLC (MH+ 210).

9.2.3. 2-(1-Methyl-1H-imidazol-4-yl)thiophen-3-amine 1-methyl-4-(3-nitrothiophen-2-yl)-1H-imidazole was reduced according to protocol F to yield 2-(1-methyl-1H-imidazol-4-yl)thiophen-3-amine. Method [6] Retention time 0.35 min by HPLC (MH+ 180).

9.2.4. 2-(4-Methoxyphenyl)-N-(2-(1-methyl-1H-imidazol-4-yl)thiophen-3-yl)acetamide The title compound was prepared from 2-(1-methyl-1H-imidazol-4-yl)thiophen-3-amine and 2-(4-methoxyphenyl)acetic acid using protocol B and was purified by HPLC. Method [8] Retention time 3.55 min by HPLC (MH+ 328). $^1$H NMR (300 MHz, DMSO) δ 10.37 (s, 1H), 8.33 (s, 1H), 7.48 (3 m, H), 7.26 (d, J=8.4 Hz, 2H), 6.92 (d, J=8.4 Hz, 2H), (s, 6H), 3.60 (s, 2H).

9.3. Synthesis of N-(2-(1H-imidazol-4-yl)thiophen-3-yl)-2-(4-methoxyphenyl)-acetamide (75)

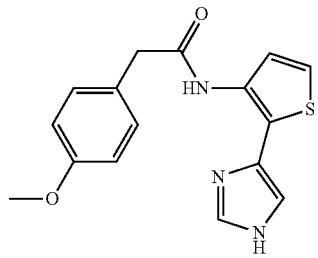 [SMILES: COc1ccc(CC(=O)Nc2ccsc2-c2c[nH]cn2)cc1]

9.3.1. 4-(Tributylstannyl)-1-trityl-1H-imidazole

3 M Ethyl magnesium bromide in THF (5.0 ml, 15.0 mmol) was added dropwise to a solution of 4-iodo-1-trityl-1H-imidazole (4.44 g, 10.2 mmol) in THF (100 ml) at −78° C. After stirring for 2 h, tributyltin chloride (5.0 ml, 18.4 mmol) was added. After stirring for an additional 2 h, the solution was concentrated under reduced pressure. The residue was flash chromatographed with 19:1, 9:1, 17:3, and 4:1 hexane:ethyl acetate as the eluant to yield 7.72 g of impure 4-(tributylstannyl)-1-trityl-1H-imidazole as a yellow solid. Method [7] Retention time 10.89 min by HPLC (MH+ 601).

9.3.2. 4-(3-Nitrothiophen-2-yl)-1-trityl-1H-imidazole

The title compound was prepared from 2-chloro-3-nitrothiophene and 4-(tributylstannyl)-1-trityl-1H-imidazole according to Protocol E. Yield: 2.43 g (56% over 2 steps from 4-iodo-1-trityl-1H-imidazole) of 4-(3-nitrothiophen-2-yl)-1-trityl-1H-imidazole as a greenish-yellow solid. Method [7] Retention time 9.92 min by HPLC (M+Na=460).

9.3.3. 2-(1-Trityl-1H-imidazol-4-yl)thiophen-3-amine

The title compound was prepared from 4-(3-nitrothiophen-2-yl)-1-trityl-1H-imidazole using protocol F (1.27 g, 95% yield) as a red viscous liquid. Method [7] Retention time 5.51 min by HPLC (M+Na=430).

9.3.4. 2-(4-Methoxyphenyl)-N-(2-(1-trityl-1H-imidazol-4-yl)thiophen-3-yl)acetamide The title compound was prepared from 2-(1-trityl-1H-imidazol-4-yl)thiophen-3-amine and 2-(4-methoxyphenyl) acetic acid using protocol B (561 mg, 59%) as a brown solid. Method [7] Retention time 9.46 min by HPLC (MH+556).

9.3.5. N-(2-(1H-Imidazol-4-yl)thiophen-3-yl)-2-(4-methoxyphenyl)acetamide 2-(4-Methoxyphenyl)-N-(2-(1-trityl-1H-imidazol-4-yl)thiophen-3-yl)acetamide (561 mg, 1.01 mmol) in TFA (10 ml) was stirred for 1 h. The solution was concentrated under reduced pressure and the residue was directly purified by HPLC to yield N-(2-(1H-imidazol-4-yl)thiophen-3-yl)-2-(4-methoxyphenyl)acetamide. Method [8] Retention time 3.37 min by HPLC (MH+ 314). $^1$H NMR (300 MHz, DMSO) δ 10.28 (s, 1H), 8.60 (s, 1H), 7.59 (s, 1H), 7.53 (d, J=5.7 Hz, 1H), 7.49 (d, J=5.7 Hz, 1H), 7.23 (d, J=8.4 Hz, 2H), 6.90 (d, J=8.4 Hz, 2H), 3.73 (s, 3H).

9.4. Synthesis of N-(2-(1H-imidazol-4-yl)thiophen-3-yl)-2-(2-oxo-3,4-dihydroquinolin-1(2H)-yl)acetamide (76)

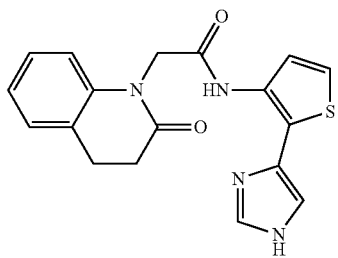 [SMILES: O=C(CN1C(=O)CCc2ccccc21)Nc1ccsc1-c1c[nH]cn1]

9.4.1. 2-(2-Oxo-3,4-dihydroquinolin-1(2H)-yl)-N-(2-(1-trityl-1H-imidazol-4-yl)thiophen-3-yl)acetamide The title compound was prepared from 2-(1-trityl-1H-imidazol-4-yl)thiophen-3-amine and 2-(2-oxo-3,4-dihydroquinolin-1(2H)-yl)acetic acid using protocol B (269 mg, 32%). Method [7] Retention time 9.32 min by HPLC (MH+ 595).

9.4.2. N-(2-(1H-Imidazol-4-yl)thiophen-3-yl)-2-(2-oxo-3,4-dihydroquinolin-1(2H)-yl)acetamide The title compound was prepared from 2-(2-oxo-3,4-dihydroquinolin-1(2H)-yl)-N-(2-(1-trityl-1H-imidazol-4-yl)thiophen-3-yl)acetamide (269 mg, 452 umol) as described in Example 9.3.5. and was purified by HPLC. Method [8] Retention time 3.74 min by HPLC (MH+ 353). $^1$H NMR (300 MHz, DMSO) δ 10.58 (s, 1H), 8.52 (s, 1H), 7.65 (s, 1H), 7.54 (s, 2H), 7.22 (m, 2H), 6.99 (m, 2H), 4.68 (s, 2H), 2.95 (m, 2H), 2.66 (m, 2H).

9.5. Synthesis of 2-(4-methoxyphenyl)-N-(2-(2-methyl-1H-imidazol-4-yl)thiophen-3-yl)acetamide (77)

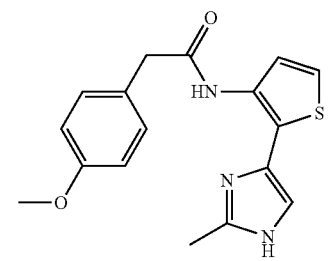 [SMILES: COc1ccc(CC(=O)Nc2ccsc2-c2c[nH]c(C)n2)cc1]

9.5.1. 2-Methyl-4-(tributylstannyl)-1-trityl-1H-imidazole

3 M Ethyl magnesium bromide in THF (6.0 ml, 18.0 mmol) was added dropwise to a solution of 4-iodo-2-methyl-1-trityl-1H-imidazole (5.30 g, 11.8 mmol) in THF (100 ml) at −78° C. After stirring for 2 h, tributyltin chloride (5.0 ml, 18.4 mmol) was added. After stirring for an additional 2 h, the solution was diluted with water and extracted with methylene chloride. The combined organic extracts were dried over magnesium sulfate, filtered and concentrated under reduced pressure to yield 8.49 g of impure 2-methyl-4-(tributylstannyl)-1-trityl-1H-imidazole as a orange liquid. Method [7] Retention time 11.32 min by HPLC (MH+ 615).

9.5.2. 2-Methyl-4-(3-nitrothiophen-2-yl)-1-trityl-1H-imidazole

The title compound was prepared from 2-methyl-4-(tributylstannyl)-1-trityl-1H-imidazole and 2-chloro-3-nitrothiophene using protocol E (3.43 g, 76% over 2 steps). Method [7] Retention time 8.87 min by HPLC (M+Na=474).

9.5.3. 2-(2-Methyl-1-trityl-1H-imidazol-4-yl)thiophen-3-amine

The title compound was prepared from 2-methyl-4-(3-nitrothiophen-2-yl)-1-trityl-1H-imidazole using protocol F (1.33 g, 100% yield). Method [7] Retention time 5.42 min by HPLC (M+Na=444).

9.5.4. 2-(4-Methoxyphenyl)-N-(2-(2-methyl-1-trityl-1H-imidazol-4-yl)thiophen-3-yl)acetamide The title compound was prepared from 2-(2-methyl-1-trityl-1H-imidazol-4-yl)thiophen-3-amine and 2-(4-methoxyphenyl)acetic acid using protocol B (540 mg, 57%). Method [7] Retention time 7.42 min by HPLC (MH+ 570).

9.5.5. 2-(4-Methoxyphenyl)-N-(2-(2-methyl-1H-imidazol-4-yl)thiophen-3-yl)acetamide 2-(4-methoxyphenyl)-N-(2-(2-methyl-1-trityl-1H-imidazol-4-yl)thiophen-3-yl)acetamide (540 mg, 948 mmol) in TFA (10 ml) was stirred for 1 h. The solution was concentrated under reduced pressure and the residue was directly purified by HPLC to yield 2-(4-methoxyphenyl)-N-(2-(2-methyl-1H-imidazol-4-yl)thiophen-3-yl)acetamide. Method [8] Retention time 3.52 min by HPLC (MH+ 328). $^1$H NMR (300 MHz, DMSO) δ 10.02 (s, 1H), 7.60 (d, J=5.4 Hz, 1H), 7.53 (s, 1H), 7.40 (d, J=5.4 Hz, 1H), 7.23 (d, J=8.7 Hz, 2H), 6.89 (d, J=8.9 Hz, 2H), 3.73 (s, 3H).

9.6. Synthesis of N-(2-(2-methyl-1H-imidazol-4-yl)thiophen-3-yl)-2-(2-oxo-3,4-dihydroquinolin-1(2H)-yl)acetamide (78)

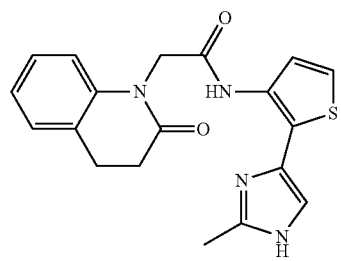 [SMILES: Cc1nc(-c2sccc2NC(=O)CN2C(=O)CCc3ccccc32)c[nH]1]

9.6.1. N-(2-(2-Methyl-1-trityl-1H-imidazol-4-yl) thiophen-3-yl)-2-(2-oxo-3,4-dihydroquinolin-1(2H)-yl)acetamide The title compound was prepared from 2-(2-methyl-1-trityl-1H-imidazol-4-yl)thiophen-3-amine and 2-(2-oxo-3,4-dihydroquinolin-1(2H)-yl)acetic acid using protocol B (125 mg). Method [7] Retention time 7.33 min by HPLC (MH+ 609).

9.6.2. N-(2-(2-Methyl-1H-imidazol-4-yl)thiophen-3-yl)-2-(2-oxo-3,4-dihydroquinolin-1(2H)-yl)acetamide N-(2-(2-methyl-1-trityl-1H-imidazol-4-yl)thiophen-3-yl)-2-(2-oxo-3,4-dihydroquinolin-1(2H)-yl)acetamide (125 mg, 205 mmol) in TFA (5 ml) was stirred for 1 h. The solution was concentrated under reduced pressure and the residue was directly purified by HPLC to yield N-(2-(2-methyl-1H-imidazol-4-yl)thiophen-3-yl)-2-(2-oxo-3,4-dihydroquinolin-1(2H)-yl)acetamide. Method [8] Retention time 4.05 min by HPLC (MH+ 367). $^1$H NMR (300 MHz, DMSO) δ 10.28 (s, 1H), 7.57 (m, 2H), 7.43 (d, J=4.8 Hz, 2H), 7.22 (m, 2H), 6.99 (m, 2H), 4.68 (s, 2H), 2.92 (m, 2H), 2.59 (m, 2H), 2.46 (s, 3H).

9.7. Synthesis of N-(2-(1H-imidazol-1-yl)thiophen-3-yl)2-(naphthalen-1-yl)acetamide (79)

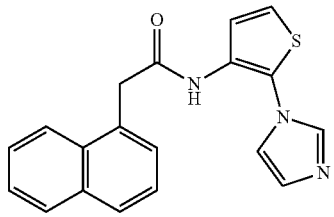 [SMILES: O=C(Cc1cccc2ccccc12)Nc1ccsc1-n1ccnc1]

9.7.1. 1-(3-Nitrothiophen-2-yl)-1H-imidazole

Imidazole (860 mg, 12.63 mmol) was added to a solution of 2-chloro-3-nitro-thiophene (1 g, 6.10 mmol) in abs. ethanol (20 mL). The reaction mixture was heated to reflux in a sealed tube for 3 days and then concentrated under reduced pressure. Purification by flash chromatography (silica, 25:75 ethyl/hexane) gave 1-(3-nitrothiophen-2-yl)-1H-imidazole (540 mg, 45%). See Erker, T. J. et al., *J. Heterocylic. Chem.* 39 (2002) 857-861. Method [3] m/z 195.9 (M+H); retention time=0.615.

9.7.2. 2-(1H-Imidazol-1-yl)thiophen-3-amine

The title compound was prepared from 1-(3-nitrothiophen-2-yl)-1H-imidazole (540 mg, 2376 mmol) using the procedures of Example 1.97.2 (431 mg, 94%) and was used without further purification. Method [4] m/z 166.0 (M+H); retention time=0.227.

9.7.4. N-(2-(1H-Imidazol-1-yl)thiophen-3-yl)-2-(naphthalen-1-yl)acetamide

To a mixture of 1-naphthyl acetic acid and 2-(1H-imidazol-1-yl)thiophen-3-amine in anhydrous CH$_2$Cl$_2$ was added O-(7-azabenzotriazol-1-yl)-N,N,N,N,-tetramethyl uronium hexafluorophosphate and 4-methylmorpholine. A small amount of DMF was added to help starting material reagents go into solution. The reaction mixture was stirred overnight under N$_2$ (g) inlet and evaporated under reduced pressure. The resulting residue was purified by flash column chromatography (silica, 10:90 methanol/methylene chloride) to afford N-(2-(1H-imidazol-1-yl)thiophen-3-yl)2-(naphthalen-1-yl)acetamide (209 mg, 33%). The desired product was purified by preparative HPLC. Method [8] m/z 334.1 (M+H); retention time=4.885. $^1$H-NMR (CD$_3$OD) δ 8.83. (s, 1H), 7.89-7.80 (m, 2H), 7.77 (d, J=7.8 Hz, 1H), 7.51 (d, J=6.3 Hz, 2H), 7.48-7.32 (m, 5H), 7.17 (d, J=6.3 Hz, 2H), 4.08 (s, 2H).

9.8. Synthesis of 2-(4-methoxyphenyl)-N-(2-(4-methyl-1H-imidazol-1-yl)thiophen-3-yl)acetamide (80)

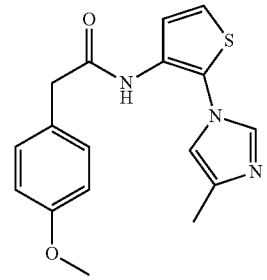 [SMILES: COc1ccc(CC(=O)Nc2ccsc2-n2cnc(C)c2)cc1]

9.8.1. 4-Methyl-1-(3-nitrothiophen-2-yl)-1H-imidazole 4-methyl-1(3-nitrothiophen-2-yl)-1H-imidazole was prepared from 2-chloro-3-nitrothiophene and 4-methyl-1H-imidazole according to the procedure described in Example 9.7.1., above. Purification by flash column chromatography (silica, 40:60 ethyl acetate/hexane) gave the nitro intermediate (1.26 g, 49%). $^1$H-NMR (CDCl$_3$) δ 7.67 (s, 1H), 7.59 (d, J=6.1 Hz, 1H), 7.19 (d, J=6.1 Hz, 1H), 6.89 (s, 1H), 2.27 (s, 3H).

9.8.2. 2-(4-Methyl-1H-imidazol-1-yl)thiophen-3-amine

2(4-methyl-1H-imidazol-1-yl)thiophen-3-amine was prepared from 4-methyl-1-(3-nitrothiophen-2-yl)-1H-imidazole according to the procedure described in Example 9.7.2., above. The amine intermediate (1.52 g, quantitative) was used without further purification. Method [4] m/z 180.1 (M+H); retention time=0.236.

9.8.3. 2-(4-Methoxyphenyl)-N-(2-(4-methyl-1H-imidazol-1-yl)thiophen-3-yl)acetamide 2-(4-methoxyphenyl)-N-(2-(4-methyl-1H-imidazol-1-yl) thiophen-3-yl)acetamide was prepared from 2-(4-methoxyphenyl)acetic acid and 2-(4-methyl-1H-imidazol-1-yl)thiophen-3-amine according to the procedure described in Example 9.7.3., above. Purification by flash column chromatography afforded the final product (silica, 75:25 ethyl acetate/hexane) (77 mg, 6%). Method [7] m/z 328.0 (M+H); retention time=1.001. $^1$H-NMR (CDCl$_3$) δ 8.00 (broad s, 1H), 7.77 (d, J=6.4 Hz, 1H), 7.16 (s, 1H), 7.13 (d, J=8.7 Hz, 2H), 6.85 (d, J=8.7 Hz, 2H), 6.50 (s, 1H), 3.81 (s, 3H), 3.65 (s, 2H), 2.15 (d, J=0.9 Hz, 2H).

Example 10

Thiophene Pyrazine Analogs

10.1. Synthesis of 2-(4-methoxyphenyl)-N-(2-(pyrazin-2-yl)thiophen-3-yl)acetamide (81)

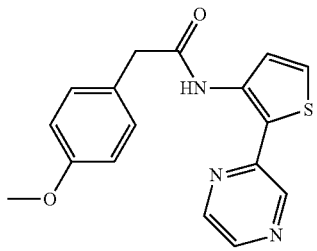 [SMILES: COc1ccc(CC(=O)Nc2ccsc2-c2cnccn2)cc1]

10.1.1. 2-(3-Nitrothiophen-2-yl)pyrazine

The title compound was prepared from 2-(tributylstannyl)pyrazine and 2-chloro-3-nitrothiophene using protocol E and was purified by flash chromatography (hexane:ethyl acetate). Method [7] Retention time 2.38 min by HPLC (MH+ 208).

10.1.2. 2-(Pyrazin-2-yl)thiophen-3-amine

The title compound was prepared from 2-(3-nitrothiophen-2-yl)pyrazine using protocol F. Method [8] Retention time 2.17 min by HPLC (MH+ 178).

10.1.3. 2-(4-Methoxyphenyl)-N-(2-(pyrazin-2-yl)thiophen-3-yl)acetamide

The title compound was prepared from 2-(pyrazin-2-yl)thiophen-3-amine and 2-(4-methoxyphenyl)acetic acid according to protocol B and was purified by HPLC. Method [7] Retention time 5.91 min by HPLC (MH+ 326). $^1$H NMR (300 MHz, DMSO) δ s (11.02, 1H), 8.81 (d, J=0.9 Hz, 1H), 8.45 (d, J=2.7 Hz, 1H), 8.26 (m, 1H), 7.92 (d, J=5.4 Hz, 1H), 7.74 (d, J=5.4 Hz, 1H), 7.33 (d, 8.7 Hz, 2H), 6.99 (d, J=8.7 Hz, 2H), 3.78 (s, 3H), 3.72 (s, 2H).

10.2. Synthesis of N-(4-cyano-3-(pyrazin-2-yl)thiophen-2-yl)-2-(quinolin-5-yl)acetamide

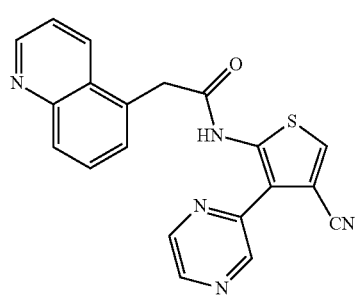 [SMILES: N#Cc1csc(NC(=O)Cc2cccc3ncccc23)c1-c1cnccn1]

10.2.1. 4-Bromo-5-nitrothiophene-3-carbonitrile

The title compound (2.8 g, 71%) was prepared from 4-bromothiophene-3-carbonitrile (2.9 g, 15.5 mmol) according to the procedure described in U.S. Patent Application Publication 20080214528 (p. 25). $R_f$=0.48 (20% EtOAc/hexanes; silica); $^1$H NMR (300 MHz, CDCl$_3$) δ 8.12 (s, 1H).

10.2.2. 5-Nitro-4-(pyrazin-2-yl)thiophene-3-carbonitrile

To a solution of 4-bromo-5-nitrothiophene-3-carbonitrile (312 mg, 1.34 mmol) in dioxane (4 mL) was added tetrakis(triphenylphosphine)palladium(0) (154 mg, 0.133 mmol) and tributylstannylpyrazine (794 mg, 2.15 mmol). This was heated by microwave irradiation to 140° C. for 30 min. The reaction mixture was concentrated under reduced pressure, and the residue purified by flash chromatography to afford the titled compound (166 mg, 53%): $R_f$=0.33 (20% EtOAc/hexanes; silica); HPLC method [4], retention time=1.45 min; MS(ESI) 233.0 (MH+).

10.2.3. 5-Amino-4-(pyrazin-2-yl)thiophene-3-carbonitrile

To 5-nitro-4-(pyrazin-2-yl)thiophene-3-carbonitrile (166 mg, 0.72 mmol) in conc HCl (3 mL) at rt was added tin(II) chloride (327 mg, 1.7 mmol). This was stirred at rt for 2 h, whereupon the reaction mixture was basified with aqueous NaOH and extracted with EtOAc. The combined organic extracts were dried (Na$_2$SO$_4$), filtered and concentrated to give a brown oil (31 mg, 21%). HPLC method [4], retention time=1.458 min; MS(ESI) 203.1 (MH+).

10.2.4. N-(4-Cyano-3-(pyrazin-2-yl)thiophen-2-yl)-2-(quinolin-5-yl)acetamide The title compound was synthesized from 5-amino-4-(pyrazin-2-yl)thiophene-3-carbonitrile (30.5 mg, 0.15 mmol) and 2-(quinolin-5-yl)acetic acid hydrochloride (36 mg, 0.16 mmol) according to protocol A. The product was purified by HPLC method [4], retention time=1.393 min; MS(ESI) 372.1 (MH+); $^1$H NMR (300 MHz, CD$_3$OD) δ 9.30 (d, J=1.5 Hz, 1H), 9.06 (dd, J=4.8, 1.3 Hz, 1H), 8.99 (d, J=8.5 Hz, 1H), 8.51 (d, J=2.6 Hz, 1H), 8.29 (t, J=1.9 Hz, 1H), 8.20 (d, J=8.6 Hz, 1H), 8.09 (dd, J=8.6, 7.1 Hz, 1H), 7.95 (s, 1H), 7.93 (d, J=6.7 Hz, 1H), 7.86 (dd, J=8.6, 4.9 Hz, 1H), 4.55 (s, 2H).

Example 11

Synthesis of 2-(isoquinolin-5-yl)-N-(4-(pyrazin-2-yl)thiazol-5-yl)acetamide (82)

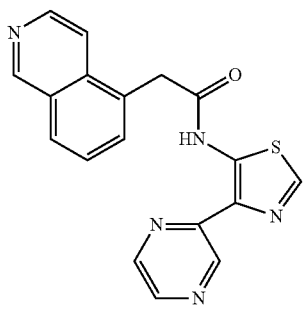 [SMILES: O=C(Cc1cccc2cnccc12)Nc1scnc1-c1cnccn1]

11.1. tert-Butyl 4-bromothiazol-5-ylcarbamate

To a solution of tert-butyl thiazol-5-ylcarbamate (WO 2007/071955) (607 mg, 3.0 mmol) in chloroform (50 mL) was added N-bromosuccinimide (542 mg, 3.04 mmol) at 0° C. After 1 h, reaction was quenched by addition of saturated NaHCO$_3$ solution (50 mL). The layers were separated, and the mixture extracted with CHCl$_3$ (3×50 mL). The combined organic extracts were dried (MgSO$_4$), filtered and concentrated. $^1$H NMR (CDCl$_3$) δ 8.37 (d, J=0.6 Hz, 1H), 7.05 (br s, 1H), 1.55 (s, 9H); MH+ 278.9.

11.2. tert-Butyl 4-(pyrazin-2-yl)thiazol-5-ylcarbamate

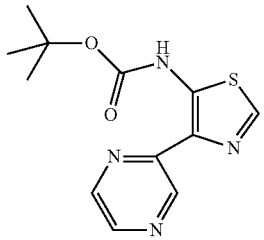 [SMILES: CC(C)(C)OC(=O)Nc1scnc1-c1cnccn1]

A mixture of tert-butyl 4-bromothiazol-5-ylcarbamate (420 mg, 1.5 mmol), tetrakis(triphenylphosphine)palladium (0) (170 mg, 0.15 mmol) and 2-tributylstannylpyrazine (930 mg, 2.5 mmol) in anhydrous dioxane (4 mL) was heated to 140° C. in a microwave reactor for 2 h. The reaction mixture was then concentrated in vacuo and purified by flash chromatography (EtOAc/hexanes) to give the desired product (260 mg, 62%). $^1$H NMR (CDCl$_3$) δ 11.10 (s, 1H), 9.47 (d, J=1.4 Hz, 1H), 8.52 (t, J=2.0 Hz, 1H), 8.45 (d, J=2.7 Hz, 1H), 8.40 (s, 1H), 1.58 (s, 9H); MH+ 279.0.

11.3. 2-(Isoquinolin-5-yl)-N-(4-(pyrazin-2-yl)thiazol-5-yl)acetamide

To a solution of tert-butyl 4-(pyrazin-2-yl)thiazol-5-ylcarbamate (260 mg, 0.94 mmol) in CH$_2$Cl$_2$ (1 mL) at 0° C. was added trifluoroacetic acid (1 mL) and the mixture was allowed to warm to rt over 1 h. The solvent was removed in vacuo and the crude product was used without further purification.

The crude 4-(pyrazin-2-yl)thiazol-5-amine was coupled with 2-(isoquinolin-5-yl)acetic acid hydrochloride using procedure A and was purified by HPLC purified to afford desired material as a white trifluoroacetic acid salt (107 mg). Method [8]: rt=3.71 min; $^1$H NMR (CDCl$_3$) δ 12.16 (s, 1H), 9.80 (s, 1H), 9.48 (d, J=1.2 Hz, 1H), 8.64 (d, J=6.4 Hz, 1H), 8.47 (s, 1H), 8.45 (d, J=2.7 Hz, 1H), 8.39 (d, J=8.5 Hz, 1H), 8.31 (d, J=6.5 Hz, 1H), 8.15 (d, J=7.2 Hz, 1H), 8.10-7.98 (m, 2H), 4.45 (s, 2H); MH+ 348.0.

Example 12

Synthesis of N-(4,4'-bithiazol-5-yl)-2-(isoquinolin-5-yl)acetamide (83)

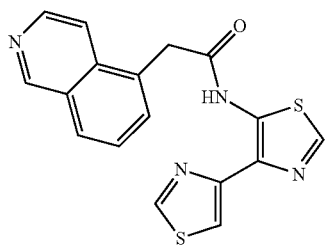 [SMILES: O=C(Cc1cccc2cnccc12)Nc1scnc1-c1cscn1]

12.1. tert-Butyl 4,4'-bithiazol-5-ylcarbamate

A mixture of tert-butyl 4-bromothiazol-5-ylcarbamate (590 mg, 2.1 mmol), tetrakis(triphenylphosphine)palladium (0) (240 mg, 0.21 mmol) and 4-tributylstannylthiazole (1.18 g, 3.2 mmol) in anhydrous dioxane (5 mL) was heated to 140° C. in a microwave reactor for 1 h. The reaction mixture was then concentrated in vacuo and purified by flash chromatography (EtOAc/hexanes elution) to give the desired product (420 mg, 71%). MH+ 283.9.

12.2. N-(4,4'-Bithiazol-5-yl)-2-(isoquinolin-5-yl)acetamide

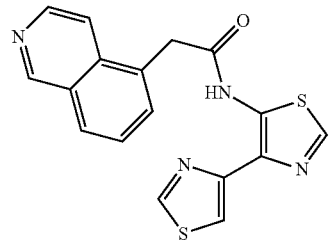 [SMILES: O=C(Cc1cccc2cnccc12)Nc1scnc1-c1cscn1]

Conversion of tert-Butyl 4,4'-bithiazol-5-ylcarbamate to the above titled compound was performed according to the procedure detailed for the synthesis of 2-(isoquinolin-5-yl)-N-(4-(pyrazin-2-yl)thiazol-5-yl)acetamide. Method [4]: rt=1.22 min; $^1$H NMR (d$_4$-MeOD) δ 9.73 (s, 1H), 8.79 (d, J=2.0 Hz, 1H), 8.63-8.45 (m, 4H), 8.30 (d, J=7.1 Hz, 1H), 8.09 (t, J=7.8 Hz, 1H), 7.86 (d, J=2.0 Hz, 1H), 4.58 (s, 2H); MH+ 353.1.

Example 13

Synthesis of 2-(4-methoxyphenyl)-N-(2-(2-oxooxazolidin-3-yl)thiophen-3-yl)acetamide (84)

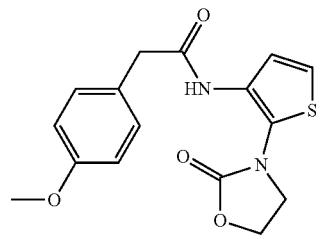 [SMILES: COc1ccc(CC(=O)Nc2ccsc2N2CCOC2=O)cc1]

13.1. 3-(3-Nitrothiophen-2-yl)oxazolidin-2-one

Potassium tert-butoxide (1.86 g, 16.6 mmol) and oxazolidin-2-one (1.90 g, 21.8 mmol) in DMF (50 ml) was stirred for 30 min. 2-chloro-3-nitrothiophene (1.64 g, 10.0 mmol) was added and after 1 h, the solution was placed into a preheated oil bath at 100° C. After stirring for 1 h, the solution was diluted with brine and extracted with diethyl ether. The combined organic extracts were dried over magnesium sulfate, filtered and concentrated under reduced pressure. The residue was flash chromatographed with 9:1, 4:1, 7:3, 3:2, and 1:1 hexane:ethyl acetate as the eluant to yield impure 3-(3-nitrothiophen-2-yl)oxazolidin-2-one. Method [3] Retention time 2.50 min by HPLC (MH+ 215) and (M+Na=237).

13.2. 3-(3-Aminothiophen-2-yl)oxazolidin-2-one

The title compound was prepared from 3-(3-nitrothiophen-2-yl)oxazolidin-2-one according to the procedures of Example 1.97.2. Method [7] Retention time 0.85 min by HPLC (MH+ 185).

13.3. 2-(4-Methoxyphenyl)-N-(2-(2-oxooxazolidin-3-yl)thiophen-3-yl)acetamide The title compound was prepared from 3-(3-aminothiophen-2-yl)oxazolidin-2-one and 2-(4-methoxyphenyl)acetic acid (510 mg, 3.06 mmol) using protocol B. The crude product was purified by HPLC. Method [7] Retention time 2.95 min by HPLC (MH+ 333). $^1$H NMR (300 MHz, CDCl$_3$) δ 8.14 (broad s, 1H), 7.39 (d, J=5.7 Hz, 1H), 7.27 (d, J=9.0 Hz, 2H), 7.06 (d, J=5.7 Hz, 1H), 6.92 (d, J=9.0 Hz, 2H), 4.47 (m, 2H), 3.89 (m, 2H), 3.83 (s, 3H), 3.64 (s, 2H).

Example 14

Determination of Kinase Activities
Abbreviations
DTT: DL-dithiothreitol; DMSO: dimethyl sulfoxide; BSA: bovine serum albumin; ATP: adenosine triphosphate; MAPK: mitogen-activated protein kinase; EDTA: ethylenediaminetetraacetic acid; HEPES: (4-(2-hydroxyethyl)-1-piperazineethanesulfonic acid).
Materials
EPIW-1
Biotin-Jun-Jun 50mer (BIOTIN-LC-Asn-Pro-Lys-Ile-Leu-Lys-Gln-Ser-Met-Thr-Leu-Asn-Leu-Ala-Asp-Pro-Val-Gly-Ser-Leu-Lys-Pro-His-Leu-Arg-Ala-Lys-Asn-Ser-Asp-Leu-Leu-Thr-Ser-Pro-Asp-Val-Gly-Leu-Leu-Lys-Leu-Ala-Ser-Pro-Glu-Arg-Glu-Arg-Leu-OH)
EPIG-1
Biotin-ELK-1 45mer (BIOTIN-LC-Pro-Gln-Lys-Gly-Arg-Lys-Pro-Arg-Asp-Leu-Glu-Leu-Pro-Leu-Ser-Pro-Ser-Leu-Leu-Gly-Gly-Pro-Gly-Pro-glu-Thr-Leu-Ser-Pro-Ile-Ala-Pro-Arg-Ser-Pro-Ala-Lys-Leu-Ser-Phe-Gln-Phe-Pro-Ser-Ser- OH)
EPIG-2
Biotin-ATF-2 35mer (BIOTIN-LC-Leu-Ala-Val-His-Lys-His-Lys-His-Glu-Met-Thr-Leu-Lys-Phe-Gly-Pro-Ala-Arg-Asn-Asp-Ser-Val-Ile-Val-Ala-Asp-Gln-Thr-Pro-Thr-Pro-Thr-Arg-Phe-Leu-OH)
aP38δ (Upstate Biotech); aP38δ (Cell Signaling Technology); SA-XL (High grade XL665-conjugated streptavidin SA-Xlent, CIS Bio International); Eu-ELK-1-Ab (Phospho-ELK-1 antibody from Cell Signaling Technology labeled by Perkin Elmer with Lance Eu W1024); Eu-ATF-2-Ab (Phospho-ATF-2 antibody from Cell Signaling Technology labeled by Perkin Elmer with Lance Eu W1024); Eu-Ser-63-Ab (Phospho-c-Jun (Ser63) II antibody from Cell Signaling Technology labeled by Perkin Elmer with Lance Eu W1024); Eu-Ser-73-Ab (Phospho-c-Jun (Ser73) II antibody from Cell Signaling Technology labeled by Perkin Elmer with Lance Eu W1024); Eu-ELK-1-Ab (Phospho-ELK-1 antibody from Cell Signaling Technology labeled by Perkin Elmer with Lance Eu W1024); aJNK1/SAPK1c, aJNK2/SAPK1a, aJNK3/SAPK1b, uJNK1/SAPK1c, uJNK2/SAPK1a, uJNK3/SAPK1b, MKK4/SKK1 active, MKK7b1 active, uMAPK2/Erk2, MEK1 (active), up38α/SAPK2α and MKK6/SKK3 (active) from Upstate Cell Signaling Solutions; K252a (A.G. Scientific); 506126 (Calbiochem).
Reagents
Reagents were prepared and stored as specified below.
JNK Buffer Stock Solution:
27 mM HEPES (free acid), 1 mM MgCl$_2$, pH 7.0, prepared by media kitchen and stored at 4° C.
JNK Detection Buffer
50 mM HEPES, 0.1% BSA, 400 mM NaCl, stored at 4° C.
0.5 M EDTA
0.5 M EDTA in DI water, stored at RT.
1 mM ATP
275.6 mg of ATP (MW 551.2) were dissolved in 500 mL DI H$_2$O and stored at −20° C.

14.1. Active MAPK TR-FRET Assay

Procedure
(1) Assay buffer #1 was prepared (JNK buffer stock solution, 0.0025% Tween, 1 mM DTT).
(2) Assay buffer #2 was prepared (assay buffer #1, 0.025% BSA).
(3) Test compound solution preparation: 5× compound solution was prepared using assay buffer #1 with 5% DMSO. The compound solution (10 µl/well) was added to a 384-well plate.
(4) aMAPK preparation: aMAPK stock (100 ug/ml) was thawed from −80° C. on ice, and aMAPK (10 ng/20 µl=0.5 ng/µl) solution using assay buffer #2 was prepared. The aMAPK solution (20 µl/well) was added to the plate. The plate was shaken and the enzyme was incubated with the compound at RT for 10 min.
(5) ATP/substrate solution preparation: ATP and substrate stocks were thawed on ice. 2.5×ATP/substrate (75 µM ATP/50 nM ELK-1) was prepared using assay buffer #1. The ATP/substrate (20 µl/well) was added to the plate. The plate was shaken and incubated at 30° C. for 1 hr.
(6) EDTA preparation: 30 mM EDTA was prepared using 0.5M EDTA stock and assay buffer #1. The EDTA (10 µl/well) was added to the plate to quench the enzyme reaction, and the plate was shaken well.
(7) Detection reagent preparation: Eu-ELK-1-Ab and SA-XL stocks were thawed on ice. 4× Eu-Anti-ELK-1/SA-XL (2 nM Eu-Anti-ELK-1/9.4 nM SA-XL) using JNK detection buffer was prepared. The 4× Eu-Anti-ELK-1/SA-XL solution (20 µl/well) was added to the plate. The plate was shaken and incubated at RT for 1 hr before reading the plate on LJL using ratiometric method named HTRF.

14.2. Active p38 TR-FRET Assay

Procedures
(1) Assay buffer #1 with 0.0025% Tween and 1 mM DTT was prepared using JNK buffer stock solution.
(2) Assay buffer #2 with 0.025% BSA was prepared using the assay buffer #1.
(3) Test compound solution preparation: 5× compound solution was prepared using assay buffer #1 with 5% DMSO. The compound solution (10 µl/well) was added to a 384-well plate (Corning, Cat No. 3654).
(4) aP38 preparation: aP38 stock (100 ug/ml) at −80° C. was thawed on ice and a P38 (30 ng/20 µl=1.5 ng/µl) solution using assay buffer #2 was prepared. The P38 solution (20 µl/well) was added to the plate. The plate was shaken and the enzyme was incubated with compound at RT for 10 min.
(5) ATP/substrate solution preparation: ATP and substrate stocks were thawed on ice. 2.5×ATP/substrate (75 µM ATP/50 nM ATF-2) was prepared using assay buffer #1. The ATP/substrate (20 µl/well) was added to the plate, the plate was shaken, and the plate was incubate at 30° C. for 1 hr.
(6) EDTA preparation: 30 mM EDTA was prepared using 0.5M EDTA stock and assay buffer #1. The EDTA (10 µl/well) was added to the plate to quench the enzyme reaction and the plate was shaken well.
(7) Detection reagent preparation: Eu-Anti-ATF-2 and SA-XL stocks were thawed on ice. 4× Eu-Anti-ATF-2/SA-XL (2 nM Eu-Anti-ATF-2/9.4 nM SA-XL) was prepared using JNK detection buffer. The Eu-Anti-ATF-2/SA-XL solution (20 µl/well) was added to the plate. The plate was shaken and incubated at RT for 1 hr before reading the plate on LJL using ratiometric method named HTRF.

14.3. Active JNK 1, 2 and 3 TR-FRET Assay

Procedures
(1) Assay buffer #1 with 0.0025% Tween and 1 mM DTT was prepared using JNK buffer stock solution.
(2) Assay buffer #2 with 0.025% BSA was prepared using the assay buffer #1.
(3) Test compound solution preparation: 5× compound solution was prepared using assay buffer #1 with 5% DMSO. The compound solution (10 µl/well) was added to a 384-well plate (Corning, Cat No. 3654).
(4) aJNK1, 2 or 3 preparation: aJNK stock (100 µg/ml) at −80° C. was thawed on ice and an aJNK (1.6 ng/ml) solution was prepared using assay buffer #2. The aJNK solution (20 µl/well) was added to the plate and the plate was shaken. The enzyme was incubated with the compound at RT for 10 min.
(5) ATP/substrate solution preparation: ATP and substrate stocks were thawed on ice. 2.5×ATP/substrate (e.g., 25 µM or 2.5 mM ATP/50 nM EPIW-1) was prepared using assay buffer #1. The ATP/substrate (20 µl/well) was added to the plate and the plate was shaken. The plate was incubated at RT for 15 min. Note: In an exemplary assay, the final ATP concentration was about 1 mM.
(6) EDTA preparation: 30 mM EDTA was prepared using 0.5M EDTA stock and assay buffer #1. The EDTA (10 µl/well) was added to the plate to quench the enzyme reaction and the plate was shaken well.
(7) Detection reagent preparation: Eu-63 and SA-XL stocks were thawed on ice. 4× Eu-63/SA-XL (2 nM Eu-63/9.4 nM SA-XL) was prepared using JNK detection buffer. The Eu-63/SA-XL solution (20 µl/well) was added to the plate and the plate was shaken. The plate was incubated at RT for 1 hr before reading the plate on LJL using ratiometric method named HTRF.

14.4. Coupled JNK 1, 2 and 3 TR-FRET Assay

Procedures
(1) Assay buffer with 0.0025% Tween, 0.01% BSA, and 1 mM DTT was prepared using JNK buffer stock solution.
(2) Test compound solution preparation: 5× compound solution, including EDTA background, was prepared using assay buffer with 5% DMSO. The compound solution (10 µl/well) was added to a 384-well plate (Corning, Cat No. 3654).
(3) uJNK1,2, or 3 activation reaction preparation: uJNK activation solution was prepared using assay buffer (1.6 ng/ml MKK4, 1.6 ng/ml MKK7, 16 ng/ml uJNK, and 20 uM ATP final). The uJNK activation solution (35 µl/well) was added to the plate, the plate was shaken, and the reaction mixture was incubated with compound at 30° C. for 60 min.
(4) c-Jun substrate solution preparation: 50 nM EPIW-1, c-Jun peptide, was prepared using assay buffer (15 nM final). The EPIW-1 solution (15 µl/well) was added to the plate, the plate was shaken and incubated at 30° C. for 60 min.
(5) EDTA preparation: 30 mM EDTA was prepared using 0.5M EDTA stock and assay buffer. The EDTA (10 µl/well) was added to the plate to quench the enzyme reaction and the plate was shaken well.
(6) Detection reagent preparation: Eu-73 and SA-XL stocks were thawed on ice. 4× Eu-73/SA-XL (2 nM Eu-73/9.4 nM SA-XL) were prepared using JNK detection buffer. The Eu-73/SA-XL solution (20 µl/well) was added to the plate. The plate was shaken and incubated at RT for 1 hr before reading the plate on LJL using ratiometric method named HTRF.

14.5. Coupled MAPK2/Erk2 TR-FRET Assay

Procedures
(1) Assay buffer with 0.0025% Tween, 0.01% BSA, and 1 mM DTT was prepared using JNK buffer stock solution.
(2) Test compound solution preparation: 5× compound solution, including EDTA background, was prepared using assay buffer with 5% DMSO. The compound solution (10 µl/well) was added to a 384-well plate (Corning, Cat No. 3654).
(3) uMAPK/Erk2 activation reaction preparation: uMAPK activation solution was prepared using assay buffer (16 ng/ml MEK1, 160 ng/ml uMAPK2/Erk2, and 60 uM ATP final). The uMAPK activation solution (35 µl/well) was added to the plate. The plate was shaken and the reaction mixture was incubated with compound at 30° C. for 60 min.
(4) ELK-1 substrate solution preparation: 50 nM ELK-1 peptide was prepared using assay buffer (15 nM final). The ELK-1 peptide solution (15 µl/well) was added to the plate. The plate was shaken and incubated at 30° C. for 60 min.
(5) EDTA preparation: 30 mM EDTA was prepared using 0.5M EDTA stock and assay buffer. The EDTA (10 µl/well) was added to the plate to quench the enzyme reaction and the plate was shaken well.
(6) Detection reagent preparation: Eu-ELK-1-Ab and SA-XL stocks were thawed on ice. 4× Eu-Anti-ELK-1/SA-XL (2 nM Eu-Anti-ELK-1/9.4 nM SA-XL) was prepared using JNK detection buffer. The Eu-Anti-ELK-1/SA-XL solution (20 µl/well) was added to the plate. The plate was shaken and incubated at RT for 60 min. before reading the plate on LJL using ratiometric method named HTRF.

14.6. Coupled p38α/SAPK2α TR-FRET Assay

Procedures
(1) Assay buffer with 0.0025% Tween, 0.01% BSA, and 1 mM DTT was prepared using JNK buffer stock solution.
(2) Test compound solution preparation: 5× compound solution, including EDTA background, was prepared using assay buffer with 5% DMSO. The compound solution (10 µl/well) was added to a 384-well plate (Corning, Cat No. 3654).
(3) up38α/SAPK2α activation reaction preparation: up38a activation solution was prepared using assay buffer (48 ng/ml MKK6, 480 ng/ml up38a and 60 uM ATP final). The up38a activation solution (35 µl/well) was added to the plate. The plate was shaken and the reaction mixture was incubated with compound at 30° C. for 60 min.
(4) ATF-2 substrate solution preparation: 50 nM ATF-2 peptide was prepared using assay buffer (15 nM final). The ATF-2 peptide solution (15 µl/well) was added to the plate, the plate was shaken, and the plate was incubate at 30° C. for 60 min.

(5) EDTA preparation: 30 mM EDTA was prepared using 0.5M EDTA stock and assay buffer. The EDTA (10 μl/well) was added to the plate to quench the enzyme reaction and the plate was shaken well.

(6) Detection reagent preparation: Eu-Anti-ATF-2 and SA-XL stocks were thawed on ice. 4× Eu-Anti-ATF-2/SA-XL (2 nM Eu-Anti-ATF-2/9.4 nM SA-XL) was prepared using JNK detection buffer. The Eu-Anti-ATF-2/SA-XL solution (20 μl/well) was added to the plate. The plate was shaken and incubated at RT for 1 hr before reading the plate on LJL using ratiometric method named HTRF.

Example 15

Inhibition of Kainic Acid Induced Phospho-cJun Upregulation in Mice Hippocampi

Excitotoxic cell death can be induced experimentally by the administration of kainic acid, a potent agonist of the kainate class of glutamate receptors. Peripheral injection of kainic acid results in recurrent seizures and degeneration of select populations of neurons in the hippocampus. Activation of jnk is observed after kainic acid treatment in vivo (see, e.g., Jeon S. H. et al., *Experimental and Molecular Medicine* 2000, 32(4): 227-230 and Kim Y.-H. et al., *Molecules and Cells* 2001, 11(2): 144-150). Mice lacking the Jnk3 gene are resistant to kainic acid induced upregulation of phosphorylated c-jun (p-cjun) and hippocampal neuronal apotosis (see e.g., Yang D. D. et al., *Nature* 1997, 389: 865-870). Phosphorylated c-jun in wildtype mice is upregulated after kainic acid administration and have demonstrated that this upregulation is inhibited by certain compounds of the present disclosure.

Methods

Female, FVB/N mice (Taconic) were treated by oral gavage (PO) with one 300 mg/kg dose of N-(4-chloro-3-(1H-1,2,4-triazol-5-yl)thiophen-2-yl)-2-(isoquinolin-5-yl) acetamide or vehicle (0.9% saline) at a 5 ml/kg dose volume. Control animals were dosed with vehicle. Thirty minutes later animals were treated interperitoneally with 25 mg/kg of kainic acid or saline at a 10 ml/kg dose volume. Kainic acid was formulated in 0.9% saline. Four hours after kainic acid administration animals were euthanized by carbon dioxide and were transcardially perfused with 0.9% saline. Brains were removed, and separated into left and right hemispheres. The hippocampus was dissected from the right hemisphere, frozen on dry ice and kept at −80° C. until used for quantitation of p-cjun levels.

Preweighed hippocampus tissues were homogenized in cold cell extraction buffer (CEB) containing 1% Triton X-100, 0.1% SDS, 0.5% deoxycholate, 20 mM $Na_4P_2O_7$, 2 mM $Na_3VO_4$, 0.1% SDS and protease inhibitors (PI, 2 mg/mL aprotinin and 1 mg/mL leupeptin) at a ratio of 9:1 CEB to wet tissue weight. Homogenized samples were analyzed using PathScan Phospho-c-Jun (Ser63) Sandwich ELISA Kit II from Cell Signaling Technology. Samples were diluted 1:10 in sample diluent provided in the kit. An 8-point standard curve was prepared by diluting a 10 ng/mL phos-c-Jun standard 1:3 in 10% CEB/PI in sample diluent. Samples and standards were added at 100 μL per well to prewetted ELISA plates which contain a phos-c-jun (ser63)-specific rabbit monoclonal capture antibody and incubated overnight at 4° C. The plate was then allowed to warm to room temperature and washed three times using TBS+ 0.05% Tween 20 (TTBS). To each well were added 100 μL of a mouse monoclonal c-Jun detection antibody and the plate was incubated at 37° C. for 1 hour. The plate was washed three times in TTBS, then 100 μL per well of an anti-mouse IgG HRP-linked antibody was added. The plate was incubated at 37° C. for 30 minutes and was then washed three times in TTBS. To each well were added 100 μL of TMB substrate and the plate was incubated for 10 minutes at 37° C. Then stop solution was added. The colorimetric reaction was read using a Molecular Devices Spectramax plate reader and sample data was calculated from the standard curve fit to a 4-parameter function.

Results

Treatment with 300 mg/kg of N-(4-chloro-3-(1H-1,2,4-triazol-5-yl)thiophen-2-yl)-2-(isoquinolin-5-yl)acetamide resulted in a statistically significant (unpaired t-test) 51% reduction of p-cjun in the hippocampus of FVB mice 4 hours after treatment with kainic acid. The results are summarized in Table 2, below.

TABLE 2

N-(4-chloro-3-(1H-1,2,4-triazol-5-yl)thiophen-2-yl)-2-(isoquinolin-5-yl)acetamide Inhibits Kainic Acid Induced Phospho-cJun Upregulation in Mice

| Group | p-cJun Mean (ng/ml) | % of SD | Vehicle | p-Value |
|---|---|---|---|---|
| Control | 0.297 | 0.03 | | |
| Kainic Acid | 1.886 | 1.18 | | |
| KainicAcid + N-(4-chloro-3-(1H-1,2,4-triazol-5-yl)thiophen-2-yl)-2-(isoquinolin-5-yl)acetamide | 0.927 | 0.43 | 49.2 | 0.0025 |

What is claimed is:

1. A compound having a structure according to Formula (I):

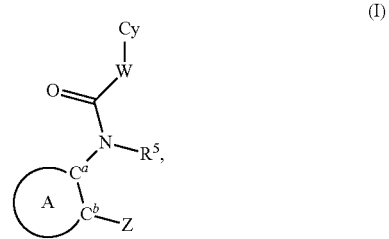

or a salt or solvate thereof,
wherein
ring A is 5-membered heteroaryl comprising a sulfur atom, wherein the heteroaryl is optionally substituted with 1 or 2 substituents independently chosen from alkyl, alkenyl, alkynyl, haloalkyl, heteroalkyl, $C_3$-$C_{10}$-cycloalkyl, 3- to 8-membered heterocycloalkyl, aryl, 5- or 6-membered heteroaryl, CN, halogen, $OR^{12}$, $SR^{12}$, $NR^{12}R^{13}$, $C(O)R^{14}$, $C(O)NR^{12}R^{13}$, $OC(O)NR^{12}R^{13}$, $C(O)OR^{12}$, $NR^{15}C(O)R^{14}$, $NR^{15}C(O)OR^{12}$, $NR^{15}C(O)NR^{12}R^{13}$, $NR^{15}C(S)NR^{12}R^{13}$, $NR^{15}S(O)_2R^{14}$, $S(O)_2NR^{12}R^{13}$, $S(O)R^{14}$ and $S(O)_2R^{14}$,
wherein
$R^{12}$, $R^{13}$ and $R^{15}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, or $R^{12}$ and $R^{13}$, together with the nitrogen atom to which they are bound form a 5- to 7-membered heterocyclic ring; and $R^{14}$ is chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl;

$C^a$ and $C^b$ are carbon atoms, which are adjacent to each other and are part of ring A;

Z is triazole optionally substituted with alkyl, cycloalkyl, alkenyl, alkynyl, heteroalkyl, heterocycloalkyl, aryl, heteroaryl, —$R^a$, —$OR^a$, —$SR^a$, =O, =$NR^a$, =N—$OR^a$, —$NR^aR^b$, -halogen, —$SiR^aR^bR^c$, —OC(O)$R^a$, —C(O)$R^c$, —C(O)$OR^a$, —C(O)$NR^aR^b$, —OC(O)$NR^aR^b$, —$NR^cC(O)R^e$, —$NR^cC(O)NR^aR^b$, —$NR^cC(S)NR^aR^b$, —$NR^cC(O)OR^a$, —$NR^cC(NR^aR^b)$=$NR^d$, —S(O)$R^e$, —S(O)$_2R^e$, —S(O)$_2NR^aR^b$, —$NR^cS(O)_2R^a$, —CN, —$NO_2$, —$N_3$, —CH(Ph)$_2$, fluoro($C_1$-$C_4$)alkoxy, and halo($C_1$-$C_4$)alkyl, $OR^{17}$, $SR^{17}$, and $NR^{17}R^{18}$, wherein $R^a$, $R^b$, $R^c$, $R^d$ and $R^e$ each independently hydrogen, $C_1$-$C_{24}$ alkyl, $C_3$-$C_{10}$ cycloalkyl, $C_1$-$C_{24}$ heteroalkyl, $C_3$-$C_{10}$ heterocycloalkyl, aryl, heteroaryl, arylalkyl and heteroarylalkyl; and wherein where two R groups are attached to the same nitrogen atom, they can be combined with the nitrogen atom to form a 5-, 6-, or 7-membered ring;

$R^{17}$ and $R^{18}$ are independently chosen from H, acyl, $C_1$-$C_6$ alkyl, 2- to 6-membered heteroalkyl, aryl, 5- or 6-membered heteroaryl, $C_3$-$C_8$ cycloalkyl, and 3- to 8-membered heterocycloalkyl, or $R^{17}$ and $R^{18}$, together with the nitrogen atom to which they are bound are optionally joined to form a 5- to 7-membered heterocyclic ring;

$R^5$ is chosen from H, acyl, substituted or unsubstituted $C_1$-$C_6$ alkyl, and $C_3$-$C_6$ cycloalkyl;

W is chosen from $C_1$-$C_4$ alkylene, wherein the alkylene is optionally substituted with 1-4 substituents independently chosen from alkyl, alkenyl, alkynyl, haloalkyl, heteroalkyl, $C_3$-$C_6$-cycloalkyl, 3- to 8-membered heterocycloalkyl, aryl, 5- or 6-membered heteroaryl, CN, halogen, $OR^{42}$, $SR^{42}$, $NR^{42}R^{43}$, $C(O)R^{44}$, $C(O)NR^{42}R^{43}$, $OC(O)NR^{42}R^{43}$, $C(O)OR^{42}$, $NR^{45}C(O)R^{44}$, $NR^{45}C(O)OR^{42}$, $NR^{45}C(O)NR^{42}R^{43}$, $NR^{45}C(S)NR^{42}R^{43}$, $NR^{45}S(O)_2R^{44}$, $S(O)_2NR^{42}R^{43}$, $S(O)R^{44}$, and $S(O)_2R^{44}$, wherein $R^{42}$, $R^{43}$ and $R^{45}$ are members independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{42}$ and $R^{43}$, together with the nitrogen atom to which they are bound are optionally joined to form a 5- to 7-membered heterocyclic ring; and $R^{44}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl;

Cy is chosen from cycloalkyl, heterocycloalkyl, aryl, and heteroaryl, wherein the cycloalkyl, heterocycloalkyl, aryl or heteroaryl is optionally substituted with 1-6 substituents independently chosen from substituted or unsubstituted alkyl, substituted or unsubstituted alkenyl, substituted or unsubstituted alkynyl, haloalkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, CN, halogen, $OR^{52}$, $SR^{52}$, =O, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$, wherein $R^{52}$, $R^{53}$ and $R^{55}$ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein $R^{52}$ and $R^{53}$, together with the nitrogen atom to which they are bound are optionally joined to form a 5- to 7-membered heterocyclic ring; and $R^{54}$ is independently chosen from acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl;

wherein the aryl groups are chosen from 5-, 6- or 7-membered, aromatic carbocyclic group having a single ring or being fused to other aromatic or non-aromatic rings; and wherein the heteroaryl groups are chosen from polyunsaturated, 5-, 6- or 7-membered aromatic moiety containing at least one heteroatom chosen from N, O, S, Si and B, wherein the nitrogen and sulphur atoms are optionally oxidized, and the nitrogen atom(s) are optionally quarternized, and wherein the heteroaryl groups can be a single ring or be fused to other aryl, heteroaryl, cycloalkyl or heterocycloalkyl rings.

2. The compound of claim 1, wherein the compound has a structure according to Formula (IV), Formula (V), Formula (VI) or Formula (VII):

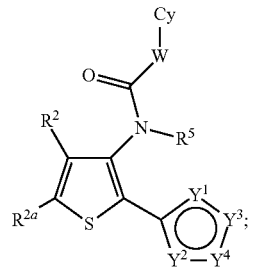

(IV)

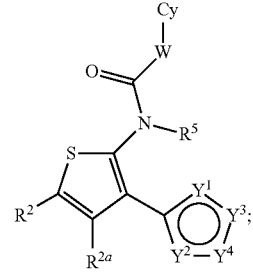

(V)

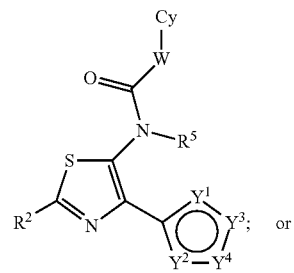

(VI)

or (VII)

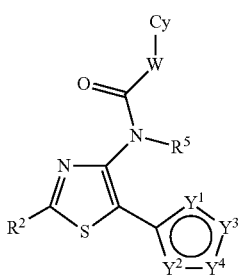

or a salt or solvate thereof,
wherein
R² and R²ᵃ are independently chosen from H, $C_1$-$C_4$-alkyl, $C_2$-$C_4$-alkenyl, $C_2$-$C_4$-alkynyl, $C_1$-$C_4$-haloalkyl, 2- to 4-membered heteroalkyl, $C_3$-$C_6$-cycloalkyl, 3- to 6-membered heterocycloalkyl, CN, and halogen;
wherein the moiety

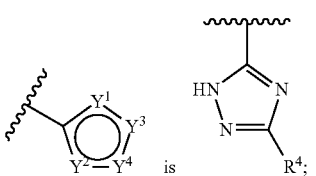

wherein R⁴ is chosen from H, $C_1$-$C_4$ alkyl, $C_2$-$C_4$-alkenyl, $C_2$-$C_4$-alkynyl, $C_1$-$C_4$ haloalkyl, $C_3$-$C_6$ cycloalkyl, 3- to 6-membered heterocycloalkyl, aryl, 5- or 6-membered heteroaryl, CN, halogen, OR¹⁷, SR¹⁷ and NR¹⁷R¹⁸,
wherein
R¹⁷ and R¹⁸ are independently chosen from H, acyl, $C_1$-$C_6$-alkyl, 2- to 6-membered heteroalkyl, aryl, 5- or 6-membered heteroaryl, $C_3$-$C_8$ cycloalkyl and 3- to 8-membered heterocycloalkyl, wherein R¹⁷ and R¹⁸, together with the nitrogen atom to which they are bound are optionally joined to form a 5- to 7-membered heterocyclic ring.

3. The compound of claim 1, wherein ring A is chosen from thiophene and thiazole, wherein the thiophene or the thiazole is optionally substituted with 1 or 2 substituents chosen from $C_1$-$C_4$-alkyl, $C_2$-$C_4$-alkenyl, $C_2$-$C_4$-alkynyl $C_1$-$C_4$-haloalkyl, 2- to 4-membered heteroalkyl, $C_3$-$C_6$-cycloalkyl, 3- to 6-membered heterocycloalkyl, CN, and halogen.

4. The compound of claim 2, wherein the compound has a structure according to Formula (IVa), Formula (Va), Formula (VIa) or Formula (VIIa):

(IVa)

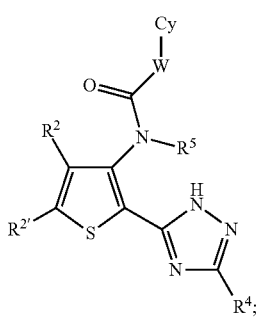

(Va)

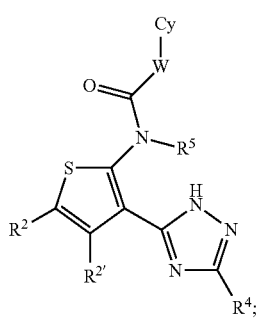

(VIa)

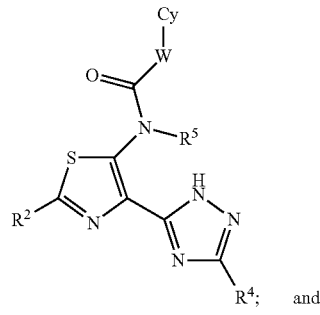

(VIIa)

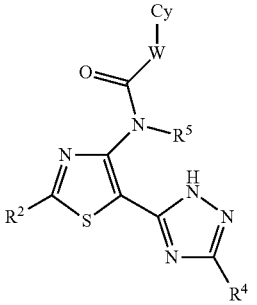

or a salt or solvate thereof,
wherein R⁴ is chosen from H, methyl, and cyclopropyl.

5. The compound of claim 1, wherein W is methylene (—CH₂—).

6. The compound of claim 1, wherein R⁵ is H.

7. The compound of claim 1, wherein Cy is chosen from phenyl, naphthyl, quinoline, isoquinoline, quinoxaline, quinazoline, quinolin-2-one, 3,4-dihydroquinolin-2-one, 3,4-dihydro-1,5-naphthyridin-2-one, and 3,4-dihydro-1,6-naphthyridin-2-one, each optionally substituted with 1-6 substituents independently chosen from $C_1$-$C_6$-alkyl, $C_2$-$C_6$-alkenyl, $C_2$-$C_6$-alkynyl, $C_1$-$C_6$-haloalkyl, 2- to 6-membered heteroalkyl, $C_3$-$C_6$-cycloalkyl, 3- to 8-membered heterocycloalkyl, aryl, 5- or 6-membered heteroaryl, CN, halogen, OR⁵², SR⁵², NR⁵²R⁵³, C(O)R⁵⁴, C(O)NR⁵²R⁵³, OC(O)NR⁵²R⁵³, C(O)OR⁵², NR⁵⁵C(O)R⁵⁴, NR⁵⁵C(O)OR⁵², NR⁵⁵C(O)NR⁵²R⁵³, NR⁵⁵C(S)NR⁵²R⁵³, NR⁵⁵S(O)₂R⁵⁴, S(O)₂NR⁵²R⁵³, S(O)R⁵⁴ and S(O)₂R⁵⁴.

8. The compound of claim 7, wherein Cy is optionally substituted quinoline.

9. The compound of claim 7, wherein Cy is optionally substituted isoquinoline.

10. The compound of claim 7, wherein Cy is optionally substituted quinolin-2-one.

11. The compound of claim 10, wherein the Cy is quinolin-2-one substituted with at least one $C_1$-$C_6$-haloalkyl.

12. The compound of claim 7, wherein Cy is optionally substituted 3,4-dihydro-1,6-naphthyridin-2-one.

13. The compound of claim 7, wherein Cy is optionally substituted 3,4-dihydro-1,5-naphthyridin-2-one.

14. The compound of claim 13, wherein Cy is unsubstituted 3,4-dihydro-1,5-naphthyridin-2-one.

15. The compound of claim 1, which is N-(4-bromo-3-(1H-1,2,4-triazol-5-yl)thiophen-2-yl)-2-(2-oxo-6-(trifluoromethyl)quinolin-1(2H)-yl)acetamide.

16. The compound of claim 1, which is N-(4-bromo-3-(1H-1,2,4-triazol-5-yl)thiophen-2-yl)-2-(2-oxo-3,4-dihydro-1,5-naphthyridin-1 (2H)-yl)acetamide.

17. The compound of claim 1, wherein Cy is selected from the group consisting of:

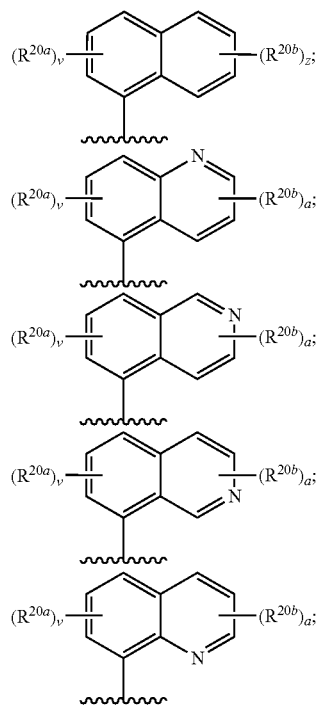

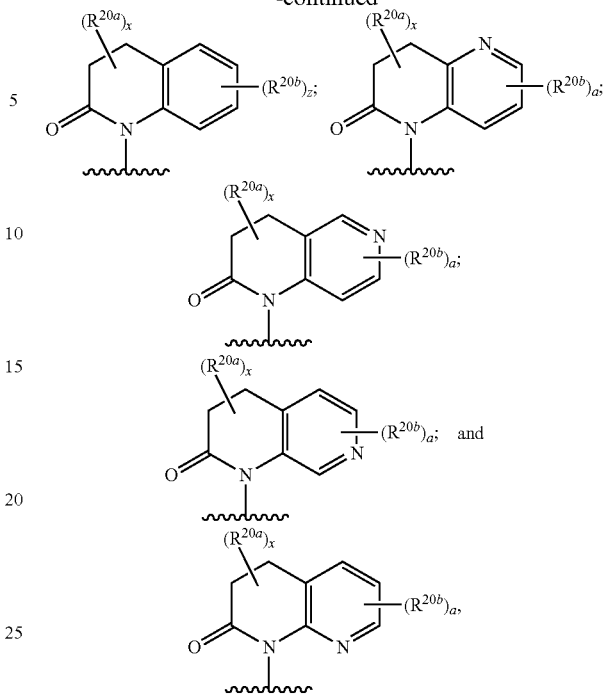

wherein:
$R^{20a}$ and $R^{20b}$ are each independently chosen from $C_1$-$C_6$-alkyl, $C_2$-$C_6$-alkenyl, $C_2$-$C_6$-alkynyl, $C_1$-$C_6$-haloalkyl, 2- to 6-membered heteroalkyl, $C_3$-$C_6$-cycloalkyl, 3- to 8-membered heterocycloalkyl, aryl, 5- or 6-membered heteroaryl, CN, halogen, $OR^{52}$, $SR^{52}$, $NR^{52}R^{53}$, $C(O)R^{54}$, $C(O)NR^{52}R^{53}$, $OC(O)NR^{52}R^{53}$, $C(O)OR^{52}$, $NR^{55}C(O)R^{54}$, $NR^{55}C(O)OR^{52}$, $NR^{55}C(O)NR^{52}R^{53}$, $NR^{55}C(S)NR^{52}R^{53}$, $NR^{55}S(O)_2R^{54}$, $S(O)_2NR^{52}R^{53}$, $S(O)R^{54}$ and $S(O)_2R^{54}$
v is an integer from 0 to 3;
x is an integer from 0 to 4;
z is an integer from 0 to 4; and
a is an integer from 0 to 3.

* * * * *